United States Patent
Brace et al.

(10) Patent No.: US 11,472,794 B2
(45) Date of Patent: Oct. 18, 2022

(54) FUSED IMIDAZOLE DERIVATIVES AS IL-17 MODULATORS

(71) Applicant: UCB Biopharma SRL, Brussels (BE)

(72) Inventors: Gareth Neil Brace, Abingdon (GB); Rose Elizabeth Bardell-Cox, Abingdon (GB); Gregory Foulkes, Abingdon (GB); James Richard Frost, Slough (GB); Helen Tracey Horsley, Slough (GB); Elizabeth Pearl Jones, Bracknell (GB); Fabien Claude Lecomte, Slough (GB); James Thomas Reuberson, Slough (GB); Monika-Sarah Elizabeth Dorothea Schulze, Slough (GB); Richard David Taylor, Slough (GB); Wei Tsung Yau, Abingdon (GB); Zhaoning Zhu, Slough (GB)

(73) Assignee: UCB Biopharma SRL, Brussels (BE)

( * ) Notice: Subject to any disclaimer, the term of this patent is extended or adjusted under 35 U.S.C. 154(b) by 0 days.

(21) Appl. No.: 16/959,339

(22) PCT Filed: Jan. 10, 2019

(86) PCT No.: PCT/EP2019/050594
§ 371 (c)(1),
(2) Date: Jun. 30, 2020

(87) PCT Pub. No.: WO2019/138017
PCT Pub. Date: Jul. 18, 2019

(65) Prior Publication Data
US 2021/0053952 A1 Feb. 25, 2021

(30) Foreign Application Priority Data

Jan. 15, 2018 (GB) .................................. 1800639.5
Dec. 11, 2018 (GB) .................................. 1820172.3

(51) Int. Cl.
| | | |
|---|---|---|
| *C07D 403/12* | (2006.01) | |
| *C07D 413/12* | (2006.01) | |
| *C07D 407/14* | (2006.01) | |
| *C07D 235/16* | (2006.01) | |
| *C07D 401/14* | (2006.01) | |
| *C07D 413/14* | (2006.01) | |

(52) U.S. Cl.
CPC ......... *C07D 407/14* (2013.01); *C07D 235/16* (2013.01); *C07D 401/14* (2013.01); *C07D 403/12* (2013.01); *C07D 413/12* (2013.01); *C07D 413/14* (2013.01)

(58) Field of Classification Search
CPC ............................. C07D 403/12; C07D 413/12
See application file for complete search history.

(56) References Cited

U.S. PATENT DOCUMENTS

| 5,948,779 A * | 9/1999 | Sperl .................... C07D 213/56 544/242 |
| 2016/0158200 A1 * | 6/2016 | Hewawasam ........ A61K 31/444 514/308 |

FOREIGN PATENT DOCUMENTS

| WO | WO2009/089036 A2 | 7/2009 | |
| WO | WO-2012/166891 A2 * | 12/2012 | ........... A61K 31/436 |
| WO | WO2013/116682 A1 | 8/2013 | |
| WO | WO2014/066726 A2 | 5/2014 | |
| WO | WO2014/181287 A1 | 11/2014 | |
| WO | WO-2016/022312 A1 * | 2/2016 | ........... C07D 401/14 |
| WO | WO2018/229079 A1 | 12/2018 | |

OTHER PUBLICATIONS

PubChem CID 843431, National Center for Biotechnology Information. "PubChem Compound Summary for CID 843431, N-(1H-Benzimidazol-2-ylmethyl)acetamide" PubChem, https://pubchem.ncbi.nlm.nih.gov/compound/N-_1H-Benzimidazol-2-ylmethyl_acetamide. Accessed Sep. 23, 2021, create date Jul. 9, 2005. (Year: 2005).*
Chemical Abstracts Registry No. 1061591-59-0, indexed in the Registry file on STN CAS Online Oct. 15, 2008. (Year: 2008).*
Chemical Abstracts Registry No. 2128700-12-7, indexed in the Registry file on STN CAS Online Sep. 19, 2017. (Year: 2017).*
Chemical Abstracts Registry No. 2249207-30-3, indexed in the Registry file on STN CAS Online Nov. 18, 2018. (Year: 2018).*
Gaffen, Sarah L., An overview of IL-17 function and signaling, Cytokine, 2008, 402-407, 43.
Korn et al., IL-17 and Th17 Cells, Annu. Rev. Immunol., 2009, 485-517, 27.
Moseley et al., Interleukin-17 family and IL-17 receptors, Cytokine Growth Factor Rev, 2003, 155-174,14.
Rouvier et al., CTLA-8, cloned from an activated T cell, bearing AU-rich messenger RNA instability sequences, and homologous to a herpesvirus saimiri gene, J. Immunol, 1993, 5445-5456, 150.
Wright et al, The human IL17/IL-17A Heterodimeric Cytokine Signals through the IL-17RA/IL-17RC Receptor Complex, J. Immunol, 2008, 2799-2805, 181.
International Search Report dated Feb. 13, 2019 for International Application No. PCT/EP2019/050594, 2 pages.

* cited by examiner

*Primary Examiner* — Laura L Stockton
(74) *Attorney, Agent, or Firm* — McDonnell Boehnen Hulbert & Berghoff LLP

(57) ABSTRACT

A series of substituted fused bicyclic imidazole derivatives, including benzimidazole derivatives and analogues thereof, being potent modulators of human IL-17 activity, are accordingly of benefit in the treatment and/or prevention of various human ailments, including inflammatory and autoimmune disorders.

12 Claims, No Drawings

FUSED IMIDAZOLE DERIVATIVES AS IL-17 MODULATORS

This application is a U.S. national phase of International Application No. PCT/EP2019/050594, filed Jan. 10, 2019, which claims priority from GB Patent Application No. 1800639.5, filed Jan. 15, 2018, and GB Patent Application No. 1820172.3, filed Dec. 11, 2018.

The present invention relates to heterocyclic compounds, and to their use in therapy. More particularly, this invention is concerned with pharmacologically active substituted fused bicyclic imidazole derivatives, including benzimidazole derivatives and analogues thereof. These compounds act as modulators of IL-17 activity, and are accordingly of benefit as pharmaceutical agents for the treatment and/or prevention of pathological conditions, including adverse inflammatory and autoimmune disorders.

IL-17A (originally named CTLA-8 and also known as IL-17) is a pro-inflammatory cytokine and the founder member of the IL-17 family (Rouvier et al., *J. Immunol.*, 1993, 150, 5445-5456). Subsequently, five additional members of the family (IL-17B to IL-17F) have been identified, including the most closely related, IL-17F (ML-1), which shares approximately 55% amino acid sequence homology with IL-17A (Moseley et al., *Cytokine Growth Factor Rev.*, 2003, 14, 155-174). IL-17A and IL-17F are expressed by the recently defined autoimmune related subset of T helper cells, Th17, that also express IL-21 and IL-22 signature cytokines (Korn et al., *Ann. Rev. Immunol.*, 2009, 27, 485-517). IL-17A and IL-17F are expressed as homodimers, but may also be expressed as the IL-17A/F heterodimer (Wright et al., *J. Immunol.*, 2008, 181, 2799-2805). IL-17A and F signal through the receptors IL-17R, IL-17RC or an IL-17RA/RC receptor complex (Gaffen, *Cytokine*, 2008, 43, 402-407). Both IL-17A and IL-17F have been associated with a number of autoimmune diseases.

The compounds in accordance with the present invention, being potent modulators of human IL-17 activity, are therefore beneficial in the treatment and/or prevention of various human ailments, including inflammatory and autoimmune disorders.

Furthermore, the compounds in accordance with the present invention may be beneficial as pharmacological standards for use in the development of new biological tests and in the search for new pharmacological agents. Thus, the compounds of this invention may be useful as radioligands in assays for detecting pharmacologically active compounds.

WO 2013/116682 and WO 2014/066726 relate to separate classes of chemical compounds that are stated to modulate the activity of IL-17 and to be useful in the treatment of medical conditions, including inflammatory diseases.

Co-pending international patent application PCT/EP2018/065558 (published on 20 Dec. 2018 as WO 2018/229079) describes a class of spirocyclic oxoindoline derivatives, and analogues thereof, that are stated to act as modulators of IL-17 activity, and thus to be of benefit in the treatment of pathological conditions including adverse inflammatory and autoimmune disorders.

None of the prior art available to date, however, discloses or suggests the precise structural class of substituted benzimidazole derivatives, and analogues thereof, as provided by the present invention.

The present invention provides a compound of formula (I) or an N-oxide thereof, or a pharmaceutically acceptable salt thereof:

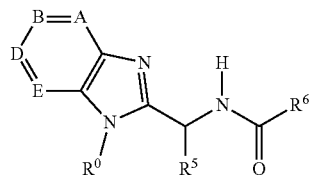

(I)

wherein
A represents C—$R^1$ or N;
B represents C—$R^2$ or N;
D represents C—$R^3$ or N;
E represents C—$R^4$ or N;
$R^0$ represents hydrogen or $C_{1-6}$ alkyl;
$R^1$, $R^2$, $R^3$ and $R^4$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$NHSO_2NR^bR^c$, —N=S(O)$R^bR^c$, —$COR^d$, —$CO_2R^d$, —$CONR^bR^c$, —$CON(OR^a)R^b$, —$SO_2NR^bR^c$ or —S(O)(N$R^e$)$R^a$; or $C_{1-6}$ alkyl, $C_{2-6}$ alkenyl, $C_{2-6}$ alkynyl, $C_{3-9}$ cycloalkyl, $C_{3-9}$ cycloalkyl($C_{1-6}$)alkyl, $C_{4-9}$ cycloalkenyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl or heteroaryl($C_{1-6}$) alkyl, any of which groups may be optionally substituted by one or more substituents;

$R^5$ represents hydrogen; or $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-6}$)alkyl, $C_{8-11}$ tricycloalkyl, $C_{8-11}$ tricycloalkyl($C_{1-6}$) alkyl, $C_{7-13}$ dispirocycloalkyl, $C_{7-13}$ dispirocycloalkyl($C_{1-6}$) alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents;

$R^6$ represents —$OR^{6a}$ or —$NR^{6b}R^{6c}$; or $R^6$ represents $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$)alkyl, any of which groups may be optionally substituted by one or more substituents;

$R^{6a}$ represents $C_{1-6}$ alkyl; or $R^{6a}$ represents $C_{3-9}$ cycloalkyl, which group may be optionally substituted by one or more substituents;

$R^{6b}$ represents hydrogen or $C_{1-6}$ alkyl;
$R^{6c}$ represents hydrogen or $C_{1-6}$ alkyl;
$R^a$ represents trifluoromethyl; or $R^a$ represents $C_{1-6}$ alkyl, $C_{3-9}$ cycloalkyl, $C_{3-9}$ cycloalkyl($C_{1-6}$)alkyl, aryl, aryl($C_{1-6}$) alkyl, $C_{3-7}$ heterocycloalkyl, $C_{3-7}$ heterocycloalkyl-($C_{1-6}$) alkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-9}$ cycloalkyl, $C_{3-9}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents; or $R^b$ and $R^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

$R^d$ represents hydrogen; or $R^d$ represents $C_{1-6}$ alkyl, $C_{3-9}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as defined above, or a pharmaceutically acceptable salt thereof.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of IL-17 function is indicated.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of IL-17 function is indicated.

The present invention also provides a method for the treatment and/or prevention of disorders for which the administration of a modulator of IL-17 function is indicated which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one, two or three substituents. Suitably, such groups will be unsubstituted, or substituted by one or two substituents.

For use in medicine, the salts of the compounds of formula (I) will be pharmaceutically acceptable salts. Other salts may, however, be useful in the preparation of the compounds of formula (I) or of their pharmaceutically acceptable salts. Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002. Suitable pharmaceutically acceptable salts of the compounds of formula (I) include acid addition salts which may, for example, be formed by mixing a solution of a compound of formula (I) with a solution of a pharmaceutically acceptable acid.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds of use in the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

Suitable $C_{2-6}$ alkenyl groups include vinyl and allyl.

Suitable $C_{2-6}$ alkynyl groups include ethynyl and propargyl.

The term "$C_{3-9}$ cycloalkyl" as used herein refers to monovalent groups of 3 to 9 carbon atoms derived from a saturated monocyclic hydrocarbon, and may comprise benzo-fused analogues thereof. Suitable $C_{3-9}$ cycloalkyl groups include cyclopropyl, cyclobutyl, benzocyclobutenyl, cyclopentyl, indanyl, cyclohexyl, cycloheptyl, cyclooctyl and cyclononanyl.

The term "$C_{4-9}$ cycloalkenyl" as used herein refers to monovalent groups of 4 to 9 carbon atoms derived from an unsaturated monocyclic hydrocarbon, and may comprise benzo-fused analogues thereof. Suitable $C_{4-9}$ cycloalkenyl groups include cyclobutenyl, cyclopentenyl, cyclohexenyl, cycloheptenyl and cyclooctenyl.

The term "$C_{4-12}$ bicycloalkyl" as used herein refers to monovalent groups of 4 to 12 carbon atoms derived from a saturated bicyclic hydrocarbon. Typical bicycloalkyl groups include bicyclo[1.1.1]pentanyl, bicyclo[3.1.0]hexanyl, bicyclo[4.1.0]heptanyl and bicyclo[2.2.2]octanyl.

The term "$C_{5-9}$ spirocycloalkyl" as used herein refers to saturated bicyclic ring systems containing 5 to 9 carbon atoms, in which the two rings are linked by a common atom. Suitable spirocycloalkyl groups include spiro[2.3]hexanyl, spiro[2.4]heptanyl, spiro[3.3]heptanyl, spiro[3.4]octanyl, spiro[3.5]nonanyl and spiro[4.4]nonanyl.

The term "$C_{8-11}$ tricycloalkyl" as used herein refers to monovalent groups of 8 to 11 carbon atoms derived from a saturated tricyclic hydrocarbon. Typical tricycloalkyl groups include adamantanyl.

The term "$C_{7-13}$ dispirocycloalkyl" as used herein refers to saturated tricyclic ring systems containing 7 to 13 carbon atoms, in which the three rings incorporate two spiro linkages. Suitable dispirocycloalkyl groups include dispiro[2.0.24.13]heptanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, tetrahydro-thiopyranyl, piperidinyl, 1,2,3,4-tetrahydroquinolinyl, 1,2,3,4-tetrahydroisoquinolinyl, piperazinyl, 1,2,3,4-tetrahydroquinoxalinyl, hexahydro-[1,2,5]thiadiazolo[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl. Additional groups include 2,5-dihydropyrrolyl, 1,2-dihydropyridinyl, 1,2,3,4-tetrahydropyridinyl, 2,3-dihydro-1,4-oxazinyl and 6,7-dihydro-5H-1,4-oxazepinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 6-oxabicyclo[3.1.0]hexanyl, 3-azabicyclo[3.1.0]hexanyl, 2-oxa-5-azabicyclo[2.2.1]heptanyl, 6-azabicyclo[3.2.0]heptanyl, 6-oxabicyclo[3.1.1]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo-[2.2.2]octanyl, 8-oxabicyclo[3.2.1]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzofuryl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups. Additional groups include 6,8-dihydro-5H-[1,2,4]triazolo[4,3-a]pyrazinyl.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$.

Similarly, by way of example, each individual carbon atom present in formula (I), or in the formulae depicted hereinafter, may be present as a $^{12}C$, $^{13}C$ or $^{14}C$ atom, preferably $^{12}C$.

In one embodiment, A represents C—$R^1$. In another embodiment, A represents N.

In one embodiment, B represents C—$R^2$. In another embodiment, B represents N.

In one embodiment, D represents C—$R^3$. In another embodiment, D represents N.

In one embodiment, E represents C—$R^4$. In another embodiment, E represents N.

In a particular embodiment, A represents C—$R^1$, B represents C—$R^2$, D represents C—$R^3$ and E represents C—$R^4$.

In another embodiment, A represents C—$R^1$, B represents C—$R^2$, D represents N and E represents C—$R^4$.

In another embodiment, A represents C—$R^1$, B represents N, D represents C—$R^3$ and E represents C—$R^4$.

In another embodiment, A represents N, B represents C—$R^2$, D represents C—$R^3$ and E represents C—$R^4$.

In another embodiment, A represents N, B represents C—$R^2$, D represents C—$R^3$ and E represents N.

In another embodiment, A represents N, B represents C—$R^2$, D represents N and E represents C—$R^4$.

Suitably, the present invention provides a compound of formula (I-1), (I-2), (I-3), (I-4), (I-5) or (I-6) or an N-oxide thereof, or a pharmaceutically acceptable salt thereof:

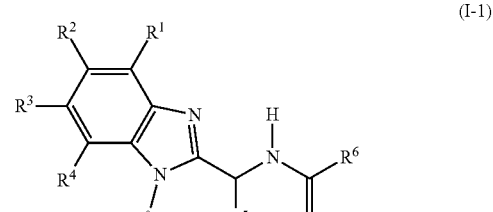

(I-1)

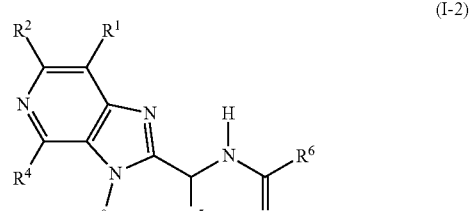

(I-2)

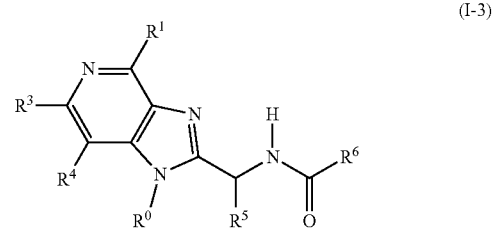

(I-3)

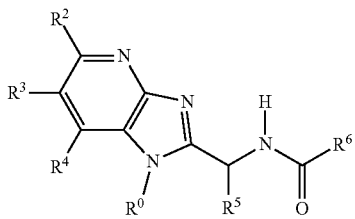

(I-4)

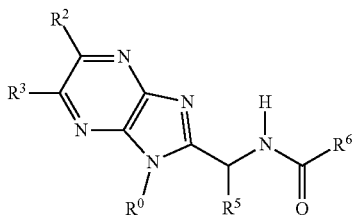

(I-5)

(I-6)

wherein $R^0$, $R^1$, $R^2$, $R^3$, $R^4$, $R^5$ and $R^6$ are as defined above.

Suitably, $R^0$ represents hydrogen or methyl.

In a particular embodiment, $R^0$ represents hydrogen. In another embodiment, $R^0$ represents $C_{1-6}$ alkyl, especially methyl.

In general, $R^1$, $R^2$, $R^3$ and $R^4$ independently represent hydrogen, halogen, cyano, nitro, hydroxy, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$NHSO_2NR^bR^c$, —$COR^d$, —$CO_2R^d$, —$CONR^bR^c$, —$CON(OR^a)R^b$, —$SO_2NR^bR^c$ or —$S(O)(NR^e)R^a$; or $C_{1-6}$ alkyl, $C_{2-6}$ alkenyl, $C_{2-6}$ alkynyl, $C_{3-9}$ cycloalkyl, $C_{3-9}$ cycloalkyl($C_{1-6}$)alkyl, $C_{4-9}$ cycloalkenyl, aryl, aryl($C_{1-6}$)-alkyl, $C_{3-7}$ heterocycloalkyl, $C_{3-7}$ heterocycloalkyl($C_{1-6}$)alkyl, $C_{3-7}$ heterocycloalkenyl, $C_{4-9}$ heterobicycloalkyl, heteroaryl or heteroaryl($C_{1-6}$)alkyl, any of which groups may be optionally substituted by one or more substituents;

More generally, $R^1$, $R^2$, $R^3$ and $R^4$ independently represent hydrogen, halogen, cyano, —$OR^a$, —$SOR^a$, —$NR^bR^c$, —$NR^cCOR^d$ or —$N=S(O)R^bR^c$; or $C_{1-6}$ alkyl, aryl, aryl($C_{1-6}$)-alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents.

Generally, $R^1$, $R^2$, $R^3$ and $R^4$ independently represent hydrogen, halogen or —$OR^a$; or $C_{3-7}$ heterocycloalkyl or $C_{3-7}$ heterocycloalkyl($C_{1-6}$)alkyl, either of which groups may be optionally substituted by one or more substituents.

Suitably, $R^1$, $R^2$, $R^3$ and $R^4$ independently represent hydrogen, halogen or —$OR^a$; or $C_{3-7}$ heterocycloalkyl, which group may be optionally substituted by one or more substituents.

Aptly, $R^1$, $R^2$, $R^3$ and $R^4$ independently represent hydrogen, fluoro, chloro, cyano, —$OR^a$, —$SOR^a$, —$NR^bR^c$, —$NR^cCOR^d$ or —$N=S(O)R^bR^c$; or methyl, ethyl, propyl, phenyl, benzyl, tetrahydrofuranyl, pyrrolidinyl, tetrahydropyranyl, piperidinyl, piperazinyl, morpholinyl, oxazepinyl, pyrrolidinylmethyl, piperidinylmethyl, piperazinylmethyl, morpholinylmethyl, 2,5-dihydropyrrolyl, 3,6-dihydro-2H-pyranyl, 1,2,3,4-tetrahydro-pyridinyl, 2,3-dihydro-1,4-oxazinyl, 6,7-dihydro-5H-1,4-oxazepinyl, furyl, pyrazolyl, 6,8-dihydro-5H-[1,2,4]triazolo[4,3-a]pyrazinyl, pyridinyl, pyrimidinyl, pyrazinyl, pyridinyl-methyl or pyridinylethyl, any of which groups may be optionally substituted by one or more substituents.

Appositely, $R^1$, $R^2$, $R^3$ and $R^4$ independently represent hydrogen, halogen or —$OR^a$; or tetrahydropyranyl, piperazinyl or piperazinylmethyl, any of which groups may be optionally substituted by one or more substituents.

Typically, $R^1$, $R^2$, $R^3$ and $R^4$ independently represent hydrogen, halogen or —$OR^a$; or tetrahydropyranyl or piperazinyl, either of which groups may be optionally substituted by one or more substituents.

Illustrative examples of optional substituents which may be present on $R^1$, $R^2$, $R^3$ or $R^4$ include one, two or three substituents independently selected from halogen, cyano, nitro, $C_{1-6}$ alkyl, trifluoromethyl, difluoroethyl, phenyl, fluorophenyl, oxetanyl, pyrrolidinyl, tetrahydropyranyl, morpholinyl, piperazinyl, oxadiazolyl, ($C_{1-6}$)alkyl-oxadiazolyl, hydroxy, hydroxy($C_{1-6}$)alkyl, oxo, $C_{1-6}$ alkoxy, difluoromethoxy, trifluoro-methoxy, pentafluorothio, $C_{1-6}$ alkylthio, $C_{1-6}$ alkylsulfinyl, ($C_{1-6}$)alkyl(imino)sulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro($C_{1-6}$)alkylamino-carbonyl, di($C_{1-6}$)alkylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)-(methyl)azetidinylcarbonyl, morpholinylcarbonyl, ($C_{1-6}$)alkylpyrazolylcarbonyl, amino-sulfonyl, $C_{1-6}$ alkylaminosulfonyl, di($C_{1-6}$)alkylaminosulfonyl, ($C_{1-6}$)alkylsulfoximinyl, trifluoromethylsulfoximinyl, [($C_{1-6}$)alkyl][N—($C_{1-6}$)alkyl]sulfoximinyl, [($C_{1-6}$)alkyl][N-carboxy($C_{1-6}$)alkyl]sulfoximinyl, [N—($C_{2-6}$)alkoxycarbonyl($C_{1-6}$)alkyl][($C_{1-6}$)alkyl]-sulfoximinyl, ($C_{3-7}$)cycloalkylsulfoximinyl, N-[di($C_{1-6}$)alkylsulfoxo]iminyl and di($C_{1-6}$)alkylsulfoximinyl.

Representative examples of optional substituents which may be present on $R^1$, $R^2$, $R^3$ or $R^4$ include one, two or three substituents independently selected from halogen, cyano, $C_{1-6}$ alkyl, oxetanyl, oxadiazolyl, ($C_{1-6}$)alkyloxadiazolyl, hydroxy, oxo, ($C_{1-6}$)alkyl-(imino)sulfinyl, $C_{1-6}$ alkylsulfonyl, $C_{2-6}$ alkylcarbonylamino, $C_{1-6}$ alkylsulfonylamino, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro($C_{1-6}$)alkylaminocarbonyl, di($C_{1-6}$)alkylaminocarbonyl, azetidinylcarbonyl, hydroxyazetidinylcarbonyl, difluoroazetidinylcarbonyl, (hydroxy)-(trifluoromethyl)azetidinylcarbonyl, (hydroxy)(methyl)azetidinylcarbonyl, morpholinyl-carbonyl and ($C_{1-6}$)alkylpyrazolylcarbonyl.

Suitable examples of optional substituents which may be present on $R^1$, $R^2$, $R^3$ or $R^4$ include one, two or three substituents independently selected from halogen, $C_{1-6}$ alkyl, trifluoromethyl, difluoroethyl, hydroxy, hydroxy($C_{1-6}$)alkyl, pentafluorothio, $C_{1-6}$ alkyl-sulphonyl, oxo, amino, carboxy, $C_{2-6}$ alkoxycarbonyl, ($C_{1-6}$)alkylsulfoximinyl, trifluoromethylsulfoximinyl, [($C_{1-6}$)alkyl][N—($C_{1-6}$)alkyl]sulfoximinyl, [($C_{1-6}$)alkyl][N-carboxy($C_{1-6}$)alkyl]

sulfoximinyl, [N—($C_{2-6}$)alkoxycarbonyl($C_{1-6}$)alkyl][($C_{1-6}$)alkyl]-sulfoximinyl, ($C_{3-7}$)cycloalkylsulfoximinyl and N-[di($C_{1-6}$)alkylsulfoxo]iminyl.

Typical examples of optional substituents which may be present on $R^1$, $R^2$, $R^3$ or $R^4$ include one, two or three substituents independently selected from $C_{1-6}$ alkyl.

Illustrative examples of specific substituents which may be present on $R^1$, $R^2$, $R^3$ or $R^4$ include one, two or three substituents independently selected from fluoro, chloro, bromo, cyano, nitro, methyl, ethyl, isopropyl, tert-butyl, trifluoromethyl, difluoroethyl, phenyl, fluorophenyl, oxetanyl, pyrrolidinyl, tetrahydropyranyl, morpholinyl, piperazinyl, oxadiazolyl, methyloxadiazolyl, hydroxy, hydroxymethyl, hydroxyisopropyl, oxo, methoxy, tert-butoxy, difluoromethoxy, trifluoromethoxy, pentafluorothio, methylthio, methylsulfinyl, (imino)(methyl)sulfinyl, methylsulfonyl, amino, aminomethyl, amino-ethyl, methylamino, tert-butylamino, dimethylamino, acetylamino, acetylaminoethyl, methoxycarbonylamino, methylsulfonylamino, formyl, acetyl, hydroxyacetyl, carboxy, methoxycarbonyl, ethoxycarbonyl, tert-butoxycarbonyl, aminocarbonyl, methylamino-carbonyl, ethylaminocarbonyl, chloropropylaminocarbonyl, dimethylaminocarbonyl, azetidinylcarbonyl, hydroxyazetidinylcarbonyl, difluoroazetidinylcarbonyl, (hydroxy)-(trifluoromethyl)azetidinylcarbonyl, (hydroxy)(methyl)azetidinylcarbonyl, morpholinyl-carbonyl, ethylpyrazolylcarbonyl, aminosulfonyl, methylaminosulfonyl, dimethylamino-sulfonyl, methylsulfoximinyl, ethylsulfoximinyl, trifluoromethylsulfoximinyl, (methyl)-(N-methyl)sulfoximinyl, (N-carboxymethyl)(methyl)sulfoximinyl, (N-tert-butoxy-carbonylmethyl)(methyl)sulfoximinyl, cyclopropylsulfoximinyl, N-(dimethylsulfoxo)-iminyl and dimethylsulfoximinyl.

Representative examples of specific substituents which may be present on $R^1$, $R^2$, $R^3$ or $R^4$ include one, two or three substituents independently selected from fluoro, cyano, methyl, oxetanyl, oxadiazolyl, methyloxadiazolyl, hydroxy, oxo, (imino)(methyl)sulfinyl, methylsulfonyl, acetylamino, methylsulfonylamino, acetyl, hydroxyacetyl, carboxy, methoxycarbonyl, ethoxycarbonyl, tert-butoxycarbonyl, aminocarbonyl, methylamino-carbonyl, ethylaminocarbonyl, chloropropylaminocarbonyl, dimethylaminocarbonyl, azetidinylcarbonyl, hydroxyazetidinylcarbonyl, difluoroazetidinylcarbonyl, (hydroxy)-(trifluoromethyl)azetidinylcarbonyl, (hydroxy)(methyl)azetidinylcarbonyl, morpholinyl-carbonyl and ethylpyrazolylcarbonyl.

Suitable examples of particular substituents on $R^1$, $R^2$, $R^3$ or $R^4$ include one, two or three substituents independently selected from fluoro, methyl, ethyl, trifluoromethyl, difluoroethyl, hydroxy, hydroxyisopropyl, pentafluorothio, methylsulphonyl, oxo, amino, carboxy, methoxycarbonyl, ethoxycarbonyl, tert-butoxycarbonyl, methylsulfoximinyl, ethylsulfoximinyl, trifluoromethylsulfoximinyl, (methyl)(N-methyl)sulfoximinyl, (N-carboxymethyl)(methyl)sulfoximinyl, (N-tert-butoxycarbonylmethyl)(methyl)-sulfoximinyl, cyclopropylsulfoximinyl and N-(dimethylsulfoxo)iminyl.

Typical examples of particular substituents on $R^1$, $R^2$, $R^3$ or $R^4$ include one, two or three substituents independently selected from methyl.

Particular values of $R^1$, $R^2$, $R^3$ or $R^4$ include hydrogen, fluoro, chloro, cyano, —$OR^a$, —$SOR^a$, —$NR^bR^c$, —$NR^c$-$COR^d$, —N=S(O)$R^bR^c$, tert-butoxycarbonylmethyl, dimethyl-aminocarbonylmethyl, acetylaminoethyl, carboxyethyl, tert-butoxycarbonylethyl, methylaminocarbonylethyl, dimethylaminocarbonylethyl, acetylaminopropyl, methylsulfonyl-phenyl, methylsulfonylaminophenyl, tert-butoxycarbonylphenyl, dimethylaminocarbonyl-phenyl, ethoxycarbonylbenzyl, carboxytetrahydrofuranyl, methoxycarbonyltetrahydro-furanyl, dimethylaminocarbonyltetrahydrofuranyl, hydroxyazetidinylcarbonyltetrahydro-furanyl, difluoroazetidinylcarbonyltetrahydrofuranyl, (hydroxy)(trifluoromethyl)-azetidinylcarbonyltetrahydrofuranyl, morpholinylcarbonyltetrahydrofuranyl, methoxy-carbonylpyrrolidinyl, tert-butoxycarbonylpyrrolidinyl, dimethylaminocarbonyl-pyrrolidinyl, difluoroazetidinylcarbonylpyrrolidinyl, (ethoxycarbonyl)(methylsulfonyl)-pyrrolidinyl, (acetyl)(ethoxycarbonyl)pyrrolidinyl, (tert-butoxycarbonyl)(difluoro-azetidinylcarbonyl)pyrrolidinyl, tetrahydropyranyl, ethoxycarbonyltetrahydropyranyl, dimethylaminocarbonyltetrahydropyranyl, piperidinyl, methylpiperidinyl, acetyl-piperidinyl, hydroxyacetylpiperidinyl, methoxycarbonylpiperidinyl, tert-butoxycarbonyl-piperidinyl, dimethylaminocarbonylpiperidinyl, ethylpyrazolylcarbonylpiperidinyl, methylpiperazinyl, morpholinyl, methyloxadiazolylmorpholinyl, methylsulfonyl-morpholinyl, acetylmorpholinyl, hydroxyacetylmorpholinyl, methoxycarbonyl-morpholinyl, ethoxycarbonylmorpholinyl, tert-butoxycarbonylmorpholinyl, ethylamino-carbonylmorpholinyl, difluoroazetidinylcarbonylmorpholinyl, oxazepinyl, tert-butoxy-carbonyloxazepinyl, oxopyrrolidinylmethyl, carboxypyrrolidinylmethyl, methoxy-carbonylpyrrolidinylmethyl, dimethylaminocarbonylpyrrolidinylmethyl, methylsulfonyl-piperidinylmethyl, piperazin- ylmethyl, methylpiperazinylmethyl, oxetanylpiperazinyl-methyl, methylsulfonylpiperazinylmethyl, acetylpiperazinylmethyl, tert-butoxycarbonyl-piperazinylmethyl, (acetyl)(tert-butoxycarbonyl)piperazinylmethyl, morpholinylmethyl, (tert-butoxycarbonyl)(difluoroazetidinylcarbonyl)-2,5-dihydropyrrolyl, 3,6-dihydro-2H-pyranyl, ethoxycarbonyl-3,6-dihydro-2H-pyranyl, dimethylaminocarbonyl-3,6-dihydro-2H-pyranyl, tert-butoxycarbonyl-1,2,3,4-tetrahydropyridinyl, tert-butoxycarbonyl-2,3-dihydro-1,4-oxazinyl, tert-butoxycarbonyl-6,7-dihydro-5H-1,4-oxazepinyl, difluoro-azetidinylcarbonylfuryl, difluoroazetidinylcarbonylpyrazolyl, acetyl-6,8-dihydro-5H-[1,2,4]triazolo[4,3-a]pyrazinyl, (imino)(methyl)sulfinylpyridinyl, ethoxycarbonyl-pyridinyl, chloropropylaminocarbonylpyridinyl, dimethylaminocarbonylpyridinyl, azetidinylcarbonylpyridinyl, difluoroazetidinylcarbonylpyridinyl, (hydroxy)(methyl)-azetidinylcarbonylpyridinyl, (dimethylaminocarbonyl)(fluoro)pyridinyl, dimethylamino-carbonylpyrimidinyl, (dimethylaminocarbonyl)(methyl)pyrimidinyl, dimethylamino-carbonylpyrazinyl, pyridinylmethyl, cyanopyridinylmethyl, oxadiazolylpyridinylmethyl, ethoxycarbonylpyridinylmethyl, aminocarbonylpyridinylmethyl, pyridinylethyl and hydroxypyridinylethyl.

Suitable values of $R^1$, $R^2$, $R^3$ or $R^4$ include hydrogen, fluoro, chloro, —$OR^a$, tetrahydropyranyl and methylpiperazinyl.

Suitably, $R^1$ represents hydrogen, halogen, cyano or —$OR^a$.

Typically, $R^1$ represents halogen or —$OR^a$.

In a first embodiment, $R^1$ represents hydrogen. In a second embodiment, $R^1$ represents halogen. In one aspect of that embodiment, $R^1$ represents fluoro. In another aspect of that embodiment, $R^1$ represents chloro. In a third embodiment, $R^1$ represents cyano. In a fourth embodiment, $R^1$ represents —$OR^a$.

Illustrative values of $R^1$ include hydrogen, fluoro, chloro, cyano and —$OR^a$.

Suitable values of $R^1$ include fluoro, chloro and —$OR^a$.

Generally, $R^2$ represents hydrogen, cyano, —$OR^a$, —$SOR^a$, —$NR^bR^c$, —$NR^cCOR^d$ or —$N=S(O)R^bR^c$; or $R^2$ represents $C_{1-6}$ alkyl, aryl, aryl($C_{1-6}$)alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one or more substituents.

Favourably, $R^2$ represents aryl, $C_{3-7}$ heterocycloalkyl or heteroaryl, any of which groups may be optionally substituted by one or more substituents.

Suitably, $R^2$ represents hydrogen; or $R^2$ represents $C_{3-7}$ heterocycloalkyl, which group may be optionally substituted by one or more substituents.

Aptly, $R^2$ represents hydrogen, cyano, —$OR^a$, —$SOR^a$, —$NR^bR^c$, —$NR^cCOR^d$ or —$N=S(O)R^bR^c$; or $R^2$ represents methyl, ethyl, propyl, phenyl, benzyl, tetrahydrofuranyl, pyrrolidinyl, tetrahydropyranyl, piperidinyl, piperazinyl, morpholinyl, oxazepinyl, pyrrolidinylmethyl, piperidinylmethyl, piperazinylmethyl, morpholinylmethyl, 2,5-dihydropyrrolyl, 3,6-dihydro-2H-pyranyl, 1,2,3,4-tetrahydropyridinyl, 2,3-dihydro-1,4-oxazinyl, 6,7-dihydro-5H-1,4-oxazepinyl, furyl, pyrazolyl, 6,8-dihydro-5H-[1,2,4]-triazolo[4,3-a]pyrazinyl, pyridinyl, pyrimidinyl, pyrazinyl, pyridinylmethyl or pyridinyl-ethyl, any of which groups may be optionally substituted by one or more substituents.

More favourably, $R^2$ represents phenyl, tetrahydrofuranyl, pyrrolidinyl, tetrahydropyranyl, piperidinyl, piperazinyl, morpholinyl, oxazepinyl, furyl, pyrazolyl, 6,8-dihydro-5H-[1,2,4]triazolo[4,3-a]pyrazinyl, pyridinyl, pyrimidinyl or pyrazinyl, any of which groups may be optionally substituted by one or more substituents.

Still more favourably, $R^2$ represents phenyl, tetrahydrofuranyl, pyrrolidinyl, morpholinyl, pyridinyl, pyrimidinyl or pyrazinyl, any of which groups may be optionally substituted by one or more substituents.

Typically, $R^2$ represents hydrogen; or $R^2$ represents tetrahydropyranyl or piperazinyl, either of which groups may be optionally substituted by one or more substituents.

Illustrative examples of optional substituents on $R^2$ include one, two or three substituents independently selected from halogen, cyano, nitro, $C_{1-6}$ alkyl, trifluoro-methyl, phenyl, fluorophenyl, oxetanyl, pyrrolidinyl, tetrahydropyranyl, morpholinyl, piperazinyl, oxadiazolyl, ($C_{1-6}$)alkyloxadiazolyl, hydroxy, hydroxy($C_{1-6}$)alkyl, oxo, $C_{1-6}$ alkoxy, difluoromethoxy, trifluoromethoxy, $C_{1-6}$ alkylthio, $C_{1-6}$ alkylsulfinyl, ($C_{1-6}$)alkyl-(imino)sulfinyl, $C_{1-6}$ alkylsulfonyl, amino, amino($C_{1-6}$)alkyl, $C_{1-6}$ alkylamino, di($C_{1-6}$)-alkylamino, $C_{2-6}$ alkylcarbonylamino, $C_{2-6}$ alkylcarbonylamino($C_{1-6}$)alkyl, $C_{2-6}$ alkoxy-carbonylamino, $C_{1-6}$ alkylsulfonylamino, formyl, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro-($C_{1-6}$)alkylaminocarbonyl, di($C_{1-6}$)alkylaminocarbonyl, azetidinylcarbonyl, hydroxyazetidinylcarbonyl, difluoroazetidinylcarbonyl, (hydroxy)(trifluoromethyl)azetidinyl-carbonyl, (hydroxy)(methyl)azetidinylcarbonyl, morpholinylcarbonyl, ($C_{1-6}$)alkylpyrazolylcarbonyl, aminosulfonyl, $C_{1-6}$ alkylaminosulfonyl, di($C_{1-6}$)alkylaminosulfonyl and di($C_{1-6}$)alkylsulfoximinyl.

Representative examples of optional substituents on $R^2$ include one, two or three substituents independently selected from halogen, cyano, $C_{1-6}$ alkyl, oxetanyl, oxadiazolyl, ($C_{1-6}$)alkyloxadiazolyl, hydroxy, oxo, ($C_{1-6}$)alkyl(imino)sulfinyl, $C_{1-6}$ alkylsulfonyl, $C_{2-6}$ alkylcarbonylamino, $C_{1-6}$ alkylsulfonylamino, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkylaminocarbonyl, chloro($C_{1-6}$)alkylaminocarbonyl, di($C_{1-6}$)alkylaminocarbonyl, azetidinylcarbonyl, hydroxyazetidinylcarbonyl, difluoroazetidinylcarbonyl, (hydroxy)-(trifluoromethyl)azetidinylcarbonyl, (hydroxy)(methyl)azetidinylcarbonyl, morpholinyl-carbonyl and ($C_{1-6}$)alkylpyrazolylcarbonyl.

Favoured examples of optional substituents on $R^2$ include one, two or three substituents independently selected from $C_{2-6}$ alkoxycarbonyl, $C_{1-6}$ alkylaminocarbonyl, di($C_{1-6}$)alkylaminocarbonyl and difluoroazetidinylcarbonyl.

Typical examples of optional substituents on $R^2$ include one, two or three substituents independently selected from $C_{1-6}$ alkyl.

Illustrative examples of specific substituents on $R^2$ include one, two or three substituents independently selected from fluoro, chloro, bromo, cyano, nitro, methyl, ethyl, isopropyl, tert-butyl, trifluoromethyl, phenyl, fluorophenyl, oxetanyl, pyrrolidinyl, tetrahydropyranyl, morpholinyl, piperazinyl, oxadiazolyl, methyloxadiazolyl, hydroxy, hydroxymethyl, oxo, methoxy, tert-butoxy, difluoromethoxy, trifluoromethoxy, methyl-thio, methylsulfinyl, (imino)(methyl)sulfinyl, methylsulfonyl, amino, aminoethyl, aminomethyl, methylamino, tert-butylamino, dimethylamino, acetylamino, acetylamino-ethyl, methoxycarbonylamino, methylsulfonylamino, formyl, acetyl, hydroxyacetyl, carboxy, methoxycarbonyl, ethoxycarbonyl, tert-butoxycarbonyl, aminocarbonyl, methyl-aminocarbonyl, ethylaminocarbonyl, chloropropylaminocarbonyl, dimethylamino-carbonyl, azetidinylcarbonyl, hydroxyazetidinylcarbonyl, difluoroazetidinylcarbonyl, (hydroxy)(trifluoromethyl)azetidinylcarbonyl, (hydroxy)(methyl)azetidinylcarbonyl, morpholinylcarbonyl, ethylpyrazolylcarbonyl, aminosulfonyl, methylaminosulfonyl, dimethylaminosulfonyl and dimethylsulfoximinyl.

Representative examples of specific substituents on $R^2$ include one, two or three substituents independently selected from fluoro, cyano, methyl, oxetanyl, oxadiazolyl, methyloxadiazolyl, hydroxy, oxo, (imino)(methyl)sulfinyl, methylsulfonyl, acetylamino, methylsulfonylamino, acetyl, hydroxyacetyl, carboxy, methoxycarbonyl, ethoxycarbonyl, tert-butoxycarbonyl, aminocarbonyl, methylaminocarbonyl, ethylaminocarbonyl, chloro-propylaminocarbonyl, dimethylaminocarbonyl, azetidinylcarbonyl, hydroxyazetidinylcarbonyl, difluoroazetidinylcarbonyl, (hydroxy)(trifluoromethyl)azetidinylcarbonyl, (hydroxy)(methyl)azetidinylcarbonyl, morpholinylcarbonyl and ethylpyrazolylcarbonyl.

Favoured examples of specific substituents on $R^2$ include one, two or three substituents independently selected from methoxycarbonyl, ethoxycarbonyl, tert-butoxycarbonyl, methylaminocarbonyl, ethylaminocarbonyl, dimethylaminocarbonyl and difluoroazetidinylcarbonyl.

Typical examples of particular substituents on $R^2$ include one, two or three substituents independently selected from methyl.

Illustrative values of $R^2$ include hydrogen, cyano, —$OR^a$, —$SOR^a$, —$NR^bR^c$, —$NR^cCOR^d$, —$N=S(O)R^bR^c$, tert-butoxycarbonylmethyl, dimethylaminocarbonylmethyl, acetylaminoethyl, carboxyethyl, tert-butoxycarbonylethyl, methylaminocarbonylethyl, dimethylaminocarbonylethyl, acetylaminopropyl, methylsulfonylphenyl, methylsulfonylaminophenyl, tert-butoxycarbonylphenyl, dimethylaminocarbonylphenyl, ethoxy-carbonylbenzyl, carboxytetrahydrofuranyl, methoxycarbonyltetrahydrofuranyl, dimethylaminocarbonyltetrahydrofuranyl, hydroxyazetidinylcarbonyltetrahydrofuranyl, difluoro-azetidinylcarbonyltetrahydrofuranyl, (hydroxy)(trifluoromethyl)azetidinylcarbonyl-tetrahydrofuranyl, morpholinylcarbonyltetrahydrofuranyl, methoxycarbonylpyrrolidinyl, tert-butoxycarbonylpyrrolidinyl, dimethylaminocarbonylpyrrolidinyl, difluoroazetidinyl-carbonylpyrrolidinyl, (ethoxycarbonyl)(methylsulfonyl)pyrrolidinyl, (acetyl)-(ethoxycarbonyl)pyrrolidinyl, (tert-butoxycarbonyl)(difluoroazetidinylcarbonyl)-pyrrolidinyl, tetrahydropyranyl, ethoxycarbonyltetrahydropyranyl, dimethylamino-carbonyltetrahydropyranyl, piperidinyl, methylpiperidinyl, acetylpiperidinyl, hydroxyacetylpiperidinyl, methoxycarbonylpiperidinyl, tert-butoxycarbonylpiperidinyl, dimethyl-aminocarbonylpiperidinyl, ethylpyrazolylcarbonylpiperidinyl, methylpiperazinyl, morpholinyl, methyloxadiazolylmorpholinyl, methylsulfonylmorpholinyl, acetyl-morpholinyl, hydroxyacetylmorpholinyl, methoxycarbonylmorpholinyl, ethoxycarbonylmorpholinyl, tert-butoxycarbonylmorpholinyl, ethylaminocarbonylmorpholinyl, difluoro-azetidinylcarbonylmorpholinyl, oxazepinyl, tert-butoxycarbonyloxazepinyl, oxo-pyrrolidinylmethyl, carboxypyrrolidinylmethyl, methoxycarbonylpyrrolidinylmethyl, dimethylaminocarbonylpyrrolidinylmethyl, methylsulfonylpiperidinylmethyl, piperazinylmethyl, methylpiperazinylmethyl, oxetanylpiperazinylmethyl, methylsulfonyl-piperazinylmethyl, acetylpiperazinylmethyl, tert-butoxycarbonylpiperazinylmethyl, (acetyl)(tert-butoxycarbonyl)piperazinylmethyl, morpholinylmethyl, (tert-butoxy-carbonyl)(difluoroazetidinylcarbonyl)-2,5-dihydropyrrolyl, 3,6-dihydro-2H-pyranyl, ethoxycarbonyl-3,6-dihydro-2H-pyranyl, dimethylaminocarbonyl-3,6-dihydro-2H-pyranyl, tert-butoxycarbonyl-1,2,3,4-tetrahydropyridinyl, tert-butoxycarbonyl-2,3-dihydro-1,4-oxazinyl, tert-butoxycarbonyl-6,7-dihydro-5H-1,4-oxazepinyl, difluoro-azetidinylcarbonylfuryl, difluoroazetidinylcarbonylpyrazolyl, acetyl-6,8-dihydro-5H-[1,2,4]triazolo[4,3-a]pyrazinyl, (imino)(methyl)sulfinylpyridinyl, ethoxycarbonyl-pyridinyl, chloropropylaminocarbonylpyridinyl, dimethylaminocarbonylpyridinyl, azetidinylcarbonylpyridinyl, difluoroazetidinylcarbonylpyridinyl, (hydroxy)(methyl)-azetidinylcarbonylpyridinyl, (dimethylaminocarbonyl)(fluoro)pyridinyl, dimethylamino-carbonylpyrimidinyl, (dimethylaminocarbonyl)(methyl)pyrimidinyl, dimethylamino-carbonylpyrazinyl, pyridinylmethyl, cyanopyridinylmethyl, oxadiazolylpyridinylmethyl, ethoxycarbonylpyridinylmethyl, aminocarbonylpyridinylmethyl, pyridinylethyl and hydroxypyridinylethyl.

Favoured values of $R^2$ include tert-butoxycarbonylphenyl, dimethylamino-carbonylphenyl, methoxycarbonyltetrahydrofuranyl, dimethylaminocarbonyl-tetrahydrofuranyl, difluoroazetidinylcarbonyltetrahydrofuranyl, methoxycarbonyl-pyrrolidinyl, tert-butoxycarbonylpyrrolidinyl, dimethylaminocarbonylpyrrolidinyl, difluoroazetidinylcarbonylpyrrolidinyl, (tert-butoxycarbonyl)(difluoroazetidinylcarbonyl)pyrrolidinyl, methoxycarbonylmorpholinyl, ethoxycarbonylmorpholinyl, tert-butoxycarbonylmorpholinyl, ethylaminocarbonylmorpholinyl, difluoroazetidinylcarbonylmorpholinyl, ethoxycarbonylpyridinyl, dimethyl-aminocarbonylpyridinyl, difluoroazetidinylcarbonylpyridinyl, dimethylaminocarbonylpyrimidinyl and dimethylaminocarbonylpyrazinyl.

Suitable values of $R^2$ include hydrogen, tetrahydropyranyl and methylpiperazinyl.

Typically, $R^3$ represents hydrogen, halogen or $-NR^bR^c$; or $R^3$ represents $C_{1-6}$ alkyl, aryl, $C_{3-7}$ heterocycloalkyl, $C_{3-7}$ heterocycloalkyl($C_{1-6}$)alkyl or heteroaryl, any of which groups may be optionally substituted by one or more substituents.

Suitably, $R^3$ represents hydrogen, fluoro or $-NR^bR^c$; or $R^3$ represents ethyl, phenyl, morpholinyl, piperidinylmethyl, piperazinylmethyl, morpholinylmethyl or pyridinyl, any of which groups may be optionally substituted by one or more substituents.

Typical examples of optional substituents on $R^3$ include one, two or three substituents independently selected from halogen, cyano, nitro, $C_{1-6}$ alkyl, trifluoro-methyl, hydroxy, hydroxy($C_{1-6}$)alkyl, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, difluoroazetidinyl-carbonyl, aminosulfonyl, $C_{1-6}$ alkylaminosulfonyl and di($C_{1-6}$)alkylaminosulfonyl.

Suitable examples of optional substituents on $R^3$ include one, two or three substituents independently selected from $C_{1-6}$ alkylsulfonyl, $C_{2-6}$ alkylcarbonyl, $C_{2-6}$ alkoxycarbonyl, di($C_{1-6}$)alkylaminocarbonyl and difluoroazetidinylcarbonyl.

Typical examples of specific substituents on $R^3$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, difluoroazetidinylcarbonyl, aminosulfonyl, methyl-aminosulfonyl and dimethylaminosulfonyl.

Suitable examples of specific substituents on $R^3$ include one, two or three substituents independently selected from methylsulfonyl, acetyl, tert-butoxycarbonyl, dimethylaminocarbonyl and difluoroazetidinylcarbonyl.

Illustrative values of $R^3$ include hydrogen, fluoro, $-NR^bR^c$, tert-butoxycarbonyl-ethyl, dimethylaminocarbonylphenyl, morpholinyl, methylsulfonylpiperidinylmethyl, methylsulfonylpiperazinylmethyl, acetylpiperazinylmethyl, morpholinylmethyl and difluoroazetidinylcarbonylpyridinyl.

In a particular embodiment, $R^3$ represents hydrogen.

Typically, $R^4$ represents hydrogen, halogen or $-OR^a$.

Suitably, $R^4$ represents hydrogen or halogen.

In a first embodiment, $R^4$ represents hydrogen. In a second embodiment, $R^4$ represents halogen. In one aspect of that embodiment, $R^4$ represents fluoro. In another aspect of that embodiment, $R^4$ represents chloro. In a third embodiment, $R^4$ represents $-OR^a$.

Typical values of $R^4$ include hydrogen, fluoro and $-OR^a$.

Suitable values of $R^4$ include hydrogen and fluoro.

Generally, $R^5$ represents hydrogen; or $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-6}$)alkyl, $C_{8-11}$ tricycloalkyl, $C_{8-11}$ tricycloalkyl($C_{1-6}$)alkyl, aryl, aryl-($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Typically, $R^5$ represents $C_{1-6}$ alkyl, $C_{3-9}$ cycloalkyl, $C_{3-9}$ cycloalkyl($C_{1-6}$)alkyl, $C_{4-9}$ cycloalkenyl, $C_{4-12}$ bicycloalkyl, $C_{5-9}$ spirocycloalkyl, $C_{5-9}$ spirocycloalkyl($C_{1-5}$)alkyl, $C_{8-11}$ tricycloalkyl, $C_{8-11}$ tricycloalkyl($C_{1-6}$)alkyl, aryl, aryl($C_{1-6}$)alkyl, $C_{3-7}$ hetero-cycloalkyl, $C_{3-7}$ heterocycloalkyl($C_{1-6}$)

alkyl, heteroaryl or heteroaryl($C_{1-6}$)alkyl, any of which groups may be optionally substituted by one or more substituents. Additionally, $R^5$ may represent $C_{7-13}$ dispirocycloalkyl, which group may be optionally substituted by one or more substituents.

Suitably, $R^5$ represents $C_{3-9}$ cycloalkyl, $C_{4-12}$ bicycloalkyl, $C_{5-9}$ spirocycloalkyl or $C_{7-13}$ dispirocycloalkyl, any of which groups may be optionally substituted by one or more substituents.

In a first embodiment, $R^5$ represents hydrogen. In a second embodiment, $R^5$ represents optionally substituted $C_{1-6}$ alkyl. In a third embodiment, $R^5$ represents optionally substituted $C_{3-9}$ cycloalkyl. In a fourth embodiment, $R^5$ represents optionally substituted $C_{3-9}$ cycloalkyl($C_{1-6}$)alkyl. In a fifth embodiment, $R^5$ represents optionally substituted $C_{4-9}$ cycloalkenyl. In a sixth embodiment, $R^5$ represents optionally substituted $C_{4-9}$ bicycloalkyl. In a seventh embodiment, $R^5$ represents optionally substituted $C_{5-9}$ spirocycloalkyl. In an eighth embodiment, $R^5$ represents optionally substituted $C_{5-9}$ spirocycloalkyl($C_{1-6}$)alkyl. In a ninth embodiment, $R^5$ represents optionally substituted $C_{8-11}$ tricycloalkyl. Ina tenth embodiment, $R^5$ represents optionally substituted $C_{8-11}$ tricycloalkyl($C_{1-6}$)alkyl. In an eleventh embodiment, $R^5$ represents optionally substituted aryl. In a twelfth embodiment, $R^5$ represents optionally substituted aryl($C_{1-6}$)alkyl. In a thirteenth embodiment, $R^5$ represents optionally substituted $C_{3-7}$ heterocycloalkyl. In a fourteenth embodiment, $R^5$ represents optionally substituted $C_{3-7}$ heterocycloalkyl($C_{1-6}$)-alkyl. In a fifteenth embodiment, $R^5$ represents optionally substituted heteroaryl. In a sixteenth embodiment, $R^5$ represents optionally substituted heteroaryl($C_{1-6}$)alkyl. In a seventeenth embodiment, $R^5$ represents optionally substituted $C_{7-13}$ dispirocycloalkyl. In an eighteenth embodiment, $R^5$ represents optionally substituted $C_{7-13}$ dispirocycloalkyl-($C_{1-6}$)alkyl.

In a particular embodiment, $R^5$ is other than hydrogen.

Typical values of $R^5$ include methyl, isopropyl, 1-methylpropyl, 2-methylpropyl, cyclopropyl, cyclopentyl, indanyl, cyclohexyl, cyclooctyl, cyclohexylmethyl, cyclo-octenyl, spiro[3.3]heptanyl, spiro[3.3]heptanylmethyl, adamantanyl, adamantanylmethyl, phenyl, benzyl, phenylethyl, naphthylmethyl, thienyl, indolyl, pyridinyl, thienylmethyl, indolylmethyl and pyridinylmethyl, any of which groups may be optionally substituted by one or more substituents. Additional values include cycloheptyl, bicyclo[4.1.0]heptanyl, spiro[2.5]octanyl and dispiro[2.0.24.13]heptanyl, any of which groups may be optionally substituted by one or more substituents.

Illustrative values of $R^5$ include cyclopentyl, cyclohexyl, cycloheptyl, cyclooctyl, bicyclo[4.1.0]heptanyl, spiro[2.5] octanyl and dispiro[2.0.24.13]heptanyl, any of which groups may be optionally substituted by one or more substituents.

Suitable values of $R^5$ include cyclohexyl and cyclooctyl, either of which groups may be optionally substituted by one or more substituents.

Typical examples of optional substituents on $R^5$ include one, two or three substituents independently selected from halogen, cyano, nitro, $C_{1-6}$ alkyl, trifluoro-methyl, phenyl, hydroxy, oxo, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkyl-aminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^5$ include one, two or three substituents independently selected from halogen, cyano, $C_{1-6}$ alkyl, trifluoromethyl, phenyl, hydroxy, $C_{1-6}$ alkoxy and aminocarbonyl, especially $C_{1-6}$ alkyl.

Illustrative examples of optional substituents on $R^5$ include one, two or three substituents independently selected from halogen and $C_{1-6}$ alkyl, especially $C_{1-6}$ alkyl.

Typical examples of specific substituents on $R^5$ include one, two or three substituents independently selected from fluoro, chloro, bromo, cyano, nitro, methyl, ethyl, isopropyl, tert-butyl, trifluoromethyl, phenyl, hydroxy, oxo, methoxy, tert-butoxy, difluoromethoxy, trifluoromethoxy, methylthio, methylsulfinyl, methylsulfonyl, amino, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, amino-sulfonyl, methylaminosulfonyl and dimethylaminosulfonyl.

Suitable examples of specific substituents on $R^5$ include one, two or three substituents independently selected from fluoro, chloro, bromo, cyano, methyl, trifluoro-methyl, phenyl, hydroxy, methoxy, tert-butoxy and aminocarbonyl, especially methyl.

Illustrative examples of specific substituents on $R^5$ include one, two or three substituents independently selected from fluoro and methyl, especially methyl.

Illustrative examples of specific values of $R^5$ include hydrogen, methyl, isopropyl, 1-methylpropyl, 2-methylpropyl, cyclopropyl, cyclopentyl, indanyl, cyclohexyl, methylcyclohexyl, cyclooctyl, cyclohexylmethyl, cyclooctenyl, spiro[3.3]heptanyl, phenyl, chlorophenyl, benzyl, fluorobenzyl, chlorobenzyl, (chloro)(fluoro)benzyl, dichlorobenzyl, bromobenzyl, cyanobenzyl, methylbenzyl, trifluoromethylbenzyl, phenylbenzyl, hydroxybenzyl, methoxybenzyl, tert-butoxybenzyl, aminocarbonylbenzyl, phenylethyl, chlorophenylethyl, naphthylmethyl, thienylmethyl, indolylmethyl and pyridinylmethyl. Additional examples include difluorocyclohexyl, dimethylcyclohexyl, cycloheptyl, bicyclo[4.1.0]heptanyl, spiro[2.5]octanyl and dispiro[2.0.24.13]heptanyl.

Apposite examples of specific values of $R^5$ include cyclopentyl, cyclohexyl, methylcyclohexyl, difluorocyclohexyl, dimethylcyclohexyl, cycloheptyl, cyclooctyl, bicyclo[4.1.0] heptanyl, spiro[2.5]octanyl and dispiro[2.0.24.13]heptanyl.

Representative examples of specific values of $R^5$ include methylcyclohexyl and cyclooctyl.

In a first embodiment, $R^5$ represents methylcyclohexyl, especially 4-methyl-cyclohexyl. In a second embodiment, $R^5$ represents cyclooctyl.

Typically, $R^6$ represents —$OR^{6a}$ or —$NR^{6b}R^6$; or R represents $C_{1-6}$ alkyl, $C_{3-9}$ cycloalkyl, $C_{3-9}$ cycloalkyl($C_{1-6}$) alkyl, aryl, aryl($C_{1-6}$)alkyl, heteroaryl or heteroaryl-($C_{1-6}$) alkyl, any of which groups may be optionally substituted by one or more substituents.

Suitably, $R^6$ represents $C_{1-6}$ alkyl, heteroaryl or heteroaryl ($C_{1-6}$)alkyl, any of which groups may be optionally substituted by one or more substituents.

Appropriately, $R^6$ represents —$OR^{6a}$; or $R^6$ represents $C_{1-6}$ alkyl, aryl or heteroaryl, any of which groups may be optionally substituted by one or more substituents.

Appositely, $R^6$ represents —$OR^{6a}$; or $R^6$ represents heteroaryl, which group may be optionally substituted by one or more substituents.

In a first embodiment, $R^6$ represents optionally substituted $C_{1-6}$ alkyl. In a second embodiment, $R^6$ represents optionally substituted $C_{3-9}$ cycloalkyl. In a third embodiment, $R^6$ represents optionally substituted $C_{3-9}$ cycloalkyl($C_{1-6}$)alkyl. In a fourth embodiment, $R^6$ represents optionally substituted aryl. In a fifth embodiment, $R^6$ represents optionally substituted aryl($C_{1-6}$)alkyl. In a sixth embodiment, $R^6$ represents optionally substituted $C_{3-7}$ heterocycloalkyl. In a seventh embodiment, $R^6$ represents optionally substituted $C_{3-7}$ heterocycloalkyl($C_{1-6}$)alkyl. In an eighth embodiment, $R^6$ represents optionally substituted heteroaryl. In a ninth embodiment, $R^6$ represents optionally substituted heteroaryl($C_{1-6}$) alkyl. In a tenth embodiment, $R^6$ represents —$OR^{6a}$. In an eleventh embodiment, $R^6$ represents —$NR^{6a}R^6$.

Typical values of $R^6$ include —$OR^{6a}$ or —$NR^{6a}R^{6b}$; and methyl, ethyl, propyl, 2-methylpropyl, butyl, cyclopropyl, cyclobutyl, cyclohexyl, cyclohexylmethyl, phenyl, benzyl, phenylethyl, pyrazolyl, isoxazolyl, pyridinyl, triazolylmethyl, benzotriazolyl-methyl or pyridinylmethyl, any of which groups may be optionally substituted by one or more substituents.

Illustrative values of $R^6$ include —$OR^{6a}$; and methyl, phenyl, pyrazolyl or isoxazolyl, any of which groups may be optionally substituted by one or more substituents.

Suitable values of $R^6$ include pyrazolyl and isoxazolyl, either of which groups may be optionally substituted by one or more substituents.

Typical examples of optional substituents on $R^6$ include one, two or three substituents independently selected from halogen, cyano, nitro, $C_{1-6}$ alkyl, trifluoro-methyl, phenyl, fluorophenyl, hydroxy, hydroxy($C_{1-6}$)alkyl, oxo, $C_{1-6}$ alkoxy, difluoro-methoxy, trifluoromethoxy, $C_{1-6}$ alkylthio, $C_{1-6}$ alkylsulfinyl, $C_{1-6}$ alkylsulfonyl, amino, amino($C_{1-6}$) alkyl, $C_{1-6}$ alkylamino, di($C_{1-6}$)alkylamino, pyrrolidinyl, tetrahydropyranyl, morpholinyl, piperazinyl, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylamino-carbonyl, aminosulfonyl, $C_{1-6}$ alkylaminosulfonyl and di($C_{1-6}$) alkylaminosulfonyl. Additional examples include di($C_{1-6}$) alkylsulfoximinyl.

Illustrative examples of optional substituents on $R^6$ include one, two or three substituents independently selected from $C_{1-6}$ alkyl, tetrahydropyranyl and di($C_{1-6}$)alkylsulfoximinyl.

Suitable examples of optional substituents on $R^6$ include one, two or three substituents independently selected from $C_{1-6}$ alkyl and tetrahydropyranyl.

Typical examples of specific substituents on $R^6$ include one, two or three substituents independently selected from fluoro, chloro, bromo, cyano, nitro, methyl, ethyl, isopropyl, tert-butyl, trifluoromethyl, phenyl, fluorophenyl, hydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, pyrrolidinyl, tetrahydropyranyl, morpholinyl, piperazinyl, acetylamino, acetylaminoethyl, methoxycarbonylamino, methylsulfonylamino, formyl, acetyl, carboxy, methoxycarbonyl, ethoxycarbonyl, tert-butoxycarbonyl, aminocarbonyl, methylaminocarbonyl, dimethylaminocarbonyl, aminosulfonyl, methylaminosulfonyl and dimethylaminosulfonyl. Additional examples include dimethylsulfoximinyl.

Illustrative examples of specific substituents on $R^6$ include one, two or three substituents independently selected from methyl, ethyl, tetrahydropyranyl and dimethyl-sulfoximinyl.

Suitable examples of specific substituents on $R^6$ include one, two or three substituents independently selected from methyl and tetrahydropyranyl.

Illustrative examples of specific values of R include methyl, difluoromethyl, methylsulfonylmethyl, aminomethyl, methylaminomethyl, difluoroethyl, carboxyethyl, difluoropropyl, 2-methylpropyl, butyl, cyanocyclopropyl, methylcyclopropyl, ethyl-cyclopropyl, dimethylcyclopropyl, trifluoromethylcyclopropyl, phenylcyclopropyl, fluorophenylcyclopropyl, hydroxycyclopropyl, aminocyclopropyl, cyclobutyl, trifluoromethylcyclobutyl, cyclohexyl, cyclohexylmethyl, phenyl, fluorophenyl, chloro-phenyl, cyanophenyl, methylphenyl, hydroxyphenyl, methylsulfonylphenyl, benzyl, fluorobenzyl, difluorobenzyl, chlorobenzyl, (chloro)(fluoro)benzyl, dichlorobenzyl, (chloro)(difluoro)benzyl, bromobenzyl, cyanobenzyl, methylbenzyl, dimethylbenzyl, trifluoromethylbenzyl, phenylbenzyl, hydroxybenzyl, hydroxymethylbenzyl, benzoyl, methoxybenzyl, dimethoxybenzyl, trifluoromethoxybenzyl, methylsulfonylbenzyl, aminomethylbenzyl, aminoethylbenzyl, dimethylaminobenzyl, pyrrolidinylbenzyl, (dimethyl)(pyrrolidinyl)benzyl, morpholinylbenzyl, (dimethyl)(morpholinyl)benzyl, piperazinylbenzyl, acetylaminoethylbenzyl, phenylethyl, chlorophenylethyl, methyl-pyrazolyl, (methyl) (tetrahydropyranyl)pyrazolyl, methylisoxazolyl, pyridinyl, triazolyl-methyl, benzotriazolylmethyl, pyridinylmethyl and aminopyridinylmethyl. Additional values include dimethylsulfoximinylphenyl, ethylpyrazolyl and ethylisoxazolyl.

Suitable examples of specific values of $R^6$ include —$OR^{6a}$, methyl, dimethyl-sulfoximinylphenyl, methylpyrazolyl, ethylpyrazolyl, (methyl)(tetrahydropyranyl)-pyrazolyl, methylisoxazolyl and ethylisoxazolyl.

Favoured values of R include methylpyrazolyl, ethylpyrazolyl, methylisoxazolyl and ethylisoxazolyl.

Typical examples of specific values of R include methylpyrazolyl, (methyl)-(tetrahydropyranyl)pyrazolyl and methylisoxazolyl.

Generally, $R^{6a}$ represents $C_{1-6}$ alkyl.

In a first embodiment, $R^{6a}$ represents $C_{1-6}$ alkyl. In a second embodiment, $R^{6a}$ represents optionally substituted $C_{3-9}$ cycloalkyl.

Typically, $R^{6a}$ represents $C_{1-6}$ alkyl; or $R^{6a}$ represents cyclobutyl, which group may be optionally substituted by one or more substituents.

Typical examples of optional substituents on $R^{6a}$ include one, two or three substituents independently selected from halogen, cyano, nitro, $C_{1-6}$ alkyl, trifluoro-methyl, hydroxy, hydroxy($C_{1-6}$)alkyl, oxo, $C_{1-6}$ alkoxy, difluoromethoxy, trifluoro-methoxy, $C_{1-6}$ alkylthio, $C_{1-6}$ alkylsulfinyl, $C_{1-6}$ alkylsulfonyl, amino, amino($C_{1-6}$)alkyl, $C_{1-6}$ alkylamino, di($C_{1-6}$)alkylamino, $C_{2-6}$ alkylcarbonylamino, $C_{2-6}$ alkoxycarbonylamino, $C_{1-6}$ alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Suitable examples of optional substituents on $R^{6a}$ include one, two or three substituents independently selected from halogen.

Typical examples of specific substituents on $R^{6a}$ include one, two or three substituents independently selected from fluoro, chloro, bromo, cyano, nitro, methyl, ethyl, isopropyl, tert-butyl, trifluoromethylhydroxy, hydroxymethyl, oxo, methoxy, tert-butoxy, difluoromethoxy, trifluoromethoxy, methylthio, methylsulfinyl, methylsulfonyl, amino, aminomethyl, aminoethyl, methylamino, tert-butylamino, dimethylamino, acetylamino, methoxycarbonylamino, methylsulfonylamino, formyl, acetyl, carboxy, methoxycarbonyl, ethoxycarbonyl, tert-butoxycarbonyl, aminocarbonyl, methylamino-carbonyl, dimethylaminocarbonyl, aminosulfonyl, methylaminosulfonyl and dimethyl-aminosulfonyl.

Suitable examples of specific substituents on $R^{6a}$ include one, two or three substituents independently selected from fluoro.

Illustrative examples of specific values of $R^{6a}$ include methyl, ethyl, n-propyl, isopropyl, n-butyl and tert-butyl. Additional examples include difluorocyclobutyl.

Suitable examples of specific values of $R^{6a}$ include tert-butyl and difluoro-cyclobutyl.

Typically, $R^{6a}$ represents tert-butyl.

Typically, $R^{6b}$ represents hydrogen or methyl.

In a first embodiment, $R^{6b}$ represents hydrogen. In a second embodiment, $R^{6b}$ represents $C_{1-6}$ alkyl, especially methyl.

Typically, $R^{6c}$ represents hydrogen or methyl.

In a first embodiment, $R^{6c}$ represents hydrogen. In a second embodiment, $R^{6c}$ represents $C_{1-6}$ alkyl, especially methyl.

Typical examples of suitable substituents on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

In general, $R^a$ represents $C_{1-6}$ alkyl, $C_{3-9}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted by one or more substituents.

Appositely, $R^a$ represents $C_{1-6}$ alkyl, $C_{3-9}$ cycloalkyl, aryl, $C_{3-7}$ heterocycloalkyl or heteroaryl, any of which groups may be optionally substituted by one or more substituents.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Illustrative values of $R^a$ include methyl, ethyl, cyclopropyl, phenyl, benzyl, oxetanyl, tetrahydropyranyl, piperidinyl, pyridinyl, pyridazinyl and isoindolylpropyl, any of which groups may be optionally substituted by one or more substituents.

Representative values of $R^a$ include methyl, cyclopentyl, phenyl, oxetanyl, tetrahydropyranyl, piperidinyl, pyridinyl and pyridazinyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo. Additional examples include $C_{1-6}$ alkylsulfonyl.

Selected examples of specific substituents on $R^a$ include methoxy and oxo. Additional examples include methylsulfonyl.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl.

In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl. In a further embodiment, $R^a$ represents optionally substituted $C_{3-9}$ cycloalkyl, e.g. cyclopentyl. In a further embodiment, $R^a$ represents optionally substituted $C_{3-7}$ heterocycloalkyl.

Particular values of $R^a$ include methyl, cyclopentyl, phenyl, oxetanyl, tetrahydropyranyl, methylsulfonylpiperidinyl, pyridinyl and pyridazinyl. Additional values include methoxyethyl, benzyl and dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$) alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-($C_{1-6}$)alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, R represents $C_{1-6}$ alkyl, especially methyl.

Selected values of R include hydrogen; or $C_{1-6}$ alkyl, $C_{3-7}$ cycloalkyl or $C_{3-7}$ heterocycloalkyl, any of which groups may be optionally substituted by one or more substituents.

Favourably, $R^c$ represents $C_{3-7}$ heterocycloalkyl, which group may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected values of $R^c$ include tetrahydropyranyl and piperidinyl, either of which groups may be optionally substituted by one or more substituents.

Selected examples of suitable substituents on $R^c$ include $C_{2-6}$ alkylcarbonyl and $C_{2-6}$ alkoxycarbonyl. Additional examples include $C_{1-6}$ alkylsulfonyl.

Selected examples of specific substituents on $R^c$ include acetyl and tert-butoxycarbonyl. Additional examples include methylsulfonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl.

Additional values include methylsulfonylpiperidinyl.

Particular values of $R^c$ include tetrahydropyranyl and methylsulfonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy($C_{1-6}$)alkyl, amino($C_{1-6}$)alkyl, cyano, oxo, $C_{2-6}$ alkylcarbonyl, carboxy, $C_{2-6}$ alkoxycarbonyl, amino, $C_{2-6}$ alkylcarbonyl-amino, $C_{2-6}$ alkylcarbonylamino($C_{1-6}$)alkyl, $C_{2-6}$ alkoxycarbonylamino, $C_{1-6}$ alkyl-sulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxy-carbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethyl-azetidin-1-yl, cyanoazetidin-1-yl, carboxyazetidin-1-yl, aminoazetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di($C_{1-6}$)alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxo-thiazolidinyl.

Selected examples of specific values for $R^d$ include hydrogen, methyl, acetoxy-methyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, $R^e$ represents optionally substituted $C_{1-6}$ alkyl, ideally unsubstituted $C_{1-6}$ alkyl, e.g. methyl or propyl, especially methyl. In another embodiment, $R^e$ represents optionally substituted aryl. In one aspect of that embodiment, $R^e$ represents unsubstituted aryl, especially phenyl. In another aspect of that embodiment, $R^e$ represents monosubstituted aryl, especially methylphenyl. In a further embodiment, $R^e$ represents optionally substituted heteroaryl.

Selected values of $R^e$ include methyl, propyl and methylphenyl.

One sub-class of compounds according to the invention is represented by the compounds of formula (IIA) and N-oxides thereof, and pharmaceutically acceptable salts thereof:

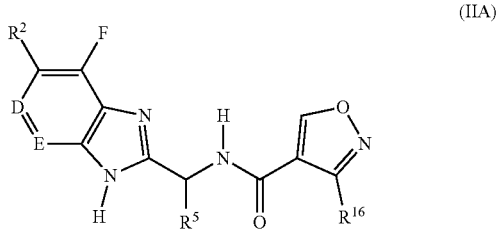

(IIA)

wherein $R^{16}$ represents methyl or ethyl; and

D, E, $R^2$ and $R^5$ are as defined above.

In a first embodiment, $R^{16}$ represents methyl. In a second embodiment, $R^{16}$ represents ethyl.

Another sub-class of compounds according to the invention is represented by the compounds of formula (IIB) and N-oxides thereof, and pharmaceutically acceptable salts thereof:

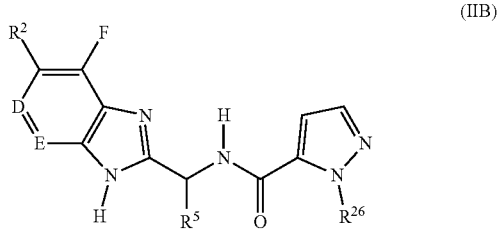

(IIB)

wherein $R^{26}$ represents methyl or ethyl; and

D, E, $R^2$ and $R^5$ are as defined above.

In a first embodiment, $R^{26}$ represents methyl. In a second embodiment, $R^{26}$ represents ethyl.

Specific novel compounds in accordance with the present invention include each of the compounds whose preparation is described in the accompanying Examples, and pharmaceutically acceptable salts and solvates thereof.

The compounds in accordance with the present invention are beneficial in the treatment and/or prevention of various human ailments, including inflammatory and autoimmune disorders.

The compounds according to the present invention are useful in the treatment and/or prophylaxis of a pathological disorder that is mediated by a pro-inflammatory IL-17 cytokine or is associated with an increased level of a pro-inflammatory IL-17 cytokine. Generally, the pathological condition is selected from the group consisting of infections (viral, bacterial, fungal and parasitic), endotoxic shock associated with infection, arthritis, rheumatoid arthritis, psoriatic arthritis, systemic onset juvenile idiopathic arthritis (JIA), systemic lupus erythematosus (SLE), asthma, chronic obstructive airways disease (COAD), chronic obstructive pulmonary disease (COPD), acute lung injury, pelvic inflammatory disease, Alzheimer's Disease, Crohn's disease, inflammatory bowel disease, irritable bowel syndrome, ulcerative colitis, Castleman's disease, ankylosing spondylitis and other spondyloarthropathies, dermatomyositis, myocarditis, uveitis, exophthalmos, autoimmune thyroiditis, Peyronie's Disease, coeliac disease, gall bladder disease, Pilonidal disease, peritonitis, psoriasis, atopic dermatitis, vasculitis, surgical adhesions, stroke, autoimmune diabetes, Type I Diabetes, lyme arthritis, meningoencephalitis, immune mediated inflammatory disorders of the central and peripheral nervous system such as multiple sclerosis and Guillain-Barr syndrome, other autoimmune disorders, pancreatitis, trauma (surgery), graft-versus-host disease, transplant rejection, fibrosing disorders including pulmonary fibrosis, liver fibrosis, renal fibrosis, scleroderma or systemic sclerosis, cancer (both solid tumours such as melanomas, hepatoblastomas, sarcomas, squamous cell carcinomas, transitional cell cancers, ovarian cancers and hematologic malignancies and in particular acute myelogenous leukaemia, chronic myelogenous leukemia, chronic lymphatic leukemia, gastric cancer and colon cancer), heart disease including ischaemic diseases such as myocardial infarction as well as atherosclerosis, intravascular coagulation, bone resorption, osteoporosis, periodontitis, hypochlorhydia and pain (particularly pain associated with inflammation).

WO 2009/089036 reveals that modulators of IL-17 activity may be administered to inhibit or reduce the severity of ocular inflammatory disorders, in particular ocular surface inflammatory disorders including Dry Eye Syndrome (DES). Consequently, the compounds in accordance with the present invention are useful in the treatment and/or prevention of an IL-17-mediated ocular inflammatory disorder, in particular an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory conditions, conjunctival scarring disorders, ocular autoimmune conditions, Pemphigoid syndrome, Stevens-Johnson syndrome, ocular allergy, severe allergic (atopic) eye disease, conjunctivitis and microbial keratitis. Particular categories of Dry Eye Syndrome include keratoconjunctivitis sicca (KCS), Sjögren syndrome, Sjögren syndrome-associated keratoconjunctivitis sicca, non-Sjögren syndrome-associated keratoconjunctivitis sicca, keratitis sicca, sicca syndrome, xerophthalmia, tear film disorder, decreased tear production, aqueous tear deficiency (ATD), meibomian gland dysfunction and evaporative loss.

Illustratively, the compounds of the present invention may be useful in the treatment and/or prophylaxis of a pathological disorder selected from the group consisting of arthritis, rheumatoid arthritis, psoriasis, psoriatic arthritis, systemic onset juvenile idiopathic arthritis (JIA), systemic lupus erythematosus (SLE), asthma, chronic obstructive airway disease, chronic obstructive pulmonary disease, atopic dermatitis, scleroderma, systemic sclerosis, lung fibrosis, inflammatory bowel diseases (including Crohn's disease and ulcerative colitis), ankylosing spondylitis and other spondylo-arthropathies, cancer and pain (particularly pain associated with inflammation).

Suitably, the compounds of the present invention are useful in the treatment and/or prophylaxis of psoriasis, psoriatic arthritis or ankylosing spondylitis.

The present invention also provides a pharmaceutical composition which comprises a compound in accordance with the invention as described above, or a pharmaceutically acceptable salt thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds according to the present invention may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds according to the present invention may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds according to the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds according to the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds according to the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration the compounds according to the present invention may be formulated in an ointment such as petrolatum.

For rectal administration the compounds according to the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound according to the present invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above may be prepared by a process which comprises reacting a carboxylic acid of formula $R^6$—$CO_2H$ with a compound of formula (III):

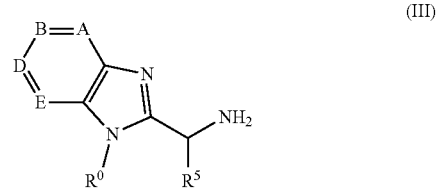

(III)

wherein A, B, D, E, $R^0$, $R^5$ and $R^6$ are as defined above.

The reaction is conveniently accomplished in the presence of a coupling agent and a base. Suitable coupling agents include 1-[bis(dimethylamino)methylene]-1H-1,2,3-triazolo[4,5-b]pyridinium 3-oxide hexafluorophosphate (HATU); and 2,4,6-tripropyl-1,3,5,2,4,6-trioxatriphosphorinane-2,4,6-trioxide. Suitable bases include organic amines, e.g. a trialkylamine such as N,N-diisopropylethylamine. The reaction is conveniently performed at ambient or elevated temperature in a suitable solvent, e.g. a cyclic ether such as tetrahydrofuran, or a dipolar aprotic solvent such as N,N-dimethylformamide, or a chlorinated solvent such as dichloromethane.

Where $R^6$ represents $C_{1-6}$ alkyl, e.g. methyl, the compounds of formula (I) above may be prepared by a process which comprises reacting a compound of formula $R^6$—COCl, e.g. acetyl chloride, with a compound of formula (III) as defined above. The reaction is conveniently accomplished in the presence of a base. Suitable bases include organic amines, e.g. a trialkylamine such as N,N-diisopropylethylamine. The reaction is conveniently performed at ambient temperature in a suitable solvent, e.g. a cyclic ether such as tetrahydrofuran.

Where $R^6$ represents $-OR^{6a}$, the compounds of formula (I) above may be prepared by a two-step process which comprises: (i) reacting a compound of formula $R^{6a}$—OH with N,N'-disuccinimidyl carbonate, ideally in the presence of a base, e.g. an organic amine such as triethylamine; and (ii) reacting the resulting material with a compound of formula (III) as defined above. Steps (i) and (ii) are conveniently performed at ambient temperature in a suitable solvent, e.g. a chlorinated solvent such as dichloromethane.

In an alternative procedure, the compounds of formula (I) above wherein $R^0$ represents hydrogen may be prepared by a process which comprises cyclising a compound of formula (IV):

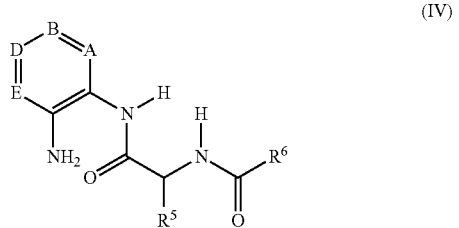

(IV)

wherein A, B, D, E, $R^5$ and $R^6$ are as defined above.

Cyclisation of compound (IV) is conveniently effected by heating in a suitable medium, e.g. acetic acid.

The intermediates of formula (IV) above may be prepared by reacting a compound of formula (V) with a carboxylic acid of formula (VI) or a salt thereof, e.g. a lithium salt thereof:

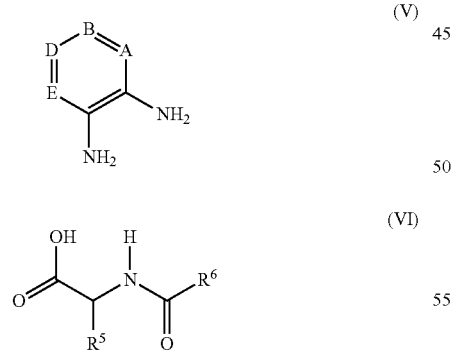

(V)

(VI)

wherein A, B, D, E, $R^5$ and $R^6$ are as defined above; under conditions analogous to those described above for the reaction between compound (III) and a carboxylic acid of formula $R^6$—$CO_2H$.

The intermediates of formula (VI) may be prepared by a two-step procedure which comprises: (i) reacting a carboxylic acid of formula $R^6$—$CO_2H$ with a compound of formula (VII):

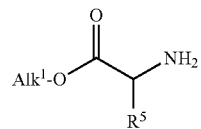

(VII)

wherein $Alk^1$ represents $C_{1-4}$ alkyl, e.g. methyl, and $R^5$ and $R^6$ are as defined above; under conditions analogous to those described above for the reaction between compound (III) and a carboxylic acid of formula $R^6$—$CO_2H$; and (ii) saponification of the resulting material by treatment with a base.

Alternative coupling agents that may usefully be employed in step (i) include N-(3-dimethylaminopropyl)-N'-ethylcarbodiimide hydrochloride (EDC.HCl) and O-(benzotriazol-1-yl)-N,N,N',N'-tetramethyluronium hexafluorophosphate (HBTU).

The saponification reaction in step (ii) will generally be effected by treatment with a base. Suitable bases include inorganic hydroxides, e.g. an alkali metal hydroxide such as lithium hydroxide. Where lithium hydroxide is employed in step (ii) of the above procedure, the product may be the lithium salt of the carboxylic acid of formula (VI).

Step (ii) is conveniently effected at ambient temperature in water and a suitable organic solvent, e.g. a cyclic ether such as tetrahydrofuran, optionally in admixture with a $C_{1-4}$ alkanol such as methanol.

The intermediates of formula (III) above wherein $R^0$ represents hydrogen may be prepared by a three-step procedure which comprises the following steps:

(i) reacting a compound of formula (V) as defined above with a compound of formula (VIII):

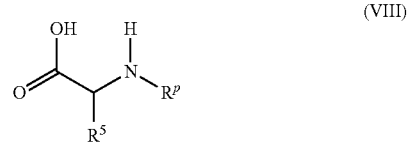

(VIII)

wherein $R^5$ is as defined above, and RP represents a N-protecting group; under conditions analogous to those described above for the reaction between compounds (V) and (VI);

(ii) cyclisation of the resulting material under conditions analogous to those described above for the cyclisation of compound (IV); and (iii) removal of the N-protecting group RP.

The N-protecting group RP will suitably be tert-butoxycarbonyl (BOC), in which case the removal thereof in step (iii) may conveniently be effected by treatment with an acid, e.g. a mineral acid such as hydrochloric acid, or an organic acid such as trifluoroacetic acid.

Alternatively, the intermediates of formula (III) above wherein $R^0$ represents hydrogen may be prepared by a procedure which comprises the following steps:

(i) reacting a compound of formula (IX) with a compound of formula (X):

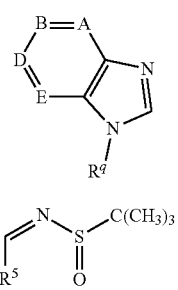

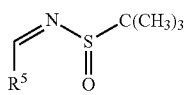

wherein A, B, D, E and $R^5$ are as defined above, and $R^q$ represents a N-protecting group; to provide a compound of formula (XI):

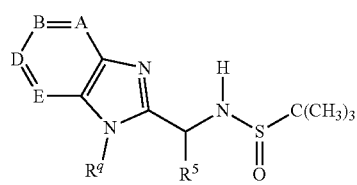

wherein A, B, D, E, $R^5$ and $R^q$ are as defined above; and (ii) removal of the tert-butylsulfinyl group and the N-protecting group $R^q$ from compound (XI).

The N-protecting group $R^q$ will suitably be 2-(trimethylsilyl)ethoxymethyl.

Step (i) is suitably effected by treatment of compound (IX) with a base, e.g. an organic base such as n-butyllithium, followed by reaction with compound (X). The reaction is conveniently accomplished in a suitable solvent, e.g. a cyclic ether such as tetrahydrofuran.

Where the N-protecting group $R^q$ is 2-(trimethylsilyl) ethoxymethyl, removal of the tert-butylsulfinyl group and the N-protecting group $R^q$ from compound (XI) in step (ii) may both be accomplished by treatment with an acid, e.g. a mineral acid such as hydrochloric acid.

Where the N-protecting group $R^q$ is 2-(trimethylsilyl) ethoxymethyl, the intermediates of formula (IX) above may be prepared by a procedure which comprises the following steps:

(i) reaction of a compound of formula (V) as defined above with formic acid; and (ii) reaction of the material thereby obtained with 2-(trimethylsilyl)ethoxymethyl chloride.

Step (i) is conveniently carried out at an elevated temperature.

Step (ii) is suitably effected by treating the reactants with a base, e.g. an inorganic base such as sodium hydride.

The intermediates of formula (X) above may be prepared by reacting an aldehyde derivative of formula $R^5$—CHO with 2-methyl-2-propanesulfinamide. The reaction is suitably effected in the presence of pyridinium p-toluenesulfonate and magnesium sulfate. The reaction is conveniently carried out at ambient temperature in a suitable solvent, e.g. a chlorinated solvent such as dichloromethane.

Where they are not commercially available, the starting materials of formula (V), (VII) and (VIII) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) comprising a N—BOC moiety (wherein BOC is an abbreviation for tert-butoxycarbonyl) may be converted into the corresponding compound comprising a N—H moiety by treatment with an acid, e.g. a mineral acid such as hydrochloric acid, or an organic acid such as trifluoroacetic acid.

A compound of formula (I) comprising a N—H functionality may be alkylated, e.g. methylated, by treatment with a suitable alkyl halide, e.g. iodomethane, typically in the presence of a base, e.g. an inorganic carbonate such as sodium carbonate.

A compound of formula (I) comprising a N—H functionality may be acylated, e.g. acetylated, by treatment with a suitable acyl halide, e.g. acetyl chloride, typically in the presence of a base, e.g. an organic base such as N,N-diisopropylethylamine or triethyl-amine. Similarly, a compound of formula (I) comprising a N—H functionality may be acylated, e.g. acetylated, by treatment with a suitable acyl anhydride, e.g. acetic anhydride, typically in the presence of a base, e.g. an organic base such as triethylamine.

Similarly, a compound of formula (I) comprising a N—H functionality may be converted into the corresponding compound comprising a N—S(O)$_2$Alk$^1$ functionality (wherein Alk$^1$ is as defined above) by treatment with the appropriate CIA alkylsulfonyl chloride reagent, e.g. methylsulfonyl chloride, typically in the presence of a base, e.g. an organic base such as triethylamine.

Similarly, a compound of formula (I) comprising a N—H functionality may be converted into the corresponding compound comprising a carbamate or urea moiety respectively by treatment with the appropriate chloroformate or carbamoyl chloride reagent, typically in the presence of a base, e.g. an organic base such as triethylamine. Alternatively, a compound of formula (I) comprising a N—H functionality may be converted into the corresponding compound comprising a urea moiety by treatment with the appropriate amine-substituted (3-methylimidazol-3-ium-1-yl)methanone iodide derivative, typically in the presence of a base, e.g. an organic base such as triethylamine. Alternatively, a compound of formula (I) comprising a N—H functionality may be converted into the corresponding compound comprising a urea moiety N—C(O)N(H)Alk$^1$ (wherein Alk$^1$ is as defined above) by treatment with the appropriate isocyanate derivative Alk$^1$-N=C=O, typically in the presence of a base, e.g. an organic base such as triethyl-amine.

A compound of formula (I) comprising a N—H functionality may be converted into the corresponding compound comprising a N—C(H) functionality by treatment with the appropriate aldehyde or ketone in the presence of a reducing agent such as sodium triacetoxyborohydride.

A compound of formula (I) comprising a C$_{1-4}$ alkoxycarbonyl moiety —CO$_2$Alk$^1$ (wherein Alk$^1$ is as defined above) may be converted into the corresponding compound comprising a carboxylic acid (—CO$_2$H) moiety by treatment with a base, e.g. an alkali metal hydroxide salt such as lithium hydroxide. Alternatively, a compound of formula (I) comprising a tert-butoxycarbonyl moiety may be converted into the corresponding compound comprising a carboxylic acid (—CO$_2$H) moiety by treatment with trifluoroacetic acid.

A compound of formula (I) comprising a carboxylic acid (—CO$_2$H) moiety may be converted into the corresponding compound comprising an amide moiety by treatment with the appropriate amine, under conditions analogous to those described above for the reaction between compound (III) and a carboxylic acid of formula $R^6$—$CO_2H$.

A compound of formula (I) comprising a $C_{1-4}$ alkoxycarbonyl moiety —$CO_2Alk^1$ (wherein $Alk^1$ is as defined above) may be converted into the corresponding compound comprising a hydroxymethyl (—$CH_2OH$) moiety by treatment with a reducing agent such as lithium aluminium hydride.

A compound of formula (I) comprising a $C_{1-4}$ alkylcarbonyloxy moiety —$OC(O)Alk^1$ (wherein $Alk^1$ is as defined above), e.g. acetoxy, may be converted into the corresponding compound comprising a hydroxy (—OH) moiety by treatment with a base, e.g. an alkali metal hydroxide salt such as sodium hydroxide.

A compound of formula (I) comprising a halogen atom, e.g. bromo, may be converted into the corresponding compound comprising an optionally substituted aryl, heterocycloalkenyl or heteroaryl moiety by treatment with the appropriately substituted aryl, heterocycloalkenyl or heteroaryl boronic acid or a cyclic ester thereof formed with an organic diol, e.g. pinacol, 1,3-propanediol or neopentyl glycol. The reaction is typically effected in the presence of a transition metal catalyst, and a base. The transition metal catalyst may be [1,1'-bis(diphenylphosphino)ferrocene]dichloropalladium(II). In the alternative, the transition metal catalyst may be tris(dibenzylideneacetone)dipalladium(0), which may advantageously be employed in conjunction with 2-dicyclohexylphosphino-2',4',6'-triisopropylbiphenyl (XPhos). Suitably, the base may be an inorganic base such as sodium carbonate or potassium carbonate.

A compound of formula (I) comprising a halogen atom, e.g. bromo, may be converted into the corresponding compound comprising an optionally substituted aryl or heteroaryl moiety via a two-step procedure which comprises: (i) reaction with bis(pinacolato)diboron; and (ii) reaction of the compound thereby obtained with an appropriately substituted bromoaryl or bromoheteroaryl derivative. Step (i) is conveniently effected in the presence of a transition metal catalyst such as [1,1'-bis-(diphenylphosphino)ferrocene]dichloropalladium(II), and potassium acetate. Step (ii) is conveniently effected in the presence of a transition metal catalyst such as [1,1'-bis-(diphenylphosphino)ferrocene]dichloropalladium(II), and a base, e.g. an inorganic base such as sodium carbonate or potassium carbonate.

A compound of formula (I) comprising a cyano (—CN) moiety may be converted into the corresponding compound comprising a 1-aminoethyl moiety by a two-step process which comprises: (i) reaction with methylmagnesium chloride, ideally in the presence of titanium(IV) isopropoxide; and (ii) treatment of the resulting material with a reducing agent such as sodium borohydride. If an excess of methylmagnesium chloride is employed in step (i), the corresponding compound comprising a 1-amino-1-methylethyl moiety may be obtained.

A compound of formula (I) comprising the moiety —S— may be converted into the corresponding compound comprising the moiety —S(O)(NH)— by treatment with (diacetoxyiodo)benzene and ammonium carbamate.

A compound of formula (I) comprising a C=C double bond may be converted into the corresponding compound comprising a CH—CH single bond by treatment with gaseous hydrogen in the presence of a hydrogenation catalyst, e.g. palladium on charcoal.

A compound of formula (I) comprising an aromatic nitrogen atom may be converted into the corresponding compound comprising an N-oxide moiety by treatment with a suitable oxidising agent, e.g. 3-chloroperbenzoic acid.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Greene's Protective Groups in Organic Synthesis*, ed. P.G.M. Wuts, John Wiley & Sons, 5$^{th}$ edition, 2014. The protecting groups may be removed at any convenient subsequent stage utilising methods known from the art.

The compounds in accordance with this invention potently inhibit the ability of IL-17A to bind to IL-17RA. When tested in the IL-17 FRET assay described below, compounds of the present invention exhibit an $IC_{50}$ value of 10 µM or less, generally of 5 µM or less, usually of 1 µM or less, typically of 500 nM or less, suitably of 100 nM or less, ideally of 50 nM or less, and preferably of 25 nM or less (the skilled person will appreciate that a lower $IC_{50}$ figure denotes a more active compound).

Moreover, certain compounds in accordance with this invention potently inhibit IL-17 induced IL-6 release from human dermal fibroblasts. Indeed, when tested in the HDF cell line assay described below, compounds of the present invention exhibit an $IC_{50}$ value of 10 µM or less, generally of 5 µM or less, usually of 1 µM or less, typically of 500 nM or less, suitably of 100 nM or less, ideally of 50 nM or less, and preferably of 25 nM or less (as before, the skilled person will appreciate that a lower $IC_{50}$ figure denotes a more active compound).

IL-17 FRET Assay

The purpose of this assay is to test the ability of compounds to disrupt the interaction between IL-17A and soluble IL-17 Receptor A (IL-17RA). The ability of a compound to inhibit IL-17A binding to IL-17RA is measured in this assay.

An IL-17AA-TEV-Human Fc construct was expressed in a CHO SXE cell system and purified by protein A chromatography and size exclusion. The protein was labelled with an amine reactive AlexaFluor 647 dye (Thermo Fisher #A20006), as per manufacturer's instruction.

Soluble IL-17RA (33-317)-HKH-TEV-Fc was expressed in an Expi HEK293 cell system and purified by protein A chromatography and size exclusion. The Fc tag was cleaved by TEV, producing IL-17RA (33-317)-HKH, and the protein was labelled with amine reactive terbium (Thermo Fisher #PV3581).

In assay buffer [Dulbecco's PBS (Sigma #14190-094), 0.05% P20 (Thermo Scientific #28320), 1 mg/mL BSA (Sigma #A2153-500G)] the following solutions were prepared:

For IL-17A Assay
  IL-17A-Fc-AF647 at 5 nM
  IL-17RA-HKH-Tb at 5 nM

Compounds were serially diluted in DMSO before receiving an aqueous dilution into a 384 well dilution plate (Greiner #781281), to give a 25% DMSO solution.

IL-17A (10 µL) was added to a black low volume assay plate (Costar #4511) and diluted compound (5 µL) was transferred from the aqueous dilution plate. The cytokine and compound were allowed to incubate for 1 h, then IL-17RA (10 µL) was added. The plates were wrapped in foil and incubated at room temperature for 18-20 h with gentle shaking (<400 rpm) before being read on a Perkin Elmer Envision plate reader (Excitation: 330 nm; Emission 615/645 nm).

The final assay concentrations were IL-17A-AF647 2 nM and IL-17RA-Tb 2 nM, 5% DMSO.

When tested in the IL-17 FRET assay, the compounds of the accompanying Examples were all found to exhibit $IC_{50}$ values of 10 µM or better.

When tested in the IL-17 FRET assay, compounds of the accompanying Examples exhibit $IC_{50}$ values generally in the range of about 0.01 nM to about 10 µM, usually in the range of about 0.01 nM to about 5 µM, typically in the range of about 0.01 nM to about 1 µM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

Inhibition of IL-17A Induced IL-6 Release from Dermal Fibroblast Cell Line

The purpose of this assay is to test the neutralising ability to IL-17 proteins, in a human primary cell system. Stimulation of normal human dermal fibroblasts (HDF) with IL-17 alone produces only a very weak signal but in combination with certain other cytokines, such as TNFα, a synergistic effect can be seen in the production of inflammatory cytokines, i.e. IL-6.

HDFs were stimulated with IL-17A (50 µM) in combination with TNF-α (25 µM). The resultant IL-6 response was then measured using a homogenous time-resolved FRET kit from Cisbio. The kit utilises two monoclonal antibodies, one labelled with Eu-Cryptate (Donor) and the second with d2 or XL665 (Acceptor). The intensity of the signal is proportional to the concentration of IL-6 present in the sample (Ratio is calculated by 665/620×104).

The ability of a compound to inhibit IL-17 induced IL-6 release from human dermal fibroblasts is measured in this assay.

HDF cells (Sigma #106-05n) were cultured in complete media (DMEM+10% FCS+2 mM L-glutamine) and maintained in a tissue culture flask using standard techniques. Cells were harvested from the tissue culture flask on the morning of the assay using TrypLE (Invitrogen #12605036). The TrypLE was neutralised using complete medium (45 mL) and the cells were centrifuged at 300×g for 3 minutes. The cells were re-suspended in complete media (5 mL) counted and adjusted to a concentration of $3.125 \times 10^4$ cells/mL before being added to the 384 well assay plate (Corning #3701) at 40 µL per well. The cells were left for a minimum of three hours, at 37° C./5% $CO_2$, to adhere to the plate.

Compounds were serially diluted in DMSO before receiving an aqueous dilution into a 384 well dilution plate (Greiner #781281), where 5 µL from the titration plate was transferred to 45 µL of complete media and mixed to give a solution containing 10% DMSO.

Mixtures of TNFα and IL-17 cytokine were prepared in complete media to final concentrations of TNFα 25 µM/IL-17A 50 µM, then 30 µL of the solution was added to a 384 well reagent plate (Greiner #781281).

10 µL from the aqueous dilution plate was transferred to the reagent plate containing 30 µL of the diluted cytokines, to give a 2.5% DMSO solution. The compounds were incubated with the cytokine mixtures for one hour at 37° C. After the incubation, 10 µL was transferred to the assay plate, to give a 0.5% DMSO solution, then incubated for 18-20 h at 37° C./5% $CO_2$.

From the Cisbio IL-6 FRET kit (Cisbio #62IL6PEB) europium cryptate and Alexa 665 were diluted in reconstitution buffer and mixed 1:1, as per kit insert. To a white low volume 384 well plate (Greiner #784075) were added FRET reagents (10 µL), then supernatant (10 µL) was transferred from the assay plate to Greiner reagent plate. The mixture was incubated at room temperature for 3 h with gentle shaking (<400 rpm) before being read on a Synergy Neo 2 plate reader (Excitation: 330 nm; Emission: 615/645 nm).

When tested in the above assay, compounds of the accompanying Examples were found to exhibit $IC_{50}$ values of 10 µM or better.

When tested in the above assay, compounds of the accompanying Examples exhibit $IC_{50}$ values generally in the range of about 0.01 nM to about 10 µM, usually in the range of about 0.01 nM to about 5 µM, typically in the range of about 0.01 nM to about 1 µM, suitably in the range of about 0.01 nM to about 500 nM, appositely in the range of about 0.01 nM to about 100 nM, ideally in the range of about 0.01 nM to about 50 nM, and preferably in the range of about 0.01 nM to about 25 nM.

The following Examples illustrate the preparation of compounds according to the invention.

EXAMPLES

Abbreviations

DCM: dichloromethane DMF: N,N-dimethylformamide
MeOH: methanol THF: tetrahydrofuran
DMSO: dimethyl sulfoxide DIPEA: N,N-diisopropylethylamine
EtOAc: ethyl acetate TFA: trifluoroacetic acid
EtOH: ethanol AcOH: acetic acid
DMAP: 4-(dimethylamino)pyridine NMP: 1-methyl-2-pyrrolidinone
9-BBN: 9-borabicyclo[3.3.1]nonane TPP: triphenylphosphine DAST: (diethylamino)sulfur trifluoride CDI: 1,1'-carbonyl-diimidazole
AIBN: 2,2'-azobis(2-methylpropionitrile) NBS: N-bromo-succinimide
HOBT: 1-hydroxybenzotriazole hydrate MCPBA: 3-chloroperbenzoic acid
MeMgCl: methylmagnesium chloride
TMEDA: N,N,N',N'-tetramethylethylenediamine
EDC.HCl: N-(3-dimethylaminopropyl)-N'-ethylcarbodiimide hydrochloride
HATU: 1-[bis(dimethylamino)methylene]-1H-1,2,3-triazolo[4,5-b]pyridinium 3-oxide hexafluorophosphate
HBTU: O-(benzotriazol-1-yl)-N,N,N',N'-tetramethyluronium hexafluorophosphate
T3P®: 2,4,6-tripropyl-1,3,5,2,4,6-trioxatriphosphorinane-2,4,6-trioxide solution
Pd(PPh$_3$)$_4$: tetrakis(triphenylphosphine)palladium(0)
Pd$_2$(dba)$_3$: tris(dibenzylideneacetone)dipalladium(0)
Pd(dppf)Cl$_2$.DCM: [1,1'-bis(diphenylphosphino)ferrocene]dichloropalladium(II), complex with dichloromethane
XPhos: 2-dicyclohexylphosphino-2',4',6'-triisopropylbiphenyl
Xantphos: 4,5-bis(diphenylphosphino)-9,9-dimethylxanthene
RuPhos: 2-dicyclohexylphosphino-2',6'-diisopropoxybiphenyl
{Ir[dF(CF$_3$)ppy]$_2$(dtbpy)}PF$_6$: [4,4'-bis(1,1-dimethylethyl)-2,2'-bipyridine-N$^1$,N$^1$']bis-{3,5-difluoro-2-[5-(trifluoromethyl)-2-pyridinyl-N]phenyl-C}iridium(III) hexafluoro-phosphate
h: hour r.t.: room temperature
M: mass RT: retention time
HPLC: High Performance Liquid Chromatography
LCMS: Liquid Chromatography Mass Spectrometry
Analytical Conditions All reactions involving air- or moisture-sensitive reagents were performed under a nitrogen atmosphere using dried solvents and glassware.

NMR spectra were recorded on a Bruker Avance III HD 500 MHz, 400 MHz, 300 MHz or 250 MHz spectrometer. HPLC-MS was performed on an Agilent 1200-6120 LC-MS system coupled to UV Detection (230 to 400 nm and 215 nm) and Mass Spec Detection Agilent 6120 Mass Spectrometer (ES) m/z 120 to 800.

Method 1
X-Bridge C18 Waters 2.1×20 mm, 2.5 µm column
Mobile Phase A: 10 mM ammonium formate in water+0.1% formic acid
Mobile Phase B: acetonitrile+5% water+0.1% formic acid
Gradient program: Flow rate Pump 1: 1 mL/minute

| Time | A % | B % |
|---|---|---|
| 0.00 | 94.00 | 6.00 |
| 1.50 | 5.00 | 95.00 |
| 2.25 | 5.00 | 95.00 |
| 2.50 | 94.00 | 6.00 |

Method 2
X-Bridge C18 Waters 2.1×20 mm, 2.5 µm column
Mobile Phase A: 10 nM ammonium formate in water+0.1% formic acid
Mobile Phase B: acetonitrile+5% water+0.1% formic acid
Gradient program: Flow rate Pump 1: 1 mL/minute

| Time | A % | B % |
|---|---|---|
| 0.00 | 95.00 | 5.00 |
| 4.00 | 5.00 | 95.00 |
| 5.00 | 5.00 | 95.00 |
| 5.10 | 96.00 | 4.00 |

Method 3
X-Bridge C18 Waters 2.1×20 mm, 2.5 µm column
Mobile Phase A: 10 nM ammonium formate in water+0.1% ammonia solution
Mobile Phase B: acetonitrile+5% water+0.1% ammonia solution
Gradient program: Flow rate 1 mL/minute

| Time | A % | B % |
|---|---|---|
| 0.00 | 96.00 | 4.00 |
| 4.00 | 5.00 | 95.00 |
| 5.00 | 5.00 | 95.00 |
| 5.10 | 96.00 | 4.00 |

Method 4
X-Bridge C18 Waters 2.1×20 mm, 2.5 µm column
Mobile Phase A: 10 mM ammonium formate in water+0.1% ammonia solution
Mobile Phase B: acetonitrile+5% water+0.1% ammonia solution
Gradient program: Flow rate 1 mL/minute

| Time | A % | B % |
|---|---|---|
| 0.00 | 96.00 | 4.00 |
| 1.50 | 5.00 | 95.00 |
| 2.25 | 5.00 | 95.00 |
| 2.50 | 96.00 | 4.00 |

Method 5
X-Select CSH C18 3×50 mm, 2.5 µm column
Mobile Phase A: 5 mM ammonium bicarbonate in water
Mobile Phase B: acetonitrile
Gradient program: Flow rate 1.2 mL/minute

| Time | A % | B % |
|---|---|---|
| 0.00 | 100 | 0 |
| 2.00 | 2.00 | 98.00 |
| 3.00 | 2.00 | 98.00 |

Method 6
X-Bridge C18 Waters 2.1×30 mm, 2.5 µm column
Mobile Phase A: 5 mM ammonium formate in water+0.1% ammonia solution
Mobile Phase B: acetonitrile+5% water+0.1% ammonia solution
Gradient program: Flow rate 1 mL/minute

| Time | A % | B % |
|---|---|---|
| 0.00 | 95.00 | 5.00 |
| 4.00 | 5.00 | 95.00 |
| 5.00 | 5.00 | 95.00 |

Automated preparative reverse phase HPLC purification was performed using a Gilson system with a Gilson 331&332 pump, a Gilson GX281 autoinjector, a Gilson GX281 fraction collector and a Gilson 159 UV detector.

Method 7

X-Bridge C18 Waters 30×100 mm, 10 μm column

Mobile Phase A: water+0.2% ammonia solution

Mobile Phase B: acetonitrile+0.2% ammonia solution

Gradient program: Flow rate 40 mL/minute

| Time | A % | B % |
|---|---|---|
| 0.00 | 70 | 30 |
| 0.55 | 70 | 30 |
| 11.00 | 5 | 95 |
| 13.10 | 5 | 95 |
| 13.31 | 70 | 30 |

Method 8

Waters Sunfire C18 Waters 30×100 mm, 10 μm column

Mobile Phase A: water+0.1% formic acid

Mobile Phase B: acetonitrile+0.1% formic acid

Gradient program: Flow rate 40 mL/minute

| Time | A % | B % |
|---|---|---|
| 0.00 | 70 | 30 |
| 0.55 | 70 | 30 |
| 11.00 | 5 | 95 |
| 13.10 | 5 | 95 |
| 13.31 | 70 | 30 |

Method 9

Phenomenex Kinetex-XB, C18 2.1×100 mm, 1.7 μm column

Mobile Phase A: 0.1% formic acid in water

Mobile Phase B: 0.1% formic acid in acetonitrile

Gradient program: Flow rate 0.6 mL/minute; column temperature 40° C.

| Time | A % | B % |
|---|---|---|
| 0.00 | 95.00 | 5.00 |
| 5.30 | 0.00 | 100.0 |
| 5.80 | 0.00 | 100.0 |
| 5.82 | 95.00 | 5.00 |
| 7.00 | 95.00 | 5.00 |

Method 10

Phenomenex Kinetex Core-Shell C8 50×2.1 mm, 5 μm column, protected by

Phenomenex 'Security Guard' column

Mobile Phase A: 0.1% formic acid in water

Mobile Phase B: 0.1% formic acid in acetonitrile

Gradient program: Flow rate 1.2 mL/minute; column temperature 40° C.

| Time | A % | B % |
|---|---|---|
| 0.00 | 95.00 | 5.00 |
| 1.20 | 0.00 | 100.0 |
| 1.30 | 0.00 | 100.0 |
| 1.31 | 95.00 | 5.00 |

Column chromatography separations were performed using a Biotage® Isolera 4 system with Biotage® SNAP KP-Sil pre-packed silica gel columns.

Intermediate 1

Methyl 2-cyclooctylidene-2-formamidoacetate

A 1M solution of potassium tert-butoxide in THF (48 mL, 48 mmol) was added dropwise to a solution of methyl isocyanoacetate (4.0 mL, 41.8 mmol) in anhydrous THF (40 mL) at approximately −65° C. under nitrogen. After stirring for 5 minutes, a solution of cyclooctanone (5 g, 39.6 mmol) in anhydrous THF (20 mL) was added slowly at −70° C. The reaction mixture was stirred at −70° C. for 30 minutes, then warmed to 20° C. and stirred under nitrogen for 60 h. The solution was quenched with water (100 mL) and stirred at 20° C. for 1 h. The residue was extracted with ethyl acetate (3×100 mL). The combined organic extracts were washed with brine (50 mL) and dried over magnesium sulfate, then filtered and concentrated in vacuo. The resulting crude orange oil was purified by flash column chromatography, using a gradient of ethyl acetate in heptane (0-90%), to afford the title compound (5.37 g, 58%) as an orange viscous oil, which solidified upon standing. δH (500 MHz, DMSO-$d_6$) 9.31 (s, 1H), 8.01 (d, J 1.5 Hz, 1H), 3.60 (s, 3H), 2.52-2.47 (m, 2H), 2.31-2.23 (m, 2H), 1.74-1.60 (m, 4H), 1.50-1.31 (m, 6H) (major rotamer). LCMS (Method 5): [M+Na]$^+$ m/z 248, RT 1.63 minutes.

Intermediate 2

Methyl 2-cyclooctyl-2-formamidoacetate

Magnesium turnings (3.15 g, 130 mmol) were added carefully to a stirred solution of Intermediate 1 (3.04 g, 12.9 mmol) in anhydrous methanol (65 mL) at 0° C. under nitrogen. The suspension was stirred at 0° C. for 1 h, then warmed to 20° C. over 2 h. Stirring of the suspension was continued at 20° C. for 16 h. An additional portion of magnesium turnings (1 g, 41.14 mmol) was added, and the suspension was stirred at 20° C. for 3.5 h under nitrogen. The mixture was carefully concentrated in vacuo. The residue was suspended in EtOAc (100 mL) and water (200 mL), then cooled to 0° C. Aqueous hydrochloric acid (1M, 100 mL) was added, and the pH was adjusted to 5 with concentrated hydrochloric acid. The organic phase was separated, and the aqueous suspension was further extracted with EtOAc (3×100 mL). The combined organic extracts were washed with brine (50 mL) and dried over magnesium sulfate, then filtered and concentrated in vacuo. The resulting crude orange oil was purified by flash column chromatography, using a gradient of ethyl acetate in heptane (0-80%), to afford the title compound (1.53 g, 48%) as an orange viscous oil. $\delta_H$ (500 MHz, DMSO-$d_6$) 8.46 (d, J 8.5 Hz, 1H), 8.06 (s, 1H), 4.29 (dd, J 8.6, 6.1 Hz, 1H), 3.64 (s, 3H), 2.04-1.93 (m, 1H), 1.73-1.19 (m, 14H) (major rotamer). LCMS (Method 4): [M+H]$^+$ m/z 228, RT 3.94 minutes.

Intermediate 3

Methyl 2-amino-2-cyclooctylacetate hydrochloride

Acetyl chloride (1.9 mL, 26.7 mmol) was added cautiously at 0° C. to a stirred solution of Intermediate 2 (1.69 g, 6.77 mmol) in methanol (68 mL) under nitrogen. After stirring for 5 minutes, the solution was heated at 50° C. for 2 h. The volatiles were concentrated in vacuo. The resulting crude orange powder was triturated with diethyl ether (40 mL). The solids were collected by filtration and washed with diethyl ether (2×20 mL), then dried in vacuo at 50° C., to afford the title compound (1.43 g, 81%) as a tan powder. $\delta_H$ (500 MHz, DMSO-$d_6$) 8.61 (br s, 3H), 3.86 (d, J 4.4 Hz, 1H), 3.73 (s, 3H), 2.19-2.09 (m, 1H), 1.68-1.37 (m, 13H), 1.32-1.20 (m, 1H). LCMS (Method 5): [M+H]$^+$ m/z 200, RT 0.75 and 0.86 minutes.

Intermediate 4

Methyl 2-cyclooctyl-2-[(2-methylpyrazole-3-carbonyl)amino]acetate

DIPEA (1.05 mL, 6.35 mmol) was added to a stirred solution of Intermediate 3 (500 mg, 2.12 mmol), 1-methyl-1H-pyrazole-5-carboxylic acid (269 mg, 2.12 mmol) and HBTU (969 mg, 2.55 mmol) in anhydrous DMF (10 mL) under a nitrogen atmosphere. The mixture was stirred at 20° C. for 18 h, then quenched with saturated aqueous sodium hydrogen carbonate solution (50 mL) and water (50 mL). The residue was extracted with EtOAc (3×50 mL). The combined organic layers were washed with brine (2×50 mL) and dried over sodium sulfate, then filtered and concentrated in vacuo. The residue was purified by flash column chromatography, using a gradient of EtOAc in heptane (0-100%), to afford the title compound (618 mg, 80%) as a yellow-orange oil. $\delta_H$ (500 MHz, DMSO-$d_6$) 8.60 (d, J 8.3 Hz, 1H), 7.46 (d, J 2.1 Hz, 1H), 7.01 (d, J 2.1 Hz, 1H), 4.37 (t, J 8.1 Hz, 1H), 4.01 (s, 3H), 3.66 (s, 3H), 2.22-2.08 (m, 1H), 1.80-1.38 (m, 13H), 1.37-1.29 (m, 1H). LCMS (Method 5): [M+H]$^+$ m/z 308, RT 1.87 minutes.

Intermediate 5

Lithium 2-cyclooctyl-2-[(2-methylpyrazole-3-carbonyl)amino]acetate

To a stirred solution of Intermediate 4 (618 mg, 1.69 mmol) in THF (9 mL) and water (4.5 mL) was added lithium hydroxide monohydrate (0.106 g, 2.53 mmol). The reaction mixture was stirred at 20° C. for 22 h, then concentrated and dried in vacuo, to afford the title compound (640 mg, quantitative) as a yellow solid. $\delta_H$ (500 MHz, DMSO-$d_6$) 7.60 (d, J 7.6 Hz, 1H), 7.42 (d, J 2.0 Hz, 1H), 6.74 (d, J 2.0 Hz, 1H), 4.01 (s, 3H), 3.88 (dd, J 7.6, 4.3 Hz, 1H), 2.11-2.01 (m, 1H), 1.74-1.22 (m, 14H). LCMS (Method 5): [M+H]$^+$ m/z 294, RT 1.71 minutes.

Intermediate 6

Methyl 2-cyclooctyl-2-[(3-methylisoxazole-4-carbonyl)amino]acetate

To a solution of 3-methylisoxazole-4-carboxylic acid (12.9 g, 66.1 mmol) in dry DMF (100 mL) at 0° C. were added DIPEA (54.9 g, 425 mmol), EDC.HCl (19.5 g, 102 mmol) and HOBT (13.8 g, 102 mmol). The reaction mixture was stirred for 15 minutes at 0° C., then Intermediate 3 (20.0 g, 84.92 mmol) was added and the mixture was stirred at r.t. for 48 h. The reaction mixture was poured into ice-cold water (500 mL) and extracted with ethyl acetate (2×400 mL). The organic layer was separated, then washed with ice-cold water (2×100 mL) and 1N hydrochloric acid (2×50 mL). The organic layer was dried over anhydrous Na$_2$SO$_4$, then filtered and evaporated under vacuum. The crude residue was purified by silica-gel flash column chromatography, using 15% EtOAc in hexane as eluting solvent, to afford the title compound (7.9 g, 41%) as a pale yellow oil. LCMS (Method 5): [M+H]$^+$ m/z 309, RT 1.07 minutes.

Intermediate 7

2-Cyclooctyl-2-[(3-methylisoxazole-4-carbonyl)amino]acetic Acid

To a solution of Intermediate 6 (11.0 g, 35.7 mmol) in THF (90 mL) at r.t. were added water (30 mL) and lithium hydroxide monohydrate (2.25 g, 53.6 mmol). The mixture was stirred for 16 h, then evaporated under vacuum. The residue was suspended in diethyl ether (50 mL), then stirred for 10 minutes and filtered. The resultant solid was washed with diethyl ether (50 mL) and pentane (50 mL), then dried under vacuum, to afford an off-white solid (9.51 g). The solid (9.0 g) was suspended in water (30 mL) and EtOAc (100 mL), then acidified with a 2M aqueous HCl solution (35 mL). The resulting mixture was extracted with EtOAc (2×75 mL). The combined organic extracts were washed with water (30 mL) and brine (50 mL), then dried over MgSO$_4$, filtered and concentrated in vacuo. The residue crystallised upon standing and was triturated with acetonitrile, to give the title compound (7.0 g, 80%) as a pale powder. $\delta_H$ (500 MHz, DMSO-$d_6$) 12.71 (s, 1H), 9.41 (d, J 0.6 Hz, 1H), 8.36 (d, J 8.6 Hz, 1H), 4.35 (dd, J 8.6, 6.6 Hz, 1H), 2.37 (s, 3H), 2.11-2.02 (m, 1H), 1.68-1.37 (m, 14H). LCMS (Method 8): [M+H]$^+$ m/z 295, RT 1.90 minutes.

Intermediate 8 (Procedure A)

N-[2-(2-Amino-3-methoxyanilino)-1-cyclooctyl-2-oxoethyl]-3-methylisoxazole-4-carboxamide To a solution of Intermediate 7 (110 mg, 0.37 mmol), 3-methoxybenzene-1,2-diamine (50 mg, 0.34 mmol) and DIPEA (0.2 mL, 1 mmol) in DMF (2 mL) was added HATU (160 mg, 0.41 mmol). The reaction mixture was stirred at r.t. for 48 h, then partitioned between DCM and water. The organic phase was separated, then dried and concentrated in vacuo. The crude residue was purified by flash column chromatography (0-100% EtOAc/hexanes) to give the title compound (28.7 mg, 20%) as a white solid. LCMS (Method 5): [M+H]$^+$ m/z 415, RT 1.31 minutes.

Intermediate 9

N-[2-(2-Amino-3-fluoroanilino)-1-cyclooctyl-2-oxoethyl]-3-methylisoxazole-4-carboxamide The title compound (134 mg, 44%) was prepared from Intermediate 7 (233 mg, 0.79 mmol) and 3-fluorobenzene-1,2-diamine (100 mg, 0.75 mmol) in accordance with Procedure A. LCMS (Method 5): [M+H]$^+$ m/z 403, RT 1.33 minutes.

Intermediate 10

N-{2-[2-Amino-3-fluoro-4-(tetrahydropyran-4-yl)anilino]-1-cyclooctyl-2-oxoethyl}-3-methylisoxazole-4-carboxamide The title compound (160 mg, 58%) was prepared from Intermediate 7 (65 mg, 0.22 mmol) and Intermediate 24 (50 mg, 0.22 mmol) in accordance with Procedure A. LCMS (Method 5): [M+H]$^+$ m/z 487, RT 2.34 minutes.

Intermediate 11

N-{2-[2-Amino-3-fluoro-4-(4-methylpiperazin-1-yl)anilino]-1-cyclooctyl-2-oxoethyl}-3-methylisoxazole-4-carboxamide The title compound (144 mg, quantitative) was prepared from Intermediate 7 (85 mg, 0.29 mmol) and 3-fluoro-4-(4-methylpiperazin-1-yl)benzene-1,2-diamine (70 mg, 0.29 mmol) in accordance with Procedure A. LCMS (Method 5): [M+H]$^+$ m/z 501, RT 1.24 minutes.

Intermediate 12

N-[2-(2-Amino-3,6-difluoroanilino)-1-cyclooctyl-2-oxoethyl]-3-methylisoxazole-4-carboxamide The title compound (40 mg, 14%) was prepared from Intermediate 7 (204 mg, 0.69 mmol) and 3,6-difluorobenzene-1,2-diamine (100 mg, 0.66 mmol) in accordance with Procedure A. LCMS (Method 5): [M+H]$^+$ m/z 421, RT 1.36 minutes.

Intermediate 13 tert-Butyl N-[2-(2-amino-3-fluoroanilino)-1-cyclooctyl-2-oxoethyl]carbamate

The title compound (2.99 g, 100%) was prepared from 2-(tert-butoxycarbonyl-amino)-2-cyclooctylacetic acid (2.26 g, 7.92 mmol) and 3-fluorobenzene-1,2-diamine (1 g, 7.53 mmol) in accordance with Procedure A. LCMS (Method 5): [M+H]$^+$ m/z 394.2, RT 1.48 minutes.

Intermediate 14

Cyclooctyl(4-fluoro-1H-benzimidazol-2-yl)methanamine

To a solution of Example 6 (2.8 g, 7.50 mmol) in DCM (30 mL) at −78° C. was added TFA (5 mL, 66.13 mmol). The reaction mixture was warmed slowly to r.t. and stirred for 24 h, then concentrated under vacuum. The residue was run down an SCX column, eluting with 7N NH$_3$ in MeOH, to give the title compound (1.67 g, 82%) as a light brown solid. LCMS (Method 5): [M+H]$^+$ m/z 276, RT 1.19 minutes.

Intermediate 15

2-(tert-Butoxycarbonylamino)-2-(4-methylcyclohexyl)acetic acid

To a solution of 2-amino-2-(4-methylcyclohexyl)acetic acid (3 g, 18 mmol), dissolved in 1,4-dioxane (35 mL) and water (17 mL), was added a 2M aqueous solution of NaOH (8.75 mL, 17.5 mmol). The reaction mixture was cooled to 0° C. Di-tert-butyl dicarbonate (5.8 g, 26 mmol) and sodium bicarbonate (1.5 g, 18 mmol) were added. The reaction mixture was stirred at r.t. for 24 h, then concentrated under vacuum to half the volume. The residue was diluted with EtOAc (40 mL), and the pH of the solution was adjusted to 2-3 with a 1M aqueous KHSO$_4$ solution. The aqueous layer was extracted with EtOAc (2×50 mL). The organic layer was washed with water, then concentrated under vacuum, to give the title compound (4.7 g, 99%) as a white solid. LCMS (Method 5): [M-BOC]$^+$ m/z 172, RT 0.96 minutes.

Intermediate 16 tert-Butyl N-[2-(2-amino-3-fluoroanilino)-1-(4-methylcyclohexyl)-2-oxoethyl]carbamate The title compound (568 mg, 99%) was prepared from Intermediate 15 (430 mg, 1.58 mmol) and 3-fluorobenzene-1,2-diamine (200 mg, 1.51 mmol) in accordance with Procedure A. LCMS (Method 5): [M+H]$^+$ m/z 380, RT 1.43 minutes.

Intermediate 17 (Procedure B)

tert-Butyl N-[(4-fluoro-1H-benzimidazol-2-yl)(4-methylcyclohexyl)methyl]carbamate A solution of Intermediate 16 (568 mg, 1.50 mmol) in AcOH (4 mL) was heated at 70° C. for 3 h, then concentrated in vacuo. The residue was purified by chromatography using an SCX column, eluting with 7N NH$_3$ in MeOH, to give the title compound (541 mg, quantitative). LCMS (Method 5): [M+H]$^+$ m/z 362, RT 1.44 minutes.

Intermediate 18

(4-Fluoro-1H-benzimidazol-2-yl)(4-methylcyclohexyl)methanamine

To a solution of Intermediate 17 (541 mg, 1.50 mmol) in DCM (6 mL) at −78° C. was added TFA (0.5 mL, 93.6 mmol). The reaction mixture was warmed slowly to r.t. and stirred for 24 h, then concentrated in vacuo. The residue was run down an SCX column, eluting with 7N NH$_3$ in MeOH, to give the title compound (397 mg, 100%). LCMS (Method 5): [M+H]$^+$ m/z 262, RT 1.16 minutes.

Intermediate 19

N-[2-(2-Amino-3-chloroanilino)-1-cyclooctyl-2-oxoethyl]-3-methylisoxazole-4-carboxamide The title compound (264 mg, 100%) was prepared from Intermediate 7 (195 mg, 0.66 mmol) and 3-chlorobenzene-1,2-diamine (100 mg, 0.63 mmol) in accordance with Procedure A. LCMS (Method 5): [M+H]$^+$ m/z 419, RT 1.38 minutes.

Intermediate 20

N-[2-(2-Amino-3-fluoroanilino)-1-cyclooctyl-2-oxoethyl]-2-methylpyrazole-3-carboxamide The title compound (60 mg, 41%) was prepared from Intermediate 5 (50 mg, 0.17 mmol) and 3-fluorobenzene-1,2-diamine (26 mg, 0.206 mmol) in accordance with Procedure A. LCMS (Method 5): [M+H]$^+$ m/z 402, RT 2.07 minutes.

Intermediate 21 tert-Butyl N-(2-amino-4-bromo-3-fluorophenyl)carbamate

To a solution of 4-bromo-3-fluorobenzene-1,2-diamine (556 mg, 2.71 mmol) in DCM (10 mL) at r.t. was added 2M aqueous sodium hydroxide solution (3.1 mL, 6.10 mmol), followed by di-tert-butyl dicarbonate (2.8 g, 12 mmol). The reaction mixture was stirred overnight, then diluted with DCM (30 mL) and washed with brine (50 mL). The organic layer was dried over sodium sulfate, filtered and evaporated to dryness. Purification by flash chromatography, eluting with EtOAc in hexanes (2-20%), gave the title compound (549 mg, 66%) as a white solid. $\delta_H$ (400 MHz, CDCl$_3$) 7.05 (dd, J 8.8, 1.6 Hz, 1H), 6.95 (dd, J 8.7, 7.1 Hz, 1H), 6.30 (s, 1H), 3.35 (s, 2H), 1.54 (s, 9H). LCMS (Method 5): [M+H]$^+$ m/z 305, RT 1.30 minutes.

Intermediate 22 tert-Butyl N-[2-amino-4-(3,6-dihydro-2H-pyran-4-yl)-3-fluorophenyl]carbamate

To a mixture of Intermediate 21 (200 mg, 0.66 mmol), 3,6-dihydro-2H-pyran-4-boronic acid pinacol ester (142 mg, 0.66 mmol) and [1,1'-bis(diphenylphosphino)-ferrocene]dichloropalladium(II) complex with dichloromethane (59 mg, 0.065 mmol) in 1,4-dioxane (2 mL) at r.t. was added aqueous sodium carbonate solution (2M, 2 mL, 4 mmol). The mixture was de-gassed under nitrogen, then heated in a microwave reactor for 60 minutes at 100° C. The reaction mixture was filtered through Celite®, washing with EtOAc (10 mL), then the combined washings were concentrated in vacuo. The residue was diluted with EtOAc (30 mL) and washed with water (50 mL), then dried over sodium sulfate, filtered and evaporated to dryness. Purification by flash chromatography, eluting with a solution of EtOAc in hexanes (15-100%), gave the title compound (176 mg, 86%) as a beige solid. $\delta_H$ (400 MHz, CDCl$_3$) 7.10 (dd, J 8.4, 1.5 Hz, 1H), 6.71 (t, J 8.3 Hz, 1H), 6.37 (s, 1H), 6.11-5.91 (m, 1H), 4.39-4.26 (m, 2H), 3.93 (t, J 5.4 Hz, 2H), 2.58-2.42 (m, 2H), 1.54 (s, 9H). LCMS (method 5): [M+H-$^t$Bu]$^+$ m/z 253, RT 1.22 minutes.

Intermediate 23 tert-Butyl N-[2-amino-3-fluoro-4-(tetrahydropyran-4-yl)phenyl]carbamate

To a solution of Intermediate 22 (176 mg, 0.57 mmol) in ethanol (10 mL) was added 10% Pd on charcoal (17 mg). The mixture was de-gassed under nitrogen, then stirred under an atmosphere of hydrogen for 2 h. The reaction mixture was filtered through Celite® and evaporated to dryness, to give the title compound (173 mg, 91%) as a grey solid. $\delta_H$ (400 MHz, CDCl$_3$) 7.11-6.96 (m, 1H), 6.72-6.59 (m, 1H), 6.27 (s, 1H), 4.15-3.99 (m, 2H), 3.65-3.49 (m, 2H), 3.17-2.97 (m, 1H), 1.92-1.76 (m, 4H), 1.75-1.66 (m, 2H), 1.54 (s, 9H). LCMS (Method 5): [M+H-$^t$Bu]$^+$ m/z 255, RT 1.20 minutes.

Intermediate 24

3-Fluoro-4-(tetrahydropyran-4-yl)benzene-1,2-diamine

To a solution of Intermediate 23 (76 mg, 0.23 mmol) in ethanol (10 mL) was added a 4M solution of hydrochloric acid in 1,4-dioxane (2 mL). The mixture was stirred for 1 h at r.t., then evaporated to dryness. The residue was dissolved in methanol (2 mL) and purified with an SCX-2 column (washed with methanol). The resulting material was treated with a 4M solution of ammonia in methanol (10 mL) and evaporated to dryness, to give the title compound (50 mg, 97%) as a beige solid. $\delta_H$ (400 MHz, CDCl$_3$) 6.56-6.35 (m, 2H), 4.12-3.91 (m, 2H), 3.62-3.44 (m, 2H), 3.09-2.89 (m, 1H), 1.87-1.58 (m, 4H). LCMS (Method 5): [M+H]$^+$ m/z 210, RT 0.79 minutes.

Intermediate 25 (Procedure C)

3-Fluoro-4-(4,4,5,5-tetramethyl-1,3,2-dioxaborolan-2-yl)benzene-1,2-diamine

A solution of 4-bromo-3-fluorobenzene-1,2-diamine (5.0 g, 24.39 mmol), bis(pinacolato)diboron (6.5 g, 26 mmol) and potassium acetate (7.2 g, 73 mmol) in 1,4-dioxane (50 mL) was degassed with N$_2$ for 10 minutes, then Pd(dppf) Cl$_2$.DCM (1.3 g, 1.58 mmol) was added. The mixture was degassed with N$_2$ for a further 10 minutes, then the reaction mixture was heated at 105° C. overnight. The reaction mixture was cooled and filtered through Celite®, washing the plug with EtOAc. The filtrate was concentrated in vacuo, then the residue was partitioned between DCM and water. The organic layers were dried over Na$_2$SO$_4$ and concentrated in vacuo, then purified by flash chromatography, eluting with EtOAc/hexanes (0-65% gradient), to give the title compound (3.7 g, 60%) as a brown solid. LCMS (Method 5): [M+H]$^+$ m/z 253, RT 1.02 minutes.

Intermediate 26 (Procedure D)

tert-Butyl N-(3-bromo-2,5-difluoro-6-nitrophenyl)-N-(tert-butoxycarbonyl)carbamate To a stirred solution of 3-bromo-2,5-difluoro-6-nitroaniline (510 mg, 2.02 mmol) in THF (10 mL) was added DIPEA (1.05 mL, 6.02 mmol), followed by di-tert-butyl dicarbonate (530 mg), at 0° C. After stirring for 10 minutes, DMAP (125 mg, 1.02 mmol) was added portionwise. The reaction mixture was stirred at 0° C. for 15 minutes, then warmed to r.t. After 1 h, further di-tert-butyl dicarbonate (790 mg) was added. The reaction mixture was stirred for 2.5 h, then concentrated in vacuo. The crude residue was purified by flash column chromatography, eluting with EtOAc/hexanes (0-50% gradient), to give the title compound (509 mg, 56%). LCMS (Method 5): [M+H−2(BOC)]$^+$ m/z 254, RT 1.66 minutes.

Intermediate 27

N,N-Dibenzyl-3-bromo-2-fluoro-6-nitroaniline

To a solution of 2,3-difluoro-4-bromonitrobenzene (1 g, 4.12 mmol) in DMSO (10 mL) were added K$_2$CO$_3$ and dibenzylamine (0.86 mL, 4.3 mmol). The reaction mixture was heated at 100° C. and stirred overnight, then partitioned between EtOAc and water. The organic layers were separated and dried over Na$_2$SO$_4$, then concentrated in vacuo. The residue was purified by flash chromatography, eluting with EtOAc/hexanes (0-50% gradient), to give the title compound (1.07 g, 52%). LCMS (Method 5): [M+H]$^+$ m/z 417, RT 1.71 minutes.

Intermediate 28 tert-Butyl N-(4-bromo-2-fluoro-6-nitrophenyl)-N-(tert-butoxycarbonyl)carbamate

The title compound (9.6 g, quantitative) was prepared from 4-bromo-2-fluoro-6-nitroaniline (5 g, 20.22 mmol) in accordance with Procedure D. LCMS (Method 5): [M+H−2(BOC)]⁺ m/z 236, RT 1.65 minutes.

Intermediate 29

3-Fluoro-4-(1H-pyrazol-3-yl)benzene-1,2-diamine

To a mixture of Intermediate 21 (200 mg, 0.65 mmol), 1-(2-tetrahydropyranyl)-1H-pyrazole-5-boronic acid pinacol ester (376 mg, 1.31 mmol) and Pd(dppf)Cl$_2$.DCM (59 mg, 0.09 mmol) in 1,4-dioxane (2 mL) was added aqueous Na$_2$CO$_3$ solution (2M, 1.9 mL). The mixture was degassed under N$_2$ sparge for 10 minutes, then heated under focused microwave irradiation for 60 minutes at 100° C. After cooling, the mixture was filtered through Celite® (1 g), washing the plug with EtOAc (20 mL). The organic layers were concentrated in vacuo, then partitioned between EtOAc and water. The organic layers were dried over Na$_2$SO$_4$, then concentrated in vacuo. The residue was purified by flash chromatography, eluting with EtOAc/hexanes (12-100% gradient). The resulting yellow glass was taken up in 4M HCl in 1,4-dioxane (2 mL). The reaction mixture was stirred for 1 h, then concentrated in vacuo. The residue was taken up in MeOH (2 mL) and eluted onto an SCX cartridge (2 g). After MeOH washing, the residue was eluted with a 4M solution of NH$_3$ in MeOH (10 mL), then concentrated in vacuo, to furnish the title compound (80 mg, 63%) as a pale yellow solid. LCMS (Method 5): [M+H]⁺ m/z 193, RT 0.49 minutes.

Intermediate 30

4-(Benzenesulfinyl)-3-fluorobenzene-1,2-diamine

To a solution of 4-bromo-3-fluorobenzene-1,2-diamine (300 mg, 1.46 mmol), thiophenol (300 μL, 2.90 mmol) and K$_2$CO$_3$ (613 mg, 4.39 mmol) in DMF (7 mL) was added copper(I) chloride. The mixture was heated in a sealed vial at 150° C. overnight, then poured onto water and filtered through Celite®, eluting with EtOAc. The organic layers were separated and dried over MgSO$_4$, then concentrated in vacuo. The residue was purified by flash chromatography, eluting with EtOAc/hexanes (0-100% gradient). The resulting dark oil was taken up in DMF (3 mL), and H$_2$O$_2$ (3 mL, 29.37 mmol, 30% mass) was added. The mixture was stirred overnight, then poured slowly onto a saturated aqueous solution of Na$_2$S$_2$O$_5$ (20 mL). The mixture was diluted with EtOAc (20 mL). The organic layers were separated and washed with brine, then dried over MgSO$_4$ and concentrated in vacuo. Purification of the residue by flash chromatography, eluting with EtOAc/hexanes (30-100% gradient), afforded the title compound (85 mg, 23% overall) as a brown solid. LCMS (Method 5): [M+H]⁺ m/z 251, RT 0.87 minutes.

Intermediate 31 tert-Butyl 2-(3,4-diamino-2-fluorophenyl)acetate

A mixture of Intermediate 27 (916 mg, 2.2 mmol), XPhos (325 mg, 0.66 mmol) and Pd$_2$(dba)$_3$ (312 mg, 0.33 mmol) in anhydrous THF (20 mL) was degassed under N$_2$ sparge for 10 minutes at r.t., then 2-tert-butoxy-2-oxoethylzinc chloride (10 mL, 5 mmol) was added. The reaction mixture was stirred for 3 h at 70° C., then cooled and diluted with EtOAc (50 mL). The organic layers were washed with saturated NH$_4$Cl solution, then dried over MgSO$_4$ and concentrated in vacuo. The residue was purified by flash chromatography, eluting with EtOAc/hexanes (0-20% gradient), then reverse-phase HPLC. The resulting yellow solid was taken up in EtOH (13 mL), and 10% Pd/C (20 mg) was added. The reaction mixture was stirred under an atmosphere of hydrogen overnight, then filtered through Celite® (1 g), washing the plug with EtOH. The residue was concentrated in vacuo to give the title compound (116 mg, 22% overall) as a red oil. LCMS (Method 5): [M+H]⁺ m/z 241, RT 1.08 minutes.

Intermediate 32 (Procedure E)

tert-Butyl 3-(3,4-diamino-2-fluorophenyl)propanoate

To a solution of 4-bromo-3-fluorobenzene-1,2-diamine (500 mg, 2.34 mmol), dissolved in DMF (1.7 mL), was added DIPEA (1.7 mL), then tert-butyl acrylate (0.43 mL, 2.9 mmol), tri-o-tolylphosphine (285 mg, 0.94 mmol) and palladium(II) acetate (26 mg, 0.12 mmol). The mixture was heated at 110° C. overnight under an atmosphere of argon, then allowed to cool, and concentrated in vacuo. The residue was partitioned between EtOAc (10 mL) and water (10 mL). The organic layers were separated and dried over MgSO$_4$, then concentrated in vacuo. The residue was purified by flash chromatography, eluting with EtOAc/hexanes (0%-70% gradient). The resulting brown oil was taken up in EtOH (56 mL), and 10% Pd/C (57 mg) was added. The reaction mixture was stirred under an atmosphere of hydrogen overnight, then filtered through Celite® (2.5 g), washing the plug with EtOH. The residue was concentrated in vacuo to give the title compound (486 mg, 82% overall) as a brown oil. $\delta_H$ (400 MHz, CDCl$_3$) 6.57-6.45 (m, 1H), 6.41 (dd, J 8.1, 1.3 Hz, 1H), 3.37 (s, 4H), 2.87-2.79 (m, 2H), 2.52-2.44 (m, 2H), 1.42 (s, 9H). LCMS (Method 5): [M+H]⁺ m/z 255, RT 1.14 minutes.

Intermediate 33 (Procedure F)

tert-Butyl 2-(3,4-diamino-2-fluorophenyl)benzoate

To a solution of 4-bromo-3-fluorobenzene-1,2-diamine (1.0 g, 4.68 mmol), 2-(tert-butoxycarbonyl)phenylboronic acid pinacol ester (2.23 g, 7.04 mmol) and K$_2$CO$_3$ (1.63 g, 11.7 mmol) in 1,4-dioxane (32 mL) and water (17 mL) was added Pd(dppf)Cl$_2$.DCM (382 mg, 0.47 mmol). The reaction mixture was degassed for 10 minutes with N$_2$ sparging, and heated at 80° C. for 48 h, then cooled, diluted with water and extracted into EtOAc. The organic layers were dried over Na$_2$SO$_4$, concentrated in vacuo and purified by flash chromatography, eluting with EtOAc/hexanes (0-100% gradient), to give the title compound (1.31 g, 84%) as a brown oil. LCMS (Method 5): [M+H]⁺ m/z 303, RT 1.21 minutes.

Intermediate 34 (Procedure G)

2-(3,4-Diamino-2-fluorophenyl)-N,N-dimethylbenzamide

A solution of Intermediate 25 (206 mg, 0.82 mmol), 2-bromo-N,N-dimethyl-benzamide (200 mg, 0.88 mmol) and K$_2$CO$_3$ (327 mg, 2.37 mmol) in water (0.5 mL) and 1,4 dioxane (3.2 mL) in a microwave vial was sparged with N$_2$ for 5 minutes, prior to the addition of Pd(dppf)Cl$_2$.DCM (35 mg, 0.05 mmol). The reaction mixture was heated under microwave irradiation for 1 h at 100° C., then concentrated in vacuo. The residue was purified using flash chromatography, eluting with EtOAc/hexanes (10-100% gradient), to furnish the title compound (150 mg, 48%) as a brown foam. LCMS (Method 5): [M+H]+ m/z 274, RT 0.48 minutes.

Intermediate 35 (Procedure H)

3-(Cyclopentyloxy)benzene-1,2-diamine

To a solution of 2,3-dinitrophenol (250 mg, 1.36 mmol) in DMF (2.5 mL) at r.t. was added $K_2CO_3$ (375 mg, 2.71 mmol), followed by cyclopentyl bromide (6.7 mL, 61 mmol). The reaction mixture was heated at 100° C. for 1 h, then cooled, poured onto water (50 mL) and extracted with diethyl ether (2×30 mL). The organic phase was separated, dried over $Na_2SO_4$ and concentrated in vacuo. The residue was purified by flash chromatography, eluting with EtOAc/hexanes (15-60% gradient). The resulting beige solid was taken up in EtOH (20 mL), and 10% Pd/C (24 mg) was added. The reaction mixture was stirred under an atmosphere of hydrogen overnight, then filtered through Celite® (1 g), washing the plug with EtOH. The residue was concentrated in vacuo to give the title compound (166 mg, 63% overall) as a brown oil. $\delta_H$ (400 MHz, $CD_3OD$) 6.63-6.52 (m, 1H), 6.43-6.33 (m, 2H), 4.84-4.73 (m, 1H), 2.04-1.76 (m, 6H), 1.75-1.57 (m, 2H). LCMS (Method 5): [M+H]+ m/z 193, RT 1.11 minutes.

Intermediate 36 (Procedure I)

3-Methoxy-4-(tetrahydropyran-4-yl)benzene-1,2-diamine

To a mixture of 4-bromo-3-methoxy-2-nitroaniline (200 mg, 0.81 mmol), 3,6-dihydro-2H-pyran-4-boronic acid pinacol ester (177 mg, 0.82 mmol) and aqueous $Na_2CO_3$ solution (2M, 2.43 mL) in 1,4-dioxane (3 mL) was added Pd(dppf)$Cl_2$.DCM (73 mg, 0.08 mmol). The reaction mixture was degassed by $N_2$ sparging for 10 minutes, then heated under focused microwave irradiation for 1 h at 100° C. The reaction mixture was cooled and filtered through Celite® (1 g), washing with MeOH (20 mL), then concentrated in vacuo. The residue was partitioned between EtOAc and water. The organic phase was separated, dried over $Na_2SO_4$ and concentrated in vacuo. The residue was purified by flash chromatography, eluting with EtOAc/hexanes (10-80% gradient). The resulting beige solid was taken up in EtOH (20 mL), and 10% Pd/C (24 mg) was added. The reaction mixture was stirred under an atmosphere of hydrogen overnight, then filtered through Celite® (1 g), washing the plug with EtOH. The residue was concentrated in vacuo to give the title compound (56 mg, 31% overall) as a brown solid. $\delta_H$ (400 MHz, $CD_3OD$) 6.58-6.42 (m, 2H), 4.09-3.95 (m, 2H), 3.74 (s, 3H), 3.62-3.52 (m, 2H), 3.12-2.99 (m, 1H), 1.82-1.60 (m, 4H). LCMS (Method 5): [M+H]+ m/z 223, RT 0.73 minutes.

Intermediate 37

3-Bromo-2,5-difluoro-6-nitroaniline

To a stirred solution of 1-bromo-2,3,5-trifluoro-4-nitrobenzene (265 mg, 0.96 mmol) in MeOH (1 mL) at 0° C. was added dropwise a 7N solution of $NH_3$ in MeOH (481 µL). The reaction mixture was stirred at r.t. for 1 h, then concentrated in vacuo. The crude residue was purified by flash chromatography, eluting with EtOAc/hexanes (5-40% gradient), to give the title compound (178 mg, 72%) as a yellow solid. $\delta_H$ (400 MHz, $CDCl_3$) 6.73 (dd, J 10.7, 5.6 Hz, 1H), 5.94 (s, 2H).

Intermediate 38

3-Fluoro-6-methoxy-4-(tetrahydropyran-4-yl)benzene-1,2-diamine

To a mixture of Intermediate 37 (178 mg, 0.70 mmol), 3,6-dihydro-2H-pyran-4-boronic acid pinacol ester (146 mg, 0.70 mmol) and aqueous $Na_2CO_3$ solution (2M, 1.74 mL) in 1,4-dioxane (3 mL) was added Pd(dppf)$Cl_2$.DCM (73 mg, 0.08 mmol). The reaction mixture was degassed by $N_2$ sparging for 10 minutes, then heated under focused microwave irradiation for 1 h at 100° C. The reaction mixture was cooled and filtered through Celite® (1 g), washing with MeOH (20 mL), then concentrated in vacuo. The residue was partitioned between EtOAc and water. The organic phase was separated, dried over $Na_2SO_4$ and concentrated in vacuo. The residue was purified by flash chromatography, eluting with EtOAc/hexanes (10-80% gradient). The resulting yellow solid was taken up in MeOH (5 mL) and stirred at 70° C. under focused microwave irradiation for 1 h. The cooled reaction mixture was concentrated in vacuo and purified by flash chromatography, eluting with EtOAc:hexanes (10-100% gradient). The resulting orange solid was taken up in EtOH (20 mL), and 10% Pd/C (8 mg) was added. The reaction mixture was stirred under an atmosphere of hydrogen overnight, then filtered through Celite® (1 g), washing the plug with EtOH. The residue was concentrated in vacuo to give the title compound (63 mg, 34% overall) as a tan glass. $\delta_H$ (400 MHz, $CD_3OD$) 6.23 (d, J 6.3 Hz, 1H), 4.10-4.01 (m, 2H), 3.82 (s, 3H), 3.62-3.49 (m, 2H), 3.08-2.93 (m, 1H), 1.90-1.64 (m, 4H). LCMS (Method 5): [M+H]+ m/z 241, RT 0.92 minutes.

Intermediate 39 (Procedure J)

3-Fluoro-5-(morpholin-4-yl)benzene-1,2-diamine

A solution of Intermediate 28 (300 mg, 0.69 mmol), morpholine (90 µL, 1.03 mmol) and $Cs_2CO_3$ (450 mg, 1.38 mmol) in toluene (12 mL) was degassed with $N_2$ for 10 minutes, then Xantphos (80 mg, 0.14 mmol) and $Pd_2(dba)_3$ (65 mg, 0.07 mmol) were added. The reaction mixture was heated at 100° C. for 1 h, then cooled and concentrated in vacuo. The crude material was purified by flash chromatography, eluting with EtOAc/hexanes (0-100% gradient). The recovered material was dissolved in DCM (5 mL), and TFA (500 µL) was added. After 1 h, the reaction mixture was run down an SCX column, eluting with a 7N solution of $NH_3$ in MeOH (10 mL). The residue was concentrated in vacuo. The resulting red solid was taken up in EtOH (2 mL), and 10% Pd/C (2 mg) was added. The reaction mixture was stirred under an atmosphere of hydrogen for 1 h, then filtered through Celite® (1 g), washing the plug with EtOH. The residue was concentrated in vacuo to give the title compound (53 mg, 34% overall). LCMS (Method 5): [M+H]+ m/z 212, RT 0.53 minutes.

Intermediate 40 (Procedure K)

2-(3,4-Diamino-2-fluorophenyl)-2-(pyridin-3-yl)acetonitrile

To a solution of pyridin-3-ylacetonitrile (0.32 mL, 3.0 mmol) in THF (10 mL) under $N_2$ at 0° C. was added potassium tert-butoxide (348 mg, 3.04 mmol) portionwise. The reaction mixture was stirred for 30 minutes, then a solution of 2,3 difluoro-6-nitro-aniline (500 mg, 2.82 mmol) in THF (3 mL) was added. The solution was stirred for a further 30 minutes. The reaction mixture was quenched with 2M aqueous HCl (1.5 mL) and stirred for 1 h, then concentrated in vacuo. The crude residue was purified by flash chromatography, eluting with EtOAc/hexanes (0-100% gradient). The resulting material was taken up in EtOH (5 mL), and 10% Pd/C (22 mg) was added. The reaction mixture was stirred under an atmosphere of hydrogen overnight, then filtered through Celite® (1 g), washing the plug with EtOAc. The residue was concentrated in vacuo to give the title compound (325 mg, 40% overall) as a brown oil. LCMS (Method 5): [M+H]$^+$ m/z 243, RT 0.78 minutes.

Intermediate 41 tert-Butyl N-tert-butoxycarbonyl-N-(2,3-difluoro-6-nitrophenyl)carbamate

The title compound (6.5 g, quantitative) was prepared from 2,3-difluoro-6-nitro-aniline (3 g, 17.23 mmol) in accordance with Procedure D. LCMS (Method 5): [M+H]$^+$ m/z 375, RT 1.08 minutes.

Intermediate 42

3-Fluoro-4-[1-(pyridin-4-yl)ethyl]benzene-1,2-diamine

To a solution of ethyl pyridin-4-ylacetate (191 mg, 0.79 mmol) in dry THF (20 mL) at 0° C. was added NaH (60% mass, 38 mg, 0.95 mmol) and the mixture was stirred for 20 minutes. A solution of Intermediate 41 (300 mg, 0.79 mmol) in THF (5 mL) was added dropwise over 5 minutes. The reaction mixture was stirred for 1 h, then quenched with saturated aqueous NH$_4$Cl solution. The mixture was extracted with EtOAc, then dried over Na$_2$SO$_4$ and concentrated in vacuo. The residue was purified by flash chromatography, eluting with EtOAc/hexanes (30-100% gradient). The resulting solid was taken up in THF (4 mL) and treated with LiOH.H$_2$O (43 mg, 1.02 mmol) in water (1 mL). The reaction mixture was stirred overnight, then neutralised with 2N aqueous HCl and concentrated in vacuo. The residue was purified by flash chromatography, eluting with EtOAc/hexanes (30-100% gradient). The resultant solid was stirred for 90 minutes in TFA (0.5 mL) and DCM (5 mL), then concentrated in vacuo. The residue was taken up in EtOH (5 mL), and 10% Pd/C (10 mg) was added. The reaction mixture was stirred under an atmosphere of hydrogen overnight, then filtered through Celite® (1 g), washing the plug with EtOAc. The residue was concentrated in vacuo to give the title compound (70 mg, 38% overall) as a brown oil. LCMS (Method 5): [M+H]$^+$ m/z 232, RT 0.92 minutes.

Intermediate 43 (Procedure L)

3-Fluoro-4-{[1-(methylsulfonyl)piperidin-4-yl]oxy}benzene-1,2-diamine

NaH (180 mg, 3.99 mmol) was added portionwise to a solution of 1-(methyl-sulfonyl)piperidin-4-ol (425 mg, 2.25 mmol) in dry THF (10 mL). After 20 minutes, 2,3 difluoro-6-nitroaniline (200 mg, 1.13 mmol) was added portionwise. The reaction mixture was stirred at 70° C. overnight, then quenched with saturated aqueous NH$_4$Cl solution (1 mL) and concentrated in vacuo. The crude residue was purified by flash chromatography, eluting with EtOAc/hexanes (0-100% gradient). The resulting material was taken up in EtOH (10 mL), and 10% Pd/C (35 mg) was added. The reaction mixture was stirred under an atmosphere of hydrogen overnight, then filtered through Celite® (1 g), washing the plug with EtOAc. The residue was concentrated in vacuo to give the title compound (150 mg, 43% overall) as a brown solid. LCMS (Method 5): [M+H]$^+$ m/z 304, RT 0.79 minutes.

Intermediate 44 (Procedure M)

3-Fluoro-4-(morpholin-4-yl)benzene-1,2-diamine

To a solution of 2,3 difluoro-6-nitroaniline (300 mg, 1.69 mmol) in NMP (1 mL) at r.t. was added morpholine (150 μL, 1.69 mmol), followed by triethylamine (710 μL, 5.1 mmol). The reaction mixture was heated under focused microwave irradiation for 1 h at 90° C., then cooled to r.t., poured onto water (80 mL) and stood at r.t. for 1 h. The mixture was cooled to 0° C. in an ice bath, then filtered and dried for 4 h on a sintered funnel under suction. The resulting yellow solid was taken up in EtOH (10 mL), and 10% Pd/C (35 mg) was added. The reaction mixture was stirred under an atmosphere of hydrogen overnight, then filtered through Celite® (1 g). The residue was concentrated in vacuo to give the title compound as a brown solid (301 mg, 92% overall). LCMS (Method 5): [M+H]$^+$ m/z 225, RT 0.36 minutes.

Intermediate 45 (Procedure N)

tert-Butyl 6-(3,4-diamino-2-fluorophenyl)-3,4-dihydro-2H-pyridine-1-carboxylate

To a solution of tert-butyl 2-oxopiperidine-1-carboxylate (1 g, 5.02 mmol) in THF (10 mL), cooled to −30° C., was added lithium bis(trimethylsilyl)amide (1M in THF, 5.52 mL) dropwise over 15 minutes. The reaction mixture was stirred for 1 h at −30° C., then diphenyl chlorophosphate (1.1 mL, 5.3 mmol) was added dropwise over 5 minutes. The reaction mixture was allowed to warm to r.t. and stirred for 48 h. The mixture was poured onto saturated aqueous NH$_4$Cl solution (10 mL) and extracted with EtOAc. The organic layers were washed with saturated aqueous NaHCO$_3$ solution and brine, then dried over Na$_2$SO$_4$. The residue was concentrated in vacuo. The resulting oil was purified by flash chromatography, eluting with EtOAc/hexanes (0-30% gradient), to furnish tert-butyl 6-diphenoxyphosphoryloxy-3,4-dihydro-2H-pyridine-1-carboxylate (1.92 g, 89%) as a colourless oil.

Intermediate 25 (200 mg, 0.79 mmol), tert-butyl 6-diphenoxyphosphoryloxy-3,4-dihydro-2H-pyridine-1-carboxylate (342 mg, 0.79 mmol), Pd(dppf)Cl$_2$.DCM (65 mg, 0.08 mmol), aqueous Na$_2$CO$_3$ solution (2M, 2.4 mL) and 1,4-dioxane (3.2 mL) were added to a microwave vial, sparged with N$_2$ for 10 minutes, then heated under microwave irradiation for 1 h at 100° C. The reaction mixture was filtered through Celite® (1 g), eluting with MeOH (20 mL). The washings were concentrated in vacuo, and the residue was partitioned between EtOAc and water. The organic layers were washed with brine and dried over MgSO$_4$, then concentrated in vacuo. The residue was purified using flash chromatography, eluting with EtOAc/hexanes (0-100% gradient), to furnish the title compound (143 mg, 59%) as a tan-coloured solid. δ$_H$ (400 MHz, CDCl$_3$) 6.58 (t, J 8.1 Hz, 1H), 6.43 (dd, J 8.2, 1.3 Hz, 1H), 5.20 (td, J 3.8, 0.9 Hz, 1H), 3.88-3.55 (m, 2H), 3.63-3.08 (br s, 4H, 2×NH$_2$), 2.25 (td, J 6.9, 3.8 Hz, 2H), 1.98-1.75 (m, 2H), 1.13 (s, 9H). LCMS (Method 5): [M+H]$^+$ m/z 308, RT 1.17 minutes.

Intermediate 46 (Procedure O)

tert-Butyl 2-(3,4-diamino-2-fluorophenyl)piperidine-1-carboxylate

To a solution of Intermediate 45 (60 mg, 0.19 mmol) in EtOH (6 mL) at r.t. was added 10% Pd/C (6 mg). The reaction mixture was stirred under an atmosphere of hydrogen overnight, then filtered through Celite® (1 g), washing with EtOAc. The residue was concentrated in vacuo to give the title compound (50 mg, 83%) as a brown solid. δ$_H$ (400 MHz, CDCl$_3$) 6.48 (td, J 8.1, 0.8 Hz, 1H), 6.43 (dd, J 8.3, 1.0 Hz, 1H), 5.41 (dd, J 6.0, 3.1 Hz, 1H), 4.11-3.99 (m, 1H, proton alpha to nitrogen), 3.55-3.23 (very br s, 4H, 2×NH$_2$), 3.04 (ddd, J 13.4, 11.9, 3.8 Hz, 1H, proton alpha to nitrogen), 2.16-2.04 (m, 1H), 1.97-1.77 (m, 1H), 1.71-1.41 (m, 4H), 1.38 (s, 9H). LCMS (Method 5): [M+H]$^+$ m/z 310, RT 1.23 minutes.

Intermediate 47 tert-Butyl 4-(3-amino-2-fluoro-4-nitroanilino)piperidine-1-carboxylate

To a solution of 2,3-difluoro-6-nitroaniline (350 mg, 1.97 mmol) in NMP (3 mL) were added tert-butyl 4-aminopiperidine-1-carboxylate (415 mg, 1.97 mmol) and triethylamine (0.82 mL, 5.9 mmol). The reaction mixture was heated under focused microwave irradiation for 1 h at 90° C. Further aliquots of tert-butyl 4-aminopiperidine-1-carboxylate (2×450 mg) were added and, after each addition, the mixture was heated for a further 1 h at 90° C. The reaction mixture was cooled, then partitioned between EtOAc and water. The organic layers were dried over Na$_2$SO$_4$ and concentrated in vacuo. The crude material was purified by flash chromatography, eluting with EtOAc/hexanes (0-100% gradient), to give the title compound (686 mg, 98%) as a solid. LCMS (Method 5): [M+H]$^+$ m/z 355, RT 1.37 minutes.

Intermediate 48 (Procedure P)

2-Fluoro-4-nitro-N$i$-(piperidin-4-yl)benzene-1,3-diamine

To a solution of Intermediate 47 (686 mg, 1.94 mmol) in DCM (10 mL) was added TFA (1 mL). The reaction mixture was stirred for 4 h at r.t., then concentrated in vacuo. The residue was taken up in MeOH, and loaded onto an SCX column, eluting with a 7N solution of NH$_3$ in MeOH. The washings were concentrated in vacuo to give the title compound (493 mg, 99%). LCMS (Method 5): [M+H]$^+$ m/z 255, RT 0.37 minutes.

Intermediate 49 (Procedure Q)

3-Fluoro-N$^4$-[1-(methylsulfonyl)piperidin-4-yl]benzene-1,2,4-triamine

Intermediate 48 (488 mg, 1.9 mmol) was taken up in DCM (5 mL). Triethylamine (268 µL, 1.92 mmol) and methanesulfonyl chloride (149 µL, 1.93 mmol) were added. The solution was stirred at r.t. overnight, then concentrated in vacuo and purified by flash column chromatography, eluting with EtOAc/hexanes (0-100% gradient). The residue was taken up in EtOH (10 mL), and 10% Pd/C (20 mg) was added. The reaction mixture was stirred under an atmosphere of hydrogen for 5 h, then filtered through Celite® (1 g), washing the plug with EtOAc. The residue was concentrated in vacuo to give the title compound (360 mg, 62% overall) as a brown solid. LCMS (Method 5): [M+H]$^+$ m/z 303, RT 0.59 minutes.

Intermediate 50 (Procedure R)

tert-Butyl 4-[(3,4-diamino-2-fluorophenyl)methyl]piperazine-1-carboxylate

A solution of 4-bromo-3-fluorobenzene-1,2-diamine (1.91 g, 8.84 mmol), potassium (4-tert-butoxycarbonylpiperazin-1-yl)methyltrifluoroborate (4.06 g, 13.3 mmol) and Cs$_2$CO$_3$ (8.64 g, 26.5 mmol) in THF (48 mL) and water (12 mL) was degassed with N$_2$ for 10 minutes, then XPhos (930 mg, 1.77 mmol) and palladium(II) acetate (200 mg, 0.89 mmol) were added. The reaction mixture was heated at 70° C. under N$_2$ overnight. After cooling, the mixture was filtered through Celite®, washing with EtOAc. The filtrate was concentrated in vacuo. The residue was purified by flash chromatography, eluting with EtOAc/hexanes (0-100% gradient), to give the title compound (2.87 g, quantitative) as a brown solid. LCMS (Method 5): [M+H]$^+$ m/z 325, RT 1.07 minutes.

Intermediate 51 tert-Butyl 4-[(3-amino-2,5-difluoro-4-nitrophenyl)methyl]piperazine-1-carboxylate The title compound (1.11 g, quantitative) was prepared from 3-bromo-2,5-difluoro-6-nitroaniline (750 mg, 2.96 mmol) in accordance with Procedure R. LCMS (Method 5): [M+H]$^+$ m/z 373, RT 1.41 minutes.

Intermediate 52

2,5-Difluoro-6-nitro-3-(piperazin-1-ylmethyl)aniline

The title compound (1.1 g, quantitative) was prepared from Intermediate 51 (1.8 g, 4.04 mmol) in accordance with Procedure P. LCMS (Method 5): [M+H]$^+$ m/z 273, RT 0.64 minutes.

Intermediate 53

3,6-Difluoro-4-{[4-(methylsulfonyl)piperazin-1-yl]methyl}benzene-1,2-diamine

The title compound (366 mg, 30%) was prepared from Intermediate 52 (1.03 g, 3.8 mmol) in accordance with Procedure Q. LCMS (Method 5): [M+H]$^+$ m/z 321, RT 0.85 minutes.

Intermediate 54 tert-Butyl 4-({4-[bis(tert-butoxycarbonyl)amino]-3-fluoro-5-nitrophenyl}methyl)-piperazine-1-carboxylate The title compound (316 mg, quantitative) was prepared from Intermediate 28 (248 mg, 0.57 mmol) in accordance with Procedure R. LCMS (Method 5): [M+H]$^+$ m/z 556, RT 1.73 minutes.

Intermediate 55

2-Fluoro-6-nitro-4-(piperazin-1-ylmethyl)aniline

The title compound (130 mg, 89%) was prepared from Intermediate 54 (316 mg, 0.57 mmol) in accordance with Procedure P. LCMS (Method 5): [M+H]$^+$ m/z 255, RT 0.68 minutes.

Intermediate 56

3-Fluoro-5-{[4-(methylsulfonyl)piperazin-1-yl]methyl}benzene-1,2-diamine

The title compound (61 mg, 39%) was prepared from Intermediate 55 (130 mg, 0.51 mmol) in accordance with Procedure Q. LCMS (Method 5): [M+H]$^+$ m/z 303, RT 0.81 minutes.

Intermediate 57

1-{4-[(3,4-diamino-5-fluorophenyl)methyl]piperazin-1-yl}ethanone

To a solution of Intermediate 55 (70 mg, 0.28 mmol) in DCM (1 mL) were added triethylamine (40 µL, 0.29 mmol) and acetic anhydride (26 µL, 0.28 mmol). The reaction mixture was stirred at r.t. for 90 minutes, then partitioned between DCM and water. The organic layers were dried over Na$_2$SO$_4$ and concentrated in vacuo. The residue was taken up in THF (1 mL), then acetonitrile (1 mL), NH$_4$Cl (33 mg, 0.62 mmol) and zinc dust (40 mg, 0.62 mmol) were added. The reaction mixture was stirred for 3 days, then two further aliquots of zinc (40 mg) and NH$_4$Cl (33 mg) were added. Stirring was continued for a further 2 days, then the mixture was filtered through Celite®, washing with EtOAc. The residue was concentrated in vacuo to give the title compound (49 mg, 66% overall) as an oil. LCMS (Method 5): [M+H]$^+$ m/z 267, RT 0.71 minutes.

Intermediate 58 (Procedure S)

tert-Butyl 4-[(3,4-diamino-2-fluorophenyl)methyl]piperidine-1-carboxylate

A mixture of tert-butyl-4-methylenepiperidine-1-carboxylate (157 mg, 0.79 mmol) and 9-BBN (1.6 mL, 0.80 mmol) was heated at 70° C. for 2 h. After cooling, 4-bromo-3-fluorobenzene-1,2-diamine (150 mg, 0.73 mmol), K$_2$CO$_3$ (133 mg, 0.95 mmol), DMF (1.46 mL), water (0.15 mL) and Pd(dppf)Cl$_2$.DCM (18 mg, 0.02 mmol) were added. The mixture was heated at 60° C. for 3 h, then cooled and partitioned between EtOAc and water. The organic layers were washed with brine and dried over MgSO$_4$, then concentrated in vacuo. The residue was purified by flash chromatography, eluting with EtOAc/hexanes (0-100% gradient), to yield the title compound (70 mg, 30%) as a yellow oil. LCMS (Method 5): [M+H-BOC]$^+$ m/z 224, RT 1.33 minutes.

Intermediate 59

3-Fluoro-4-(piperazin-1-ylmethyl)benzene-1,2-diamine

The title compound (2.10 g, quantitative) was prepared from Intermediate 50 (2.88 g, 8.88 mmol) in accordance with Procedure P. LCMS (Method 5): [M+H]$^+$ m/z 255, RT 0.68 minutes.

Intermediate 60

1-{4-[(3,4-diamino-2-fluorophenyl)methyl]piperazin-1-yl}ethanone

To a solution of Intermediate 59 (2.14 g, 9.56 mmol) in DCM (25 mL) at 0° C. was added triethylamine (1.3 mL, 9.3 mmol), followed by acetic anhydride (0.9 mL, 10 mmol). The reaction mixture was warmed to r.t. and stirred for 4 h, then partitioned between EtOAc and water. The organic layers were dried over Na$_2$SO$_4$ and concentrated in vacuo. The residue was purified by flash chromatography, eluting with MeOH/EtOAc (0-20% gradient), to give the title compound (501 mg, 20%). LCMS (Method 5): [M+H]$^+$ m/z 267, RT 0.63 minutes.

Intermediate 61 (Procedure T)

Ethyl 5-(3,4-diamino-2-fluorophenyl)-3,6-dihydro-2H-pyran-4-carboxylate

To a solution of ethyl 3-oxotetrahydro-2H-pyran-4-carboxylate (1.01 g, 5.58 mmol,) dissolved in DCM (28 mL) and cooled under N$_2$ to −78° C., was added DIPEA (1.2 mL, 6.9 mmol). The reaction mixture was stirred under N$_2$, then a 1M solution of trifluoromethanesulfonic anhydride in DCM (6.07 mL, 6.07 mmol) was added. The reaction mixture was stirred at −78° C. for 30 minutes, then warmed to r.t. and stirred for 4 h. Saturated aqueous NaHCO$_3$ solution (30 mL) was added. The mixture was stirred rapidly at room temperature for 5 minutes, then filtered. The organic layer was concentrated in vacuo to afford ethyl 5-(trifluoromethylsulfonyloxy)-3,6-dihydro-2H-pyran-4-carboxylate (1.7 g, quantitative) as a brown oil.

To a solution of ethyl 5-(trifluoromethylsulfonyloxy)-3,6-dihydro-2H-pyran-4-carboxylate (1.7 g, 5.58 mmol) in 1,4-dioxane (20 mL) were added Intermediate 25 (1.12 g, 4.41 mmol), K$_2$CO$_3$ (2.32 g, 16.81 mmol) and water (6 mL), and the mixture was sparged with N$_2$. Pd(dppf)Cl$_2$.DCM (440 mg, 0.57 mmol) was added, and the mixture was further sparged with N$_2$, then heated at 100° C. overnight. The mixture was cooled and concentrated in vacuo, then the residue was partitioned between DCM and water. The organic layers were separated and concentrated in vacuo. The crude residue was purified by flash chromatography, eluting with EtOAc/hexanes (0-100% gradient), yielding the title compound (541 mg, 35%) as an orange solid. LCMS (Method 5): [M+H]$^+$ m/z 281, RT 1.20 minutes.

Intermediate 62 (Procedure U)

Ethyl 3-(3,4-diamino-2-fluorophenyl)tetrahydropyran-4-carboxylate

To a solution of Intermediate 61 (156 mg, 0.56 mmol) in EtOH (8 mL) was added 10% Pd/C (130 mg). The reaction mixture was stirred under an atmosphere of hydrogen for three days, then filtered through Celite® (1 g), washing with DCM. The residue was concentrated in vacuo to give the title compound (1:1 mixture of cis isomers) (156 mg, quantitative) as a brown solid. LCMS (Method 5): [M+H]$^+$ m/z 283, RT 0.89 minutes.

Intermediate 63 tert-Butyl 2-[3-(dibenzylamino)-2-fluoro-4-nitrophenyl]acetate

A mixture of Intermediate 27 (916 mg, 2.21 mmol), XPhos (325 mg, 0.66 mmol) and Pd$_2$(dba)$_3$ (312 mg, 0.33 mmol) in anhydrous THF was degassed under a $N_2$ sparge for 10 minutes at r.t., then 2-tert-butoxy-2-oxoethylzinc chloride (10 mL, 5 mmol) was added. The reaction mixture was stirred at r.t. for 10 minutes under $N_2$, then at 70° C. for 3 h, then cooled to r.t. and concentrated in vacuo. The residue was dissolved in EtOAc (50 mL) and washed with saturated aqueous $NH_4Cl$ solution (20 mL), then dried over $MgSO_4$ and concentrated in vacuo. The residue was purified by flash chromatography, eluting with EtOAc/hexanes (0-20% gradient), then preparative HPLC, to give the title compound (517 mg, 52%) as an off-white solid. LCMS (Method 5): $[M+H]^+$ m/z 451, RT 1.84 minutes.

Intermediate 64

2-(3,4-Diamino-2-fluorophenyl)-N,N-dimethylacetamide

To a solution of Intermediate 63 (248 mg, 0.55 mmol) in DCM (2 mL) was added TFA (0.35 mL). The mixture was stirred at r.t. overnight, then concentrated in vacuo. The residue was taken up in DCM (3 mL), then HATU (260 mg, 0.66 mmol), DIPEA (0.55 mL, 1.1 mmol) and a 2M solution of dimethylamine in THF (0.55 mL, 1.1 mmol) were added. After 2 h, the mixture was partitioned between DCM and water. The organic layers were dried over $Na_2SO_4$ and concentrated in vacuo. The residue was dissolved in EtOH (10 mL), to which was added 10% Pd/C (20 mg), then stirred under an atmosphere of hydrogen for 2 h. The reaction mixture was filtered through Celite® (1 g), washing with EtOAc. The residue was concentrated in vacuo to give the title compound (63 mg, 56% overall). LCMS (Method 5): $[M+H]^+$ m/z 212, RT 0.35 minutes.

Intermediate 65

6-Bromo-2-methoxypyridine-3,4-diamine

A suspension of 6-bromo-2-chloropyridine-3,4-diamine (1 g, 4.49 mmol) and sodium methoxide (4.86 g, 90.0 mmol) in MeOH (38 mL) was stirred at 140° C. in an autoclave. After 55 h, the reaction mixture was partitioned between EtOAc and water. The organic layers were washed with brine, dried over $Na_2SO_4$ and concentrated in vacuo. The residue was purified by flash column chromatography, eluting with MeOH/DCM (0-10% gradient), to give the title compound (357 mg, 36% yield). LCMS (Method 5): $[M+H]^+$ m/z 220, RT 0.77 minutes.

Intermediate 66 tert-Butyl 4-[(3-amino-4-nitrophenyl)methyl]piperazine-1-carboxylate

The title compound (779 mg, quantitative) was prepared from 5-bromo-2-nitro-aniline (500 mg, 2.30 mmol) in accordance with Procedure R. LCMS (Method 5): $[M+H]^+$ m/z 337, RT 1.31 minutes.

Intermediate 67 tert-Butyl 4-[(3,4-diaminophenyl)methyl]piperazine-1-carboxylate

To a solution of Intermediate 66 (779 mg, 2.32 mmol) in EtOH (10 mL) at r.t. was added 10% Pd/C (10 mg). The reaction mixture was stirred under a hydrogen atmosphere overnight, then filtered through Celite®, washing with EtOAc. The filtrate was concentrated in vacuo. Purification by flash chromatography, eluting with MeOH/EtOAc (0-20% gradient) gave the title compound (248 mg, 35%). LCMS (Method 5): $[M+H]^+$ m/z 307, RT 1.03 minutes.

Intermediate 68 tert-Butyl 4-[(3-fluoro-5-methoxy-4-nitrophenyl)methyl]piperazine-1-carboxylate

The title compound (594 mg, 64%) was prepared from 5-bromo-1-fluoro-3-methoxy-2-nitrobenzene (663 mg, 2.52 mmol) in accordance with Procedure R. LCMS (Method 5): $[M+H]^+$ m/z 370, RT 1.51 minutes.

Intermediate 69 tert-Butyl 4-[(3,4-diamino-5-methoxyphenyl)methyl]piperazine-1-carboxylate

To a solution of Intermediate 68 (594 mg, 1.61 mmol) in DMSO (2 mL) was added sodium azide (115 mg, 1.77 mmol). The reaction mixture was heated at 50° C. for 6 h, then further sodium azide (115 mg, 1.77 mmol) was added and the mixture was stirred overnight. A final aliquot of sodium azide (115 mg, 1.77 mmol) was added. The mixture was left for 3 h, then cooled, and partitioned between EtOAc and water. The organic layers were washed with brine and dried over $Na_2SO_4$, then concentrated in vacuo. The crude residue was taken up in EtOH (20 mL), and 10% Pd/C (50 mg) was added. The reaction mixture was stirred at r.t. under an atmosphere of hydrogen overnight, then filtered through Celite®, washing with EtOAc. The filtrate was concentrated in vacuo. The residue was purified by flash chromatography, eluting with EtOAc/hexanes (50-100% gradient), to give the title compound (117 mg, 22% overall). $\delta_H$ (400 MHz, DMSO-$d_6$) 6.19 (d, J 1.7 Hz, 1H), 6.14 (d, J 1.7 Hz, 1H), 4.46 (s, 2H), 3.91 (s, 2H), 3.70 (s, 3H), 3.29 (d, J 4.9 Hz, 4H), 3.23 (s, 2H), 2.25 (t, J 5.0 Hz, 4H), 1.38 (s, 9H).

Intermediates 70 to 99

The following diamines were prepared from the indicated starting materials in accordance with the indicated Procedures:

| Int. | Name | Starting Material(s) | Proc | LCMS (Method 5) | |
|---|---|---|---|---|---|
| | | | | $[M + H]^+$ | RT (min) |
| 70 | tert-Butyl 3-(3,4-diamino-5-fluoro-phenyl)propanoate | 5-Bromo-3-fluorobenzene-1,2-diamine | E | 255.0 | 1.12 |

-continued

| Int. | Name | Starting Material(s) | Proc | LCMS (Method 5) [M + H]+ | RT (min) |
|---|---|---|---|---|---|
| 71 | 3,5-Difluoro-4-(tetrahydropyran-4-yl)benzene-1,2-diamine | 3-Chloro-2,4-difluoro-6-nitro-aniline and 2-(3,6-dihydro-2H-pyran-4-yl)-4,4,5,5-tetramethyl-1,3,2-dioxaborolane | I | 229.0 | 0.91 |
| 72 | 3,6-Difluoro-4-(tetrahydropyran-4-yl)benzene-1,2-diamine | Intermediate 37 and 2-(3,6-dihydro-2H-pyran-4-yl)-4,4,5,5-tetramethyl-1,3,2-dioxaborolane | I | 229.0 | 0.92 |
| 73 | 3-Fluoro-4-(tetrahydropyran-3-yl)-benzene-1,2-diamine | 4-Bromo-3-fluorobenzene-1,2-diamine and 2-(3,4-dihydro-2H-pyran-5-yl)-4,4,5,5-tetramethyl-1,3,2-dioxaborolane | I | 211.2 | 0.63 |
| 74 | tert-Butyl 4-(3,4-diamino-2-fluoro-phenyl)piperidine-1-carboxylate | 4-Bromo-3-fluorobenzene-1,2-diamine and tert-butyl 4-(4,4,5,5-tetramethyl-1,3,2-dioxaborolan-2-yl)-3,6-dihydro-2H-pyridine-1-carboxylate | I | 254.0 | 1.26 |
| 75 | Ethyl 2-(3,4-diamino-2-fluoro-phenyl)-2-(pyridin-3-yl)acetate | Ethyl pyridin-3-ylacetate and 2,3-difluoro-6-nitroaniline | K | 290.0 | 0.92 |
| 76 | Ethyl 2-(3,4-diamino-2-fluoro-phenyl)-2-(pyridin-4-yl)acetate | Ethyl pyridin-4-ylacetate and 2,3-difluoro-6-nitroaniline | K | 290.0 | 0.68 |
| 77 | 2-(3,4-Diamino-2-fluorophenyl)-2-(pyridin-4-yl)acetonitrile | Pyridin-4-ylacetonitrile and 2,3-difluoro-6-nitroaniline | K | 243.0 | 0.92 |
| 78 | Ethyl 2-(3,4-diamino-2-fluoro-phenyl)-2-phenylacetate | Ethyl 2-phenylacetate and 2,3-difluoro-6-nitroaniline | K | 289.0 | 1.20 |
| 79 | 3-Fluoro-6-methoxybenzene-1,2-diamine | 4-Fluoro-2,3-dinitrophenol and methyl iodide | H | 157.0 | 0.68 |
| 80 | 5-Fluoro-3-[(tetrahydropyran-4-yl)-oxy]benzene-1,2-diamine | 3,5-Difluoro-2-nitroaniline and 4-hydroxytetrahydropyran | L | 227.0 | 0.87 |
| 81 | 3-Fluoro-4-[(pyridazin-4-yl)oxy]-benzene-1,2-diamine | 4-Hydroxypyridazine and 2,3-difluoro-6-nitroaniline | L | 221.0 | 0.21 |
| 82 | 3-Fluoro-4-[(pyridin-4-yl)oxy]-benzene-1,2-diamine | 4-Hydroxypyridine and 2,3-difluoro-6-nitroaniline | L | 220.0 | 0.17 |
| 83 | 3-Fluoro-4-[(tetrahydropyran-4-yl)-oxy]benzene-1,2-diamine | 4-Hydroxytetrahydropyran and 2,3-difluoro-6-nitroaniline | L | 227.0 | 0.70 |
| 84 | 3-Fluoro-4-[(oxetan-3-yl)oxy]-benzene-1,2-diamine | 3-Hydroxyoxetane and 2,3-difluoro-6-nitroaniline | L | 199.0 | 0.35 |
| 85 | Methyl (2S)-1-(3,4-diamino-2-fluorophenyl)pyrrolidine-2-carboxylate | Methyl (2S)-pyrrolidine-2-carboxylate and 2,3-difluoro-6-nitroaniline | M | 254.0 | 0.85 |
| 86 | Methyl (2R)-1-(3,4-diamino-2-fluorophenyl)pyrrolidine-2-carboxylate | Methyl (2R)-pyrrolidine-2-carboxylate and 2,3-difluoro-6-nitroaniline | M | 254.0 | 0.85 |
| 87 | Methyl 1-(3,4-diamino-2-fluoro-phenyl)piperidine-2-carboxylate | Methyl piperidine-2-carboxylate and 2,3-difluoro-6-nitroaniline | M | 268.0 | 0.93 |
| 88 | (2S)-1-(3,4-Diamino-2-fluoro-phenyl)-N,N-dimethylpiperidine-2-carboxamide | (2S)-N,N-Dimethylpiperidine-2-carboxamide and 2,3-difluoro-6-nitroaniline | M | 281.0 | 0.91 |
| 89 | 3-Fluoro-N4-(tetrahydropyran-4-yl)-benzene-1,2,4-triamine | 4-Aminotetrahydropyran and 2,3-difluoro-6-nitroaniline | M | 226.0 | 0.45 |
| 90 | tert-Butyl 5-(3,4-diamino-2-fluoro-phenyl)-2,3-dihydropyrrole-1-carboxylate | tert-Butyl 2-oxopyrrolidine-1-carboxylate and Intermediate 25 | N | 238 (-tBu) | 1.12 |
| 91 | tert-Butyl 2-(3,4-diamino-2-fluoro-phenyl)pyrrolidine-1-carboxylate | Intermediate 90 | O | 240 (-tBu) | 1.12 |
| 92 | tert-Butyl 5-(3,4-diamino-2-fluoro-phenyl)-2,3-dihydro-1,4-oxazine-4-carboxylate | tert-Butyl 3-oxomorpholine-4-carboxylate and Intermediate 25 | N | 254 (-tBu) | 1.05 |
| 93 | tert-Butyl 3-(3,4-diamino-2-fluoro-phenyl)-6,7-dihydro-5H-1,4-oxazepine-4-carboxylate | tert-Butyl 3-oxo-1,4-oxazepane-4-carboxylate and Intermediate 25 | N | 268 (-tBu) | 1.10 |
| 94 | tert-Butyl 4-[(3,4-diamino-5-fluoro-phenyl)methyl]piperidine-1-carboxylate | 5-Bromo-3-fluorobenzene-1,2-diamine and tert-butyl-4-methylenepiperidine-1-carboxylate | S | 224.2 (-BOC) | 1.33 |
| 95 | Methyl 4-(3,4-diamino-2-fluoro-phenyl)-2,5-dihydrofuran-3-carboxylate | Methyl 4-oxotetrahydrofuran-3-carboxylate and Intermediate 25 | T | 253.0 | 0.80 |
| 96 | Methyl 4-(3,4-diamino-2-fluoro-phenyl)tetrahydrofuran-3-carboxylate | Intermediate 95 | U | 255.2 | 0.63 |
| 97 | O1-tert-Butyl O3-ethyl 4-(3,4-diamino-2-fluorophenyl)-2,5-dihydropyrrole-1,3-dicarboxylate | O1-tert-Butyl O3-ethyl 4-oxo-pyrrolidine-1,3-dicarboxylate and Intermediate 25 | T | 266.2 (-BOC) | 1.20 |

| Int. | Name | Starting Material(s) | Proc | [M + H]+ | RT (min) |
|---|---|---|---|---|---|
| | | | | LCMS (Method 5) | |
| 98 | O¹-tert-butyl O³-ethyl 4-(3,4-diamino-2-fluorophenyl)-pyrrolidine-1,3-dicarboxylate | Intermediate 97 | U | 268.2 (-BOC) | 1.14 |
| 99 | 2-(3,4-Diamino-2,6-difluoro-phenyl)-N,N-dimethylbenzamide | 3-Chloro-2,4-difluoro-6-nitro-aniline and N,N-dimethyl-2-(4,4,5,5-tetramethyl-1,3,2-dioxa-borolan-2-yl)benzamide | I | 292.2 | 0.89 |

Intermediate 100 tert-Butyl 3-(3,4-diamino-2-fluorophenyl)morpholine-4-carboxylate

To a solution of Intermediate 92 (1.78 g, 5.75 mmol) in methanol (20 mL) was added Pd/C (metal loading 20%; 480 mg, 0.9 mmol). The mixture was placed in a stainless steel reactor and hydrogenated at 70° C. at 10 bar for 140 h. The mixture was cooled down to r.t., then passed through a pad of Celite®, washing thoroughly with MeOH. The filtrate was concentrated in vacuo and purified by flash chromatography, eluting with EtOAc/heptane (30-50% gradient), to give the title compound (1.18 g, 60%) as a colourless oil. LCMS (Method 5): [M+H-BOC]+ m/z 212, RT 1.01 minutes.

Intermediate 101 tert-Butyl 3-(3,4-diamino-2-fluorophenyl)-1,4-oxazepane-4-carboxylate

To a solution of Intermediate 93 (130 mg, 0.40 mmol) in MeOH (3 mL) was added 10% Pd/C (4.2 mg, 0.004 mmol). The mixture was placed in a stainless steel reactor and hydrogenated at 60° C. at 20 bar for 16 h. The mixture was cooled down to r.t., then passed through a pad of Celite®, washing thoroughly with DCM. The filtrate was concentrated in vacuo to give the title compound (99 mg, 76%) as a colourless oil. LCMS (Method 5): [M+H-BOC]+ m/z 226, RT 1.01 minutes.

Intermediate 102

Ethyl 4-(3,4-diamino-2-fluorophenyl)pyrrolidine-3-carboxylate

To a solution of Intermediate 98 (241 mg, 0.66 mmol) in MeOH (9 mL) was added 4N HCl in 1,4-dioxane (1.64 mL, 6.56 mmol). The reaction mixture was stirred for 6 h, then concentrated in vacuo. The residue was run down an SCX column, eluting with a 7N solution of NH₃ in MeOH, to give the title compound (1:1 mixture of cis isomers) (157 mg, 90%). LCMS (Method 5): [M+H]+ m/z 268, RT 0.30 minutes.

Intermediate 103

Ethyl 4-(3,4-diamino-2-fluorophenyl)-1-(methylsulfonyl)pyrrolidine-3-carboxylate To a solution of Intermediate 102 (80 mg, 0.29 mmol) in DCM (2 mL) at 0° C. were added triethylamine (42 µL, 0.30 mmol) and methanesulfonyl chloride (23 µL, 0.30 mmol). The reaction mixture was warmed to r.t. and stirred overnight. After standing for 4 days, the mixture was partitioned between DCM and water. The organic layers were separated and dried over Na₂SO₄, then concentrated in vacuo, to give the title compound (1:1 mixture of cis isomers) (100 mg, 97%). LCMS (Method 5): [M+H]+ m/z 346, RT 0.80 minutes.

Intermediate 104

Ethyl 1-acetyl-4-(3,4-diamino-2-fluorophenyl)pyrrolidine-3-carboxylate

To a solution of Intermediate 102 (80 mg, 0.29 mmol) in DCM (2 mL) at 0° C. were added triethylamine (42 µL, 0.30 mmol) and acetic anhydride (28 µL, 0.30 mmol). The reaction mixture was warmed to r.t. and stirred overnight. After standing for 4 days, the mixture was partitioned between DCM and water. The organic layers were separated and dried over Na₂SO₄, then concentrated in vacuo, to yield the title compound (1:1 mixture of cis isomers) (91 mg, 99%). LCMS (Method 5): [M+H]+ m/z 310, RT 0.69

Intermediate 105

Ethyl 2-{3-[bis(tert-butoxycarbonyl)amino]-2-fluoro-4-nitrophenyl}-2-(pyridin-4-yl)-acetate To a suspension of NaH (1.7 g, 43 mmol) in DMF (100 mL) at 0° C. was added ethyl pyridin-4-ylacetate (6.6 mL, 43 mmol) dropwise over 10 minutes. Intermediate 41 (6.28 g, 16.8 mmol) was then added portionwise over 10 minutes. The mixture was allowed to warm to r.t. overnight. Saturated aqueous NH₄Cl solution (10 mL) was added, and the mixture was extracted with EtOAc. The organic layers were washed with brine and dried over MgSO₄, then concentrated in vacuo. The crude residue was purified using flash chromatography, eluting with EtOAc/hexanes (0-100% gradient), to give the title compound (5.97 g, 69%) as a yellow oil. LCMS (Method 5): [M+H]+ m/z 520, RT 1.51 minutes.

Intermediate 106 tert-Butyl N-{2-fluoro-3-[(5-methyl-1,3,4-oxadiazol-2-yl)(pyridin-4-yl)methyl]-6-nitrophenyl}carbamate Intermediate 105 (2.3 g, 4.4 mmol) was dissolved in MeOH (8 mL) and hydrazine monohydrate (25% in water, 2.0 mL, 10 mmol) was added. The mixture was heated at 70° C. for several hours, then concentrated in vacuo. The residue was partitioned between EtOAc and water. The organic layers were again concentrated in vacuo. The isolated material was dissolved in acetonitrile (30 mL) and cooled to 0° C., then acetic anhydride (0.28 mL, 3.0 mmol) was added dropwise. After 2 h, the reaction mixture was concentrated in vacuo. The residue was dissolved in DMF (30 mL) and T3P® (2.1 mL, 3.6 mmol) was added. The reaction mixture was heated at 90° C., then concentrated in vacuo. The crude material was purified by flash chromatography, eluting with EtOAc/hexanes (0-100% gradient), to furnish the title compound (1.0 g, 53% overall) as a yellow oil. LCMS (Method 5): [M+H]$^+$ m/z 430, RT 1.43 minutes.

Intermediate 107

3-Fluoro-4-[(5-methyl-1,3,4-oxadiazol-2-yl)(pyridin-4-yl)methyl]benzene-1,2-diamine To a solution of Intermediate 106 (1.2 g, 2.8 mmol) in EtOH (40 mL) was added 10% Pd/C (150 mg). The mixture was stirred under an atmosphere of hydrogen for three days, then filtered through Celite® (1 g), washing with DCM. The residue was concentrated in vacuo. The crude material was taken up in DCM (10 mL) and TFA (3 mL) was added. The reaction mixture was stirred for 3 h, then concentrated in vacuo. The residue was dissolved in EtOAc, and washed with saturated aqueous NaHCO$_3$ solution. The organic layers were dried over Na$_2$SO$_4$, then concentrated in vacuo, to give the title compound (388 mg, 46% overall) as a brown oil. LCMS (Method 5): [M+H]$^+$ m/z 300, RT 0.88 minutes.

Intermediate 108 tert-Butyl N-(3-fluoro-4-formyl-2-nitrophenyl)carbamate

To a solution of 4-bromo-3-fluoro-2-nitroaniline (100 g, 426 mmol) in DMF (1000 mL) was added NaH (25.5 g, 638 mmol) at 0° C. The reaction mixture was stirred for 30 minutes, then di-tert-butyl dicarbonate (196 mL, 851 mmol) was added at 0° C. The reaction mixture was stirred at room temperature for 12 h, then poured into ice-cold water (2 L) and extracted with EtOAc (2×1 L). The organic layer was separated, dried over anhydrous Na$_2$SO$_4$ and concentrated in vacuo. The crude residue was purified by column chromatography, eluting with EtOAc/hexanes (5-10% gradient). The resulting solid was taken up in 1,4-dioxane (300 mL) and water (90 mL), then 4,4,5,5-tetramethyl-2-vinyl-1,3,2-dioxaborolane (12.7 g, 82.7 mmol) and Na$_2$CO$_3$ (21.9 g, 207 mmol) were added at 0° C. The reaction mixture was purged with nitrogen for 30 minutes. Pd(PPh$_3$)$_4$ (7.97 g, 6.89 mmol) was added, and the reaction mixture was again purged with N$_2$ for 30 minutes. The reaction mixture was heated at 100° C. for 16 h, then diluted with water (400 mL) and extracted with EtOAc (3×400 mL). The organic layer was separated, dried over anhydrous Na$_2$SO$_4$ and concentrated in vacuo. The crude residue was purified by column chromatography (silica, 100-200 mesh, 8% EtOAc in hexanes) and taken up in DCM (1.2 L), then purged with ozone gas at −78° C. for 4 h. The reaction mixture was warmed to r.t., and TPP (33.5 g, 128 mmol) was added. The reaction mixture was stirred at r.t. for 16 h, then concentrated in vacuo. The crude material was purified by column chromatography, eluting with EtOAc/hexanes (20-30% gradient), to furnish the title compound (15.0 g, 12% overall) as a light yellow solid. $\delta_H$ (400 MHz, DMSO-d$_6$) 10.28 (s, 1H), 10.09 (s, 1H), 7.96-8.00 (m, 1H), 7.46 (d, J 8.80 Hz, 1H), 1.44 (s, 9H).

Intermediate 109

Methyl (2S)-1-{[4-(tert-butoxycarbonylamino)-2-fluoro-3-nitro-phenyl]methyl}-pyrrolidine-2-carboxylate DIPEA (0.2 mL, 1.15 mmol) was added to a stirred suspension of Intermediate 108 (250 mg, 0.88 mmol) and methyl L-prolinate hydrochloride (1:1) (175 mg, 1.06 mmol) in anhydrous 1,2-dichloroethane (3 mL). The resulting solution was stirred at 20° C. for 5 minutes under N$_2$. Sodium triacetoxyborohydride (280 mg, 1.32 mmol) was added in one portion, and the suspension was stirred at 0° C. for 64 h. The reaction mixture was quenched with saturated aqueous NaHCO$_3$ solution (10 mL) and the biphasic mixture was stirred at 20° C. for 30 minutes. The residue was extracted with DCM (3×20 mL), using a hydrophobic frit, and the organic filtrate was concentrated in vacuo. The resultant yellow viscous oil was separated by flash column chromatography (KP-NH SiO$_2$), eluting with EtOAc/heptane (0-40% gradient), to afford the title compound (309 mg, 86%) as a viscous golden yellow oil. LCMS (Method 1): [M+H]$^+$ m/z 398, RT 1.77 minutes.

Intermediate 110

Methyl (2R)-1-{[4-(tert-butoxycarbonylamino)-2-fluoro-3-nitrophenyl]methyl}-pyrrolidine-2-carboxylate Prepared in an analogous fashion to Intermediate 109 from methyl D-prolinate hydrochloride (1:1) (175 mg, 1.06 mmol) and Intermediate 108 (250 mg, 0.88 mmol), furnishing the title compound (322 mg, 86%) as a viscous golden yellow oil. LCMS (Method 1): [M+H]$^+$ m/z 398, RT 1.77 minutes.

Intermediate 111

Methyl (2S)-1-{[3-amino-4-(tert-butoxycarbonylamino)-2-fluorophenyl]methyl}-pyrrolidine-2-carboxylate Iron powder (336 mg, 6.02 mmol) was added to a stirred suspension of Intermediate 109 (309 mg, 0.75 mmol) in an 8:1:1 mixture of MeOH-water-saturated aqueous NH$_4$Cl solution (10 mL). The mixture was heated at 60° C. under N$_2$ for 3 h. After cooling to 20° C., the mixture was diluted with EtOAc (50 mL). The solids were removed by filtration through kieselguhr, washing with EtOAc (2×25 mL), MeOH (20 mL) and water (50 mL). The organic phase was separated, and the aqueous layer was extracted with EtOAc (2×50 mL). The combined organic extracts were washed with brine (50 mL) and dried over MgSO$_4$, then concentrated in vacuo, to afford the title compound (255 mg, 88%) as an off-white gum. LCMS (Method 1): [M+H]$^+$ m/z 368, RT 1.45 minutes.

Intermediate 112

Methyl (2R)-1-{[3-amino-4-(tert-butoxycarbonylamino)-2-fluorophenyl]methyl}-pyrrolidine-2-carboxylate Prepared in an analogous fashion to Intermediate 111 from Intermediate 110 (322 mg, 0.81 mmol), furnishing the title compound (255 mg, 80%) as an off-white gum. LCMS (Method 1): [M+H]$^+$ m/z 368, RT 1.45 minutes.

Intermediate 113

Methyl (2S)-1-[(3,4-diamino-2-fluorophenyl) methyl]pyrrolidine-2-carboxylate

TFA (0.50 mL, 6.73 mmol) was added to a solution of Intermediate 111 (258 mg, 0.67 mmol) in anhydrous DCM (3.5 mL). The mixture was stirred at 20° C. under N$_2$ for 19 h, then quenched with saturated aqueous NaHCO$_3$ solution (pH 11, 10 mL). The residue was extracted successively with DCM (3×20 mL) and 4:1 DCM-isopropanol (4×25 mL), using a hydrophobic frit to separate the phases. The organic filtrate was concentrated in vacuo to afford the title compound (221 mg, quantitative) as a brown viscous oil. LCMS (Method 3): [M+H]$^+$ m/z 268, RT 1.96 minutes.

Intermediate 114

Methyl (2R)-1-[(3,4-diamino-2-fluorophenyl) methyl]pyrrolidine-2-carboxylate

Prepared in an analogous fashion to Intermediate 113 from Intermediate 112 (255 mg, 0.70 mmol), furnishing the title compound (250 mg, quantitative) as a brown viscous oil. LCMS (Method 5): [M+H]$^+$ m/z 268, RT 1.95 minutes.

Intermediate 115 (Procedure V)

Ethyl 2-amino-2-(3,3-dimethylcyclohexyl)acetate

To a solution of TiCl$_4$ (1M in DCM, 15.4 mL, 15.4 mmol) in THF (7.7 mL) at 0° C. was added ethyl nitroacetate (0.85 mL, 7.70 mmol) dropwise over 5 minutes. The reaction mixture was stirred for 5 minutes, then 3,3-dimethylcyclohexanone (1.10 mL, 7.70 mmol) was added dropwise over 5 minutes. Following an additional 15 minutes at 0° C., a solution of 4-methylmorpholine (3.40 mL, 30.8 mmol) in THF (31 mL) was added via syringe pump dropwise over 2 h. The reaction mixture was slowly warmed to r.t. over 2 days, then diluted with EtOAc (30 mL) and H$_2$O (30 mL). The layers were separated. The aqueous layer was re-extracted with EtOAc (2×50 mL), and the combined organic layers were dried (MgSO$_4$) and concentrated in vacuo. The residue was purified by flash column chromatography, eluting with EtOAc/hexanes (0-20% gradient). The isolated material was taken up in CHCl$_3$ (24 mL) and isopropanol (7.2 mL). To this solution was added silica (3.82 g), followed by NaBH$_4$ (365 mg, 9.26 mmol), portionwise over 5 minutes. The mixture was stirred vigorously at r.t. over 16 h, then AcOH (0.56 mL) was added. The mixture was filtered and concentrated in vacuo. The residue was re-dissolved in DCM (30 mL), and water (30 mL) was added. The aqueous layer was re-extracted with DCM (2×50 mL), and the combined organic layers were dried (MgSO$_4$) and concentrated in vacuo. The crude material was re-dissolved in EtOH (56 mL), and 10% Pd/C (56 mg) was added. The suspension was evacuated and back-filled three times with hydrogen, then left to stir at r.t. under a hydrogen atmosphere for 2 days. The mixture was filtered through a pad of Celite® (10 g) under suction using EtOH (100 mL), and concentrated in vacuo. Purification by flash column chromatography, eluting with EtOAc/hexanes (0-100% gradient), gave the title compound (1:1 mixture of diastereomers) (80 mg, 16% overall) as a colourless oil. R$_f$ 0.14 (EtOAc: isohexanes, 70:30), KMnO$_4$ stain.

Intermediate 116

Ethyl 2-(3,3-dimethylcyclohexyl)-2-[(3-methylisoxazole-4-carbonyl)amino]acetate

The title compound (114 mg, 74%) was prepared from Intermediate 115 (102 mg, 0.48 mmol) and 3-methylisoxazole-4-carboxylic acid (61 mg, 0.48 mmol) in accordance with Procedure A. LCMS (Method 5): [M+H]$^+$ m/z 323, RT 1.37 minutes.

Intermediate 117 (Procedure W)

2-(3,3-Dimethylcyclohexyl)-2-[(3-methylisoxazole-4-carbonyl)amino]acetic Acid

To a solution of Intermediate 116 (100 mg, 0.31 mmol) in THF (2.8 mL) and water (0.70 mL) at r.t. was added LiOH.H$_2$O (19.5 mg, 0.47 mmol) in one portion. The mixture was stirred at r.t. for 3 days, then acidified to pH 3 using 2N aqueous HCl and extracted with EtOAc (3×10 mL). The combined organic layers were dried (MgSO$_4$), then concentrated in vacuo, to give the title compound (1:1 mixture of diastereomers) (100 mg, quantitative) as a pale yellow oil. LCMS (Method 5): [M+H]$^+$ m/z 295, RT 0.84 minutes.

Intermediate 118

Ethyl 2-amino-2-(spiro[2.5]octan-7-yl)acetate

The title compound (126 mg, 5%) was prepared from spiro[2.5]octan-7-one (1.50 g, 12.0 mmol) in accordance with Procedure V. R$_f$ 0.16 (EtOAc:isohexanes, 70:30), KMnO$_4$ stain.

Intermediate 119

Ethyl 2-[(3-ethylisoxazole-4-carbonyl)amino]-2-(spiro[2.5]octan-7-yl)acetate

The title compound (117 mg, 59%) was prepared from Intermediate 118 (126 mg, 0.59 mmol) and 3-ethylisoxazole-4-carboxylic acid (84 mg, 0.59 mmol) in accordance with Procedure A. LCMS (Method 5): [M+H]$^+$ m/z 335, RT 1.38 minutes.

Intermediate 120

2-[(3-Ethylisoxazole-4-Carbonyl)amino]-2-(spiro [2.5]octan-7-Yl)acetic acid

The title compound (100 mg, 93%) was prepared from Intermediate 119 (117 mg, 0.35 mmol) in accordance with Procedure W. LCMS (Method 5): [M+H]$^+$ m/z 307, RT 0.86 minutes.

Intermediate 121

Ethyl 2-amino-2-(3,3-difluorocyclohexyl)acetate

To a solution of ethyl 2-nitro-2-(3-oxocyclohexyl)acetate (1.00 g, 4.14 mmol) in DCM (8.6 mL) at 0° C. was added DAST (1.10 mL, 8.33 mmol) dropwise over 10 minutes. The reaction mixture was warmed to r.t. slowly over 16 h, then poured onto ice (10 g) and neutralised with saturated aqueous Na$_2$CO$_3$ solution. The layers were separated, and the aqueous layer was re-extracted with DCM (2×30 mL). The combined organic layers were dried (MgSO$_4$) and concentrated in vacuo. The residue was purified by flash column chromatography, eluting with EtOAc/hexanes (0-12% gradient). The resulting colourless oil was taken up in AcOH (13 mL) at r.t., to which was added Zn (470 mg, 7.04 mmol) in one portion. The mixture was stirred vigorously for 16 h, then filtered through Celite® (1 g), eluting with AcOH (2×10 mL). The filtrate was concentrated in vacuo to about one-third volume, then diluted with water (10 mL). The mixture was basified dropwise with aqueous NH$_4$OH solution, and extracted with DCM (3×20 mL). The combined organic layers were washed with brine (2×20 mL), dried (MgSO$_4$) and concentrated in vacuo. Purification by flash column chromatography, eluting with EtOAc/hexanes (0-100% gradient), gave the title compound (1:1 mixture of diastereomers) (183 mg, 20% overall) as a colourless oil. $R_f$ 0.30 (EtOAc:isohexanes, 70:30), KMnO$_4$ stain.

Intermediate 122

Ethyl 2-(3,3-difluorocyclohexyl)-2-[(3-ethylisoxazole-4-carbonyl)amino]acetate

The title compound (312 mg, quantitative) was prepared from Intermediate 121 (183 mg, 0.82 mmol) and 3-ethylisoxazole-4-carboxylic acid (117 mg, 0.82 mmol) in accordance with Procedure A. LCMS (Method 5): [M+H]$^+$ m/z 345, RT 1.23 minutes.

Intermediate 123

2-(3,3-Difluorocyclohexyl)-2-[(3-ethylisoxazole-4-carbonyl)amino]acetic Acid

The title compound (264 mg, 92%) was prepared from Intermediate 122 (312 mg, 0.91 mmol) in accordance with Procedure W. LCMS (Method 5): [M+H]$^+$ m/z 317, RT 0.76 minutes.

Intermediate 124

2-Cyclooctyl-2-[(2-ethylpyrazole-3-carbonyl)amino] acetic Acid

To a solution of 1-ethyl-1H-pyrazole-5-carboxylic acid (315 mg, 2.14 mmol) and Intermediate 3 (500 mg, 2.12 mmol) in DMF (4 mL) at 0° C. was added HATU (1 g, 2.55 mmol), followed by DIPEA (1.5 mL, 8.6 mmol). The reaction mixture was warmed to r.t. and stirred for 3 days, then diluted with water (100 mL) and extracted with EtOAc (2×80 mL). The organic extracts were dried over Na$_2$SO$_4$, filtered and concentrated in vacuo. The residue was purified by flash column chromatography, eluting with EtOAc/hexanes (0-80% gradient), and the residue was taken up in THF (5 mL). LiOH.H$_2$O (55 mg, 1.31 mmol) in water (1 mL) was added. The reaction mixture was stirred at r.t. overnight, then diluted with water, acidified to pH 3 with 2N aqueous HCl solution, and extracted with EtOAc. The organic layers were dried over Na$_2$SO$_4$ and filtered, then concentrated in vacuo, to give the title compound (271 mg, 41% overall). LCMS (Method 5): [M+H]$^+$ m/z 308, RT 0.94 minutes.

Intermediate 125

(2S)-2-[(2-Ethylpyrazole-3-carbonyl)amino]-2-(4-methylcyclohexyl)acetic Acid

The title compound (130 mg, quantitative) was prepared in an analogous fashion to Intermediate 124 from trans-methyl (2S)-2-amino-2-(4-methylcyclohexyl)acetate (82 mg, 0.44 mmol) and 1-ethyl-1H-pyrazole-5-carboxylic acid (80 mg, 0.54 mmol). LCMS (Method 5): [M+H]$^+$ m/z 294, RT 0.83 minutes.

Intermediate 126

(2S)-2-(9H-Fluoren-9-ylmethoxycarbonylamino)-2-(4-methylcyclohexyl)acetic Acid (Trans Isomer)

To a solution of trans-methyl (2S)-2-amino-2-(4-methylcyclohexyl)acetate (3 g, 16.2 mmol) in 1,4-dioxane (25 mL) and water (12.5 mL) at r.t. was added NaHCO$_3$ (3.4 g, 40 mmol). The stirred suspension was treated with 9-fluorenylmethyl chloroformate (4.19 g, 16.2 mmol) portionwise over 5 minutes. The reaction mixture was stirred at r.t. for 50 h, then partitioned between EtOAc (100 mL) and water (100 mL). The organic layer was washed with 1N aqueous HCl (100 mL) and brine (100 mL), then dried over Na$_2$SO$_4$ and concentrated in vacuo. The residue was purified by flash column chromatography, eluting with EtOAc/hexanes (0-15% gradient). The recovered material was suspended in water (46 mL), then 4M HCl in 1,4-dioxane (55 mL, 221 mmol) was added dropwise. The mixture was heated at 80° C. overnight, then further 4M HCl in 1,4-dioxane (18.4 mL) was added, and the mixture was heated at 80° C. for another 24 h. The residue was concentrated in vacuo, then partitioned between EtOAc (100 mL) and water (50 mL). The organic layers were separated, dried over Na$_2$SO$_4$ and concentrated in vacuo. The residue was purified by flash chromatography, eluting with EtOAc/hexanes (0-100% gradient), to yield the title compound (3.1 g, 49% overall) as a white solid. LCMS (Method 5): [M+H]$^+$ m/z 394.2, RT 1.12 minutes.

Intermediate 127 (Procedure X)

1-[4-({2-[(S)-Amino(4-methylcyclohexyl)methyl]-4-fluoro-1H-benzimidazol-5-yl}-methyl)piperazin-1-yl]ethanone (Trans Isomer)

To a solution of trans-(2S)-2-(tert-butoxycarbonylamino)-2-(4-methylcyclohexyl)acetic acid (380 mg, 1.4 mmol) and Intermediate 60 (396 mg, 1.49 mmol) in DCM (8 mL) were added HATU (660 mg, 1.68 mmol) and DIPEA (0.5 mL, 3.0 mmol). The reaction mixture was stirred at r.t. for 5 h, then partitioned between DCM and water. The organic layers were dried over Na$_2$SO$_4$, then concentrated in vacuo. The residue was taken up in AcOH (10 mL) and stirred at reflux temperature for 16 h. The residue was concentrated in vacuo, then stirred in a mixture of MeOH (15 mL) and 4M HCl in 1,4-dioxane (5 mL). After 18 h, the reaction mixture was concentrated in vacuo. The isolated material was purified by flash chromatography, eluting with a 7N solution of NH$_3$ in MeOH/EtOAc (0-20% gradient), to give the title compound (376 mg, 62% overall) as a solid. LCMS (Method 5): [M+H]$^+$ m/z 402, RT 1.04 minutes.

Intermediate 128

[4-Fluoro-5-(tetrahydropyran-4-yl)-1H-benzimidazol-2-yl](4-methylcyclohexyl)-methanamine The title compound (137 mg, 27%) was prepared from Intermediate 15 (385 mg, 1.42 mmol) and Intermediate 24 (313 mg, 1.49 mmol) in accordance with Procedure X. LCMS (Method 5): [M+H]$^+$ m/z 346, RT 1.24 minutes.

Intermediate 129

2-{2-[(S)-Amino(4-methylcyclohexyl)methyl]-4-fluoro-1H-benzimidazol-5-yl}-N,N-dimethylbenzamide (Trans Isomer)

The title compound (157 mg, 97%) was prepared from trans-(2S)-2-(tert-butoxycarbonylamino)-2-(4-methylcyclohexyl)acetic acid (106 mg, 0.39 mmol) and Intermediate 34 (150 mg, 0.40 mmol) in accordance with Procedure X. LCMS (Method 5): [M+H]$^+$ m/z 409, RT 1.14 minutes.

Intermediate 130 (Procedure Y)

tert-Butyl N-[(5-bromo-4-fluoro-1H-benzimidazol-2-yl)(cyclooctyl)methyl]carbamate To a solution of 2-(tert-butoxycarbonylamino)-2-cyclooctylacetic acid (1.35 g, 4.74 mmol), 4-bromo-3-fluorobenzene-1,2-diamine (1.00 g, 4.70 mmol) and DIPEA (1.23 mL, 7.07 mmol) in DMF (6 mL) was added T3P® (2.8 mL, 4.7 mmol). The reaction mixture was heated overnight at 70° C., then concentrated in vacuo, and partitioned between EtOAc and water. The organic layers were dried over Na$_2$SO$_4$, then the solvent was removed in vacuo. The residue was taken up in AcOH (10 mL) and heated in a sealed vial at 70° C. overnight. The reaction mixture was concentrated in vacuo. The residue was purified by flash column chromatography, eluting with EtOAc/hexanes (0-100% gradient), to give the title compound (862 mg, 37% overall) as a brown foam. LCMS (Method 5): [M+H]$^+$ m/z 456.0, RT 1.59 minutes.

Intermediate 131 tert-Butyl N-{cyclooctyl[4-fluoro-5-(4,4,5,5-tetramethyl-1,3,2-dioxaborolan-2-yl)-1H-benzimidazol-2-yl]methyl}carbamate The title compound (108 mg, 52%) was prepared from Intermediate 130 (146 mg, 0.32 mmol) in accordance with Procedure C. LCMS (Method 5): [M+H]$^+$ m/z 502, RT 1.59 minutes.

Intermediate 132 tert-Butyl N-(cyclooctyl{5-[2-(dimethylcarbamoyl)phenyl]-4-fluoro-1H-benzimidazol-2-yl}methyl)carbamate The title compound (30 mg, 82%) was prepared from Intermediate 131 (54 mg, 0.07 mmol) and 2-bromo-N,N-dimethylbenzamide (24 mg, 0.10 mmol) in accordance with Procedure G. LCMS (Method 5): [M+H]$^+$ m/z 523, RT 1.45 minutes.

Intermediate 133 (Procedure Z)

2-{2-[Amino(cyclooctyl)methyl]-4-fluoro-1H-benzimidazol-5-yl}-N,N-dimethyl-benzamide To a solution of Intermediate 132 (30 mg, 0.06 mmol) in DCM (5 mL) was added 4N HCl in 1,4-dioxane (0.26 mL). The reaction mixture was stirred overnight, then concentrated in vacuo. The residue was dissolved in MeOH (2 mL) and eluted onto an Isolute SCX-2 cartridge (5 g), washing through with MeOH (20 mL). The material was released with a 7M solution of NH$_3$ in MeOH (20 mL), and concentrated in vacuo, to give the title compound (25 mg, quantitative) as a straw-coloured oil. LCMS (Method 5): [M+H]$^+$ m/z 423, RT 1.10 minutes.

Intermediate 134

Ethyl 3-{2-[amino(cyclooctyl)methyl]-4-fluoro-1H-benzimidazol-5-yl}pyridine-4-carboxylate The title compound (39 mg, 47%) was prepared from Intermediate 131 (108 mg, 0.17 mmol) and ethyl 3-bromoisonicotinate (65 mg, 0.28 mmol) in a sequential fashion in accordance with Procedures G and Z. LCMS (Method 5): [M+H]$^+$ m/z 425, RT 1.23 minutes.

Intermediate 135

1-(3-Bromo-6,8-dihydro-5H-[1,2,4]triazolo[4,3-a]pyrazin-7-yl)ethanone

To a suspension of 3-bromo-5,6,7,8-tetrahydro-[1,2,4]triazolo[4,3-a]pyrazine hydrochloride (142 mg, 0.59 mmol) in DCM (5 mL) and triethylamine (0.17 mL, 1.2 mmol) was added acetic anhydride (0.06 mL, 0.6 mmol). The reaction mixture was stirred under N$_2$ at r.t. overnight, then concentrated in vacuo. The residue was purified by flash chromatography, eluting with EtOAc/hexanes (0-100% gradient) then MeOH/DCM (0-30% gradient), to furnish the title compound (101 mg, 70%) as a straw-coloured oil. $\delta_H$ NMR (400 MHz, DMSO-d$_6$) 4.91-4.71 (m, 2H), 4.06-3.83 (m, 4H), 2.18-2.07 (m, 3H). LCMS (Method 5): [M+H]$^+$ m/z 425, RT 1.23 minutes.

Intermediate 136

1-(3-{2-[Amino(cyclooctyl)methyl]-4-fluoro-1H-benzimidazol-5-yl}-6,8-dihydro-5H-[1,2,4]triazolo[4,3-a]pyrazin-7-yl)ethanone The title compound (35 mg, 44%) was prepared from Intermediate 131 (108 mg, 0.17 mmol) and Intermediate 135 (65 mg, 0.28 mmol) in a sequential fashion in accordance with Procedures G and Z. LCMS (Method 5): [M+H]$^+$ m/z 440, RT 0.96 minutes.

Intermediate 137

(S)-[4-Fluoro-5-(tetrahydropyran-3-yl)-1H-benzimidazol-2-yl](4-methylcyclohexyl)-methanamine (Trans Isomer)

The title compound (77 mg, 28%) was prepared from Intermediate 73 (170 mg, 0.81 mmol) and trans-(2S)-2-(tert-butoxycarbonylamino)-2-(4-methylcyclohexyl)acetic acid (224 mg, 0.83 mmol) in accordance with Procedure X. LCMS (Method 5): [M+H]$^+$ m/z 346, RT 1.19 minutes.

Intermediate 138 (Procedure AA)

tert-Butyl N-[(S)-(5-bromo-4-fluoro-1H-benzimidazol-2-yl)(4-methylcyclohexyl)methyl]-carbamate (Trans Isomer)

To a solution of trans-(2S)-2-(tert-butoxycarbonylamino)-2-(4-methylcyclohexyl)acetic acid (5 g, 18.42 mmol) in DCM were added 4-bromo-3-fluorobenzene-1,2-diamine (3.97 g, 19.4 mmol), HATU (8.67 g, 22.1 mmol) and DIPEA (6.4 mL, 37 mmol). The mixture was stirred at r.t. overnight, then partitioned between DCM and water. The organic layers were dried over $Na_2SO_4$, then concentrated in vacuo. The residue was taken up in AcOH (40 mL) and heated at reflux temperature overnight, then poured onto saturated aqueous $NaHCO_3$ solution and partitioned between EtOAc and water. The organic layers were washed with brine, dried over $Na_2SO_4$ and concentrated in vacuo. The crude residue was purified by flash chromatography, eluting with EtOAc/hexanes (0-50% gradient), giving the title compound (7.04 g, 87% overall). LCMS (Method 5): [M+H]$^+$ m/z 442, RT 1.52 minutes.

Intermediate 139 tert-Butyl N-{(S)-[4-fluoro-5-(4,4,5,5-tetramethyl-1,3,2-dioxaborolan-2-yl)-1H-benzimidazol-2-yl](4-methylcyclohexyl)methyl}carbamate The title compound (538 mg, 49%) was prepared from Intermediate 138 (1 g, 2.27 mmol) in accordance with Procedure C. LCMS (Method 5): [M+H]$^+$ m/z 488, RT 1.54 minutes.

Intermediate 140

3-Bromo-5-fluoro-N,N-dimethylpyridine-4-carboxamide

The title compound (312 mg, quantitative) was prepared from 3-bromo-5-fluoro-isonicotinic acid (255 mg, 1.16 mmol) and a 2M solution of dimethylamine in THF (1.2 mL, 2.4 mmol) in accordance with Procedure A, with DCM (5 mL) as solvent. LCMS (Method 5): [M+H]$^+$ m/z 249, RT 0.62 minutes.

Intermediate 141

3-{2-[(S)-Amino(4-methylcyclohexyl)methyl]-4-fluoro-1H-benzimidazol-5-yl}-5-fluoro-N,N-dimethylpyridine-4-carboxamide (Trans Isomer)

The title compound (56 mg, 52%) was prepared from Intermediate 139 (100 mg, 0.21 mmol) and Intermediate 140 (56 mg, 0.23 mmol) in a sequential fashion in accordance with Procedures G and Z. LCMS (Method 5): [M+H]$^+$ m/z 528, RT 1.29 minutes.

Intermediate 142

3-{2-[(S)-Amino(4-methylcyclohexyl)methyl]-4-fluoro-1H-benzimidazol-5-yl}-N,N-dimethylpyridine-4-carboxamide (Trans Isomer)

The title compound (54 mg, 67%) was prepared from Intermediate 139 (100 mg, 0.21 mmol) and 3-bromo-N,N-dimethylpyridine-4-carboxamide (52 mg, 0.23 mmol) in a sequential fashion in accordance with Procedures G and Z. LCMS (Method 5): [M+H]$^+$ m/z 410, RT 0.99 minutes.

Intermediate 143

2-{2-[(S)-Amino(4-methylcyclohexyl)methyl]-4-fluoro-1H-benzimidazol-5-yl}-N,N-dimethylpyridine-3-carboxamide (Trans Isomer)

The title compound (25 mg, 29%) was prepared from Intermediate 139 (100 mg, 0.21 mmol) and 2-bromo-N,N-dimethylnicotinamide (55 mg, 0.23 mmol) in a sequential fashion in accordance with Procedures G and Z. LCMS (Method 5): [M+H]$^+$ m/z 410, RT 0.97 minutes.

Intermediate 144

Ethyl 5-{2-[(S)-amino(4-methylcyclohexyl)methyl]-4-fluoro-1H-benzimidazol-5-yl}-3,6-dihydro-2H-pyran-4-carboxylate (Trans Isomer)

The title compound (240 mg, 83%) was prepared from Intermediate 61 (151 mg, 0.56 mmol) and trans-(2S)-2-(tert-butoxycarbonylamino)-2-(4-methylcyclohexyl)acetic acid (151 mg, 0.55 mmol) in accordance with Procedure X. LCMS (Method 5): [M+H]$^+$ m/z 416, RT 1.19 minutes.

Intermediate 145

5-{2-[(S)-Amino(4-methylcyclohexyl)methyl]-4-fluoro-1H-benzimidazol-5-yl}-N,N-dimethyl-3,6-dihydro-2H-pyran-4-carboxamide (Trans Isomer)

To a solution of trans-(2S)-2-(tert-butoxycarbonylamino)-2-(4-methylcyclohexyl)acetic acid (151 mg, 0.55 mmol) and Intermediate 61 (151 mg, 0.55 mmol) in DCM (5 mL) were added HATU (255 mg, 0.65 mmol) and DIPEA (0.19 mL, 1.1 mmol). The reaction mixture was stirred at r.t. for 5 h, then partitioned between DCM and water. The organic layers were dried over $Na_2SO_4$, then concentrated in vacuo. The residue was taken up in AcOH (5 mL) and stirred at reflux temperature for 16 h, then concentrated in vacuo. The residue was taken up in THF (2.5 mL) and water (2.5 mL), and LiOH.H$_2$O (100 mg) was added. The mixture was stirred for 24 h at 70° C., then cooled and concentrated in vacuo. The residue was taken up in DCM (5 mL) and DMF (3 mL), then DIPEA (0.25 mL, 1.4 mmol), HATU (242 mg, 0.61 mmol) and a 2M solution of dimethylamine in THF (0.49 mL, 0.98 mmol) were added. After stirring for 3 days, further 2M dimethylamine solution in THF (1.0 mL), HATU (245 mg) and DIPEA (0.25 mL) were added. The mixture was stirred at r.t. for a further 24 h, then partitioned between water and EtOAc. The organic layers were washed with water and aqueous LiCl solution, then dried over $Na_2SO_4$ and concentrated in vacuo. The residue was purified by flash chromatography, eluting with EtOAc/hexanes (0-100% gradient). The resulting solid was taken up in DCM (5 mL) and treated with 4M HCl in 1,4-dioxane (2 mL). After 3 h, the reaction mixture was concentrated in vacuo to give the title compound (117 mg, 47% overall) as a straw-coloured oil. LCMS (Method 5): [M+H]⁺ m/z 415.2, RT 1.09 minutes.

Intermediate 146

Ethyl 3-{2-[(S)-amino(4-methylcyclohexyl)methyl]-4-fluoro-1H-benzimidazol-5-yl}-tetrahydropyran-4-carboxylate (Trans Isomer)

The title compound (62 mg, 22%) was prepared from Intermediate 62 (157 mg, 0.56 mmol) and trans-(2S)-2-(tert-butoxycarbonylamino)-2-(4-methylcyclohexyl)acetic acid (146 mg, 0.54 mmol) in accordance with Procedure X. LCMS (Method 5): [M+H]⁺ m/z 418, RT 1.19 minutes.

Intermediate 147

Methyl 4-{2-[(S)-amino(4-methylcyclohexyl)methyl]-4-fluoro-1H-benzimidazol-5-yl}-tetrahydro-furan-3-carboxylate (Trans Isomer)

The title compound (367 mg, 93%) was prepared from trans-(2S)-2-(tert-butoxycarbonylamino)-2-(4-methylcyclohexyl)acetic acid (275 mg, 1.01 mmol) and Intermediate 96 (272 mg, 1.07 mmol) in accordance with Procedure X. LCMS (Method 5): [M+H]⁺ m/z 409, RT 1.14 minutes.

Intermediate 148

Ethyl 2-{2-[amino(cyclooctyl)methyl]-4-fluoro-1H-benzimidazol-5-yl}-2-(pyridin-3-yl)-acetate The title compound (80 mg, 18%) was prepared from 2-(tert-butoxycarbonyl-amino)-2-cyclooctylacetic acid (296 mg, 1.04 mmol) and Intermediate 75 (294 mg, 1.02 mmol) in a sequential fashion in accordance with Procedures Y and Z. LCMS (Method 5): [M+H]⁺ m/z 439, RT 1.21 minutes.

Intermediate 149

Ethyl 2-{2-[(tert-butoxycarbonylamino)(cyclooctyl)methyl]-4-fluoro-1H-benzimidazol-5-yl}-2-(pyridin-4-yl)acetate The title compound (390 mg, 22%) was prepared from 2-(tert-butoxycarbonyl-amino)-2-cyclooctylacetic acid (951 mg, 3.33 mmol) and Intermediate 76 (953 mg, 3.29 mmol) in accordance with Procedure Y. LCMS (Method 5): [M+H]⁺ m/z 539, RT 1.46 minutes.

Intermediate 150

Ethyl 2-{2-[amino(cyclooctyl)methyl]-4-fluoro-1H-benzimidazol-5-yl}-2-(pyridin-4-yl)-acetate The title compound (45 mg, quantitative) was prepared from Intermediate 149 (56 mg, 0.10 mmol) in accordance with Procedure P. LCMS (Method 5): [M+H]⁺ m/z 439, RT 1.26 minutes.

Intermediate 151

Cyclooctyl[4-fluoro-5-(pyridin-4-ylmethyl)-1H-benzimidazol-2-yl]methanamine

To a solution of Intermediate 150 (58 mg, 0.11 mmol) in EtOH (3 mL) was added LiOH.H₂O, dissolved in water (1 mL). The reaction mixture was stirred at r.t. overnight. The acidity was adjusted to pH 1 with 2M aqueous HCl solution, and water (10 mL) was added. The reaction mixture was concentrated in vacuo. The residue was purified by flash chromatography, eluting with MeOH/DCM (0-35% gradient), to give the title compound (39 mg, 17%). LCMS (Method 5): [M+H]⁺ m/z 367, RT 1.21 minutes.

Intermediate 152 tert-Butyl N-[{5-[cyano(pyridin-4-yl)methyl]-4-fluoro-1H-benzimidazol-2-yl}-(cyclooctyl)methyl] carbamate The title compound (800 mg, 12%) was prepared from 2-(tert-butoxycarbonyl-amino)-2-cyclooctylacetic acid (4.0 g, 14.0 mmol) and Intermediate 77 (3.4 g, 14.0 mmol) in accordance with Procedure Y. LCMS (Method 5): [M+H]⁺ m/z 492, RT 1.16 minutes.

Intermediate 153

2-{2-[Amino(cyclooctyl)methyl]-4-fluoro-1H-benzimidazol-5-yl}-2-(pyridin-4-yl)-acetamide To a cooled (0° C.) solution of Intermediate 152 (55 mg, 0.11 mmol) in DCM (2 mL) was added H₂SO₄ (40 µL, 0.7 mmol). The reaction mixture was warmed to r.t. overnight with stirring, then concentrated in vacuo. The residue was purified by flash chromatography, eluting with MeOH/DCM (0-70% gradient). The relevant fractions were concentrated in vacuo to give the title compound (19 mg, 41%) as an off-white solid. LCMS (Method 5): [M+H]⁺ m/z 410, RT 1.00 minutes.

Intermediate 154

Cyclooctyl{4-fluoro-5-[(5-methyl-1,3,4-oxadiazol-2-yl)(pyridin-4-yl)methyl]-1H-benzimidazol-2-yl}methanamine The title compound (160 mg, 27%) was prepared from 2-(tert-butoxycarbonyl-amino)-2-cyclooctylacetic acid (370 mg, 1.30 mmol) and Intermediate 107 (388 mg, 1.30 mmol) in a sequential fashion in accordance with Procedures Y and Z. LCMS (Method 5): [M+H]⁺ m/z 449, RT 1.09 minutes.

Intermediate 155 tert-Butyl 3-{2-[(S)-(9H-fluoren-9-ylmethoxycarbonylamino)(4-methylcyclohexyl)-methyl]-4-fluoro-1H-benzimidazol-5-yl}morpholine-4-carboxylate (Trans Isomer)

To a solution of Intermediate 126 (800 mg, 2.03 mmol) and Intermediate 100 (665 mg, 2.14 mmol) in DCM (11 mL) were added HATU (928 mg, 2.44 mmol) and DIPEA (0.71 mL, 4.1 mmol). The reaction mixture was stirred at r.t. overnight, then partitioned between DCM and water. The organic layers were dried over MgSO₄, and concentrated in vacuo. The residue was taken up in AcOH (7 mL), and heated at 70° C. After 5 h, the reaction mixture was cooled, and concentrated in vacuo. The residue was purified by flash chromatography, eluting with EtOAc/hexanes (0-100% gradient), to give the title compound (1.15 g, 85% overall) as an orange foam. LCMS (Method 5): [M+H]⁺ m/z 669, RT 1.67 minutes.

Intermediate 156

1-(3-{2-[(S)-Amino(4-methylcyclohexyl)methyl]-4-fluoro-1H-benzimidazol-5-yl}morpholin-4-yl)-2-hydroxyethanone To a solution of Intermediate 155 (60 mg, 0.09 mmol) in DCM (2 mL) was added TFA (0.5 mL). The reaction mixture was stirred for 2 h, then concentrated in vacuo. The crude material was taken up in DCM (3 mL), and triethylamine (16 μL, 0.11 mmol) was added, followed by acetoxyacetyl chloride (13 μL, 0.12 mmol). The reaction mixture was stirred at r.t. for 1 h, then concentrated in vacuo. The residue was dissolved in MeOH (5 mL) and water (1 mL), then NaOH (70 μL, 0.1 mmol) was added. The reaction mixture was stirred overnight, then concentrated in vacuo, and partitioned between DCM and water. The organic layers were separated and dried over $Na_2SO_4$, then concentrated in vacuo. The crude orange glass was dissolved in acetonitrile (1 mL), and diethylamine (250 μL, 2.4 mmol) was added. After 2 h at r.t. the reaction mixture was concentrated in vacuo, to give the title compound (14 mg, 37% overall). LCMS (Method 5): [M+H]+ m/z 405, RT 0.95 minutes.

Intermediate 157

(2S)-1-{2-[(S)-Amino(4-methylcyclohexyl)methyl]-4-fluoro-1H-benzimidazol-5-yl}-N,N-dimethylpiperidine-2-carboxamide (Trans Isomer)

The title compound (174 mg, 66%) was prepared from Intermediate 88 (179 mg, 0.64 mmol) and trans-(2S)-2-(tert-butoxycarbonylamino)-2-(4-methylcyclohexyl)acetic acid (115 mg, 0.42 mmol) in accordance with Procedure X. LCMS (Method 5): [M+H]+ m/z 416, RT 1.12 minutes.

Intermediate 158

2-{2-[(S)-Amino(4-methylcyclohexyl)methyl]-4-fluoro-1H-benzimidazol-5-yl}-N,N-dimethylacetamide (Trans Isomer)

The title compound (102 mg, 96%) was prepared from Intermediate 64 (63 mg, 0.30 mmol) and trans-(2S)-2-(tert-butoxycarbonylamino)-2-(4-methylcyclohexyl)acetic acid (80 mg, 0.29 mmol) in accordance with Procedure X. LCMS (Method 5): [M+H]+ m/z 347, RT 1.01 minutes.

Intermediate 159

Ethyl 4-{2-[(S)-amino(4-methylcyclohexyl)methyl]-4-fluoro-1H-benzimidazol-5-yl}-1-(methylsulfonyl)pyrrolidine-3-carboxylate (Trans Isomer)

The title compound (144 mg, quantitative) was prepared from Intermediate 103 (100 mg, 0.30 mmol) and trans-(2S)-2-(tert-butoxycarbonylamino)-2-(4-methylcyclohexyl)acetic acid (80 mg, 0.30 mmol) in accordance with Procedure X. LCMS (Method 5): [M+H]+ m/z 481, RT 1.13 minutes.

Intermediate 160

Ethyl 1-acetyl-4-{2-[(S)-amino(4-methylcyclohexyl)methyl]-4-fluoro-1H-benzimidazol-5-yl}pyrrolidine-3-carboxylate (Trans Isomer)

The title compound (133 mg, quantitative) was prepared from Intermediate 104 (91 mg, 0.30 mmol) and trans-(2S)-2-(tert-butoxycarbonylamino)-2-(4-methylcyclohexyl)acetic acid (80 mg, 0.29 mmol) in accordance with Procedure X. LCMS (Method 5): [M+H]+ m/z 446, RT 1.05 minutes.

Intermediate 161

2-{2-[(S)-amino(4-methylcyclohexyl)methyl]-4,6-difluoro-H-benzimidazol-5-yl}-N,N-dimethylbenzamide (Trans Isomer)

The title compound (274 mg, 95%) was prepared from Intermediate 99 (165 mg, 0.57 mmol) and trans-(2S)-2-(tert-butoxycarbonylamino)-2-(4-methylcyclohexyl)acetic acid (161 mg, 0.59 mmol) in accordance with Procedure X. LCMS (Method 5): [M+H]+ m/z 427, RT 1.18 minutes.

Intermediate 162

(5-Bromo-4-fluoro-1H-benzimidazol-2-yl)(cyclooctyl)methanamine

The title compound (186 mg, quantitative) was prepared from Intermediate 130 (235 mg, 0.48 mmol) in accordance with Procedure Z. LCMS (Method 5): [M+H]+ m/z 354, RT 1.08 minutes.

Intermediate 163

N-[(5-Bromo-4-fluoro-1H-benzimidazol-2-yl)(cyclooctyl)methyl]-2-ethylpyrazole-3-carboxamide The title compound (184 mg, 81%) was prepared from Intermediate 162 (165 mg, 0.57 mmol) and 1-ethyl-1H-pyrazole-5-carboxylic acid (78 mg, 0.55 mmol) in accordance with Procedure A. LCMS (Method 5): [M+H]+ m/z 476, RT 1.45 minutes.

Intermediate 164 tert-Butyl N-[(S)-(5-bromo-1H-imidazo[4,5-b]pyridin-2-yl)(4-methylcyclohexyl)methyl]-carbamate (Trans Isomer)

To a solution of trans-(2S)-2-(tert-butoxycarbonylamino)-2-(4-methylcyclohexyl)acetic acid (350 mg, 1.29 mmol) and 6-bromopyridine-2,3-diamine (280 mg, 1.42 mmol) in DCM (5 mL) were added HATU (590 mg, 1.55 mmol) and DIPEA (0.45 mL, 2.6 mmol). The reaction mixture was stirred at r.t. for 2 days, then partitioned between DCM and water. The organic layers were separated and dried over $Na_2SO_4$, then concentrated in vacuo. The residue was taken up in EtOH (5.4 mL) and water (0.6 mL), and NaOH (260 mg, 6.5 mmol) was added. The reaction mixture was heated at 80° C. overnight, then concentrated in vacuo. The residue was purified by flash chromatography, eluting with EtOAc/hexanes (50-100% gradient), to give the title compound (69 mg, 12%). LCMS (Method 5): [M+H]+ m/z 423, RT 1.36 minutes.

Intermediate 165

(S)-(5-Bromo-1H-imidazo[4,5-b]pyridin-2-yl)(4-methylcyclohexyl)methanamine (Trans Isomer)

The title compound (30 mg, 58%) was prepared from Intermediate 164 (69 mg, 0.16 mmol) in accordance with Procedure Z. LCMS (Method 5): [M+H]+ m/z 325, RT 1.08 minutes.

Intermediate 166

N-[(S)-(5-Bromo-1H-imidazo[4,5-b]pyridin-2-yl)(4-methylcyclohexyl)methyl]-2-ethyl-pyrazole-3-carboxamide (Trans Isomer)

The title compound (38 mg, 92%) was prepared from Intermediate 165 (30 mg, 0.09 mmol) and 1-ethyl-1H-pyrazole-5-carboxylic acid (17 mg, 0.11 mmol) in accordance with Procedure A. LCMS (Method 5): [M+H]$^+$ m/z 447, RT 1.27 minutes.

Intermediate 167

N-[(6-Bromo-4-methoxy-1H-imidazo[4,5-c]pyridin-2-yl)(cyclooctyl)methyl]-2-methyl-pyrazole-3-carboxamide To a solution of Intermediate 5 (400 mg, 1.36 mmol), Intermediate 65 (297 mg, 1.36 mmol) and DIPEA (0.36 mL, 2.1 mmol) in DMF (3 mL) was added T3P® (0.81 mL, 1.4 mmol). The reaction mixture was heated overnight at 70° C., then concentrated in vacuo, and partitioned between EtOAc and water. The organic layers were dried over Na$_2$SO$_4$, then the solvent was removed in vacuo. The residue was taken up in EtOH (5.4 mL) and water (0.6 mL), and NaOH (260 mg, 6.5 mmol) was added. The reaction mixture was heated at 80° C. overnight, then concentrated in vacuo, to furnish the title compound (155 mg, 61% overall). LCMS (Method 5): [M+H]$^+$ m/z 423, RT 1.36 minutes.

Intermediate 168

N-[(5-Bromo-4-fluoro-1H-benzimidazol-2-yl)(cyclooctyl)methyl]-3-methylisoxazole-4-carboxamide The title compound (82 mg, 12%) was prepared from Intermediate 7 (362 mg, 1.23 mmol) and 4-bromo-3-fluorobenzene-1,2-diamine (251 mg, 1.18 mmol) in accordance with Procedure Y. LCMS (Method 5): [M+H]$^+$ m/z 465, RT 1.45 minutes.

Intermediate 169 tert-Butyl 4-(2-{cyclooctyl[(3-methylisoxazole-4-carbonyl)amino]methyl}-4-fluoro-1H-benzimidazol-5-yl)piperidine-1-carboxylate The title compound (463 mg, 75%) was prepared from Intermediate 7 (444 mg, 1.51 mmol) and Intermediate 74 (476 mg, 1.51 mmol) in accordance with Procedure Y. LCMS (Method 5): [M+H]$^+$ m/z 568, RT 1.65 minutes.

Intermediate 170

O$^1$-tert-Butyl O$^3$-ethyl 4-{2-[(S)-benzyloxycarbonylamino(4-methylcyclohexyl)methyl]-4-fluoro-1H-benzimidazol-5-yl}pyrrolidine-1,3-dicarboxylate (Trans Isomer)

The title compound (220 mg, quantitative) was prepared from trans-(2S)-2-(benzyloxycarbonylamino)-2-(4-methylcyclohexyl)acetic acid (125 mg, 0.33 mmol) and Intermediate 98 (162 mg, 0.44 mmol) in accordance with Procedure AA. LCMS (Method 5): [M+H]$^+$ m/z 637, RT 1.56 minutes.

Intermediate 171 tert-Butyl 3-{2-[(S)-benzyloxycarbonylamino(4-methylcyclohexyl)methyl]-4-fluoro-1H-benzimidazol-5-yl}-4-(dimethylcarbamoyl)pyrrolidine-1-carboxylate (Trans Isomer)

To a solution of LiOH.H$_2$O (10 mg, 0.42 mmol) in water (0.5 mL) was added Intermediate 170 (220 mg, 0.35 mmol) in EtOH (2 mL). The reaction mixture was stirred for 8 h, then concentrated in vacuo. The residue was suspended in DCM (3 mL), and HATU (165 mg, 0.42 mmol), DIPEA (0.35 mL, 46.8 mmol) and a 2M solution of dimethylamine in THF (0.35 mL, 0.7 mmol) were added. The mixture was stirred under N$_2$ for 4 days, then partitioned between DCM and water. The organic layers were separated, dried over Na$_2$SO$_4$ and concentrated in vacuo. The crude material was flashed down an SCX column, eluting with a 7N solution of NH$_3$ in MeOH, to give the title compound (153 mg, 69%). LCMS (Method 5): [M+H]$^+$ m/z 636.4, RT 1.44 minutes.

Intermediate 172 tert-Butyl 3-(dimethylcarbamoyl)-4-(2-{(S)-[(3-ethylisoxazole-4-carbonyl)amino](4-methylcyclohexyl)methyl}-4-fluoro-1H-benzimidazol-5-yl)pyrrolidine-1-carboxylate (Trans Isomer)

To a solution of Intermediate 171 (153 mg, 0.24 mmol) in EtOH at r.t. was added 10% Pd/C (20 mg). The reaction mixture was stirred under an atmosphere of hydrogen for 2 h, then filtered through Celite®, washing with EtOAc. The filtrate was concentrated in vacuo. The residue was taken up in DCM (2 mL), and HATU (110 mg, 0.28 mmol), 3-ethylisoxazole-4-carboxylic acid (42 mg, 0.28 mmol) and DIPEA (80 µL, 0.5 mmol) were added. The reaction mixture was stirred at r.t. overnight, then partitioned between DCM and water. The organic layers were dried over Na$_2$SO$_4$, then concentrated in vacuo, to yield the crude title compound (205 mg. 60% overall). LCMS (Method 5): [M+H]$^+$ m/z 625, RT 1.37 minutes.

Intermediate 173 tert-Butyl 4-[(2-{cyclooctyl[(3-methylisoxazole-4-carbonyl)amino]methyl}-1H-benzimidazol-5-yl)methyl]piperazine-1-carboxylate The title compound (94 mg, 20%) was prepared from Intermediate 7 (240 mg, 0.82 mmol) and Intermediate 67 (248 mg, 0.81 mmol) in accordance with Procedure Y. LCMS (Method 5): [M+H]$^+$ m/z 565, RT 1.49 minutes.

Intermediate 174

N-{Cyclooctyl[5-(piperazin-1-ylmethyl)-1H-benzimidazol-2-yl]methyl}-3-methyl-isoxazole-4-carboxamide The title compound (80 mg, quantitative) was prepared from Intermediate 173 (94 mg, 0.17 mmol) in accordance with Procedure P. LCMS (Method 5): [M+H]$^+$ m/z 465, RT 1.09 minutes.

Intermediate 175 tert-Butyl 4-[(2-{cyclooctyl[(2-methylpyrazole-3-carbonyl)amino]methyl}-4-methoxy-1H-imidazo[4,5-c]pyridin-6-yl)methyl]piperazine-1-carboxylate The title compound (122 mg, quantitative) was prepared from Intermediate 167 (98 mg, 0.21 mmol) in accordance with Procedure R. LCMS (Method 5): [M+H]$^+$ m/z 595, RT 1.42 minutes.

Intermediate 176

N-{Cyclooctyl[4-methoxy-6-(piperazin-1-ylmethyl)-1H-imidazo[4,5-c]pyridin-2-yl]-methyl}-2-methylpyrazole-3-carboxamide The title compound (100 mg, quantitative) was prepared from Intermediate 175 (122 mg, 0.21 mmol) in accordance with Procedure P. LCMS (Method 5): [M+H]$^+$ m/z 495, RT 1.25 minutes.

Intermediate 177

2-[(S)-Amino(4-methylcyclohexyl)methyl]-4-fluoro-1H-benzimidazole-5-carbonitrile (Trans Isomer)

The title compound (157 mg, 97%) was prepared from trans-(2S)-2-(tert-butoxycarbonylamino)-2-(4-methylcyclohexyl)acetic acid (1 g, 3.69 mmol) and 3,4-diamino-2-fluorobenzonitrile (585 mg, 3.87 mmol) in accordance with Procedure X. LCMS (Method 5): [M+H]$^+$ m/z 287, RT 1.13 minutes.

Intermediate 178 tert-Butyl 4-[(2-{cyclooctyl[(3-methylisoxazole-4-carbonyl)amino]methyl}-7-methoxy-3H-benzimidazol-5-yl)methyl]piperazine-1-carboxylate The title compound (33 mg, 16%) was prepared from Intermediate 7 (103 mg, 0.35 mmol) and Intermediate 69 (117 mg, 0.35 mmol) in accordance with Procedure Y. LCMS (Method 5): [M+H]$^+$ m/z 595, RT 1.47 minutes.

Intermediate 179

N-{Cyclooctyl[4-methoxy-6-(piperazin-1-ylmethyl)-1H-benzimidazol-2-yl]methyl}-3-methylisoxazole-4-carboxamide The title compound (25 mg, 93%) was prepared from Intermediate 178 (33 mg, 0.05 mmol) in accordance with Procedure P. LCMS (Method 5): [M+H]$^+$ m/z 495, RT 1.17 minutes.

Intermediate 180 tert-Butyl 4-[(2-{cyclooctyl[(3-methylisoxazole-4-carbonyl)amino]methyl}-4-fluoro-1H-benzimidazol-5-yl)methyl]piperidine-1-carboxylate The title compound (45 mg, 16%) was prepared from Intermediate 7 (67 mg, 0.23 mmol) and Intermediate 58 (70 mg, 0.22 mmol) in accordance with Procedure Y. LCMS (Method 5): [M+H]$^+$ m/z 582, RT 1.56 minutes.

Intermediate 181

N-{Cyclooctyl[4-fluoro-5-(piperidin-4-ylmethyl)-1H-benzimidazol-2-yl]methyl}-3-methylisoxazole-4-carboxamide The title compound (19 mg, 59%) was prepared from Intermediate 180 (45 mg, 0.03 mmol) in accordance with Procedure P. LCMS (Method 5): [M+H]$^+$ m/z 482, RT 1.17 minutes.

Intermediate 182 tert-Butyl 4-[(2-{cyclooctyl[(3-methylisoxazole-4-carbonyl)amino]methyl}-7-fluoro-3H-benzimidazol-5-yl)methyl]piperidine-1-carboxylate The title compound (277 mg, 24%) was prepared from Intermediate 7 (423 mg, 1.44 mmol) and Intermediate 94 (443 mg, 1.37 mmol) in accordance with Procedure Y. LCMS (Method 5): [M+H]$^+$ m/z 582, RT 1.68 minutes.

Intermediate 183

N-{Cyclooctyl[4-fluoro-6-(piperidin-4-ylmethyl)-1H-benzimidazol-2-yl]methyl}-3-methylisoxazole-4-carboxamide The title compound (210 mg, quantitative) was prepared from Intermediate 182 (255 mg, 0.44 mmol) in accordance with Procedure P. LCMS (Method 5): [M+H]$^+$ m/z 482, RT 1.20 minutes.

Intermediate 184

N-[(6-Bromo-4-fluoro-1H-benzimidazol-2-yl)(cyclooctyl)methyl]-3-methylisoxazole-4-carboxamide The title compound (220 mg, 46%) was synthesized from Intermediate 7 (300 mg, 0.99 mmol) and 5-bromo-3-fluorobenzene-1,2-diamine (210 mg, 1.03 mmol) in accordance with Procedure Y. LCMS (Method 5): [M+H]$^+$ m/z 463, RT 2.61 minutes.

Intermediate 185

Methyl (2S)-1-({2-[(S)-amino(4-methylcyclohexyl)methyl]-4-fluoro-1H-benzimidazol-5-yl}methyl)pyrrolidine-2-carboxylate (Trans Isomer)

The title compound (127 mg, 57%), an off white powder, was prepared from Intermediate 113 (221 mg, 0.55 mmol) and trans-(2S)-2-(tert-butoxycarbonylamino)-2-(4-methylcyclohexyl)acetic acid (181 mg, 0.67 mmol) in accordance with Procedure X. LCMS (Method 1): [M+H]$^+$ m/z 403, RT 1.39 minutes.

Intermediate 186

Methyl (2R)-1-({2-[(S)-amino(4-methylcyclohexyl)methyl]-4-fluoro-1H-benzimidazol-5-yl}methyl)pyrrolidine-2-carboxylate (Trans Isomer)

The title compound (125 mg, 62%), a tan gum, was prepared from Intermediate 114 (220 mg, 0.50 mmol) and trans-(2S)-2-(tert-butoxycarbonylamino)-2-(4-methyl-cyclohexyl)acetic acid (163 mg, 0.50 mmol) in accordance with Procedure X. LCMS (Method 1): [M+H]$^+$ m/z 403, RT 1.40 minutes.

Intermediate 187 (Procedure BB)

(NE)-N-(Cycloheptylmethylene)-2-methylpropane-2-sulfinamide

To a solution of cycloheptane carbaldehyde (170 mg, 1.35 mmol) in DCM (2 mL) at r.t. were added 2-methylpropane-2-sulfinamide (1.35 mmol), MgSO$_4$ (6 mmol) and pyridinium p-toluenesulfonate (0.07 mmol) sequentially. The reaction mixture was stirred for 16 h, then filtered. The filtrate was concentrated in vacuo. Purification of the residue by flash column chromatography, eluting with EtOAc/hexanes (0-50% gradient), gave the title compound (134 mg, 43%) as a colourless oil. LCMS (Method 5): [M+H]$^+$ m/z 230, RT 1.53 minutes.

Intermediate 188

(NE)-N-(Cyclohexylmethylene)-2-methylpropane-2-sulfinamide

The title compound (740 mg, 86%) was prepared from cyclohexane carbaldehyde (0.50 mL, 4.00 mmol) in accordance with Procedure BB. LCMS (Method 5): [M+H]$^+$ m/z 216, RT 1.37 minutes.

Intermediate 189

(NE)-N-(Dispiro[2.0.24.13]heptan-7-ylmethylene)-2-methylpropane-2-sulfinamide

The title compound (189 mg, 53%) was prepared from dispiro[2.0.24.13]heptane-7-carbaldehyde (192 mg, 1.57 mmol) in accordance with Procedure BB. LCMS (Method 5): [M+H]$^+$ m/z 226, RT 1.33 minutes.

Intermediate 190

(NE)-2-Methyl-N-(norcaran-3-ylmethylene)propane-2-sulfinamide

The title compound (254 mg, 77%) was prepared from norcarane-3-carbaldehyde (179 mg, 1.44 mmol) in accordance with Procedure BB. LCMS (Method 5): [M+H]$^+$ m/z 228, RT 1.44 minutes.

Intermediate 191

(NE)-2-Methyl-N-[(3-methylcyclohexyl)methylene]propane-2-sulfinamide

The title compound (666 mg, 73%) was prepared from 3-methylcyclohexane carbaldehyde (500 mg, 3.96 mmol) in accordance with Procedure BB. LCMS (Method 5): [M+H]$^+$ m/z 230, RT 1.53 minutes.

Intermediate 192

(NE)-2-Methyl-N-(norcaran-7-ylmethylene)propane-2-sulfinamide

The title compound (332 mg, 91%) was prepared from rac-(1S,6R)-norcarane-7-carbaldehyde (200 mg, 1.61 mmol) in accordance with Procedure BB. LCMS (Method 5): [M+H]$^+$ m/z 228, RT 1.35 minutes.

Intermediate 193

(NE)-2-Methyl-N-[(2-methylcyclohexyl)methylene]propane-2-sulfinamide

The title compound (391 mg, 43%) was prepared from 2-methylcyclohexane carbaldehyde (500 mg, 3.96 mmol) in accordance with Procedure BB. LCMS (Method 5): [M+H]$^+$ m/z 230, RT 1.50 minutes.

Intermediate 194

(NE)-N-[(3,5-Dimethylcyclohexyl)methylene]-2-methylpropane-2-sulfinamide

The title compound (395 mg, 48%) was prepared from 3,5-dimethylcyclohexane carbaldehyde (470 mg, 3.35 mmol) in accordance with Procedure BB. LCMS (Method 5): [M+H]$^+$ m/z 244, RT 1.54 and 1.56 minutes (observable diastereomer separation).

Intermediate 195

2-{[7-Fluoro-6-(tetrahydropyran-4-yl)benzimidazol-1-yl]methoxy}ethyl(trimethyl)silane A solution of Intermediate 24 (1 g, 4.75 mmol) in formic acid (24 mL) was heated at 110° C. overnight. The reaction mixture was cooled, then concentrated in vacuo. The residue was dissolved in EtOAc (30 mL). The organic layers were washed with saturated aqueous NaHCO$_3$ solution (30 mL), dried over MgSO$_4$, and concentrated in vacuo. The crude residue was purified by flash column chromatography, eluting with EtOAc (100%) then MeOH/DCM (gradient 0-10%). NaH (60% by mass, 185 mg, 4.64 mmol) was suspended in DMF (8 mL), and the purified solid was added as a solution in DMF (8 mL) dropwise over 10 minutes. After a further 90 minutes, 2-(trimethylsilyl)ethoxymethyl chloride (0.82 mL, 4.6 mmol) was added dropwise over 10 minutes. The mixture was stirred at r.t. overnight. Water (50 mL) was added, and the mixture was extracted with EtOAc (100 mL). The organic layers were separated, dried over MgSO$_4$, and concentrated in vacuo. The crude residue was purified by flash chromatography, eluting with EtOAc/hexanes (30-80% gradient), to furnish the title compound (1.34 g, 80%) as a colourless oil. LCMS (Method 5): [M+H]$^+$ m/z 351, RT 1.45 minutes.

Intermediate 196

Methyl 1-(3,4-diamino-2-fluorophenyl)piperidine-3-carboxylate

The title compound (299 mg, 79%) was prepared from 2,3-difluoro-6-nitroaniline (250 mg, 1.40 mmol) and methyl piperidine-3-carboxylate (425 mg, 2.82 mmol) in accordance with Procedure M. LCMS (Method 5): [M+H]$^+$ m/z 268, RT 0.90 minutes.

Intermediate 197

6-Fluoro-N$^4$-(tetrahydropyran-4-yl)benzene-1,2,4-triamine

The title compound (132 mg, 84%) was prepared from Intermediate 28 (300 mg, 0.70 mmol) and tetrahydropyran- 4-amine (110 mg, 1.03 mmol) in accordance with Procedure J. LCMS (Method 5): [M+H]⁺ m/z 226, RT 0.59 minutes.

Intermediate 198

3-Bromo-N,N-dimethylpyrazine-2-carboxamide

The title compound (548 mg, 70%) was prepared from 3-bromopyrazine-2-carboxylic acid (502 mg, 2.47 mmol) and a 2M solution of dimethylamine in THF (2.5 mL, 5.0 mmol) in accordance with Procedure A, with DCM (5 mL) as solvent. LCMS (Method 5): [M+H]⁺ m/z 230, RT 0.30 minutes.

Intermediate 199

3-{2-[(S)-Amino(4-methylcyclohexyl)methyl]-4-fluoro-1H-benzimidazol-5-yl}-N,N-dimethylpyrazine-2-carboxamide (Trans Isomer)

The title compound (41 mg, 44%) was prepared from Intermediate 139 (103 mg, 0.21 mmol) and Intermediate 198 (109 mg, 0.35 mmol) in a sequential fashion in accordance with Procedures G and Z. LCMS (Method 5): [M+H]⁺ m/z 411, RT 0.98

Intermediate 200

5-{2-[(S)-(tert-Butoxycarbonylamino)(4-methylcyclohexyl)methyl]-4-fluoro-1H-benzimidazol-5-yl}-2-methylpyrimidine-4-carboxylic Acid (Trans Isomer)

The title compound (82 mg, 80%) was prepared from Intermediate 139 (100 mg, 0.21 mmol) and 5-bromo-2-methylpyrimidine-4-carboxylic acid (58 mg, 0.27 mmol) in accordance with Procedure G. LCMS (Method 5): [M+H]⁺ m/z 498, RT 1.02 minutes.

Intermediate 201 tert-Butyl N-[(S)-{5-[4-(dimethylcarbamoyl)-2-methylpyrimidin-5-yl]-4-fluoro-1H-benzimidazol-2-yl}(4-methylcyclohexyl)methyl]carbamate (Trans Isomer)

The title compound (6.4 mg, 7%) was prepared from Intermediate 200 (82 mg, 0.16 mmol) and a 2M solution of dimethylamine in THF (0.17 mL, 0.34 mmol) in accordance with Procedure A. LCMS (Method 5): [M+H]⁺ m/z 525, RT 1.24 minutes.

Intermediate 202

5-{2-[(S)-Amino(4-methylcyclohexyl)methyl]-4-fluoro-1H-benzimidazol-5-yl}-N,N,2-trimethylpyrimidine-4-carboxamide (Trans Isomer)

The title compound (5.6 mg, quantitative) was prepared from Intermediate 201 (6.4 mg, 0.012 mmol) in accordance with Procedure Z. LCMS (Method 5): [M+H]⁺ m/z 425, RT 1.00 minute.

Intermediate 203

(3-Bromopyridin-4-yl)(3,3-difluoroazetidin-1-yl)methanone

The title compound (384 mg, 55%) was prepared from 3-bromopyridine-4-carboxylic acid (523 mg, 2.50 mmol) and 3,3-difluoroazetidine hydrochloride (679 mg, 5.24 mmol) in accordance with Procedure A, with DCM (5 mL) as solvent. LCMS (Method 5): [M+H]⁺ m/z 277, RT 0.75 minutes.

Intermediate 204

(3-{2-[(S)-Amino(4-methylcyclohexyl)methyl]-4-fluoro-1H-benzimidazol-5-yl}pyridin-4-yl)(3,3-difluoroazetidin-1-yl)methanone (Trans Isomer)

The title compound (24 mg, 49%) was prepared from Intermediate 139 (51 mg, 0.10 mmol) and Intermediate 203 (32 mg, 0.12 mmol) in a sequential fashion in accordance with Procedures G and Z. LCMS (Method 5): [M+H]⁺ m/z 458, RT 1.07 minutes.

Intermediate 205

(3-Bromopyridin-4-yl)(3-hydroxy-3-methylazetidin-1-yl)methanone

The title compound (148 mg, 23%) was prepared from 3-bromopyridine-4-carboxylic acid (523 mg, 2.50 mmol) and 3-methylazetidin-3-ol hydrochloride (661 mg, 5.08 mmol) in accordance with Procedure A, with DCM (5 mL) as solvent. LCMS (Method 5): [M+H]⁺ m/z 273, RT 0.31 minutes.

Intermediate 206

(3-{2-[(S)-Amino(4-methylcyclohexyl)methyl]-4-fluoro-1H-benzimidazol-5-yl}pyridin-4-yl)(3-hydroxy-3-methylazetidin-1-yl)methanone (Trans Isomer)

The title compound (42 mg, 86%) was prepared from Intermediate 139 (51 mg, 0.10 mmol) and Intermediate 205 (48 mg, 0.18 mmol) in a sequential fashion in accordance with Procedures G and Z. LCMS (Method 5): [M+H]⁺ m/z 452, RT 0.95 minutes.

Intermediate 207

Azetidin-1-yl(3-bromopyridin-4-yl)methanone

The title compound (302 mg, 52%) was prepared from 3-bromopyridine-4-carboxylic acid (523 mg, 2.50 mmol) and azetidine (0.24 mL, 3.60 mmol) in accordance with Procedure A, with DCM (5 mL) as solvent. LCMS (Method 5): [M+H]⁺ m/z 241, RT 0.59 minutes.

Intermediates 208 & 209

(3-{2-[(S)-Amino(4-methylcyclohexyl)methyl]-4-fluoro-1H-benzimidazol-5-yl}pyridin-4-yl)(azetidin-1-yl)methanone (trans isomer) (Intermediate 208)

3-{2-[(S)-Amino(4-methylcyclohexyl)methyl]-4-fluoro-1H-benzimidazol-5-yl}-N-(3-chloropropyl)pyridine-4-carboxamide (trans isomer) (Intermediate 209)

Intermediate 139 (101 mg, 0.21 mmol), 1,4-dioxane (3 mL), water (0.5 mL), K₂CO₃ (100 mg, 0.72 mmol) and Intermediate 207 (111 mg, 0.46 mmol) were sparged with N₂ for 5 minutes, then Pd(dppf)Cl₂.DCM (13 mg, 0.02 mmol)

was added. The reaction mixture was further sparged with N₂ for 5 minutes, then heated at 110° C. in a PLS synthesiser overnight. The reaction mixture was cooled to r.t. and water (5 mL) was added, followed by DCM (10 mL). The mixture was filtered through a phase separation frit, washing further with DCM. The organic phase was concentrated in vacuo. The residue was purified by flash column chromatography, eluting with EtOAc/hexanes (0-100% gradient) then MeOH/DCM (0-20% gradient). The recovered material was taken up in DCM (5 mL) and treated with 4M HCl in dioxane (1 mL). The reaction mixture was stirred for 4 h, then concentrated in vacuo, to provide the title compounds (85 mg). LCMS confirmed that the product was a mixture of Intermediate 208 and Intermediate 209 in a ratio of 85:11 respectively. LCMS (Method 5): [M+H]⁺ m/z 422, RT 0.99 minutes (Intermediate 208); and [M+H]⁺ m/z 458, RT 1.05 minutes (Intermediate 209).

Intermediate 210

(S)-{4-Fluoro-5-[4-(methylsulfanyl)pyridin-3-yl]-1H-benzimidazol-2-yl}(4-methyl-cyclohexyl)methanamine (Trans Isomer)

The title compound (82 mg, 68%) was prepared from Intermediate 139 (150 mg, 0.31 mmol) and 3-bromo-4-(methylthio)pyridine (65 mg, 0.32 mmol) in a sequential fashion in accordance with Procedures G and Z. LCMS (Method 5): [M+H]⁺ m/z 385, RT 1.14 minutes.

Intermediate 211

3-Ethyl-N-[(S)-{4-fluoro-5-[4-(methylsulfanyl)pyridin-3-yl]-1H-benzimidazol-2-yl}(4-methylcyclohexyl)methyl]isoxazole-4-carboxamide (Trans Isomer)

The title compound (109 mg, quantitative) was prepared from Intermediate 210 (82 mg, 0.21 mmol) and 3-ethyl-isoxazole-4-carboxylic acid (40 mg, 0.27 mmol) in accordance with Procedure A, with DCM (5 mL) as solvent. LCMS (Method 5): [M+H]⁺ m/z 508, RT 1.31 minutes.

Intermediate 212

3-(2-{(S)-[(2-Ethylpyrazole-3-carbonyl)amino](4-methylcyclohexyl)methyl}-1H-imidazo[4,5-b]pyridin-5-yl)pyridine-4-carboxylic Acid (Trans Isomer)

The title compound (93 mg, 42%) was prepared from Intermediate 166 (204 mg, 0.46 mmol) and 3-boronoisonicotinic acid (102 mg, 0.55 mmol) in accordance with Procedure G. LCMS (Method 5): [M+H]⁺ m/z 488, RT 0.91 minutes.

Intermediate 213

N-[(S)-(5-Bromo-1H-imidazo[4,5-b]pyridin-2-yl)(4-methylcyclohexyl)methyl]-2-methyl-pyrazole-3-carboxamide (Trans Isomer)

The title compound (612 mg, 65%) was prepared from Intermediate 165 (707 mg, 2.19 mmol) and 1-methyl-1H-pyrazole-5-carboxylic acid (350 mg, 2.64 mmol) in accordance with Procedure A, with DCM (5 mL) as solvent. LCMS (Method 5): [M+H]⁺ m/z 431, RT 1.18 minutes.

Intermediate 214

Methyl 4-(2-{(S)-(4-methylcyclohexyl)[(2-methylpyrazole-3-carbonyl)amino]methyl}-1H-imidazo[4,5-b]pyridin-5-yl)furan-3-carboxylate (Trans Isomer)

The title compound (124 mg, 55%) was prepared from Intermediate 213 (204 mg, 0.47 mmol) and 4-(methoxycarbonyl)furan-3-boronic acid pinacol ester (150 mg, 0.58 mmol) in accordance with Procedure G. LCMS (Method 5): [M+H]⁺ m/z 477, RT 1.25 minutes.

Intermediate 215

4-(2-{(S)-(4-Methylcyclohexyl)[(2-methylpyrazole-3-carbonyl)amino]methyl}-1H-imidazo[4,5-b]pyridin-5-yl)furan-3-carboxylic Acid (Trans Isomer)

A solution of LiOH.H₂O (10 mg, 0.42 mmol) in water (0.5 mL) was added to a solution of Intermediate 214 (124 mg, 0.26 mmol) in EtOH (2 mL). The mixture was stirred at r.t. for 3.5 h, then concentrated in vacuo, to give the title compound (120 mg, quantitative). LCMS (Method 5): [M+H]⁺ m/z 463, RT 0.95 minutes.

Intermediate 216 tert-Butyl 3-{2-[(S)-amino(4-methylcyclohexyl)methyl]-4-fluoro-1H-benzimidazol-5-yl}-morpholine-4-carboxylate (Trans Isomer)

To a solution of Intermediate 155 (1.15 g, 1.72 mmol) in acetonitrile (24 mL) at r.t. was added diethylamine (6 mL, 57.95 mmol). The mixture was stirred overnight, then concentrated in vacuo. The residue was filtered through an SCX column, washing with MeOH before eluting with a 7N solution of NH₃ in MeOH. The washings were concentrated in vacuo and purified by flash chromatography, eluting with EtOAc/hexanes (0-100% gradient) then MeOH/DCM (0-10% gradient), to give the title compound (608 mg, 79%) as a foam. LCMS (Method 5): [M+H]⁺ m/z 447, RT 1.26 minutes.

Intermediate 217

Methyl 4-{2-[(S)-(tert-butoxycarbonylamino)(cyclopentyl)methyl]-4-fluoro-1H-benzimidazol-5-yl}tetrahydrofuran-3-carboxylate The title compound (272 mg, 41%) was prepared from Intermediate 96 (321 mg, 1.26 mmol) and (2S)-2-(tert-butoxycarbonylamino)-2-cyclopentylacetic acid (310 mg, 1.21 mmol) in accordance with Procedure AA. LCMS (Method 5): [M+H]⁺ m/z 462, RT 1.20 minutes.

Intermediate 218

4-{2-[(S)-(tert-Butoxycarbonylamino)(cyclopentyl)methyl]-4-fluoro-1H-benzimidazol-5-yl}tetrahydrofuran-3-carboxylic Acid A solution of LiOH.H₂O (20 mg, 0.84 mmol) in water (0.5 mL) was added to a solution of Intermediate 217 (318 mg, 0.69 mmol) in EtOH (2 mL). The mixture was stirred at r.t. for 3.5 h, then concentrated in vacuo, to give the title

Intermediate 219

Methyl 4-{2-[(S)-amino(cyclopentyl)methyl]-4-fluoro-1H-benzimidazol-5-yl}-tetrahydrofuran-3-carboxylate The title compound (194 mg, quantitative) was prepared from Intermediate 217 (271 mg, 0.52 mmol) in accordance with Procedure Z. LCMS (Method 5): [M+H]+ m/z 362, RT 0.94 minutes.

Intermediate 220

Methyl 4-(2-{(S)-cyclopentyl[(3-ethylisoxazole-4-carbonyl)amino]methyl}-4-fluoro-1H-benzimidazol-5-yl)tetrahydrofuran-3-carboxylate The title compound (229 mg, 88%) was prepared from Intermediate 219 (194 mg, 0.54 mmol) and 3-ethylisoxazole-4-carboxylic acid (100 mg, 0.67 mmol) in accordance with Procedure A, with DCM (5 mL) as solvent. LCMS (Method 5): [M+H]+ m/z 485, RT 1.14 minutes.

Intermediate 221

4-(2-{(S)-Cyclopentyl[(3-ethylisoxazole-4-carbonyl)amino]methyl}-4-fluoro-1H-benzimidazol-5-yl)tetrahydrofuran-3-carboxylic acid A solution of LiOH.H$_2$O (15 mg, 0.63 mmol) in water (0.5 mL) was added to a solution of Intermediate 220 (229 mg, 0.47 mmol) in EtOH (2 mL). The mixture was stirred at r.t. for 3.5 h, then concentrated in vacuo, to give the title compound (222 mg, quantitative). LCMS (Method 5): [M+H]+ m/z 471, RT 0.87 minutes.

Intermediate 222

(4-{2-[(S)-Amino(cyclopentyl)methyl]-4-fluoro-1H-benzimidazol-5-yl}tetrahydrofuran-3-yl)(3,3-difluoroazetidin-1-yl)methanone The title compound (234 mg, 80%) was prepared from Intermediate 218 (309 mg, 0.69 mmol) and 3,3-difluoroazetidine hydrochloride (145 mg, 1.40 mmol) in a sequential manner in accordance with Procedures A and Z. LCMS (Method 5): [M+H]+ m/z 423, RT 0.93 minutes.

Intermediate 223

(S)-(5-Bromo-4-fluoro-1H-benzimidazol-2-yl)(4-methylcyclohexyl)methanamine (Trans Isomer)

The title compound (3.9 g, quantitative) was prepared from Intermediate 138 (3.8 g, 8.7 mmol) in accordance with Procedure Z. LCMS (Method 5): [M+H]+ m/z 342, RT 1.27 minutes.

Intermediate 224

N-[(S)-(5-Bromo-4-fluoro-1H-benzimidazol-2-yl)(4-methylcyclohexyl)methyl]-2-methyl-pyrazole-3-carboxamide (Trans Isomer)

The title compound (4.6 g, 61%) was prepared from Intermediate 223 (5.7 g, 16.7 mmol) and 1-methyl-1H-pyrazole-5-carboxylic acid (2.65 g, 19.9 mmol) in accordance with Procedure A, using DCM as solvent. LCMS (Method 5): [M+H]+ m/z 451, RT 1.36

Intermediate 225

N-{(S)-[4-Fluoro-5-(4,4,5,5-tetramethyl-1,3,2-dioxaborolan-2-yl)-1H-benzimidazol-2-yl]-(4-methylcyclohexyl)methyl}-2-methylpyrazole-3-carboxamide (Trans Isomer)

The title compound (1.77 g, 50%) was prepared from Intermediate 224 (1 g, 2.27 mmol) in accordance with Procedure C. LCMS (Method 5): [M+H]+ m/z 451, RT 1.36 minutes.

Intermediate 226

(4-Bromo-1H-pyrazol-3-yl)(3,3-difluoroazetidin-1-yl)methanone

The title compound (143 mg, 38.7%) was prepared from 4-bromo-1H-pyrazole-3-carboxylic acid (266 mg, 1.39 mmol) and 3,3-difluoroazetidine hydrochloride (197 mg, 1.52 mmol) in accordance with Procedure A, with DCM (5 mL) as solvent. LCMS (Method 5): [M+H]+ m/z 268, RT 0.71 minutes.

Intermediate 227

(5-Bromo-2-methylpyrimidin-4-yl)(3,3-difluoroazetidin-1-yl)methanone

The title compound (415 mg, 61%) was prepared from 5-bromo-2-methyl-pyrimidine-4-carboxylic acid (510 mg, 2.62 mmol) and 3,3-difluoroazetidine hydrochloride (340 mg, 2.62 mmol) in accordance with Procedure A, with DCM (5 mL) as solvent. LCMS (Method 5): [M+H]+ m/z 294, RT 0.79 minutes.

Intermediate 228

(5-Bromopyrimidin-4-yl)(3,3-difluoroazetidin-1-yl)methanone

The title compound (68 mg, 11%) was prepared from 5-bromopyrimidine-4-carboxylic acid (468 mg, 2.30 mmol) and 3,3-difluoroazetidine hydrochloride (354 mg, 2.73 mmol) in accordance with Procedure A, with DCM (5 mL) as solvent. LCMS (Method 5): [M+H]+ m/z 280, RT 0.66 minutes.

Intermediate 229

[4-(Dimethylcarbamoyl)pyridin-3-yl]boronic Acid

A 2.5M solution of n-butyllithium in hexane (6.1 mL, 15.3 mmol) was added over 10 minutes to a stirred solution of diisopropylamine (2.2 mL, 16.0 mmol) in anhydrous THF (16 mL) at −10° C. under N$_2$. The orange solution was stirred at −10° C. for 5 minutes, then at 0° C. for 10 minutes. The resultant orange solution was added over approximately 10 minutes to a stirred solution of N,N-dimethylisonicotinamide (2.00 g, 13.3 mmol) and triisopropyl borate (4.0 mL, 17.3 mmol) in anhydrous THF (22 mL) at approximately −5° C. under N$_2$. The mixture was stirred between −5° C. and 5° C. under nitrogen over 50 minutes. To the resulting brown suspension was added pinacol (2.36 g, 20.0 mmol), and the suspension was stirred at 20° C. under nitrogen for 1 h. The resultant canary yellow suspension was diluted with DCM (25 mL) and filtered through a Celite® pad, washing with DCM (4×25 mL). The filtrate was stood at r.t. overnight and the additional precipitated solids were removed by filtration, washing with DCM (2×30 mL). The filtrate was concentrated in vacuo. The resultant orange solid was purified by flash column chromatography, eluting with EtOAc/heptane (25-100% gradient) followed by MeOH/EtOAc (0-40% gradient), to afford the title compound (688 mg, 20%) as an orange powder. $\delta_H$ (500 MHz, DMSO-$d_6$) 8.73-8.71 (m, 1H), 8.19 (d, J 4.9 Hz, 1H), 6.84 (d, J 4.8 Hz, 1H), 2.96 (s, 3H), 2.75 (s, 3H). LCMS (Method 2): [M+H]$^+$ m/z 195, RT 0.11 minutes.

Intermediate 230

(3,3-Difluoroazetidin-1-yl)(3-methylimidazol-3-ium-1-yl)methanone Iodide

To a solution of 3,3-difluoroazetidine hydrochloride (1.00 g, 10.7 mmol) in acetonitrile (10.8 mL, 205 mmol) and DMF (3.30 mL, 43.0 mmol) at r.t. was added CDI (1.98 g, 11.8 mmol) in one portion. The mixture was stirred at r.t. for 16 h, then concentrated in vacuo. The residue was purified by flash column chromatography, eluting with EtOAc/hexanes (0-100% gradient) then MeOH/DCM (0-10% gradient). The resulting yellow oil was taken up in acetonitrile (18.9 mL) at r.t., to which was added iodomethane (2.88 mL, 45.8 mmol). The mixture was stirred at r.t. over 2 days, then concentrated in vacuo, to afford the title compound (2.49 g, quantitative overall) as a yellow solid. LCMS (Method 5): [M+H]$^+$ m/z 202, RT 0.46 minutes.

Intermediate 231

Mixture of tert-butyl N-[(S)-{5-bromo-4-fluoro-1-[2-(trimethylsilyl)ethoxymethyl]-benzimidazol-2-yl}(4-methylcyclohexyl)methyl]carbamate (trans isomer) and tert-butyl N-[(S)-{6-bromo-7-fluoro-1-[2-(trimethylsilyl)ethoxymethyl]benzimidazol-2-yl}(4-methylcyclohexyl)methyl]carbamate (Trans Isomer)

2-(Trimethylsilyl)ethoxymethyl chloride (0.11 mL, 0.62 mmol) was added to a stirred suspension of Intermediate 138 (250 mg, 0.57 mmol) and K$_2$CO$_3$ (196 mg, 1.42 mmol) in anhydrous DMF (5.7 mL). The reaction mixture was stirred at 20° C. under N$_2$ for 64 h. An additional portion of 2-(trimethylsilyl)ethoxymethyl chloride (0.03 mL, 0.17 mmol) was added, and stirring continued at 20° C. under N$_2$ for 24 h. The mixture was quenched with water (30 mL), and the resulting material was extracted with tert-butyl methyl ether (3×30 mL). The combined organic extracts were washed sequentially with water (20 mL) and brine (2×20 mL), then dried over MgSO$_4$ and concentrated in vacuo. The resultant viscous oil was purified by flash column chromatography, eluting with EtOAc/heptane (0-20% gradient), to afford the title compounds (55:45 ratio of regio-isomers) (266 mg, 82%) as a viscous oil. LCMS (Method 1): [M+H]$^+$ m/z 570 and 572, RT 2.70 and 2.76 minutes.

Intermediate 232

Mixture of tert-butyl N-[(S)-(5-{[dimethyl(oxo)-$\lambda^6$-sulfanylidene]amino}-4-fluoro-1-[2-(trimethylsilyl)ethoxymethyl]benzimidazol-2-yl)(4-methylcyclohexyl)methyl]carbamate (Trans Isomer) and tert-butyl N-[(S)-(6-{[dimethyl(oxo)-$\lambda^6$-sulfanylidene]amino}-7-fluoro-1-[2-(trimethylsilyl)ethoxymethyl]benzimidazol-2-yl)(4-methylcyclohexyl)-methyl]carbamate (Trans Isomer)

A sealed tube was charged with Intermediate 231 (55:45 mixture of isomers, 116 mg, 0.20 mmol), S,S-dimethylsulfoximine (38 mg, 0.41 mmol), Cs$_2$CO$_3$ (200 mg, 0.61 mmol), Pd$_2$(dba)$_3$ (9.3 mg, 0.01 mmol) and RuPhos (9.5 mg, 0.02 mmol) under N$_2$. The reagents were suspended in anhydrous 1,4-dioxane (2 mL), and the mixture was degassed by sparging with N$_2$ whilst sonicating for 5 minutes. The reaction mixture was sealed under N$_2$ and heated at 110° C. for 24 h. After cooling, the mixture was diluted with EtOAc (20 mL), and the solids were removed by filtration through a Celite® pad. The residue was washed with EtOAc (2×20 mL), and the filtrate was concentrated in vacuo. The resultant orange viscous oil was separated by flash column chromatography, eluting with EtOAc/heptane (0-100% gradient), to afford the title compounds (91 mg total mass, 76% overall) as tan powders. LCMS (Method 1): [M+H]$^+$ m/z 583, RT 2.22 minutes and 2.23 minutes.

Intermediate 233 tert-Butyl N-(6-chloro-5-fluoropyridin-3-yl)carbamate

A dried sealed tube was charged with 5-bromo-2-chloro-3-fluoropyridine (1.00 g, 4.75 mmol), tert-butyl carbamate (612 mg, 5.22 mmol) and Cs$_2$CO$_3$ (3.10 g, 9.51 mmol), and the reagents were suspended in anhydrous 1,4-dioxane (9.5 mL). The mixture was sparged with N$_2$ for 5 minutes whilst sonicating. The reaction mixture was charged with Pd$_2$(dba)$_3$ (109 mg, 0.12 mmol) and Xantphos (137 mg, 0.24 mmol), and the mixture was sparged with N$_2$ for 5 minutes whilst sonicating. The mixture was sealed under N$_2$ and heated at 85° C. for 24 h. After cooling, the mixture was diluted with EtOAc (10 mL) and the solids were removed via filtration through a Celite® pad, washing with EtOAc (3×20 mL). The filtrate was concentrated in vacuo. The resultant orange viscous oil was purified by flash column chromatography, eluting with EtOAc/heptane (0-20% gradient), to afford the title compound (844 mg, 67%) as an off-white powder. $\delta_H$ (500 MHz, CDCl$_3$) 8.04 (d, J 8.7 Hz, 1H), 7.98 (d, J 2.4 Hz, 1H), 6.71 (s, 1H), 1.52 (s, 9H). LCMS (Method 1): [M+H]$^+$ m/z 247 and 249, RT 1.88 minutes.

Intermediate 234 tert-Butyl N-(6-chloro-5-fluoro-4-iodopyridin-3-yl)carbamate

A 2.5 µM solution of n-butyllithium in hexanes (4.1 mL, 10.2 mmol) was added dropwise to a stirred solution of Intermediate 233 (840 mg, 3.41 mmol) and TMEDA (1.5 mL, 10.2 mmol) in anhydrous diethyl ether (17 mL) at −78° C. After 5 minutes, the light orange solution was warmed to −20° C. and stirred for 1.5 h. The resultant olive-green suspension was cooled to −78° C. and a solution of iodine (2.70 g, 10.6 mmol) in anhydrous THF (4.7 mL) was added dropwise. The mixture was allowed to warm to 20° C. over 16 h, then quenched with 1M aqueous HCl (20 mL). The material was extracted with tert-butyl methyl ether (40 mL). The organic layer was washed with 1M aqueous HCl (10 mL), and the combined aqueous washings were extracted with tert-butyl methyl ether (2×40 mL). The combined organic extracts were washed with water (30 mL), saturated aqueous $Na_2CO_3$ solution (30 mL), saturated aqueous $Na_2S_2O_3$ solution (30 mL) and brine (30 mL). The organic phase was dried over $MgSO_4$, filtered and concentrated in vacuo. The resultant light-yellow powder was purified by flash column chromatography, eluting with EtOAc/heptane (0-20% gradient), to afford the title compound (1.03 g, 81%) as an off-white powder. $\delta_H$ (500 MHz, $CDCl_3$) 8.82 (s, 1H), 6.71 (br s, 1H), 1.55 (s, 9H). LCMS (Method 1): $[M+H]^+$ m/z 373 and 375, RT 1.97 minutes.

Intermediate 235 tert-Butyl N-[4-(benzhydrylideneamino)-6-chloro-5-fluoropyridin-3-yl]carbamate

A dried sealed tube was charged with Intermediate 234 (100 mg, 0.27 mmol), $Cs_2CO_3$ (262 mg, 0.81 mmol), $Pd_2(dba)_3$ (12 mg, 0.01 mmol) and Xantphos (16 mg, 0.03 mmol), and the tube was evacuated and back-filled with $N_2$ three times. The reagents were suspended in anhydrous 1,4-dioxane (1.1 mL), and 1,1-diphenylmethanimine (0.05 mL, 0.30 mmol) was added. The suspension was sparged with $N_2$ whilst sonicating for 5 minutes. The mixture was sealed under $N_2$ and heated at 100° C. for 24 h. After cooling to r.t., the mixture was diluted with EtOAc (10 mL) and filtered through a Celite® pad, washing with EtOAc (3×10 mL). The filtrate was concentrated in vacuo. The resultant viscous oil was purified by flash column chromatography, eluting with EtOAc/heptane (0-20% gradient), to afford the title compound (55 mg, 45%) as an orange powder. $\delta_H$ (500 MHz, $CDCl_3$) 8.89 (br s, 1H), 7.89-7.75 (m, 2H), 7.67-7.56 (m, 1H), 7.55-7.30 (m, 5H), 7.11 (d, J 7.0 Hz, 2H), 6.65 (s, 1H), 1.53 (s, 9H). LCMS (Method 1): $[M+H]^+$ m/z 426 and 428, RT 2.20 minutes.

Intermediate 236

6-Chloro-5-fluoropyridine-3,4-diamine 2M aqueous HCl (2 mL) was added to a stirred solution of Intermediate 235 (213 mg, 0.44 mmol) in anhydrous THF (2 mL). The mixture was heated at 60° C. under $N_2$ for 5 h. After cooling to r.t., the mixture was diluted with water (10 mL) and 1M aqueous HCl (10 mL), then washed with tert-butyl methyl ether (2×20 mL). The combined organic washings were extracted with 1M aqueous HCl (20 mL). The combined aqueous extracts were treated with 5M aqueous NaOH (pH 14) and extracted with EtOAc (4×25 mL). The combined organic extracts were dried over $MgSO_4$ and filtered, then concentrated in vacuo, to afford the title compound (56 mg, 79%) as a pale tan powder. $\delta_H$ (500 MHz, $CDCl_3$) 7.59 (s, 1H), 4.10 (br s, 2H), 3.27 (br s, 2H). LCMS (Method 1): $[M+H]^+$ m/z 162 and 164, RT 0.34 minutes.

Intermediate 237

(S)-(6-Chloro-7-fluoro-3H-imidazo[4,5-c]pyridin-2-yl)(4-methylcyclohexyl)methanamine (Trans Isomer)

DIPEA (0.20 mL, 1.15 mmol) was added to a stirred suspension of Intermediate 236 (76 mg, 0.47 mmol), trans-(2S)-2-(tert-butoxycarbonylamino)-2-(4-methylcyclohexyl) acetic acid (153 mg, 0.56 mmol) and HATU (232 mg, 0.61 mmol) in anhydrous DCM (4.7 mL). The mixture was stirred at 20° C. under $N_2$ for 40 h. Additional portions of trans-(2S)-2-(tert-butoxycarbonylamino)-2-(4-methylcyclohexyl) acetic acid (25 mg, 0.09 mmol), HATU (39 mg, 0.10 mmol) and DIPEA (0.07 mL, 0.41 mmol) were added, and stirring was continued at 20° C. under $N_2$ for 24 h. The mixture was diluted with DCM (10 mL), and quenched with saturated aqueous $Na_2CO_3$ solution (5 mL) and water (5 mL). The biphasic mixture was stirred at 20° C. for 30 minutes, then the organic phase was separated using a hydrophobic frit. The aqueous layer was extracted with DCM (2×20 mL), and the organic filtrate was concentrated in vacuo. The resultant tan powder was dissolved in EtOH (7 mL), and $K_2CO_3$ (280 mg, 2.02 mmol) was added. The suspension was heated at 80° C. in a sealed vial for 16 h. After cooling, the mixture was diluted with water (20 mL), and the material was extracted with DCM (3×30 mL). The combined organic extracts were washed with brine (30 mL), dried over $MgSO_4$ and concentrated in vacuo. The resultant tan viscous oil was dissolved in DCM (2 mL), and TFA (0.12 mL, 1.62 mmol) was added. The mixture was stirred at 20° C. under air for 22 h. The volatiles were removed in vacuo. The resultant brown viscous oil was dissolved in DCM (2 mL) and adsorbed onto an SCX-2 column (2 g). The column was eluted sequentially with DCM, MeOH and a 1M solution of ammonia in MeOH. The ammonia-MeOH fractions were combined, then concentrated in vacuo, to afford the title compound (53 mg, 28% overall) as a light brown viscous oil. $\delta_H$ (500 MHz, $CDCl_3$) 8.49 (s, 1H), 4.19 (d, J 5.3 Hz, 1H), 1.98-1.87 (m, 1H), 1.76-1.67 (m, 2H), 1.67-1.54 (m, 2H), 1.32-1.07 (m, 3H), 0.99-0.87 (m, 2H), 0.85 (d, J 6.5 Hz, 3H). LCMS (Method 1): $[M+H]^+$ m/z 297 and 299, RT 1.60 minutes.

Intermediate 238 tert-Butyl N-[(S)-(2-chloro-7H-purin-8-yl)(4-methylcyclohexyl)methyl]carbamate (Trans Isomer)

DIPEA (0.35 mL, 2.03 mmol) was added to a stirred suspension of 2-chloro-4,5-diaminopyrimidine (100 mg, 0.69 mmol), trans-(2S)-2-(tert-butoxycarbonylamino)-2-(4-methylcyclohexyl)acetic acid (271 mg, 0.99 mmol) and HATU (410 mg, 1.08 mmol) in DCM (5 mL) at 20° C. The reaction mixture was stirred at 20° C. for 18 h, then diluted with DCM (15 mL) and washed with saturated aqueous $NaHCO_3$ solution (10 mL). The organic layer was filtered through a hydrophobic frit, and the solvent was concentrated in vacuo. The resulting dark brown oil was dissolved in EtOH (10 mL), and $K_2CO_3$ (398 mg, 2.88 mmol) was added. The suspension was heated at 80° C. in a sealed vial for 40 h. After cooling, the mixture was diluted with water (10 mL), and the aqueous layer was extracted with DCM (3×15 mL). The combined organic extracts were filtered through a hydrophobic frit, and the solvent was concentrated in vacuo. The resultant dark brown oil was separated by flash column chromatography, eluting with EtOAc/heptane (0-50% gradient), to afford the title compound (80 mg, 30%) as a yellow oil that slowly solidified on standing. $\delta_H$ (250 MHz, $CDCl_3$) 11.73 (br s, 1H), 8.90 (s, 1H), 5.87-5.64 (m, 1H), 4.74-4.62 (m, 1H), 1.75-1.68 (m, 4H), 1.41 (s, 9H), 1.28-1.04 (m, 6H), 0.88-0.84 (m, 3H). LCMS (Method 10): $[M+H]^+$ m/z 380 and 382, RT 1.18 minutes.

Intermediate 239

(S)-(2-Chloro-7H-purin-8-yl)(4-methylcyclohexyl)methanamine (Trans Isomer)

TFA (0.31 mL, 4.23 mmol) was added to a stirred solution of Intermediate 238 (80 mg, 0.19 mmol) in DCM (4 mL) at 20° C. The reaction mixture was stirred at 20° C. for 2 h, then diluted with DCM (11 mL) and quenched with saturated aqueous $NaHCO_3$ solution (10 mL). The biphasic mixture was stirred at 20° C. for 15 minutes, then the organic layer was separated using a hydrophobic frit. The aqueous layer was extracted with 4:1 $CHCl_3$/isopropanol (2×30 mL). The combined organic extracts were filtered through a hydrophobic frit, then the solvent was concentrated in vacuo, to afford the title compound (43 mg, 78%) as a pale brown solid. LCMS (Method 10): $[M+H]^+$ m/z 280 and 282, RT 0.81 minutes.

Intermediate 240

N-[(S)-(2-Chloro-7H-purin-8-yl)(4-methylcyclohexyl)methyl]-2-ethylpyrazole-3-carboxamide (Trans Isomer)

DIPEA (65 µL, 0.37 mmol) was added to a stirred suspension of Intermediate 239 (43 mg, 0.15 mmol), 1-ethylpyrazole-4-carboxylic acid (31 mg, 0.22 mmol) and HATU (91 mg, 0.24 mmol) in DCM (2 mL) at 20° C. The reaction mixture was stirred at 20° C. for 24 h, then diluted with DCM (5 mL) and washed with saturated aqueous $NaHCO_3$ solution (5 mL). The organic layer was filtered through a hydrophobic frit, and the solvent was concentrated in vacuo. The resulting dark yellow oil was separated by flash column chromatography, eluting with EtOAc/heptane (0-100% gradient), to afford the title compound (52 mg, 62%) as a yellow solid. LCMS (Method 10): $[M+H]^+$ m/z 402 and 404, RT 1.09 minutes.

Intermediate 241

N-[(5-Bromo-1H-imidazo[4,5-b]pyrazin-2-yl)(4-methylcyclohexyl)methyl]-2-ethyl-pyrazole-3-carboxamide (Trans Isomer)

A sealed tube was charged with Intermediate 125 (509 mg, 1.73 mmol) in DCM (5 mL), and EDC.HCl (333 mg, 1.73 mmol) was added at 20° C. The reaction mixture was stirred at 20° C. for 3 h. The solvent was removed under a flow of $N_2$. The residue was dissolved in THF (5 mL), and 5-bromopyrazine-2,3-diamine (183 mg, 0.97 mmol) was added. The reaction mixture was sealed and stirred at 80° C. for 60 h. The reaction mixture was re-treated twice with 5-bromopyrazine-2,3-diamine (91.6 mg, 0.485 mmol) whilst stirring at 80° C. for an additional 48 h. After cooling, the reaction mixture was diluted with saturated aqueous $NaHCO_3$ solution (20 mL) and extracted with EtOAc (3×30 mL). The combined organic extracts were washed with saturated aqueous $NaHCO_3$ solution (20 mL) and brine (2×20 mL), then dried over $Na_2SO_4$. The solvent was concentrated in vacuo. The resulting brown solid was dissolved in EtOH (25 mL), and $K_2CO_3$ (688 mg, 4.98 mmol) was added. The reaction mixture was heated at 80° C. in a sealed vial for 6 h. After cooling, the solvent was concentrated in vacuo. The residue was diluted with water (10 mL) and extracted with 4:1 $CHCl_3$/isopropanol (2×30 mL). The combined organic extracts were washed with brine (20 mL) and dried over $Na_2SO_4$. The solvent was concentrated in vacuo. The reddish-brown solid was purified by flash column chromatography, eluting with EtOAc/heptane (0-100% gradient), to afford the title compound (116 mg, 15% overall) as a beige solid. $\delta_H$ (500 MHz, DMSO-$d_6$) 3.77 (s, 1H), 9.04-8.78 (m, 1H), 8.60-8.42 (m, 1H), 7.49 (d, J 2.0 Hz, 1H), 7.04 (d, J 2.0 Hz, 1H), 5.02 (t, J 8.2 Hz, 1H), 4.42 (q, J 7.1 Hz, 2H), 2.15-2.01 (m, 1H), 1.98-1.85 (m, 1H), 1.76-1.57 (m, 2H), 1.45-1.33 (m, 1H), 1.31-1.20 (m, 1H), 1.24 (t, J 7.1 Hz, 3H), 1.17-1.03 (m, 2H), 0.95-0.78 (m, 5H). LCMS (Method 10): $[M+H]^+$ m/z 446 and 448, RT 1.15 minutes.

Intermediate 242 tert-Butyl N-[3-Bromo-6-(tert-butoxycarbonylamino)-2-fluorophenyl]carbamate

Di-tert-butyl dicarbonate (1.33 g, 6.09 mmol) was added to a stirred solution of 4-bromo-3-fluorobenzene-1,2-diamine (500 mg, 2.44 mmol) in tert-butanol (24 mL). The mixture was stirred at 20° C. under $N_2$ for a total of 122 h, and at 50° C. for a further 96 h, re-treating twice with di-tert-butyl dicarbonate (0.5 g, 2.29 mmol). The volatiles were removed in vacuo. The resultant brown viscous oil was separated by flash column chromatography, eluting with EtOAc/heptane (0-30% gradient), to afford the title compound (675 mg, 63%) as an off-white powder. $\delta_H$ (500 MHz, DMSO-$d_6$) 8.55 (br s, 1H), 8.46 (br s, 1H), 7.52-7.46 (m, 2H), 1.47 (s, 9H), 1.43 (s, 9H). LCMS (Method 1): $[M+Na]^+$ m/z 427 and 429, RT 2.09 minutes.

Intermediate 243 tert-Butyl N-{2-(tert-butoxycarbonylamino)-3-fluoro-4-[(2-oxopyrrolidin-1-yl)methyl]-phenyl}carbamate 2-tert-Butyl-1,1,3,3-tetramethylguanidine (0.15 mL, 0.74 mmol) was added to a solution of Intermediate 242 (100 mg, 0.25 mmol), (2-oxopyrrolidin-1-yl)acetic acid (106 mg, 0.74 mmol), {Ir[dF($CF_3$)ppy]2(dtbpy)}$PF_6$ (2.8 mg, 0.025 mmol), dichloronickel, 1,2-dimethoxyethane (5.4 mg, 0.024 mmol) and 4,4'-di-tert-butyl-2,2'-bipyridyl (10 mg, 0.037 mmol) in anhydrous DMF (12 mL). The mixture was sparged with $N_2$ whilst sonicating for 10 minutes. The mixture was sealed under $N_2$ and irradiated with a 40W blue LED lamp whilst stirring for 24 h at approximately 21° C. The mixture was diluted with water (20 mL), and the material was extracted with EtOAc (3×30 mL). The combined organic extracts were washed with saturated aqueous $Na_2CO_3$ solution (20 mL), 1M aqueous HCl (20 mL) and brine (2×20 mL), then dried over $MgSO_4$ and concentrated in vacuo. The resultant brown viscous oil was purified by flash column chromatography, eluting with EtOAc/heptane (20-100% gradient), to afford the title compound (28 mg, 24%) as an orange viscous oil. $\delta_H$ (500 MHz, $CDCl_3$) 7.59 (d, J 8.3 Hz, 1H), 7.34 (br s, 1H), 7.12 (t, J 8.3 Hz, 1H), 6.23 (br s, 1H), 4.47 (s, 2H), 3.27 (t, J 7.1 Hz, 2H), 2.40 (t, J 8.1 Hz, 2H), 2.02-1.92 (m, 2H), 1.51 (s, 9H), 1.50 (s, 9H). LCMS (Method 10): $[M+H]^+$ m/z 424, RT 1.86 minutes.

Intermediate 244

1-[(3,4-Diamino-2-fluorophenyl)methyl]pyrrolidin-2-one

4M HCl in 1,4-dioxane (0.6 mL, 2.4 mmol) was added to a stirred solution of Intermediate 243 (100 mg, 0.24 mmol)

in DCM (2.4 mL) at 20° C. under N₂. The solution was stirred at 20° C. for 26 h, re-treating once with 4M HCl in 1,4-dioxane (0.3 mL, 1.2 mmol). The volatiles were removed in vacuo, to afford the title compound (59 mg, 96%) as a light cream powder (assumed to be an HCl salt of indeterminate stoichiometry). $\delta_H$ (500 MHz, DMSO-d₆) 6.85 (d, J 8.2 Hz, 1H), 6.55 (app. t, J 7.9 Hz, 1H), 4.33 (s, 2H), 3.24-3.20 (obs. m, 2H), 2.25 (t, J 8.1 Hz, 2H), 1.91 (p, J 7.5 Hz, 2H). LCMS (Method 10): [M+H]⁺ m/z 224, RT 0.47 minutes.

Intermediate 245 tert-Butyl N-[(S)-{4-fluoro-5-[(2-oxopyrrolidin-1-yl)methyl]-1H-benzimidazol-2-yl}(4-methylcyclohexyl)methyl]carbamate (Trans Isomer)

The title compound (55 mg, 53%) was prepared from trans-(2S)-2-(tert-butoxycarbonylamino)-2-(4-methylcyclohexyl)acetic acid (75 mg, 0.28 mmol) and Intermediate 244 (59 mg, 0.23 mmol) in accordance with Procedure Y. LCMS (Method 1): [M+H]⁺ m/z 459, RT 1.90 minutes.

Intermediate 246

1-({2-[(S)-Amino(4-methylcyclohexyl)methyl]-4-fluoro-1H-benzimidazol-5-yl}methyl)-pyrrolidin-2-one (Trans Isomer)

TFA (0.10 mL, 1.35 mmol) was added to a stirred solution of Intermediate 245 (55 mg, 0.12 mmol) in DCM (1.2 mL). The mixture was stirred at 20° C. under air for 16 h, then quenched with saturated aqueous Na₂CO₃ solution (10 mL). The material was extracted with DCM (3×10 mL), using a hydrophobic frit to separate the phases. The organic filtrate was concentrated in vacuo to afford the title compound (40 mg, 84%) as a tan viscous oil. $\delta_H$ (500 MHz, CDCl₃) 10.86 (br s, 1H), 7.22 (br s, 1H), 7.12-7.06 (m, 1H), 4.62 (s, 2H), 4.10 (d, J 5.7 Hz, 1H), 3.32 (t, J 7.1 Hz, 2H), 2.40 (t, J 8.1 Hz, 2H), 1.96 (p, J 7.6 Hz, 2H), 1.91-1.80 (m, 1H), 1.76-1.52 (m, 3H), 1.34-1.07 (m, 4H), 0.94-0.79 (m, 5H). LCMS (Method 1): [M+H]⁺ m/z 359, RT 1.54 minutes.

Intermediate 247

N-[(S)-(5-Bromo-4-fluoro-1H-benzimidazol-2-yl)(4-methylcyclohexyl)methyl]-2-ethyl-pyrazole-3-carboxamide (Trans Isomer)

The title compound (1.9 g, 81.2%) was prepared from Intermediate 223 (1.7 g, 4.5 mmol) and 1-ethyl-1H-pyrazole-5-carboxylic acid (714.5 mg, 5.1 mmol) in accordance with Procedure A, using DCM as solvent. LCMS (Method 5): [M+H]⁺ m/z 462.0 and 464.0, RT 1.39 minutes.

Intermediate 248

2-Ethyl-N-{(S)-[4-fluoro-5-(4,4,5,5-tetramethyl-1,3,2-dioxaborolan-2-yl)-1H-benzimidazol-2-yl](4-methylcyclohexyl)methyl}pyrazole-3-carboxamide (Trans Isomer)

The title compound (765.2 mg, 70%) was prepared from Intermediate 247 (1 g, 2.2 mmol) in accordance with Procedure C. LCMS (Method 5): [M+H]⁺ m/z 510.2, RT 1.45 minutes.

Intermediate 249

O¹-tert-Butyl O³-ethyl 4-(2-{(S)-[(2-ethylpyrazole-3-carbonyl)amino](4-methyl-cyclohexyl)methyl}-4-fluoro-1H-benzimidazol-5-yl)-2,5-dihydropyrrole-1,3-dicarboxylate (Trans Isomer)

The title compound (553 mg, 44%) was prepared from O¹-tert-butyl O³-ethyl 4-oxopyrrolidine-1,3-dicarboxylate (550 mg, 2.03 mmol) and Intermediate 248 (765 mg, 1.50 mmol) according to Procedure T. LCMS (Method 5): [M+H]⁺ m/z 623.2, RT 1.52 minutes.

Intermediate 250

Mixture of N-[(S)-(5-bromo-4-fluoro-1-methylbenzimidazol-2-yl)(4-methylcyclohexyl)-methyl]-2-methylpyrazole-3-carboxamide (trans isomer) and N-[(S)-(6-bromo-7-fluoro-1-methylbenzimidazol-2-yl)(4-methylcyclohexyl)methyl]-2-methylpyrazole-3-carboxamide (Trans Isomer)

To Intermediate 224 (500 mg, 1.11 mmol) and sodium carbonate (130 mg, 1.23 mmol) in DMF (5 mL) was added iodomethane (237 mg, 1.67 mmol). The mixture was stirred at r.t. for 24 h, then diluted with ethyl acetate (50 mL), washed with saturated brine (30 mL), dried (sodium sulfate) and concentrated in vacuo. The residue was purified by chromatography (silica, gradient of 0-65% EtOAc in isohexanes) to afford the mixture of title compounds (150 mg, 29%) as a white solid, which was utilised without separation. LCMS (pH 10): [M+H]⁺ m/z 462/464 (Br isotopes), RT 2.37 and 2.45 minutes (~1:1).

Example 1

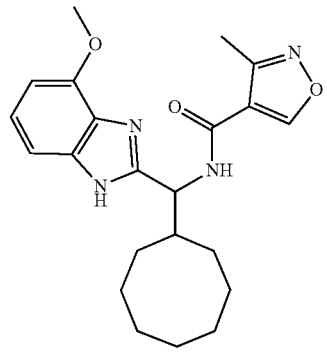 [SMILES: COc1cccc2[nH]c(C(NC(=O)c3conc3C)C3CCCCCCC3)nc12]

N-[Cyclooctyl(4-methoxy-1H-benzimidazol-2-yl)methyl]-3-methylisoxazole-4-carboxamide The title compound (2 mg, 7%), a white solid, was prepared from Intermediate 8 (30 mg, 0.09 mmol) in accordance with Procedure B. $\delta_H$ (400 MHz, DMSO-d₆) 12.21 (s, 1H), 9.38 (d, J 0.6 Hz, 1H), 8.39 (s, 1H), 7.04 (m, 2H), 6.64 (s, 1H), 5.13 (d, J 7.7 Hz, 1H), 3.94 (s, 3H), 2.48-2.32 (m, 4H), 1.96-1.08 (m, 14H). LCMS (Method 7): [M+H]⁺, 100%, m/z 397, RT 2.20 minutes. LCMS (Method 6): [M+H]⁺, 100%, m/z 397, RT 1.92 minutes.

Example 2

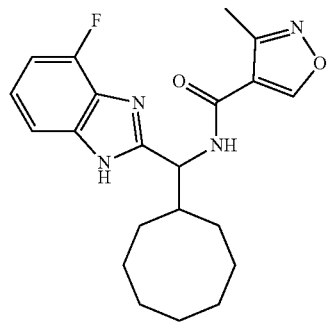 [SMILES: Cc1nocc1C(=O)NC(c1nc2c(F)cccc2[nH]1)C1CCCCCCC1]

N-[Cyclooctyl(4-fluoro-1H-benzimidazol-2-yl)methyl]-3-methylisoxazole-4-carboxamide The title compound (29 mg, 3%), a white solid, was prepared from Intermediate 9 (133.9 mg, 0.33 mmol) in accordance with Procedure B. $\delta_H$ (300 MHz, DMSO-d$_6$) 12.80 (s, 1H), 9.45 (s, 1H), 8.85 (d, J 8.2 Hz, 1H), 7.31 (d, J 6.7 Hz, 1H), 7.14 (td, J 8.0, 5.0 Hz, 1H), 6.96 (t, J 9.4 Hz, 1H), 5.12 (t, J 8.7 Hz, 1H), 2.47-2.29 (m, 4H), 1.78-1.26 (m, 14H). LC-MS (Method 7): [M−H]$^-$, 100%, m/z 383, RT 2.28 minutes. LCMS (Method 6): [M−H]$^-$, 100%, m/z 383, RT 2.26 minutes.

Example 3

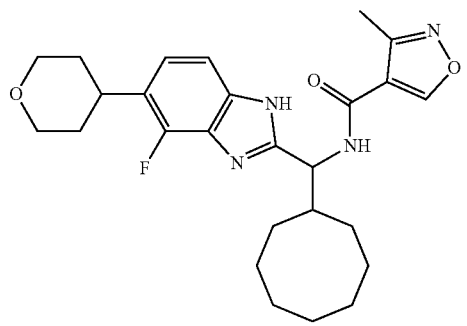 [SMILES: Cc1nocc1C(=O)NC(c1nc2c(F)c(C3CCOCC3)ccc2[nH]1)C1CCCCCCC1]

N-{Cyclooctyl[4-fluoro-5-(tetrahydropyran-4-yl)-1H-benzimidazol-2-yl]methyl}-3-methylisoxazole-4-carboxamide The title compound (20.5 mg, 34%), a beige solid, was prepared from Intermediate 10 (160 mg, 0.13 mmol) in accordance with Procedure B. $\delta_H$ (400 MHz, DMSO-d$_6$) 12.61 (s, 1H), 9.43 (d, J 0.7 Hz, 1H), 9.00-8.56 (m, 1H), 7.44-6.92 (m, 2H), 5.24-4.96 (m, 1H), 4.15-3.85 (m, 2H), 3.61-3.42 (m, 2H), 3.24-3.10 (m, 1H), 2.44-2.25 (m, 4H), 1.93-1.14 (m, 18H). LCMS (Method 7): [M+H]$^+$ m/z 469, RT 2.34 minutes.

Example 4

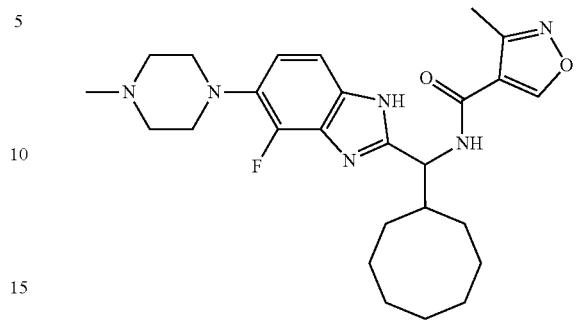

N-{Cyclooctyl[4-fluoro-5-(4-methylpiperazin-1-yl)-1H-benzimidazol-2-yl]methyl}-3-methylisoxazole-4-carboxamide The title compound (23 mg, 17%), a white solid, was prepared from Intermediate 11 (89 mg, 0.12 mmol) in accordance with Procedure B. $\delta_H$ (400 MHz, DMSO-d$_6$) 13.11-12.17 (m, 1H), 9.43 (s, 1H), 8.98-8.55 (m, 1H), 7.41-7.07 (m, 1H), 7.04-6.82 (m, 1H), 5.17-4.96 (m, 1H), 3.08-2.89 (m, 4H), 2.50-2.43 (m, 4H), 2.43-2.30 (m, 4H), 2.23 (s, 3H), 1.82-1.16 (m, 14H). LCMS (Method 7): [M+H]$^+$ m/z 483, RT 2.08 minutes.

Example 5

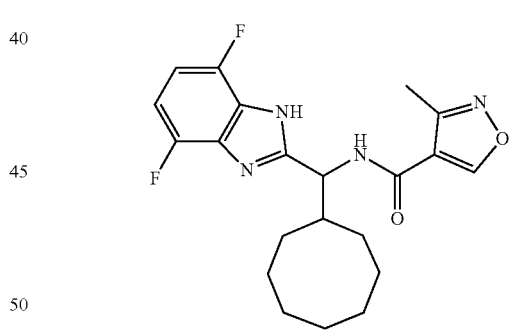

N-[Cyclooctyl(4,7-difluoro-1H-benzimidazol-2-yl)methyl]-3-methylisoxazole-4-carboxamide The title compound (7 mg, 18%), a white solid, was prepared from Intermediate 12 (40 mg, 0.10 mmol) in accordance with Procedure B. $\delta_H$ (300 MHz, DMSO-d$_6$) 13.39 (s, 1H), 9.45 (d, J 0.6 Hz, 1H), 8.87 (d, J 9.0 Hz, 1H), 7.15-6.82 (m, 2H), 5.13 (t, J 8.8 Hz, 1H), 2.48-2.25 (m, 4H), 1.86-1.11 (m, 14H). LC-MS (method 7): [M−H]$^-$, 100%, m/z 401.2, RT 2.38 minutes. LCMS (Method 6): [M−H]$^-$ m/z 401, RT 2.40 minutes.

Example 6

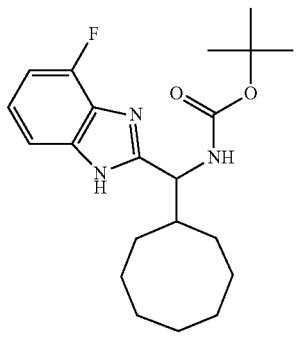 [SMILES: CC(C)(C)OC(=O)NC(c1nc2c(F)cccc2[nH]1)C1CCCCCCC1]

tert-Butyl N-[cyclooctyl(4-fluoro-1H-benzimidazol-2-yl)methyl]carbamate

The title compound (13.9 mg, 1%), a white solid, was prepared from Intermediate 13 (2.99 g, 7.60 mmol) in accordance with Procedure B. $\delta_H$ (400 MHz, DMSO-d$_6$) 12.28 (s, 1H), 7.31 (s, 1H), 7.12 (td, J 8.0, 4.9 Hz, 1H), 6.93 (t, J 9.2 Hz, 1H), 6.78 (s, 1H), 4.69-4.61 (m, 1H), 2.19 (d, J 7.3 Hz, 1H), 1.97-0.95 (m, 23H). LCMS (Method 6): [M−H]⁻ m/z 374, RT 2.51 minutes.

Example 7

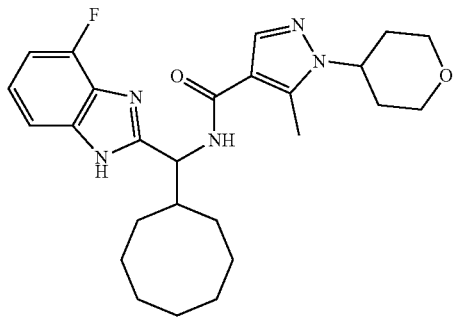 [SMILES: Cc1c(C(=O)NC(c2nc3c(F)cccc3[nH]2)C2CCCCCCC2)cnn1C1CCOCC1]

N-[Cyclooctyl(4-fluoro-1H-benzimidazol-2-yl)methyl]-5-methyl-1-(tetrahydropyran-4-yl)pyrazole-4-carboxamide The title compound (17.5 mg, 10%), a white solid, was prepared from Intermediate 14 (100 mg, 0.36 mmol) and 5-methyl--(tetrahydropyran-4-yl)-1H-pyrazole-4-carboxylic acid (85 mg, 0.38 mmol) in accordance with Procedure A. $\delta_H$ (400 MHz, DMSO-d$_6$, T=350 K) 12.42 (s, 1H), 8.04 (s, 1H), 7.94 (d, J 7.7 Hz, 1H), 7.31 (d, J 7.2 Hz, 1H), 7.12 (td, J 8.0, 4.9 Hz, 1H), 6.92 (dd, J 10.8, 8.1 Hz, 1H), 5.16 (t, J 8.6 Hz, 1H), 4.42 (tt, J 11.2, 4.3 Hz, 1H), 3.97 (dtd, J 11.6, 4.8, 1.5 Hz, 2H), 3.60-3.39 (m, 2H), 2.53 (s, 3H), 2.47-2.32 (m, 1H), 2.30-0.77 (m, 18H). LCMS (Method 7): [M+H]⁺ m/z 468, RT 2.20 minutes. LCMS (Method 6): [M−H]⁻ m/z 466, RT 2.15 minutes.

Example 8

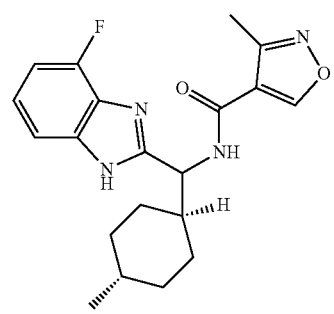 [SMILES: Cc1nocc1C(=O)NC(c1nc2c(F)cccc2[nH]1)[C@H]1CC[C@H](C)CC1]

N-[(4-Fluoro-1H-benzimidazol-2-yl)(trans-4-methylcyclohexyl)methyl]-3-methyl-isoxazole-4-carboxamide The title compound (28 mg, 15%) a white solid, was prepared from Intermediate 18 (130 mg, 0.50 mmol) and 3-methylisoxazole-4-carboxylic acid (70 mg, 0.52 mmol) in accordance with Procedure A. $\delta_H$ (300 MHz, DMSO-d$_6$) 12.63 (s, 1H), 9.45 (d, J 0.7 Hz, 1H), 8.85 (d, J 8.4 Hz, 1H), 7.30 (s, 1H), 7.14 (td, J 8.0, 5.0 Hz, 1H), 7.04-6.87 (m, 1H), 5.04 (t, J 8.5 Hz, 1H), 2.36 (s, 3H), 2.10-1.80 (m, 2H), 1.78-1.55 (m, 2H), 1.44-1.26 (m, 2H), 1.19-0.77 (m, 7H). LCMS (Method 7): [M+H]⁺ m/z 371, RT 2.62 minutes. LCMS (Method 6): [M+H]⁺ m/z 371, RT 2.61 minutes.

Example 9

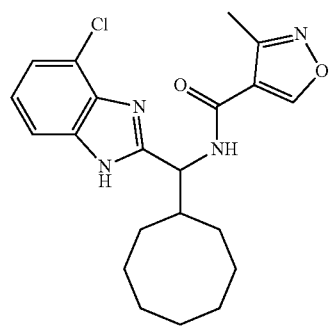 [SMILES: Cc1nocc1C(=O)NC(c1nc2c(Cl)cccc2[nH]1)C1CCCCCCC1]

N-[(4-Chloro-1H-benzimidazol-2-yl)(cyclooctyl)methyl]-3-methylisoxazole-4-carboxamide The title compound (15 mg, 6%), a white solid, was prepared from Intermediate 19 (264 mg, 0.63 mmol) in accordance with Procedure B. $\delta_H$ (300 MHz, DMSO-d$_6$) 13.15-12.50 (m, 1H), 9.66-9.28 (m, 1H), 9.13-8.65 (m, 1H), 7.59-7.32 (m, 1H), 7.28-7.04 (m, 2H), 5.32-4.93 (m, 1H), 2.46-2.22 (m, 4H), 1.83-1.24 (m, 14H). LCMS (Method 7): [M+H]⁺ m/z 401, RT 2.39 minutes. LCMS (Method 6): [M−H]⁻ m/z 399, RT 2.35 minutes.

Example 10

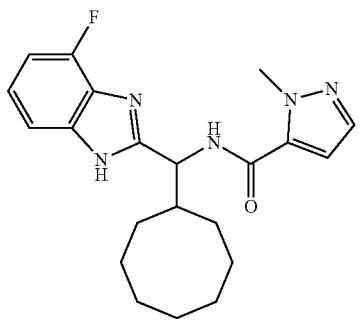 [SMILES: Cn1nccc1C(=O)NC(c1nc2c(F)cccc2[nH]1)C1CCCCCCC1]

N-[Cyclooctyl(4-fluoro-1H-benzimidazol-2-yl)methyl]-2-methylpyrazole-3-carboxamide The title compound (26 mg, 54%), a white solid, was prepared from Intermediate 20 (50 mg, 0.125 mmol) in accordance with Procedure B. $\delta_H$ (400 MHz, DMSO-$d_6$) 12.72 (br s, 1H), 8.90 (d, J 8.8 Hz, 1H), 7.46 (d, J 2.0 Hz, 1H), 7.30 (d, J 7.8 Hz, 1H), 7.12-7.17 (m, 1H), 7.07 (d, J 2.0 Hz, 1H), 6.92-6.97 (m, 1H), 5.05-5.15 (m, 1H), 4.02 (s, 3H), 1.21-1.71 (m, 15H). LCMS (Method 10): [M+H]$^+$ m/z 384, RT 2.83 minutes.

Example 11

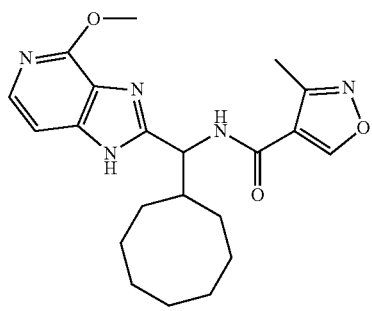 [SMILES: COc1nccc2[nH]c(C(NC(=O)c3conc3C)C3CCCCCCC3)nc12]

N-[Cyclooctyl(4-methoxy-1H-imidazolo[4,5-c]pyridin-2-yl)methyl]-3-methylisoxazole-4-carboxamide HATU (310 mg, 0.82 mmol) was added to a stirred suspension of 2-methoxy-pyridine-3,4-diamine (104 mg, 0.75 mmol), Intermediate 7 (200 mg, 0.68 mmol) and DIPEA (0.17 mL, 1.03 mmol) in anhydrous DMF (4 mL). The mixture was stirred at 20° C. under N$_2$ for 22 h, then saturated aqueous NaHCO$_3$ solution (50 mL), water (50 mL) and EtOAc (50 mL) were added. The layers were separated, then the aqueous phase was further extracted with EtOAc (2×50 mL). The combined organic extracts were washed with brine (2×50 mL) and dried over MgSO$_4$, then filtered and concentrated in vacuo. The crude residue was taken up in AcOH (4 mL) and heated at 100° C. for 18 h. Upon cooling to r.t., water (30 mL) was added, followed by 4M aqueous NaOH solution (40 mL). The mixture was extracted with EtOAc (3×40 mL) and the combined organic extracts were dried over MgSO$_4$, then filtered and concentrated in vacuo. The residue was purified by preparative HPLC to afford the title compound (2.3 mg, 1%) as a pale yellow solid. $\delta_H$ (250 MHz, 353K, DMSO-$d_6$) 9.37 (s, 1H), 8.48 (br s, 1H), 7.80 (d, J 5.7 Hz, 1H), 7.12 (d, J 5.7 Hz, 1H), 6.15 (br s, 1H), 5.36-5.02 (m, 1H), 4.02 (s, 3H), 2.44-2.27 (m, 4H), 1.98-1.12 (m, 14H). LCMS (Method 2): [M+H]$^+$ m/z 398, RT 2.93 minutes.

Example 12

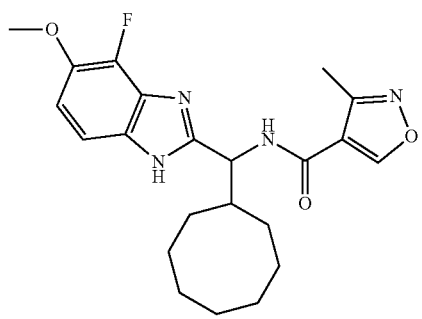 [SMILES: COc1ccc2[nH]c(C(NC(=O)c3conc3C)C3CCCCCCC3)nc2c1F]

N-[Cyclooctyl(4-fluoro-5-methoxy-1H-benzimidazol-2-yl)methyl]-3-methylisoxazole-4-carboxamide The title compound (38 mg, 18%), a white solid, was prepared from Intermediate 7 (150 mg, 0.51 mmol) and 3-fluoro-4-methoxybenzene-1,2-diamine (57 mg, 0.34 mmol) in accordance with Procedure Y. $\delta_H$ (400 MHz, DMSO-$d_6$) 12.59 (s, 1H), 9.43 (s, 1H), 8.81 (s, 1H), 7.22 (s, 1H), 7.05 (t, J 8.2 Hz, 1H), 5.08 (t, J 8.6 Hz, 1H), 3.85 (s, 3H), 2.41-2.28 (m, 4H), 1.86-1.15 (m, 14H). LCMS (Method 6): [M+H]$^+$ m/z 415, RT 2.22 minutes.

Example 13

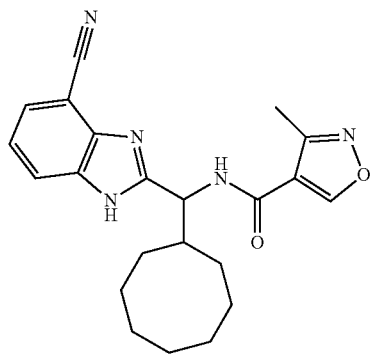 [SMILES: Cc1nocc1C(=O)NC(c1nc2c(C#N)cccc2[nH]1)C1CCCCCCC1]

N-[(4-Cyano-1H-benzimidazol-2-yl)(cyclooctyl)methyl]-3-methylisoxazole-4-carboxamide The title compound (7 mg, 1%), a white solid, was prepared from Intermediate 7 (412 mg, 1.4 mmol) and 2,3-diaminobenzonitrile (196 mg, 1.4 mmol) in accordance with Procedure Y. $\delta_H$ (300 MHz, DMSO-$d_6$) 13.04 (s, 1H), 9.43 (d, J 0.7 Hz, 1H), 8.90 (d, J 8.6 Hz, 1H), 7.81 (d, J 8.0 Hz, 1H), 7.63 (d, J 7.5 Hz, 1H), 7.30 (t, J 7.8 Hz, 1H), 5.12

(t, J 8.7 Hz, 1H), 2.47-2.39 (m, 1H), 2.36 (s, 3H), 1.75-1.26 (m, 14H). LCMS (Method 6): [M+H]⁺ m/z 392, RT 2.21 minutes.

Example 14

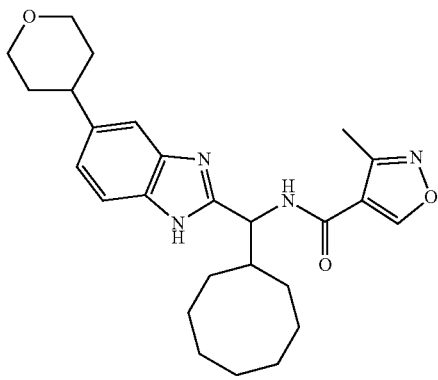 [SMILES: Cc1nocc1C(=O)NC(c1nc2cc(C3CCOCC3)ccc2[nH]1)C1CCCCCCC1]

N-{Cyclooctyl[5-(tetrahydropyran-4-yl)-1H-benz-imidazol-2-yl]methyl}-3-methyl-isoxazole-4-carboxamide The title compound (30 mg, 27%), a light brown solid, was prepared from Intermediate 7 (198 mg, 0.67 mmol) and 4-(tetrahydropyran-4-yl)benzene-1,2-diamine (129 mg, 0.67 mmol) in accordance with Procedure Y. $\delta_H$ (300 MHz, DMSO-$d_6$) 12.27 (s, 1H), 9.43 (d, J 0.7 Hz, 1H), 8.74 (d, J 8.8 Hz, 1H), 7.53-7.22 (m, 2H), 7.06 (d, J 8.2 Hz, 1H), 5.08 (t, J 8.6 Hz, 1H), 4.01-3.91 (m, 2H), 3.53-3.38 (m, 2H), 2.84 (s, 1H), 2.44-2.30 (m, 4H), 1.77-1.10 (m, 18H). LCMS (Method 6): [M+H]⁺ m/z 451, RT 2.24 minutes.

Example 15

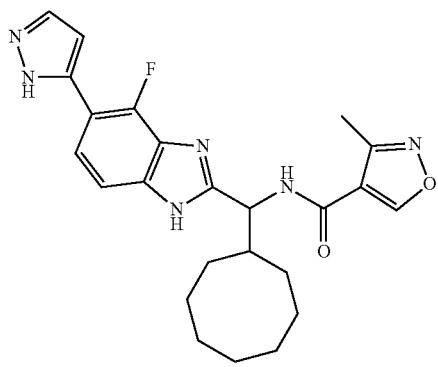 [SMILES: Cc1nocc1C(=O)NC(c1nc2c(F)c(-c3ccn[nH]3)ccc2[nH]1)C1CCCCCCC1]

N-{Cyclooctyl[4-fluoro-5-(1H-pyrazol-5-yl)-1H-benzimidazol-2-yl]methyl}-3-methyl-isoxazole-4-carboxamide The title compound (20 mg, 25%), a white solid, was prepared from Intermediate 7 (123 mg, 0.42 mmol) and Intermediate 29 (80 mg, 0.42 mmol) in accordance with Procedure Y. $\delta_H$ (300 MHz, DMSO-$d_6$) 3.40-12.05 (m, 2H), 9.45 (s, 1H), 8.97-8.71 (m, 1H), 7.87-7.54 (m, 2H), 7.43-7.25 (m, 1H), 6.70-6.57 (m, 1H), 5.20-5.04 (m, 1H), 2.44-2.22 (m, 4H), 1.88-1.02 (m, 14H). LCMS (Method 6): [M+H]⁺, m/z 451, RT 2.07 minutes.

Example 16

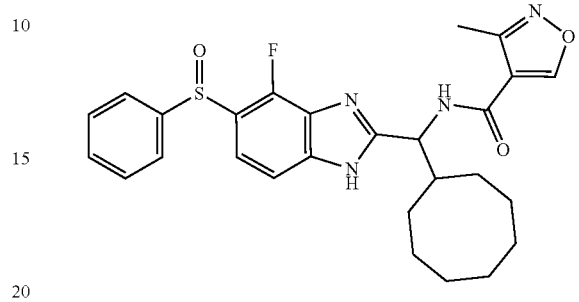

N-{[5-(Benzenesulfinyl)-4-fluoro-1H-benzimidazol-2-yl](cyclooctyl)methyl}-3-methyl-isoxazole-4-carboxamide The title compound (1:1 mixture of diastereomers) (2 mg, 3%), a white solid, was prepared from Intermediate 7 (49 mg, 0.17 mmol) and Intermediate 30 (40 mg, 0.16 mmol) in accordance with Procedure Y. $\delta_H$ (400 MHz, DMSO-$d_6$) 12.36 (s, 1H), 9.44 (s, 1H), 8.70 (s, 1H), 7.68-7.61 (m, 2H), 7.57-7.46 (m, 3H), 7.43-7.36 (m, 1H), 7.32-7.18 (m, 1H), 5.08 (t, J 8.6 Hz, 1H), 2.36 (m, 4H), 2.05-0.88 (m, 14H). LCMS (Method 6): [M+H]⁺ m/z 509, RT 2.45 minutes.

Example 17

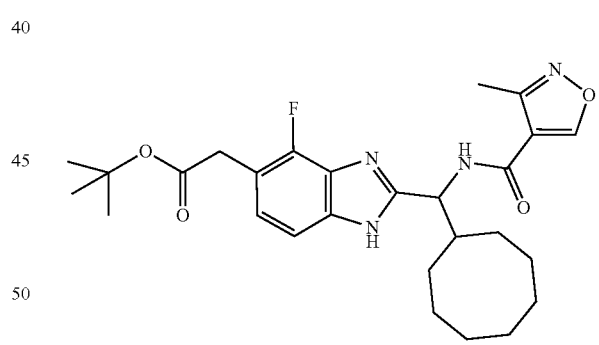

tert-Butyl 2-(2-{cyclooctyl[(3-methylisoxazole-4-carbonyl)amino]methyl}-4-fluoro-1H-benzimidazol-5-yl)acetate The title compound (43 mg, 18%), a white solid, was prepared from Intermediate 7 (150 mg, 0.51 mmol) and Intermediate 31 (116 mg, 0.49 mmol) in accordance with Procedure Y. $\delta_H$ (300 MHz, DMSO-$d_6$) 12.69 (s, 1H), 9.43 (d, J 0.7 Hz, 1H), 8.82 (s, 1H), 7.33-7.15 (m, 1H), 7.13-6.98 (m, 1H), 5.10 (t, J 8.7 Hz, 1H), 3.67 (s, 2H), 2.37 (m, 4H), 1.85-1.11 (m, 14H), 1.40 (s, 9H). LCMS (Method 6): [M+H]⁺ m/z 499, RT 2.90 minutes.

Examples 18 & 19

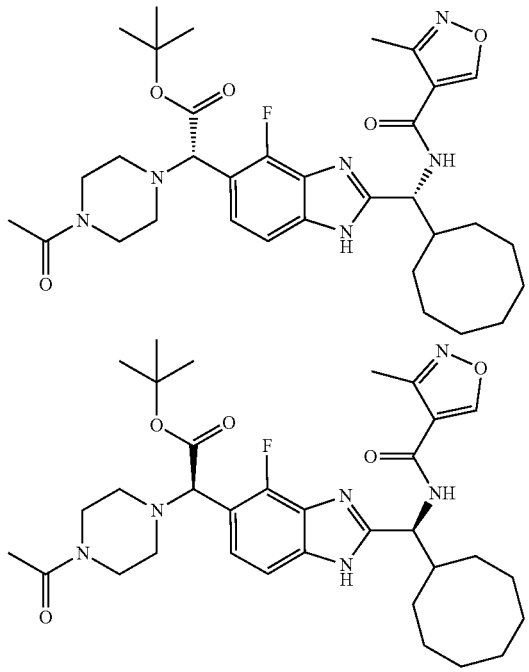

tert-Butyl rel-(2S)-2-(4-acetylpiperazin-1-yl)-2-(4-fluoro-2-{rel-(S)-cyclooctyl[(3-methyl-isoxazole-4-carbonyl)amino]methyl}-1H-benzimidazol-5-yl)acetate (Example 18) tert-Butyl rel-(2R)-2-(4-acetylpiperazin-1-yl)-2-(4-fluoro-2-{rel-(R)-cyclooctyl[(3-methylisoxazole-4-carbonyl)amino]methyl}-1H-benzimidazol-5-yl)acetate (Example 19)

To a solution of Example 17 (40 mg, 0.08 mmol) in CHCl$_3$ (1 mL) were added AIBN (2 mg, 0.01 mmol) and NBS (15 mg, 0.08 mmol) under N$_2$. The reaction mixture was heated at reflux temperature overnight, then further aliquots of AIBN (2 mg) and NBS (15 mg) were added. The mixture was heated at reflux temperature for a further 6 h, then cooled and concentrated in vacuo. The residue was taken up in acetonitrile (1 mL). DIPEA (18 μL, 0.10 mmol) and 1-acetylpiperazine (14 mg, 0.11 mmol) were added, and the mixture was stirred at r.t. overnight. Further aliquots of DIPEA (18 μL, 0.10 mmol) and 1-acetylpiperazine (14 mg, 0.11 mmol) were added, and the mixture was stirred at r.t. for 24 h, then concentrated in vacuo. The residue was subject to reverse-phase HPLC, to yield the title compounds (Peak 1, 0.5 mg, 1%: and Peak 2, 1 mg, 2%) as white solids.

Peak 1 (diastereomer 1): δ$_H$ (400 MHz, CD$_3$OD) 9.18 (d, J 0.7 Hz, 1H), 7.38-7.32 (m, 2H), 5.15 (d, J 8.1 Hz, 1H), 4.51 (s, 1H), 3.60-3.51 (m, 4H), 2.57-2.47 (m, 4H), 2.44-2.36 (m, 4H), 2.05 (s, 3H), 1.76-1.44 (m, 14H), 1.38 (s, 9H). LCMS (Method 6): [M+H]$^+$ m/z 625, RT 2.29 minutes.

Peak 2 (diastereomer 2): δ$_H$ (400 MHz, CD$_3$OD) 9.20 (d, J 0.7 Hz, 1H), 7.41-7.33 (m, 2H), 5.17 (d, J 8.2 Hz, 1H), 4.53 (s, 1H), 3.62-3.53 (m, 4H), 2.58-2.48 (m, 4H), 2.47-2.40 (m, 4H), 2.06 (s, 3H), 1.80-1.46 (m, 14H), 1.41 (s, 9H). LCMS (Method 6): [M+H]$^+$ m/z 625, RT 2.33 minutes.

Example 20

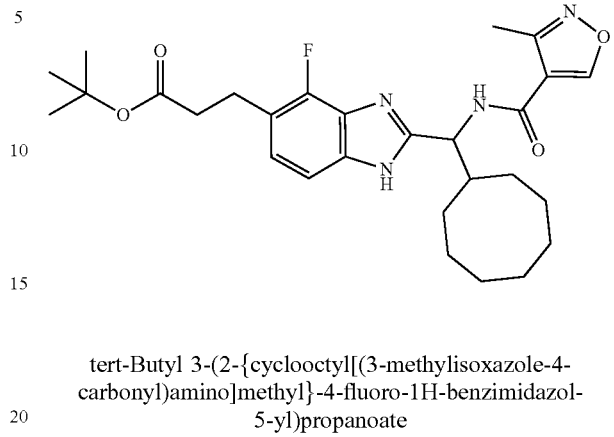

tert-Butyl 3-(2-{cyclooctyl[(3-methylisoxazole-4-carbonyl)amino]methyl}-4-fluoro-1H-benzimidazol-5-yl)propanoate The title compound (210 mg, 210%), a white solid, was prepared from Intermediate 7 (591 mg, 2.01 mmol) and Intermediate 32 (486 mg, 1.91 mmol) in accordance with Procedure Y. δ$_H$ (400 MHz, DMSO-d$_6$) 12.88-12.63 (m, 1H), 9.44 (s, 1H), 8.86-8.73 (m, 1H), 7.32-7.20 (m, 1H), 7.05 (t, J 7.3 Hz, 1H), 5.12-5.08 (t, J 8.8 Hz, 1H), 2.98-2.87 (m, 2H), 2.56-2.46 (m, 2H), 2.36 (m, 4H), 1.77-1.21 (m, 14H), 1.34 (s, 9H). LCMS (Method 6): [M+H]$^+$ m/z 513, RT 2.74 minutes.

Example 21

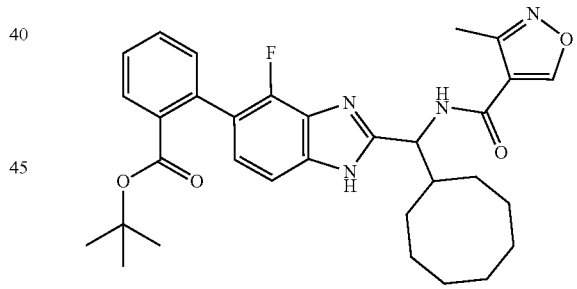

tert-Butyl 2-(2-{cyclooctyl[(3-methylisoxazole-4-carbonyl)amino]methyl}-4-fluoro-1H-benzimidazol-5-yl)benzoate The title compound (63 mg, 12%), a white solid, was prepared from Intermediate 7 (279 mg, 0.95 mmol) and Intermediate 33 (300 mg, 0.90 mmol) in accordance with Procedure Y. δ$_H$ (400 MHz, DMSO-d$_6$) 13.06-12.81 (s, 1H), 9.44 (s, 1H), 8.92-8.77 (m, 1H), 7.31 (d, J 7.7 Hz, 1H), 7.68-7.59 (i, 1H), 7.55-7.47 (m, 1H), 7.41 (d, J 7.7 Hz, 1H), 7.35 (d, J 8.2 Hz, 1H), 7.11-7.02 (m, 1H), 5.16-5.09 (m, 1H), 2.45-2.34 (m, 4H), 1.81-1.17 (m, 14H), 1.07 (s, 9H). LCMS (Method 6): [M+H]$^+$ m/z 561, RT 2.86 minutes.

Example 22

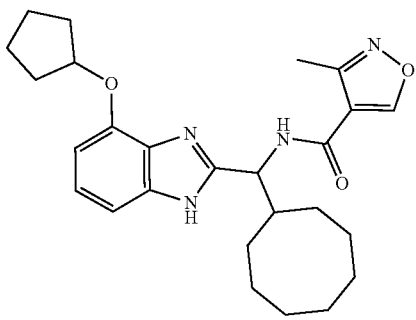 [SMILES: Cc1nocc1C(=O)NC(c1nc2c(OC3CCCC3)cccc2[nH]1)C1CCCCCCC1]

N-{Cyclooctyl[4-(cyclopentoxy)-1H-benzimidazol-2-yl]methyl}-3-methylisoxazole-4-carboxamide The title compound (26 mg, 14%), an off-white solid, was prepared from Intermediate 7 (125 mg, 0.43 mmol) and Intermediate 35 (82 mg, 0.43 mmol) in accordance with Procedure Y. $\delta_H$ (400 MHz, DMSO-$d_6$) 12.39 (s, 1H), 9.42 (s, 1H), 8.99-8.50 (m, 1H), 7.31-6.88 (m, 2H), 6.80-6.52 (m, 1H), 5.24-4.82 (m, 2H), 2.40-2.19 (m, 4H), 2.07-1.14 (m, 22H). LCMS (Method 6): [M+H]$^+$ m/z 451, RT 2.75 minutes.

Example 23

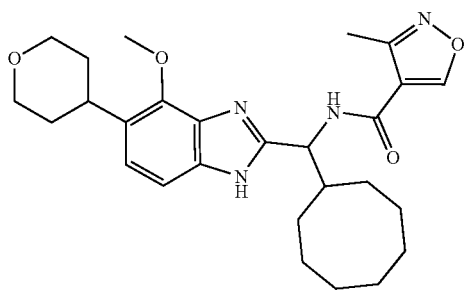 [SMILES: COc1c(C2CCOCC2)ccc2[nH]c(C(NC(=O)c3conc3C)C3CCCCCCC3)nc12]

N-{Cyclooctyl[7-methoxy-6-(tetrahydropyran-4-yl)-1H-benzimidazol-2-yl]methyl}-3-methylisoxazole-4-carboxamide The title compound (33.7 mg, 27%), an off-white solid, was prepared from Intermediate 7 (75 mg, 0.26 mmol) and Intermediate 36 (56 mg, 0.25 mmol) in accordance with Procedure Y. $\delta_H$ (400 MHz, DMSO-$d_6$) 12.70-12.06 (m, 1H), 9.60-9.30 (m, 1H), 8.88-8.54 (m, 1H), 7.38-6.90 (m, 2H), 5.22-4.95 (m, 1H), 4.20 (s, 2H), 4.08-3.77 (m, 3H), 3.54-3.39 (m, 2H), 3.28-3.15 (m, 1H), 2.37 (d, J 3.4 Hz, 4H), 1.86-1.17 (m, 18H). LCMS (Method 6): [M+H]$^+$ m/z 481, RT 2.34 minutes.

Example 24

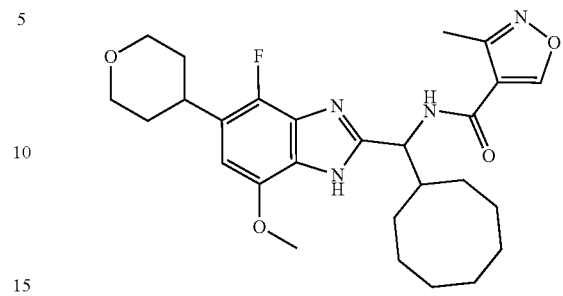

N-{Cyclooctyl[4-fluoro-7-methoxy-5-(tetrahydroyran-4-yl)-1H-benzimidazol-2-yl]-methyl}-3-methyl-isoxazole-4-carboxamide The title compound (5 mg, 4%), a white solid, was prepared from Intermediate 7 (70 mg, 0.24 mmol) and Intermediate 38 (63 mg, 0.26 mmol) in accordance with Procedure Y. $\delta_H$ (300 MHz, DMSO-$d_6$) 12.87 (s, 1H), 9.45 (s, 1H), 8.79 (s, 1H), 6.60 (s, 1H), 5.27-4.99 (m, 1H), 4.07-3.82 (m, 5H), 3.55-3.41 (m, 2H), 3.23-3.08 (m, 1H), 2.39-2.24 (m, 4H), 1.96-1.78 (m, 2H), 1.77-1.37 (m, 14H), 1.31-1.22 (m, 2H). LCMS (Method 6): [M+H]$^+$ m/z 499, RT 2.43 minutes.

Example 25

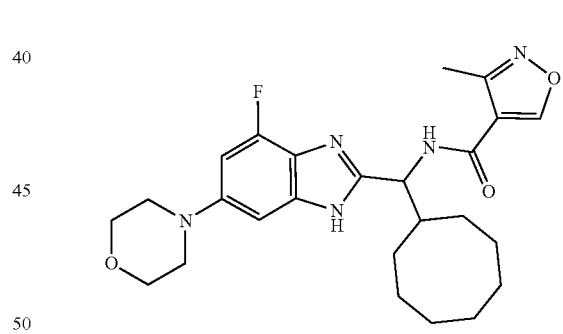

N-{Cyclooctyl[4-fluoro-6-(morpholin-4-yl)-1H-benzimidazol-2-yl]methyl}-3-methyl-isoxazole-4-carboxamide The title compound (mixture of diastereomers) (2 mg, 2%), a white solid, was prepared from Intermediate 7 (70 mg, 0.24 mmol) and Intermediate 39 (50 mg, 0.24 mmol) in accordance with Procedure Y. $\delta_H$ (300 MHz, CD$_3$OD) 9.18 (s, 1H), 6.89-6.67 (m, 2H), 5.11 (d, J 8.1 Hz, 1H), 3.88-3.82 (m, 4H), 3.17-3.10 (m, 4H), 2.50-2.33 (m, 4H), 1.80-1.42 (m, 14H). LCMS (Method 6): [M+H]$^+$ m/z 470, RT 2.18 minutes.

Example 26

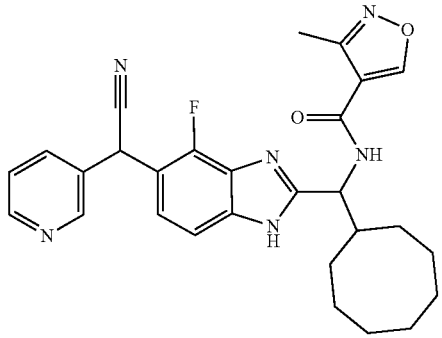 [SMILES: Cc1nocc1C(=O)NC(c1nc2c(F)c(C(C#N)c3cccnc3)ccc2[nH]1)C1CCCCCCC1]

N-[{5-[Cyano(pyridin-3-yl)methyl]-4-fluoro-1H-benzimidazol-2-yl}(cyclooctyl)methyl]-3-methyl-isoxazole-4-carboxamide The title compound (mixture of diastereomers) (2 mg, 2%), a white solid, was prepared from Intermediate 7 (59 mg, 0.20 mmol) and Intermediate 40 (46 mg, 0.19 mmol) in accordance with Procedure Y. $\delta_H$ (400 MHz, DMSO-$d_6$) 9.42 (s, 1H), 8.92-8.73 (m, 1H), 8.63 (d, J 2.4 Hz, 1H), 8.56 (dd, J 4.8, 1.6 Hz, 1H), 7.81 (d, J 8.1 Hz, 1H), 7.52-7.34 (m, 2H), 7.28 (t, J 7.4 Hz, 1H), 6.17 (s, 1H), 5.08 (t, J 8.7 Hz, 1H), 2.40-2.32 (m, 4H), 1.76-1.25 (m, 16H). LCMS (Method 6): [M+H]$^+$ m/z 501, RT 2.32 minutes.

Example 27

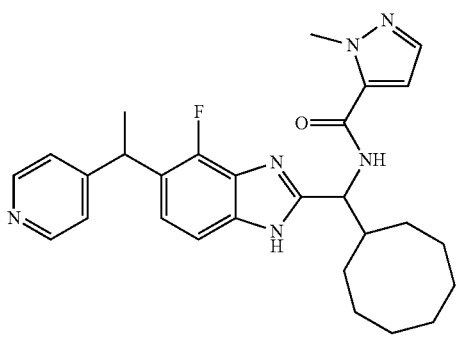 [SMILES: CC(c1ccncc1)c1ccc2[nH]c(C(NC(=O)c3ccnn3C)C3CCCCCCC3)nc2c1F]

N-(Cyclooctyl{4-fluoro-5-[1-(pyridin-4-yl)ethyl]-1H-benzimidazol-2-yl}methyl)-2-methylpyrazole-3-carboxamide The title compound (mixture of diastereomers) (14 mg, 10%), a white solid, was prepared from Intermediate 5 (90 mg, 0.30 mmol) and Intermediate 42 (70 mg, 0.30 mmol) in accordance with Procedure Y. $\delta_H$ (300 MHz, DMSO-$d_6$) 12.71 (s, 1H), 8.88 (s, 1H), 8.61-8.28 (m, 2H), 7.45 (dt, J 2.1, 1.1 Hz, 1H), 7.37-7.19 (m, 3H), 7.15-7.08 (m, 1H), 7.06 (d, J 2.1 Hz, 1H), 5.06 (t, J 8.8 Hz, 1H), 4.53 (q, J 7.3 Hz, 1H), 4.02 (d, J 0.7 Hz, 3H), 2.47-2.38 (m, 1H), 1.69-1.23 (m, 17H). LCMS (Method 6): [M+H]$^+$ m/z 489, RT 2.42 minutes.

Example 28

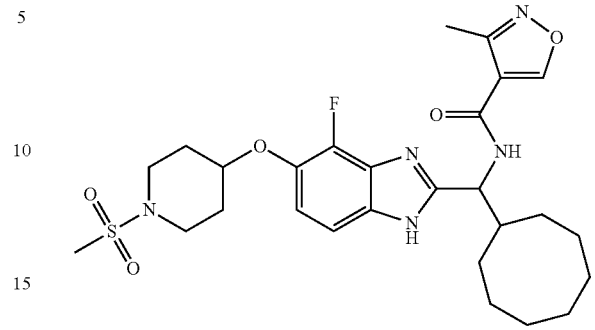

N-[Cyclooctyl(4-fluoro-5-{[1-(methylsulfonyl)piperidin-4-yl]oxy}-1H-benzimidazol-2-yl)methyl]-3-methylisoxazole-4-carboxamide The title compound (56 mg, 20%), a white solid, was prepared from Intermediate 7 (145 mg, 0.49 mmol) and Intermediate 43 (149 mg, 0.49 mmol) in accordance with Procedure Y. $\delta_H$ (400 MHz, DMSO-$d_6$) 12.99-12.60 (m, 1H), 9.43 (s, 1H), 8.91-8.71 (m, 1H), 7.38-7.15 (m, 1H), 7.06 (t, J 8.0 Hz, 1H), 5.06 (t, J 8.8 Hz, 1H), 4.41-4.31 (m, 1H), 3.37 (ddd, J 11.5, 7.4, 3.7 Hz, 2H), 3.09 (ddd, J 11.7, 7.8, 3.6 Hz, 2H), 2.90 (s, 3H), 2.46-2.30 (m, 4H), 2.02-1.91 (m, 2H), 1.86-1.11 (m, 16H). LCMS (Method 6): [M+H]$^+$ m/z 562, RT 2.42 minutes.

Example 29

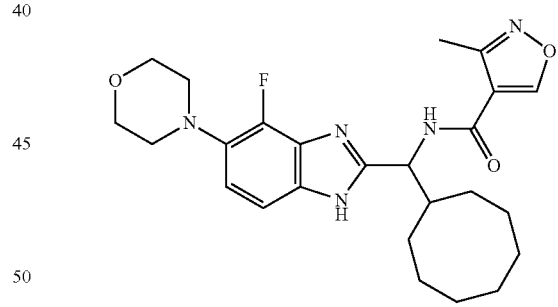

N-{Cyclooctyl[4-fluoro-5-(morpholin-4-yl)-1H-benzimidazol-2-yl]methyl}-3-methyl-isoxazole-4-carboxamide The title compound (33 mg, 21%), a beige solid, was prepared from Intermediate 7 (139 mg, 0.47 mmol) and Intermediate 44 (100 mg, 0.47 mmol) in accordance with Procedure Y. $\delta_H$ (400 MHz, DMSO-$d_6$) 13.03-12.31 (m, 1H), 9.43 (d, J 0.7 Hz, 1H), 8.97-8.61 (m, 1H), 7.40-7.12 (m, 1H), 7.05-6.81 (m, 1H), 5.22-4.95 (m, 1H), 3.88-3.65 (m, 4H), 3.10-2.87 (m, 4H), 2.42-2.23 (m, 4H), 1.86-1.15 (m, 14H). LCMS (Method 6): [M+H]$^+$ m/z 470, RT 2.17 minutes.

Example 30

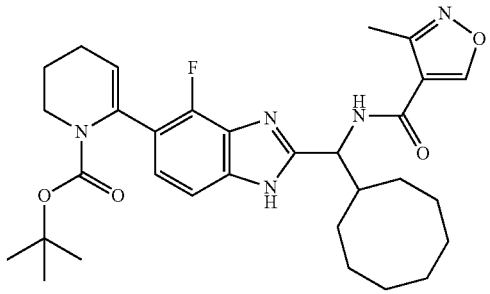 [SMILES: Cc1nocc1C(=O)NC(c1nc2c(F)c(C3=CCCCN3C(=O)OC(C)(C)C)ccc2[nH]1)C1CCCCCCC1]

tert-Butyl 6-(2-{cyclooctyl[(3-methylisoxazole-4-carbonyl)amino]methyl}-4-fluoro-1H-benzimidazol-5-yl)-3,4-dihydro-2H-pyridine-1-carboxylate The title compound (16 mg, 12%), a white solid, was prepared from Intermediate 7 (70.4 mg, 0.24 mmol) and Intermediate 45 (70 mg, 0.23 mmol) in accordance with Procedure Y. $\delta_H$ (400 MHz, DMSO-$d_6$) 12.91-12.66 (m, 1H), 9.46-9.44 (m, 1H), 8.90-8.74 (m, 1H), 7.21 (d, J 8.3 Hz, 1H), 7.21 (dd, J 8.3 Hz, 1H), 5.28-5.22 (m, 1H), 5.14-5.07 (m, 1H), 3.74-3.65 (m, 1H), 3.65-3.57 (m, 1H), 2.36 (m, 4H), 2.30-2.21 (m, 2H), 1.85-1.76 (m, 2H), 1.75-1.17 (m, 14H), 0.88 (s, 9H). LCMS (Method 6): [M+H]$^+$ m/z 566, RT 3.02 minutes.

Example 31

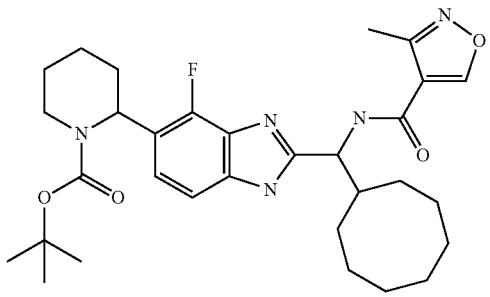 [SMILES: Cc1nocc1C(=O)NC(c1nc2c(F)c(C3CCCCN3C(=O)OC(C)(C)C)ccc2[nH]1)C1CCCCCCC1]

tert-Butyl 2-(2-{cyclooctyl[(3-methylisoxazole-4-carbonyl)amino]methyl}-4-fluoro-1H-benzimidazol-5-yl)piperidine-1-carboxylate The title compound (1:1 mixture of diastereomers) (2.6 mg, 3%), a white solid, was prepared from Intermediate 7 (50 mg, 0.17 mmol) and Intermediate 46 (50 mg, 0.16 mmol) in accordance with Procedure Y. $\delta_H$ (400 MHz, DMSO-$d_6$) 12.70 (s, 1H), 9.45 (s, 1H), 8.77 (s, 1H), 7.33-7.09 (m, 1H), 7.03-6.77 (m, 1H), 5.49-5.43 (m, 1H), 5.12-5.02 (m, 1H), 4.02-3.94 (m, 1H), 3.14 (t, J 12.7 Hz, 1H), 2.37 (m, 4H), 2.10-2.00 (m, 1H), 1.91-1.79 (m, 1H), 1.79-1.19 (m, 18H), 1.28 (s, 9H). LCMS (Method 6): [M+H]$^+$ m/z 568, RT 2.88 minutes.

Example 32

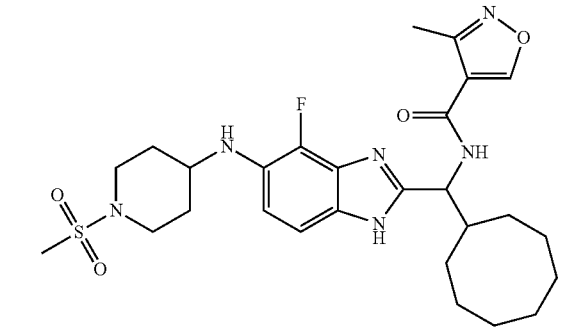 [SMILES: Cc1nocc1C(=O)NC(c1nc2c(F)c(NC3CCN(S(C)(=O)=O)CC3)ccc2[nH]1)C1CCCCCCC1]

N-[Cyclooctyl(4-fluoro-5-{[1-(methylsulfonyl)piperidin-4-yl]amino}-1H-benzimidazol-2-yl)methyl]-3-methylisoxazole-4-carboxamide The title compound (636 mg, 95%), a white solid, was prepared from Intermediate 7 (350 mg, 1.2 mmol) and Intermediate 49 (360 mg, 1.2 mmol) in accordance with Procedure Y. $\delta_H$ (300 MHz, DMSO-$d_6$) 12.53-12.24 (m, 1H), 9.44 (d, J 0.6 Hz, 1H), 8.88-8.60 (m, 1H), 7.25-7.03 (m, 1H), 6.77 (t, J 7.6 Hz, 1H), 5.11-4.97 (m, 1H), 4.91-4.57 (m, 1H), 3.56 (d, J 12.0 Hz, 2H), 3.48-3.36 (m, 1H), 2.97-2.70 (m, 5H), 2.45-2.22 (m, 4H), 1.97 (d, J 11.4 Hz, 2H), 1.80-1.20 (m, 16H). LCMS (Method 6): [M+H]$^+$ m/z 561, RT 2.31 minutes.

Example 33

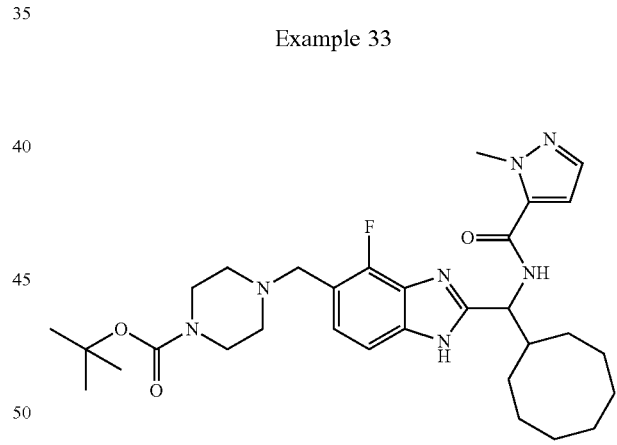

tert-Butyl 4-[(2-{cyclooctyl[(2-methylpyrazole-3-carbonyl)amino]methyl}-4-fluoro-1H-benzimidazol-5-yl)methyl]piperazine-1-carboxylate The title compound (510 mg, 55%), a white solid, was prepared from Intermediate 5 (475 mg, 1.6 mmol) and Intermediate 50 (522 mg, 1.6 mmol) in accordance with Procedure Y. $\delta_H$ (400 MHz, DMSO-$d_6$) 12.69 (s, 1H), 8.91 (d, J 8.4 Hz, 1H), 7.45 (d, J 2.1 Hz, 1H), 7.24 (d, J 8.2 Hz, 1H), 7.14 (t, J 7.2 Hz, 1H), 7.06 (s, 1H), 5.06 (t, J 9.0 Hz, 1H), 4.02 (d, J 2.1 Hz, 3H), 3.60 (s, 2H), 3.28 (s, 4H), 2.33 (s, 4H), 1.74-1.27 (m, 24H). LCMS (Method 6): [M+H]$^+$ m/z 582, RT 2.72 minutes.

Example 34

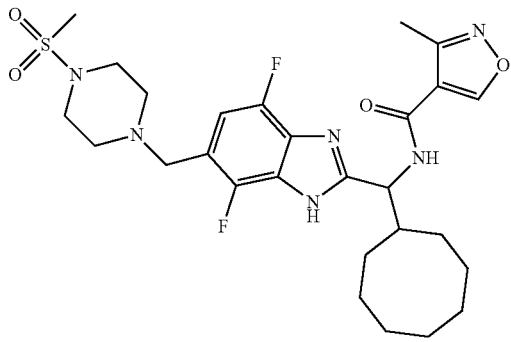 [SMILES: Cc1nocc1C(=O)NC(c1nc2c(F)cc(CN3CCN(S(C)(=O)=O)CC3)c(F)c2[nH]1)C1CCCCCCC1]

N-[Cyclooctyl(4,7-difluoro-6-{[4-(methylsulfonyl)piperazin-1-yl]methyl}-1H-benzimidazol-2-yl)methyl]-3-methylisoxazole-4-carboxamide The title compound (26 mg, 16%), a white solid, was prepared from Intermediate 7 (85 mg, 0.29 mmol) and Intermediate 53 (92 mg, 0.29 mmol) in accordance with Procedure Y. $\delta_H$ (300 MHz, DMSO-$d_6$) 13.32 (s, 1H), 9.43 (d, J 0.7 Hz, 1H), 8.84 (d, J 8.6 Hz, 1H), 6.98 (s, 1H), 5.10 (t, J 8.7 Hz, 1H), 3.64 (s, 2H), 3.08 (d, J 5.3 Hz, 4H), 2.85 (s, 3H), 2.50-2.47 (m, 4H), 2.44-2.25 (m, 4H), 1.81-1.21 (m, 14H). LCMS (Method 6): [M+H]$^+$ m/z 579, RT 2.25 minutes.

Example 35

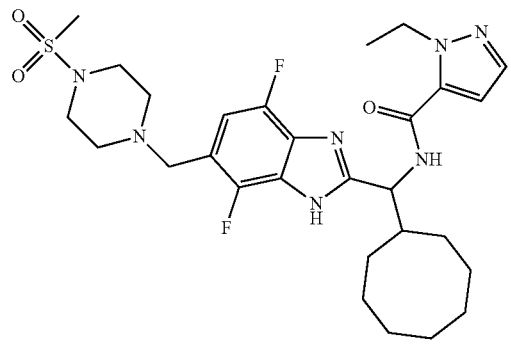 [SMILES: CCn1nccc1C(=O)NC(c1nc2c(F)cc(CN3CCN(S(C)(=O)=O)CC3)c(F)c2[nH]1)C1CCCCCCC1]

N-[Cyclooctyl(4,7-difluoro-6-{[4-(methylsulfonyl)piperazin-1-yl]methyl}-1H-benzimidazol-2-yl)methyl]-2-ethylpyrazole-3-carboxamide The title compound (70 mg, 14%), a white solid, was prepared from Intermediate 124 (272 mg, 0.88 mmol) and Intermediate 53 (275 mg, 0.86 mmol) in accordance with Procedure Y. $\delta_H$ (300 MHz, DMSO-$d_6$) 13.32 (s, 1H), 8.90-8.86 (m, 1H), 7.47 (d, J 2.0 Hz, 1H), 7.02 (d, J 2.1 Hz, 1H), 6.97 (s, 1H), 5.09 (t, J 9.0 Hz, 1H), 4.45 (q, J 7.1 Hz, 2H), 3.64 (s, 2H), 3.08 (d, J 5.3 Hz, 4H), 2.85 (s, 3H), 2.52-2.36 (m, 5H), 1.76-1.22 (m, 17H). LCMS (Method 6): [M+H]$^+$ m/z 592, RT 2.31 minutes.

Examples 36 & 37

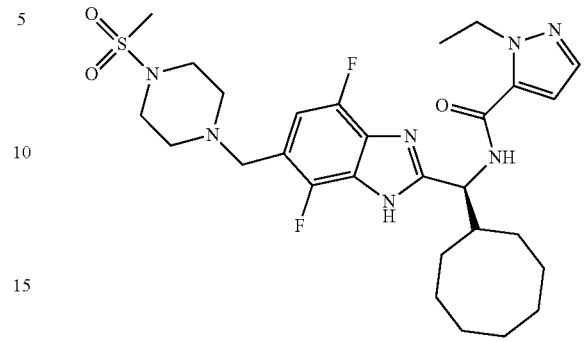

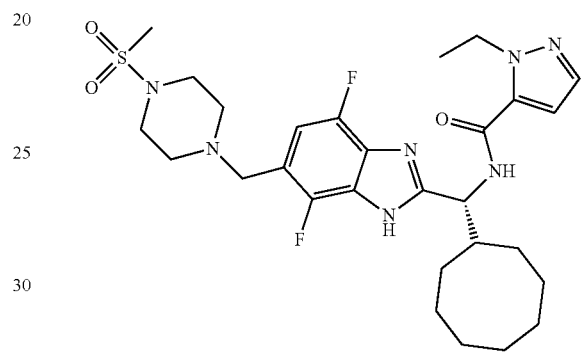

N-[(S)-Cyclooctyl(4,7-difluoro-6-{[4-(methylsulfonyl)piperazin-1-yl]methyl}-1H-benzimidazol-2-yl)methyl]-2-ethylpyrazole-3-carboxamide (Example 36)

N-[(R)-Cyclooctyl(4,7-difluoro-6-{[4-(methylsulfonyl)piperazin-1-yl]methyl}-1H-benzimidazol-2-yl)methyl]-2-ethylpyrazole-3-carboxamide (Example 37)

Example 35 (70 mg) was subject to chiral HPLC (Waters Prep 100-SQD2 equipped with a CHIRALCEL OJ-H 20×250 mm, 5 μm column), flow rate 5 mL/min, eluting with MeOH (+0.1% NH$_4$OH) and water (gradient of 5-15%), to yield, after freeze-drying, the title compounds (Peak 1, 19 mg, 27%; and Peak 2, 20 mg, 29%) as white solids.

Peak 1: $\delta_H$ (300 MHz, DMSO-$d_6$) 13.35 (s, 1H), 8.90 (d, J 8.8 Hz, 1H), 7.47 (d, J 2.0 Hz, 1H), 7.03 (d, J 2.1 Hz, 1H), 6.98 (s, 1H), 5.10 (t, J 8.9 Hz, 1H), 4.45 (q, J 7.1 Hz, 2H), 3.64 (s, 2H), 3.09 (t, J 4.8 Hz, 4H), 2.85 (s, 3H), 2.50-2.36 (m, 5H), 1.74-1.22 (m, 17H). LCMS (Method 6): [M+H]$^+$ m/z 592, RT 2.31 minutes.

Peak 2: $\delta_H$ (300 MHz, DMSO-$d_6$) 13.37 (s, 1H), 8.91 (d, J 8.7 Hz, 1H), 7.47 (d, J 2.0 Hz, 1H), 7.03 (d, J 2.1 Hz, 1H), 6.98 (s, 1H), 5.10 (t, J 9.0 Hz, 1H), 4.45 (q, J 7.1 Hz, 2H), 3.64 (s, 2H), 3.09 (t, J 4.9 Hz, 4H), 2.85 (s, 3H), 2.50-2.32 (m, 5H), 1.80-1.19 (m, 17H). LCMS (Method 6): [M+H]$^+$ m/z 592, RT 2.31 minutes.

Example 38

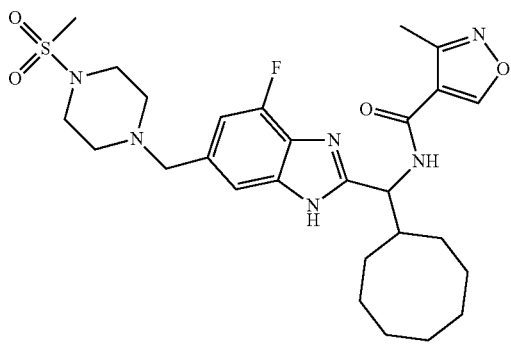 [SMILES: Cc1nocc1C(=O)NC(c1nc2c(F)cc(CN3CCN(S(C)(=O)=O)CC3)cc2[nH]1)C1CCCCCCC1]

N-[Cyclooctyl(4-fluoro-6-{[4-(methylsulfonyl)piperazin-1-yl]methyl}-1H-benzimidazol-2-yl)methyl]-3-methylisoxazole-4-carboxamide The title compound (3 mg, 3%), a white solid, was prepared from Intermediate 7 (60 mg, 0.2 mmol) and Intermediate 56 (61 mg, 0.2 mmol) in accordance with Procedure Y. $\delta_H$ (400 MHz, DMSO-$d_6$) 12.75 (s, 1H), 9.43 (s, 1H), 8.81 (s, 1H), 7.20 (s, 1H), 6.89 (s, 1H), 5.08 (t, J 8.6 Hz, 1H), 3.59 (s, 2H), 3.10 (d, J 5.2 Hz, 4H), 2.86 (s, 3H), 2.48-2.44 (m, 4H), 2.41-2.36 (m, 4H), 1.20-1.80 (m, 14H). LCMS (Method 6): [M+H]+ m/z 561, RT 2.01 minutes.

Example 39

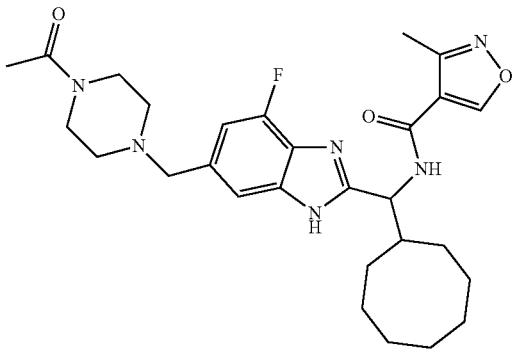 [SMILES: CC(=O)N1CCN(Cc2cc(F)c3nc(C(NC(=O)c4conc4C)C4CCCCCCC4)[nH]c3c2)CC1]

N-[{6-[(4-Acetylpiperazin-1-yl)methyl]-4-fluoro-1H-benzimidazol-2-yl}(cyclooctyl)-methyl]-3-methylisoxazole-4-carboxamide The title compound (3 mg, 3%), a white solid, was prepared from Intermediate 7 (55 mg, 0.19 mmol) and Intermediate 57 (50 mg, 0.19 mmol) in accordance with Procedure Y. $\delta_H$ (300 MHz, DMSO-$d_6$) 12.70 (s, 1H), 9.43 (s, 1H), 8.85-8.81 (m, 1H), 7.21 (s, 1H), 6.90 (d, J 12.0 Hz, 1H), 5.08 (t, J 8.7 Hz, 1H), 3.56 (s, 2H), 3.41 (d, J 5.0 Hz, 4H), 2.40-2.25 (m, 8H), 1.96 (s, 3H), 1.74-1.30 (m, 14H). LCMS (Method 6): [M+H]+ m/z 525, RT 2.00 minutes.

Example 40

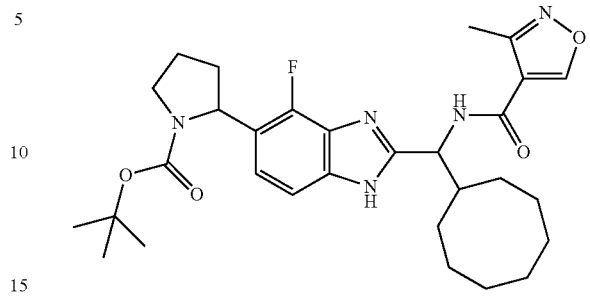

tert-Butyl 2-(2-{cyclooctyl[(3-methylisoxazole-4-carbonyl)amino]methyl}-4-fluoro-1H-benzimidazol-5-yl)pyrrolidine-1-carboxylate The title compound (1:1 mixture of diastereomers) (23.1 mg, 14%), a white solid, was prepared from Intermediate 7 (95.3 mg, 0.32 mmol) and Intermediate 91 (91.1 mg, 0.31 mmol) in accordance with Procedure Y. $\delta_H$ (400 MHz, DMSO-$d_6$) 12.88-12.65 (s, 1H), 9.44 (s, 1H), 8.84 (s, 1H), 7.39-7.14 (m, 1H), 7.01-6.81 (m, 1H), 5.19-5.00 (m, 2H), 3.63-3.40 (m, 2H), 2.36 (m, 4H), 1.95-1.19 (m, 18H), 1.04 (s, 9H). LCMS (Method 6): [M+H]+ m/z 554, RT 2.67 minutes.

Example 41

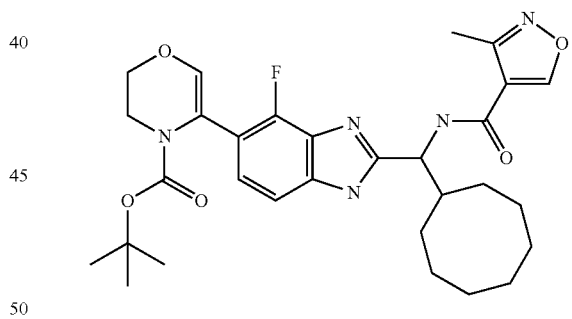

tert-Butyl 5-(2-{cyclooctyl[(3-methylisoxazole-4-carbonyl)amino]methyl}-4-fluoro-1H-benzimidazol-5-yl)-2,3-dihydro-1,4-oxazine-4-carboxylate The title compound (2 mg, 2%), a white solid, was prepared from Intermediate 7 (50 mg, 0.17 mmol) and Intermediate 92 (50 mg, 0.16 mmol) in accordance with Procedure Y. $\delta_H$ (400 MHz, DMSO-$d_6$) 12.86 (s, 1H), 9.47 (s, 1H), 8.92 (s, 1H), 7.25-7.11 (m, 1H), 7.02-6.87 (m, 1H), 6.22 (s, 1H), 5.08 (t, J 8.1 Hz, 1H), 4.19-4.09 (m, 2H), 3.81-3.64 (m, 2H), 2.36 (m, 4H), 1.77-1.19 (m, 14H), 0.92 (s, 9H). LCMS (Method 6): [M+H]+ m/z 568, RT 2.77 minutes.

Example 42

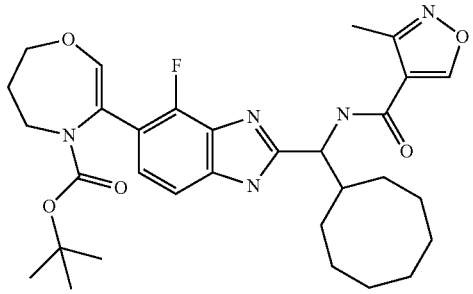 [SMILES: Cc1nocc1C(=O)NC(c1nc2c(F)c(C3=COCCCN3C(=O)OC(C)(C)C)ccc2[nH]1)C1CCCCCCC1]

tert-Butyl 3-(2-{cyclooctyl[(3-methylisoxazole-4-carbonyl)amino]methyl}-4-fluoro-1H-benzimidazol-5-yl)-6,7-dihydro-5H-1,4-oxazepine-4-carboxylate The title compound (33 mg, 14%), a white solid, was prepared from Intermediate 7 (123 mg, 0.42 mmol) and Intermediate 93 (129 mg, 0.40 mmol) in accordance with Procedure Y. $\delta_H$ (400 MHz, DMSO-$d_6$) 12.93-12.69 (s, 1H), 9.44 (s, 1H), 8.88-8.76 (m, 1H), 7.37-7.21 (m, 1H), 7.06-6.95 (m, 1H), 6.28-6.23 (m, 1H), 5.09 (t, J 8.3 Hz, 1H), 4.15-4.00 (m, 2H), 3.88-3.77 (m, 2H), 2.37 (m, 4H), 2.07-1.91 (m, 2H), 1.77-1.18 (m, 14H), 0.93 (s, 9H). LCMS (Method 6): [M+H]$^+$ m/z 582, RT 2.86 minutes.

Example 43

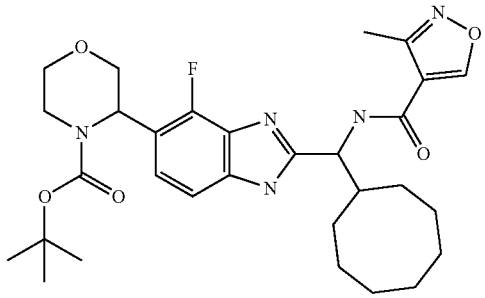

tert-Butyl 3-(2-{cyclooctyl[(3-methylisoxazole-4-carbonyl)amino]methyl}-4-fluoro-1H-benzimidazol-5-yl)morpholine-4-carboxylate The title compound (1:1 mixture of diastereomers) (18 mg, 5%), a white solid, was prepared from Intermediate 7 (217 mg, 0.73 mmol) and Intermediate 100 (219 mg, 0.70 mmol) in accordance with Procedure Y. $\delta_H$ (300 MHz, DMSO-$d_6$) 12.71 (s, 1H), 9.44 (s, 1H), 8.83 (s, 1H), 7.32-7.21 (m, 2H), 5.27 (s, 1H), 5.09 (t, J 8.7 Hz, 1H), 4.17-3.99 (m, 1H), 3.99-3.64 (m, 3H), 3.53 (td, J 11.4, 3.1 Hz, 1H), 3.36-3.23 (m, 1H), 2.37 (m, 4H), 1.85-1.08 (m, 14H), 1.33 (s, 9H). LCMS (Method 6): [M+H]$^+$ m/z 570, RT 2.80

Example 44

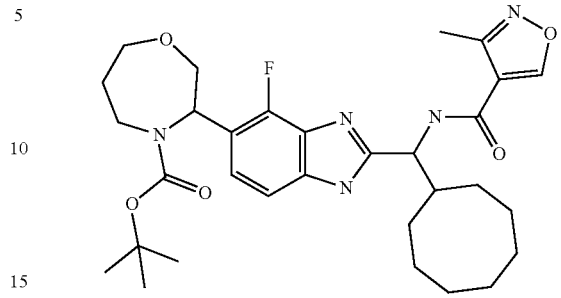

tert-Butyl 3-(2-{cyclooctyl[(3-methylisoxazole-4-carbonyl)amino]methyl}-4-fluoro-1H-benzimidazol-5-yl)-1,4-oxazepane-4-carboxylate The title compound (1:1 mixture of diastereomers) (54 mg, 19%), a white solid, was prepared from Intermediate 7 (85.5 mg, 0.29 mmol) and Intermediate 101 (90 mg, 0.28 mmol) in accordance with Procedure Y. $\delta_H$ (400 MHz, DMSO-$d_6$) 12.74 (s, 1H), 9.45 (s, 1H), 8.81 (s, 1H), 7.36-7.14 (m, 1H), 7.06-6.86 (m, 1H), 5.57-5.23 (m, 1H), 5.16-4.99 (m, 1H), 4.31-4.87 (m, 3H), 3.77-3.41 (m, 3H), 2.37 (m, 4H), 1.83-1.08 (m, 16H), 1.16 (s, 9H). LCMS (Method 6): [M+H]$^+$ m/z 584, RT 2.78 minutes.

Example 45

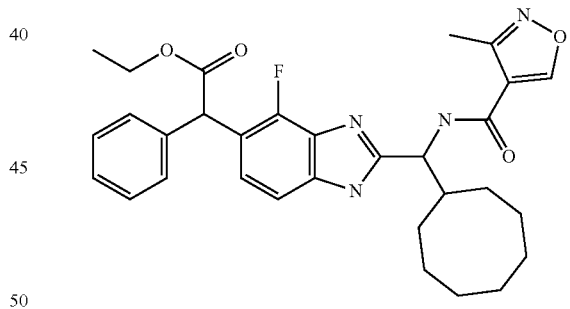

Ethyl 2-(2-{cyclooctyl[(3-methylisoxazole-4-carbonyl)amino]methyl}-4-fluoro-1H-benzimidazol-5-yl)-2-phenylacetate The title compound (1:1 mixture of diastereomers) (208 mg, 23%), a white solid, was prepared from Intermediate 7 (510 mg, 1.73 mmol) and Intermediate 78 (476 mg, 1.65 mmol) in accordance with Procedure Y. $\delta_H$ (400 MHz, DMSO-$d_6$) 13.00-12.75 (m, 1H), 9.43-9.42 (m, 1H), 8.86-8.75 (m, 1H), 7.40-7.22 (m, 6H), 7.01-7.93 (m, 1H), 5.44-5.42 (m, 1H), 5.11-5.07 (m, 1H), 4.21-4.11 (m, 2H), 2.43-2.32 (m, 4H), 1.79-1.22 (m, 14H), 1.20-1.13 (m, 3H). LCMS (Method 6): [M+H]$^+$ m/z 547, RT 2.98 minutes.

Example 46

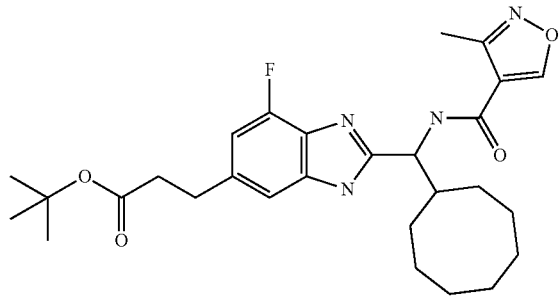

tert-Butyl 3-(2-{cyclooctyl[(3-methylisoxazole-4-carbonyl)amino]methyl}-7-fluoro-3H-benzimidazol-5-yl)propanoate The title compound (49 mg, 23%), a white solid, was prepared from Intermediate 7 (128.9 mg, 0.44 mmol) and Intermediate 70 (114 mg, 0.42 mmol) in accordance with Procedure Y. $\delta_H$ (400 MHz, DMSO-d$_6$) 12.65 (s, 1H), 9.43 (s, 1H), 8.81 (d, J 9.0 Hz, 1H), 7.13 (s, 1H), 6.85 (d, J 12.0 Hz, 1H), 5.08 (t, J 8.7 Hz, 1H), 2.89 (t, J 7.4 Hz, 2H), 2.52 (t, J 7.4 Hz, 2H), 2.42-2.32 (m, 4H), 1.77-1.18 (m, 14H), 1.36 (s, 9H). LCMS (Method 6): [M+H]⁺ m/z 513, RT 2.76 minutes.

Example 47

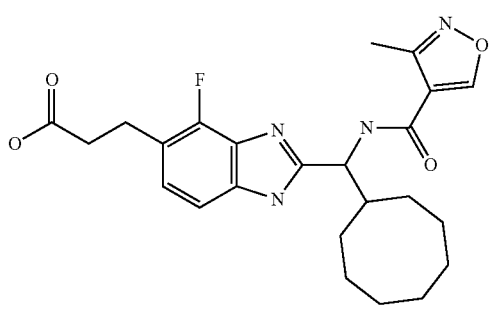

3-(2-{Cyclooctyl[(3-methylisoxazole-4-carbonyl)amino]methyl}-4-fluoro-1H-benzimidazol-5-yl)propanoic Acid To a solution of Example 20 (119 mg, 0.23 mmol) in DCM (3 mL) was added TFA (0.56 mL, 7.4 mmol). The reaction mixture was stirred overnight at r.t., then concentrated in vacuo. The crude material was subject to purification by reverse-phase HPLC to yield the title compound (26 mg, 23%) as a white solid. $\delta_H$ (300 MHz, DMSO-d6) 12.79 (s, 1H), 12.03 (br s, 1H), 9.45 (s, 1H), 8.96-8.84 (m, 1H), 7.37-7.19 (m, 1H), 7.11-7.02 (m, 1H), 5.08 (t, J 8.9 Hz, 1H), 2.93 (t, J 7.7 Hz, 2H), 2.57-2.48 (m, 2H), 2.44-2.30 (m, 4H), 1.81-1.20 (m, 14H). LCMS (Method 6): [M+H]⁺ m/z 457, RT 1.54

Example 48

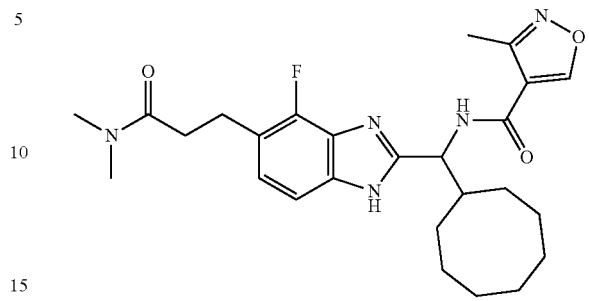

N-(Cyclooctyl{5-[3-(dimethylamino)-3-oxopropyl]-4-fluoro-1H-benzimidazol-2-yl}-methyl)-3-methyl-isoxazole-4-carboxamide The title compound (12 mg, 38%), a white solid, was prepared from Example 47 (30 mg, 0.07 mmol) and a 2M solution of dimethylamine in THF (33 μL, 0.07 mmol) in accordance with Procedure A. $\delta_H$ (400 MHz, DMSO-d$_6$) 12.63 (s, 1H), 9.44 (s, 1H), 8.83 (s, 1H), 7.19 (d, J 8.2 Hz, 1H), 7.07 (t, J 7.4 Hz, 1H), 5.09 (d, J 9.0 Hz, 1H), 2.93 (s, 3H), 2.89 (t, J 8.0 Hz, 2H), 2.82 (s, 3H), 2.59 (t, J 7.9 Hz, 2H), 2.42-2.34 (m, 4H), 1.89-1.14 (m, 14H). LCMS (Method 6): [M+H]⁺ m/z 484, RT 2.05 minutes.

Example 49

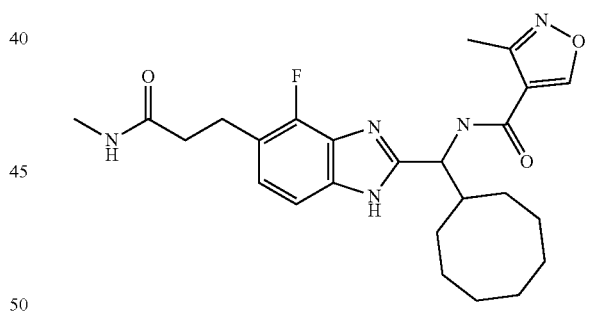

N-(Cyclooctyl{4-fluoro-5-[3-(methylamino)-3-oxopropyl]-1H-benzimidazol-2-yl}-methyl)-3-methyl-isoxazole-4-carboxamide The title compound (11 mg, 36%), a white solid, was prepared from Example 47 (30 mg, 0.07 mmol) and a 2M solution of methylamine in THF (33 μL, 0.07 mmol) in accordance with Procedure A. $\delta_H$ (400 MHz, DMSO-d$_6$) 12.94-12.72 (m, 1H), 9.44 (s, 1H), 8.90-8.81 (m, 1H), 7.75 (d, J 5.1 Hz, 1H), 7.35-7.18 (m, 1H), 7.01 (t, J 7.5 Hz, 1H), 5.07 (t, J 8.7 Hz, 1H), 3.38-3.26 (m, 2H), 2.90 (t, J 7.7 Hz, 2H), 2.55 (d, J 4.6 Hz, 3H), 2.41-2.32 (m, 4H), 1.79-1.18 (m, 14H). LCMS (Method 6): [M+H]⁺ m/z 470, RT 1.94

Example 50

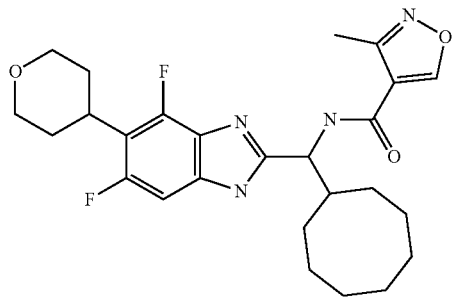

N-{Cyclooctyl[4,6-difluoro-5-(tetrahydropyran-4-yl)-1H-benzimidazol-2-yl]methyl}-3-methylisoxazole-4-carboxamide The title compound (9 mg, 7%), a beige solid, was prepared from Intermediate 7 (80 mg, 0.27 mmol) and Intermediate 71 (80 mg, 0.29 mmol) in accordance with Procedure Y. $\delta_H$ (400 MHz, DMSO-$d_6$) 12.86 (s, 1H), 9.42 (s, 1H), 8.82 (d, J 7.7 Hz, 1H), 7.18 (d, J 10.8 Hz, 1H), 5.25-4.87 (m, 1H), 4.29-3.86 (m, 2H), 3.55-3.42 (m, 2H), 3.30-3.17 (m, 2H), 2.41-2.25 (m, 4H), 2.17-1.96 (m, 2H), 1.86-1.10 (m, 15H). LCMS (Method 6): [M+H]$^+$ m/z 487, RT 2.44 minutes.

Example 51

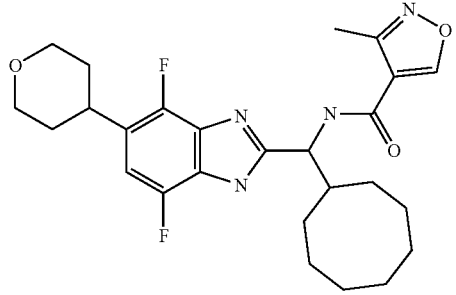

N-{Cyclooctyl[4,7-difluoro-5-(tetrahydropyran-4-yl)-1H-benzimidazol-2-yl]methyl}-3-methylisoxazole-4-carboxamide The title compound (5 mg, 3%), a white solid, was prepared from Intermediate 7 (89 mg, 0.30 mmol) and Intermediate 72 (121 mg, 0.42 mmol) in accordance with Procedure Y. $\delta_H$ (400 MHz, DMSO-$d_6$) 13.16 (s, 1H), 9.44 (s, 1H), 8.82 (s, 1H), 6.96 (s, 1H), 5.10 (t, J 8.8 Hz, 1H), 4.02-3.90 (m, 2H), 3.54-3.40 (m, 2H), 3.24-3.07 (m, 1H), 2.40-2.29 (m, 4H), 1.87-1.23 (m, 18H). LCMS (Method 6): [M+H]$^+$ m/z 487, RT 2.46

Example 52

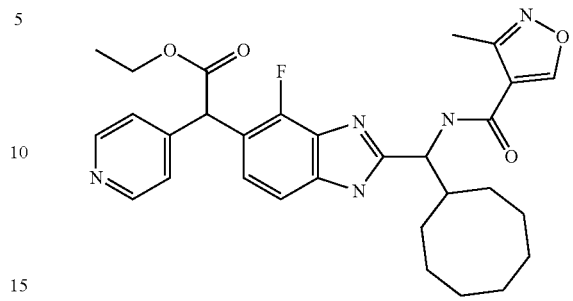

Ethyl 2-(2-{cyclooctyl[(3-methylisoxazole-4-carbonyl)amino]methyl}-4-fluoro-1H-benzimidazol-5-yl)-2-(pyridin-4-yl)acetate The title compound (mixture of diastereomers) (29 mg, 7%), a white solid, was prepared from Intermediate 7 (220 mg, 0.71 mmol) and Intermediate 76 (240 mg, 0.72 mmol) in accordance with Procedure Y. $\delta_H$ (400 MHz, DMSO-$d_6$) 12.86 (s, 1H), 9.43 (d, J 2.4 Hz, 1H), 9.01-8.75 (m, 1H), 8.53 (dt, J 4.5, 1.7 Hz, 2H), 7.47-7.20 (m, 3H), 7.10-6.93 (m, 1H), 5.50 (s, 1H), 5.19-4.98 (m, 1H), 4.28-4.06 (m, 2H), 2.43-2.22 (m, 4H), 1.77-1.24 (m, 14H), 1.21-1.06 (m, 3H). LCMS (Method 6): [M+H]$^+$ m/z 548, RT 2.31 minutes.

Example 53

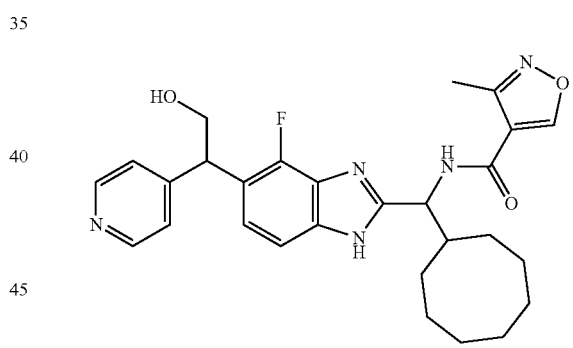

N-(Cyclooctyl{4-fluoro-5-[2-hydroxy-1-(pyridin-4-yl)ethyl]-1H-benzimidazol-2-yl}-methyl)-3-methyl-isoxazole-4-carboxamide A solution of Example 52 (23 mg, 0.04 mmol) in THF (1 mL) at −70° C. was treated with a 2M solution of LiAlH$_4$ in THF (25 µL, 0.05 mmol). The solution was allowed to warm to 0° C. and stirred for 2 h, then cooled again to −70° C. A further aliquot of a 2M solution of LiAlH$_4$ in THF (25 µL, 0.05 mmol) was added. After 1 h at r.t., the reaction mixture was quenched with saturated aqueous NaHCO$_3$ solution and extracted with EtOAc (3×10 mL). The organic layers were combined, dried over Na$_2$SO$_4$ and concentrated in vacuo. The crude material was purified by reverse-phase HPLC to yield the title compound (mixture of diastereomers) (6 mg, 28%) as a white solid. $\delta_H$ (300 MHz, DMSO-$d_6$) 12.73 (s, 1H), 9.44 (s, 1H), 8.87 (s, 1H), 8.60-8.26 (m, 2H), 7.41-7.18 (m, 3H), 7.16-7.05 (m, 1H), 5.06 (t, J 8.8 Hz, 1H), 5.01-4.91

(m, 1H), 4.47 (t, J 7.2 Hz, 1H), 4.17-3.88 (m, 2H), 2.43-2.25 (m, 4H), 1.75-1.26 (m, 14H). LCMS (Method 6): [M+H]⁺ m/z 506, RT 1.96 minutes.

Example 54

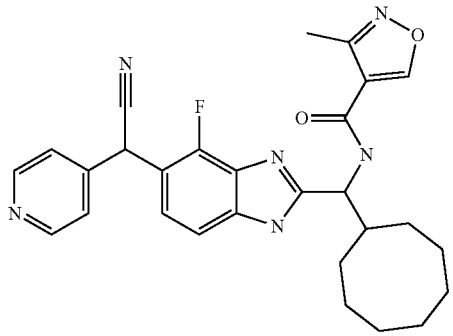

N-[{5-[Cyano(pyridin-4-yl)methyl]-4-fluoro-1H-benzimidazol-2-yl}(cyclooctyl)methyl]-3-methyl-isoxazole-4-carboxamide The title compound (mixture of diastereomers) (26 mg, 4%), a white solid, was prepared from Intermediate 7 (447 mg, 1.52 mmol) and Intermediate 77 (324 mg, 1.34 mmol) in accordance with Procedure Y. $\delta_H$ (400 MHz, DMSO-$d_6$) 12.71 (s, 1H), 9.48-9.38 (m, 1H), 8.92-8.51 (m, 2H), 7.66-7.00 (m, 4H), 6.57-6.10 (m, 1H), 5.93 (s, 1H), 5.17-5.02 (m, 1H), 2.44-2.30 (m, 4H), 1.83-1.19 (m, 14H). LCMS (Method 6): [M+H]⁺ m/z 501, RT 2.33 minutes.

Example 55

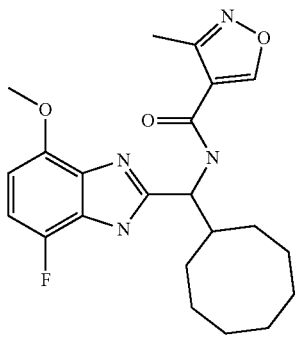

N-[Cyclooctyl(7-fluoro-4-methoxy-1H-benzimidazol-2-yl)methyl]-3-methylisoxazole-4-carboxamide The title compound (22 mg, 18%), a white solid, was prepared from Intermediate 7 (85 mg, 0.29 mmol) and Intermediate 79 (52 mg, 0.31 mmol) in accordance with Procedure Y. $\delta_H$ (300 MHz, DMSO-$d_6$) 12.85 (s, 1H), 9.57-9.37 (m, 1H), 8.90-8.63 (m, 1H), 7.00-6.78 (m, 1H), 6.75-6.48 (m, 1H), 5.13 (t, J 8.8 Hz, 1H), 3.90 (s, 3H), 2.43-2.22 (m, 4H), 1.78-1.38 (m, 12H), 1.33-1.22 (m, 2H). LCMS (Method 6): [M+H]⁺ m/z 415, RT 2.35 minutes.

Example 56

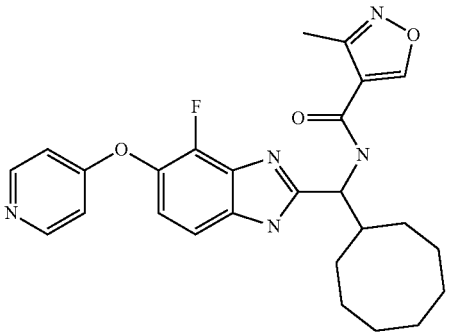

N-{Cyclooctyl[4-fluoro-5-(pyridin-4-yloxy)-1H-benzimidazol-2-yl]methyl}-3-methyl-isoxazole-4-carboxamide The title compound (27 mg, 23%), a white solid, was prepared from Intermediate 7 (200 mg, 0.65 mmol) and Intermediate 82 (180 mg, 0.82 mmol) in accordance with Procedure Y. $\delta_H$ (300 MHz, DMSO-$d_6$) 9.45 (s, 1H), 9.03 (d, J 8.6 Hz, 1H), 7.94-7.76 (m, 2H), 7.50-7.40 (m, 1H), 7.37-7.26 (m, 1H), 6.30-6.12 (m, 2H), 5.12 (t, J 8.7 Hz, 1H), 2.37 (s, 4H), 1.88-1.01 (m, 14H). LCMS (Method 6): [M+H]⁺ m/z 478, RT 1.82 minutes.

Example 57

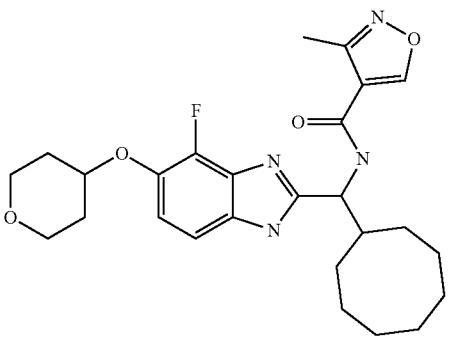

N-{Cyclooctyl[4-fluoro-5-(tetrahydropyran-4-yloxy)-1H-benzimidazol-2-yl]methyl}-3-methyl-isoxazole-4-carboxamide The title compound (53 mg, 45%), a beige solid, was prepared from Intermediate 7 (147 mg, 0.50 mmol) and Intermediate 83 (130 mg, 0.42 mmol) in accordance with Procedure Y. $\delta_H$ (400 MHz, DMSO-$d_6$) 12.65 (s, 1H), 9.43 (s, 1H), 8.83 (s, 1H), 7.20 (s, 1H), 7.12-6.95 (m, 1H), 5.07 (t, J 8.7 Hz, 1H), 4.38 (s, 1H), 3.95-3.77 (m, 2H), 3.60-3.38 (m, 2H), 2.42-2.27 (m, 4H), 2.00-1.85 (m, 2H), 1.81-1.18 (m, 16H). LCMS (Method 6): [M+H]⁺ m/z 485, RT 2.27 minutes.

Example 58

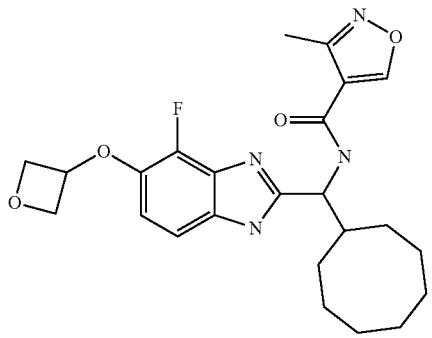

N-{Cyclooctyl[4-fluoro-5-(oxetan-3-yloxy)-1H-benzimidazol-2-yl]methyl}-3-methyl-isoxazole-4-carboxamide The title compound (45 mg, 39%), a beige solid, was prepared from Intermediate 7 (147 mg, 0.49 mmol) and Intermediate 84 (120 mg, 0.52 mmol) in accordance with Procedure Y. $\delta_H$ (400 MHz, DMSO-d$_6$) 12.67 (s, 1H), 9.43 (s, 1H), 8.82 (s, 1H), 7.19 (s, 1H), 6.79 (t, J 8.1 Hz, 1H), 5.37-5.20 (m, 1H), 5.08 (t, J 8.7 Hz, 1H), 4.95-4.81 (m, 2H), 4.69-4.56 (m, 2H), 2.41-2.24 (m, 4H), 1.88-1.10 (m, 14H). LCMS (Method 6): [M+H]$^+$ m/z 457, RT 2.12 minutes.

Example 59

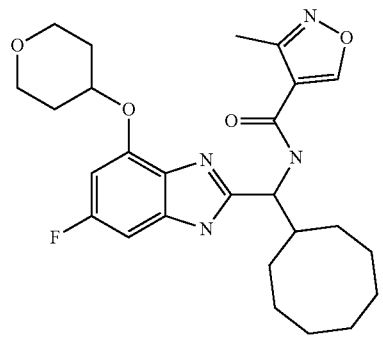

N-{Cyclooctyl[6-fluoro-4-(tetrahydropyran-4-yloxy)-1H-benzimidazol-2-yl]methyl}-3-methyl-isoxazole-4-carboxamide The title compound (58 mg, 16%), a white solid, was prepared from Intermediate 7 (230 mg, 0.78 mmol) and Intermediate 80 (175 mg, 0.77 mmol) in accordance with Procedure Y. $\delta_H$ (300 MHz, DMSO-d$_6$) 12.80-12.32 (m, 1H), 9.42 (s, 1H), 8.81 (d, J 9.4 Hz, 1H), 7.08-6.50 (m, 2H), 5.22-4.62 (m, 2H), 3.90 (d, J 11.0 Hz, 2H), 3.48 (d, J 11.2 Hz, 2H), 2.36 (m, 4H), 2.02 (d, J 12.5 Hz, 2H), 1.80-1.18 (m, 16H). LCMS (Method 6): [M+H]$^+$ m/z 485, RT 2.36 minutes.

Example 60

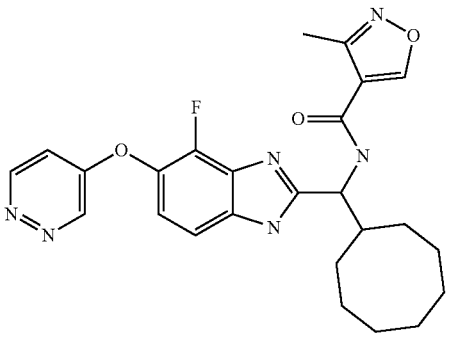

N-{Cyclooctyl[4-fluoro-5-(pyridazin-4-yloxy)-1H-benzimidazol-2-yl]methyl}-3-methyl-isoxazole-4-carboxamide The title compound (39 mg, 11%), a white solid, was prepared from Intermediate 7 (211 mg, 0.72 mmol) and Intermediate 81 (158 mg, 0.72 mmol) in accordance with Procedure Y. $\delta_H$ (300 MHz, DMSO-d$_6$) 13.14 (s, 1H), 9.64-9.27 (m, 1H), 8.99 (d, J 8.3 Hz, 1H), 8.64-8.49 (m, 1H), 7.96 (d, J 2.7 Hz, 1H), 7.56-7.30 (m, 2H), 6.51 (dd, J 7.9, 3.2 Hz, 1H), 5.13 (t, J 8.8 Hz, 1H), 2.48-2.30 (m, 4H), 1.77-1.29 (m, 14H). LCMS (Method 6): [M+H]$^+$ m/z 479, RT 2.00 minutes.

Example 61

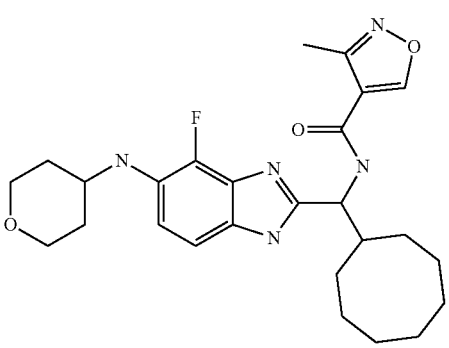

N-{Cyclooctyl[4-fluoro-5-(tetrahydropyran-4-ylamino)-1H-benzimidazol-2-yl]methyl}-3-methyl-isoxazole-4-carboxamide The title compound (15 mg, 5%), an off-white solid, was prepared from Intermediate 7 (100 mg, 0.34 mmol) and Intermediate 89 (92 mg, 0.34 mmol) in accordance with Procedure Y. $\delta_H$ (400 MHz, DMSO-d$_6$) 12.47 (s, 1H), 9.45 (s, 1H), 9.13-8.64 (m, 1H), 7.07 (s, 1H), 6.91-6.62 (m, 1H), 5.04 (t, J 8.8 Hz, 1H), 4.88-4.34 (m, 1H), 4.00-3.77 (m, 2H), 3.57-2.95 (m, 3H), 2.37 (s, 4H), 1.89-1.81 (m, 2H), 1.74-1.18 (m, 16H). LCMS (Method 6): [M+H]$^+$ m/z 484, RT 2.12 minutes.

Example 62

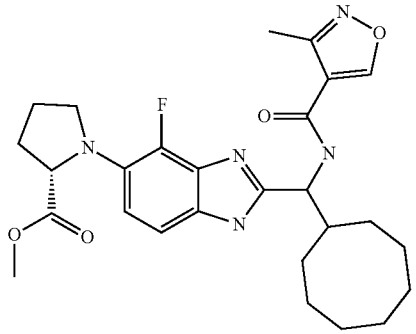

Methyl (2S)-1-(2-{cyclooctyl[(3-methylisoxazole-4-carbonyl)amino]methyl}-4-fluoro-1H-benzimidazol-5-yl)pyrrolidine-2-carboxylate The title compound (36 mg, 10%), a white solid, was prepared from Intermediate 7 (208 mg, 0.71 mmol) and Intermediate 85 (179 mg, 0.71 mmol) in accordance with Procedure Y. $\delta_H$ (400 MHz, DMSO-d$_6$) 12.53-12.32 (m, 1H), 9.43 (d, J 1.7 Hz, 1H), 8.82-8.64 (m, 1H), 7.24-7.07 (m, 1H), 6.80-6.60 (m, 1H), 5.09-5.00 (m, 1H), 4.51-4.43 (m, 1H), 3.67-3.47 (m, 4H), 3.41-3.34 (m, 1H), 2.42-2.22 (m, 5H), 2.00-1.88 (m, 3H), 1.79-1.19 (m, 14H). LCMS (Method 6): [M+H]$^+$ m/z 512, RT 2.04 minutes.

Example 63

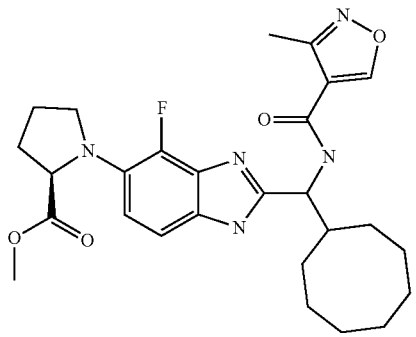

Methyl (2R)-1-(2-{cyclooctyl[(3-methylisoxazole-4-carbonyl)amino]methyl}-4-fluoro-1H-benzimidazol-5-yl)pyrrolidine-2-carboxylate The title compound (9 mg, 6%), a white solid, was prepared from Intermediate 7 (85 mg, 0.29 mmol) and Intermediate 86 (204 mg, 0.29 mmol) in accordance with Procedure Y. $\delta_H$ (400 MHz, DMSO-d$_6$) 12.52 (s, 1H), 9.48-9.42 (m, 1H), 8.79 (s, 1H), 7.09 (s, 1H), 6.69-6.62 (m, 1H), 5.08-5.01 (m, 1H), 4.50-4.42 (m, 1H), 3.62-3.47 (m, 4H), 2.39-2.24 (m, 5H), 1.94 (q, J 8.2, 6.8 Hz, 3H), 1.76-1.19 (m, 15H). LCMS (Method 6): [M+H]$^+$ m/z 512, RT 2.41 minutes.

Example 64

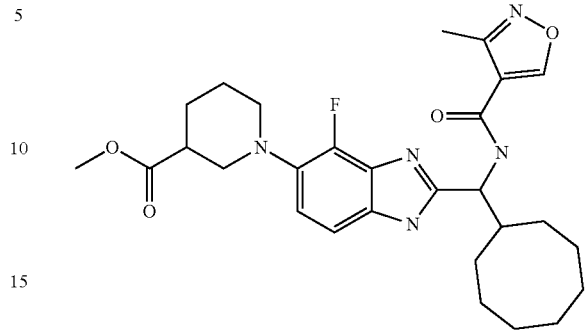

Methyl 1-(2-{cyclooctyl[(3-methylisoxazole-4-carbonyl)amino]methyl}-4-fluoro-1H-benzimidazol-5-yl)piperidine-3-carboxylate The title compound (mixture of diastereomers) (78 mg, 13%), a white solid, was prepared from Intermediate 7 (330 mg, 1.12 mmol) and Intermediate 196 (299 mg, 1.12 mmol) in accordance with Procedure Y. $\delta_H$ (400 MHz, DMSO-d$_6$) 12.78-12.50 (m, 1H), 9.43 (s, 1H), 8.90-8.68 (m, 1H), 7.31-7.15 (m, 1H), 6.97 (d, J 8.4 Hz, 1H), 5.11-4.99 (m, 1H), 3.62 (s, 3H), 3.31-3.23 (m, 1H), 3.09 (d, J 11.1 Hz, 1H), 2.90 (t, J 10.3 Hz, 1H), 2.80-2.68 (m, 2H), 2.42-2.29 (m, 4H), 1.95-1.87 (m, 1H), 1.83-1.20 (m, 17H). LCMS (Method 6): [M+H]$^+$ m/z 526, RT 2.49 minutes.

Example 65

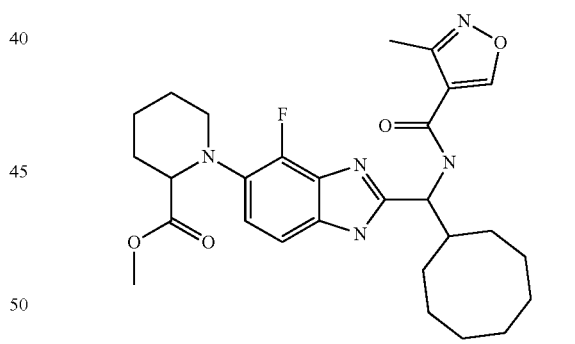

Methyl 1-(2-{cyclooctyl[(3-methylisoxazole-4-carbonyl)amino]methyl}-4-fluoro-1H-benzimidazol-5-yl)piperidine-2-carboxylate The title compound (mixture of diastereomers) (9.8 mg, 7%), a white solid, was prepared from Intermediate 7 (80 mg, 0.27 mmol) and Intermediate 87 (70 mg, 0.26 mmol) in accordance with Procedure Y. $\delta_H$ (400 MHz, DMSO-d$_6$) 12.87-12.38 (m, 1H), 9.43 (d, J 2.9 Hz, 1H), 8.96-8.66 (m, 1H), 7.31-7.05 (m, 1H), 7.05-6.84 (m, 1H), 5.16-4.94 (m, 1H), 4.24-4.03 (m, 1H), 3.52-3.39 (m, 4H), 2.99-2.78 (m, 1H), 2.36 (s, 3H), 2.00-1.85 (m, 2H), 1.78-1.22 (m, 19H). LCMS (Method 6): [M+H]$^+$ m/z 526, RT 2.54

Example 66

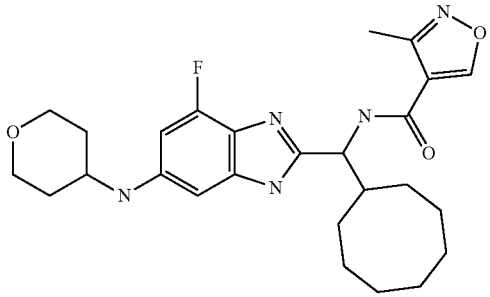

N-{Cyclooctyl[4-fluoro-6-(tetrahydropyran-4-ylamino)-1H-benzimidazol-2-yl]methyl}-3-methyl-isoxazole-4-carboxamide The title compound (9 mg, 3%), a white solid, was prepared from Intermediate 7 (175 mg, 0.6 mmol) and Intermediate 197 (135 mg, 0.6 mmol) in accordance with Procedure Y. $\delta_H$ (300 MHz, DMSO-$d_6$) 12.29 (s, 1H), 9.45 (s, 1H), 8.86 (s, 1H), 6.44-6.22 (m, 2H), 5.41 (s, 1H), 5.00 (t, J 8.2 Hz, 1H), 3.93-3.76 (m, 2H), 3.47-3.36 (m, 2H), 2.41-2.22 (m, 4H), 1.96-1.80 (m, 2H), 1.76-1.17 (m, 17H). LCMS (Method 6): [M+H]$^+$ m/z 484, RT 2.15 minutes.

Example 67

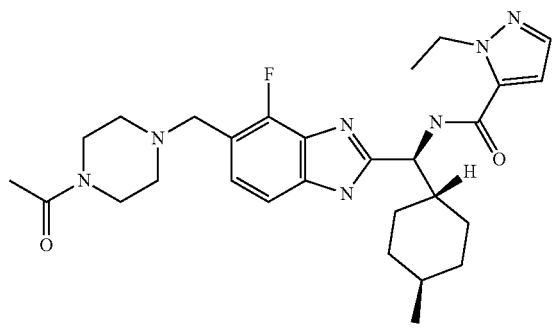

N-[(S)-{5-[(4-Acetylpiperazin-1-yl)methyl]-4-fluoro-1H-benzimidazol-2-yl}(4-methyl-cyclohexyl)methyl]-2-ethylpyrazole-3-carboxamide (Trans Isomer)

The title compound (199 mg, 41%), a white solid, was prepared from Intermediate 127 (376 mg, 0.94 mmol) and 2-ethylpyrazole-3-carboxylic acid (166 mg, 0.94 mmol) in accordance with Procedure A. $\delta_H$ (400 MHz, DMSO-$d_6$) 12.65 (s, 1H), 8.87 (d, J 8.5 Hz, 1H), 7.48 (d, J 2.0 Hz, 1H), 7.26 (d, J 8.2 Hz, 1H), 7.14 (dd, J 8.2, 6.3 Hz, 1H), 7.04 (d, J 2.1 Hz, 1H), 5.00 (t, J 8.6 Hz, 1H), 4.50-4.40 (m, 2H), 3.63 (s, 2H), 3.39 (q, J 5.4 Hz, 4H), 2.39 (t, J 5.0 Hz, 2H), 2.32 (t, J 4.8 Hz, 2H), 2.11-1.99 (m, 1H), 1.99-1.86 (m, 4H), 1.71 (d, J 12.8 Hz, 1H), 1.62 (d, J 12.2 Hz, 1H), 1.38-1.21 (m, 5H), 1.15-0.99 (m, 2H), 0.96-0.78 (m, 5H). LCMS (Method 6): [M+H]$^+$ m/z 524, RT 1.89 minutes.

Example 68

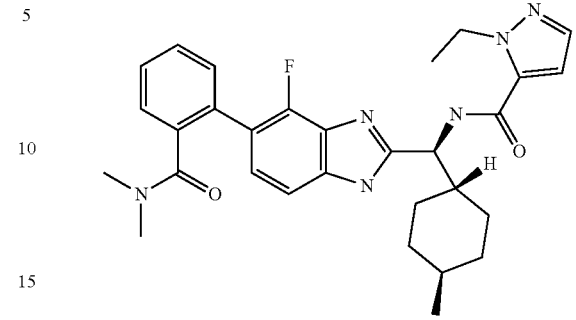

N-[(S)-{5-[2-(Dimethylcarbamoyl)phenyl]-4-fluoro-1H-benzimidazol-2-yl}(4-methyl-cyclohexyl)methyl]-2-ethylpyrazole-3-carboxamide (Trans Isomer)

The title compound (77 mg, 38%), a white solid, was prepared from Intermediate 129 (157 mg, 0.38 mmol) and 2-ethylpyrazole-3-carboxylic acid (68 mg, 0.49 mmol) in accordance with Procedure A, using DCM (5 mL) as solvent. $\delta_H$ (400 MHz, DMSO-$d_6$) 12.69 (s, 1H), 9.00-8.72 (m, 1H), 7.55-7.24 (m, 6H), 7.08-6.97 (m, 2H), 5.05 (t, J 8.7 Hz, 1H), 4.47 (qd, J 7.1, 1.4 Hz, 2H), 2.73 (s, 3H), 2.63 (s, 3H), 2.15-1.98 (m, 1H), 1.92 (d, J 12.7 Hz, 1H), 1.68 (dd, J 31.3, 12.8 Hz, 2H), 1.42 (d, J 12.4 Hz, 1H), 1.36-1.20 (m, 4H), 1.20-0.99 (m, 2H), 0.98-0.78 (m, 5H). LCMS (Method 6): [M+H]$^+$ m/z 531, RT 2.20 minutes.

Example 69

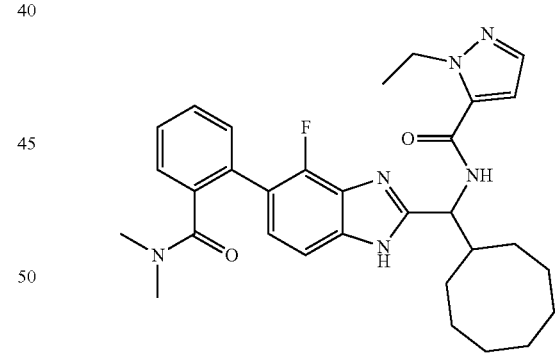

N-(Cyclooctyl{5-[2-(dimethylcarbamoyl)phenyl]-4-fluoro-1H-benzimidazol-2-yl}-methyl)-2-ethylpyrazole-3-carboxamide The title compound (16 mg, 31%), a white solid, was prepared from Intermediate 133 (44 mg, 0.10 mmol) and 2-ethylpyrazole-3-carboxylic acid (16.6 mg, 0.12 mmol) in accordance with Procedure A. $\delta_H$ (300 MHz, DMSO-$d_6$) 8.87 (br s, 1H), 7.56-7.21 (m, 8H), 7.09-6.92 (m, 2H), 5.13 (t, J 8.7 Hz, 1H), 4.48 (q, J 7.1 Hz, 2H), 2.73 (s, 3H), 2.63 (s, 3H), 1.84-1.22 (m, 18H). LCMS (Method 6): [M+H]$^+$ m/z 545, RT 2.47 minutes.

Example 70

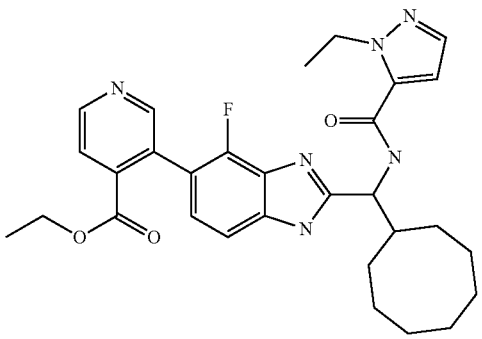

Ethyl 3-(2-{cyclooctyl[(2-ethylpyrazole-3-carbonyl)amino]methyl}-4-fluoro-1H-benzimidazol-5-yl)pyridine-4-carboxylate The title compound (14 mg, 31%), a white solid, was prepared from Intermediate 134 (39 mg, 0.08 mmol) and 2-ethylpyrazole-3-carboxylic acid (24 mg, 0.17 mmol) in accordance with Procedure A. $\delta_H$ (400 MHz, DMSO-$d_6$) 13.32-12.58 (m, 1H), 9.12-8.79 (m, 1H), 8.79-8.67 (m, 2H), 7.76 (d, J 4.9 Hz, 1H), 7.48 (d, J 2.0 Hz, 1H), 7.39 (d, J 8.0 Hz, 1H), 7.14 (s, 1H), 7.03 (d, J 2.0 Hz, 1H), 5.11 (t, J 8.7 Hz, 1H), 4.47 (q, J 7.1 Hz, 2H), 4.15-3.95 (m, 2H), 1.79-1.24 (m, 18H), 0.91 (t, J 7.1 Hz, 3H). LCMS (Method 6): [M+H]$^+$ m/z 547, RT 2.34 minutes.

Example 71

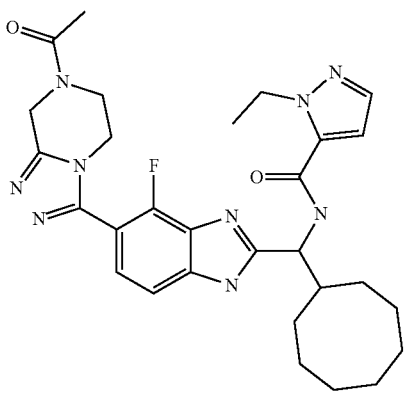

N-{[5-(7-Acetyl-6,8-dihydro-5H-[1,2,4]triazolo[4,3-a]pyrazin-3-yl)-4-fluoro-1H-benzimidazol-2-yl}(cyclooctyl)methyl]-2-ethylpyrazole-3-carboxamide The title compound (4 mg, 10%), a white solid, was prepared from Intermediate 136 (35.4 mg, 0.074 mmol) and 2-ethylpyrazole-3-carboxylic acid (14.8 mg, 0.11 mmol) in accordance with Procedure A. $\delta_H$ (300 MHz, DMSO-$d_6$) 12.80 (s, 1H), 8.85 (s, 1H), 7.52-7.37 (m, 2H), 7.35-7.17 (m, 1H), 7.03 (d, J 2.0 Hz, 1H), 5.13 (t, J 8.7 Hz, 1H), 5.02-4.78 (m, 2H), 4.47 (q, J 7.1 Hz, 2H), 4.06-3.78 (m, 4H), 2.21-2.08 (m, 3H), 1.82-1.23 (m, 18H). LCMS (Method 6): [M+H]$^+$ m/z 562, RT 1.93 minutes.

Example 72

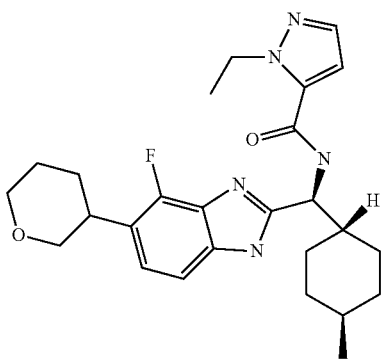 [SMILES: CCn1nccc1C(=O)N[C@H](c1nc2c(F)c(C3CCCOC3)ccc2[nH]1)[C@H]1CC[C@H](C)CC1]

2-Ethyl-N-{(S)-[4-fluoro-5-(tetrahydropyran-3-yl)-1H-benzimidazol-2-yl](4-methyl-cyclohexyl)methyl}pyrazole-3-carboxamide (Trans Isomer)

The title compound (17 mg, 15%), a white solid, was prepared from Intermediate 137 (214 mg, 0.23 mmol) and 2-ethylpyrazole-3-carboxylic acid (106 mg, 0.76 mmol) in accordance with Procedure A, using DCM (5 mL) as solvent. $\delta_H$ (400 MHz, DMSO-$d_6$) 13.07-12.38 (m, 1H), 8.97-8.58 (m, 1H), 7.48 (d, J 2.1 Hz, 1H), 7.43-7.19 (m, 1H), 7.11 (dd, J 8.4, 6.3 Hz, 1H), 7.04 (d, J 2.0 Hz, 1H), 4.99 (t, J 8.7 Hz, 1H), 4.45 (q, J 7.1 Hz, 2H), 3.89 (d, J 11.2 Hz, 1H), 3.85-3.75 (m, 1H), 3.48-3.37 (m, 2H), 3.24-3.08 (m, 1H), 2.13-1.97 (m, 1H), 1.97-1.78 (m, 3H), 1.78-1.57 (m, 4H), 1.39-1.19 (m, 5H), 1.19-0.97 (m, 2H), 0.97-0.78 (m, 5H). LCMS (Method 6): [M+H]$^+$ m/z 468, RT 2.42 minutes.

Example 73

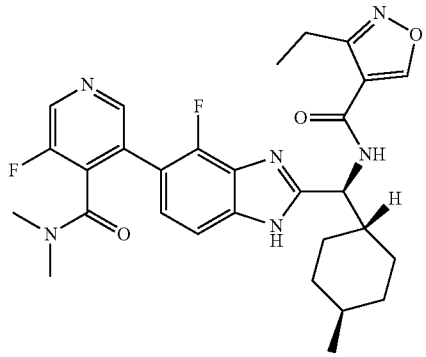 [SMILES: CCc1nocc1C(=O)N[C@H](c1nc2c(F)c(-c3cncc(F)c3C(=O)N(C)C)ccc2[nH]1)[C@H]1CC[C@H](C)CC1]

N-[(S)-{5-[4-(Dimethylcarbamoyl)-5-fluoropyridin-3-yl]-4-fluoro-1H-benzimidazol-2-yl}(4-methylcyclohexyl)methyl]-3-ethylisoxazole-4-carboxamide (Trans Isomer)

The title compound (21 mg, 36%), a white solid, was prepared from Intermediate 141 (45 mg, 0.11 mmol) and 3-ethylisoxazole-4-carboxylic acid (19 mg, 0.13 mmol) in accordance with Procedure A. $\delta_H$ (400 MHz, DMSO-$d_6$) 12.85 (s, 1H), 9.43 (d, J 1.3 Hz, 1H), 8.87-8.78 (m, 1H), 8.72 (s, 1H), 8.57 (s, 1H), 7.40-7.33 (m, 1H), 7.10-7.01 (m, 1H), 5.05 (t, J 8.4 Hz, 1H), 2.93-2.69 (m, 8H), 2.05-1.96 (m, 1H), 1.92-1.86 (m, 1H), 1.71 (d, J 12.8 Hz, 1H), 1.63 (d, J 12.9 Hz, 1H), 1.45-1.37 (m, 1H), 1.32-1.25 (m, 1H), 1.18-1.01 (m, 5H), 0.95-0.79 (m, 5H). LCMS (Method 6): [M+H]$^+$ m/z 551, RT 2.15 minutes.

Example 74

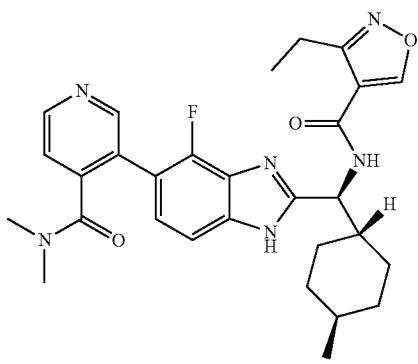 [SMILES: CCc1nocc1C(=O)N[C@H](c1nc2c(F)c(-c3cnccc3C(=O)N(C)C)ccc2[nH]1)[C@H]1CC[C@H](C)CC1]

N-[(S)-{5-[4-(Dimethylcarbamoyl)pyridin-3-yl]-4-fluoro-1H-benzimidazol-2-yl}(4-methylcyclohexyl)methyl]-3-ethylisoxazole-4-carboxamide (Trans Isomer)

The title compound (30 mg, 420%), a white solid, was prepared from Intermediate 142 (55 mg, 0.14 mmol) and 3-ethylisoxazole-4-carboxylic acid (25 mg, 0.17 mmol) in accordance with Procedure A. $\delta_H$ (400 MHz, DMSO-$d_6$) 12.87 (s, 1H), 9.43 (s, 1H), 8.86 (s, 1H), 8.69-8.62 (i, 2H), 7.43 (d, J 5.0 Hz, 1H), 7.35 (d, J 8.3 Hz, 1H), 7.08-7.02 (m, 1H), 5.06 (t, J 8.5 Hz, 1H), 2.83 (qd, J 7.5, 2.4 Hz, 2H), 2.78-2.62 (m, 6H), 2.04-1.98 (m, 1H), 1.90 (d, J 12.9 Hz, 1H), 1.71 (d, J 12.8 Hz, 1H), 1.64 (d, J 12.9 Hz, 1H), 1.41 (d, J 12.5 Hz, 1H), 1.32-1.26 (m, 1H), 1.16 (t, J 7.5 Hz, 3H), 1.11-1.01 (m, 2H), 0.97-0.79 (m, 5H). LCMS (Method 6): [M+H]$^+$ m/z 533, RT 2.02 minutes.

Example 75

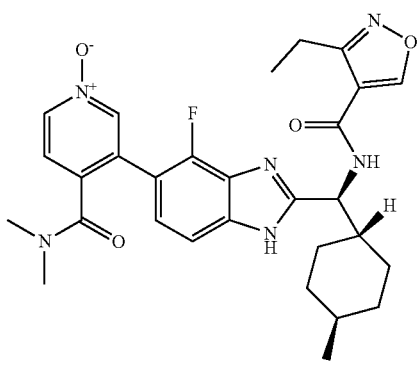 [SMILES: CCc1nocc1C(=O)N[C@H](c1nc2c(F)c(-c3c[n+]([O-])ccc3C(=O)N(C)C)ccc2[nH]1)[C@H]1CC[C@H](C)CC1]

N-[(S)-{5-[4-(Dimethylcarbamoyl)-1-oxopyridin-3-yl]-4-fluoro-1H-benzimidazol-2-yl}-(4-methylcyclohexyl)methyl]-3-ethylisoxazole-4-carboxamide (Trans Isomer)

To a solution of Example 74 (10 mg, 0.02 mmol) in DCM (1 mL) was added MCPBA (4 mg, 0.02 mmol). The reaction mixture was stirred at r.t. for 3 h, then quenched with water and saturated aqueous Na$_2$CO$_3$ solution. The material was extracted with DCM. The organic layers were separated, dried over Na$_2$SO$_4$ and concentrated in vacuo. The crude material was purified by HPLC to give, after freeze-drying, the title compound (2 mg, 19%) as a white solid. $\delta_H$ (400 MHz, CD$_3$OD) 9.19 (s, 1H), (8.49 (t, J 1.5 Hz, 1H), 8.42 (dd, J 6.6, 1.8 Hz, 1H), 7.63 (d, J 6.7 Hz, 1H), 7.44 (d, J 8.4 Hz, 1H), 7.21 (dd, J 8.3, 6.6 Hz, 1H), 5.08 (d, J 8.35 Hz, 1H), 5.02-4.51 (m, 2H), 2.98-2.81 (m, 5H), 2.77 (s, 3H), 2.10-1.95 (m, 2H), 1.80 (dt, J 13.1, 3.0 Hz, 1H), 1.71 (dt, J 13.1, 2.9 Hz, 1H), 1.46 (dt, J 12.8, 3.0 Hz, 1H), 1.35 (dtd, J 10.9, 7.5, 6.7, 4.1 Hz, 1H), 1.26-1.09 (m, 5H), 1.00 (dtd, J 21.1, 12.5, 12.0, 3.3 Hz, 2H), 0.90 (d, J 6.5 Hz, 3H). LCMS (Method 6): [M+H]$^+$ m/z 549, RT 1.75 minutes.

Example 76

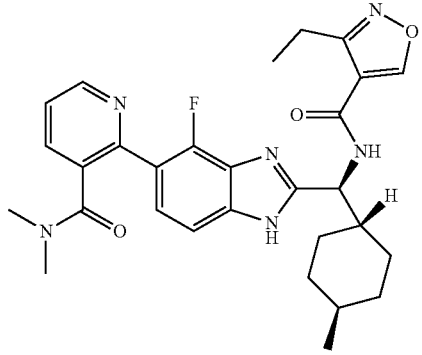 [SMILES: CCc1nocc1C(=O)N[C@H](c1nc2c(F)c(-c3ncccc3C(=O)N(C)C)ccc2[nH]1)[C@H]1CC[C@H](C)CC1]

N-[(S)-{5-[3-(Dimethylcarbamoyl)pyridin-2-yl]-4-fluoro-1H-benzimidazol-2-yl}(4-methylcyclohexyl)methyl]-3-ethylisoxazole-4-carboxamide (Trans Isomer)

The title compound (27 mg, 83%), a white solid, was prepared from Intermediate 143 (25 mg, 0.06 mmol) and 3-ethylisoxazole-4-carboxylic acid (11 mg, 0.07 mmol) in accordance with Procedure A. $\delta_H$ (400 MHz, DMSO-$d_6$) 12.85 (s, 1H), 9.44 (s, 1H), 8.83 (s, 1H), 8.72 (dd, J 4.8, 1.8 Hz, 1H), 7.83 (d, J 7.7 Hz, 1H), 7.47 (dd, J 7.7, 4.8 Hz, 1H), 7.34-7.28 (m, 1H), 7.18-7.11 (m, 1H), 5.06 (t, J 8.4 Hz, 1H), 2.98-2.68 (m, 8H), 1.88 (d, J 12.8 Hz, 1H), 1.71 (d, J 12.7 Hz, 1H), 1.63 (d, J 12.9 Hz, 1H), 1.42 (d, J 12.6 Hz, 1H), 1.32-1.24 (m, 1H), 1.16 (t, J 7.5 Hz, 3H), 1.12-1.00 (m, 2H), 0.96-0.78 (m, 5H). LCMS (Method 6): [M+H]$^+$ m/z 533, RT 1.96 minutes.

Example 77

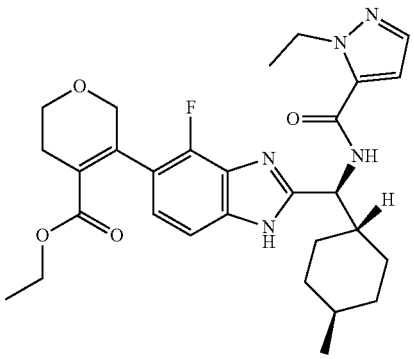 [SMILES: CCOC(=O)C1=C(c2ccc3[nH]c([C@@H](NC(=O)c4ccnn4CC)[C@H]4CC[C@H](C)CC4)nc3c2F)COCC1]

Ethyl 5-(2-{(S)-[(2-ethylpyrazole-3-carbonyl)amino](4-methylcyclohexyl)methyl}-4-fluoro-1H-benzimidazol-5-yl)-3,6-dihydro-2H-pyran-4-carboxylate (Trans Isomer)

The title compound (15 mg, 5%), a white solid, was prepared from Intermediate 144 (241 mg, 0.53 mmol) and 2-ethylpyrazole-3-carboxylic acid (82 mg, 0.59 mmol) in accordance with Procedure A, using DCM (5 mL) as the solvent. $\delta_H$ (400 MHz, DMSO-$d_6$) 13.10-12.49 (m, 1H), 9.00-8.63 (m, 1H), 7.48 (d, J 2.0 Hz, 1H), 7.43-7.19 (m, 1H), 7.04 (d, J 2.1 Hz, 1H), 6.99-6.89 (m, 1H), 5.00 (t, J 8.6 Hz, 1H), 4.45 (q, J 7.1 Hz, 2H), 4.25 (s, 2H), 3.94-3.76 (m, 4H), 2.48-2.42 (m, 2H), 2.11-1.97 (m, 1H), 1.90 (d, J 12.5 Hz, 1H), 1.71 (d, J 12.6 Hz, 1H), 1.62 (d, J 12.8 Hz, 1H), 1.37-1.22 (m, 5H), 1.16-0.97 (m, 2H), 0.97-0.90 (m, 1H), 0.90-0.80 (m, 4H), 0.72 (t, J 7.1 Hz, 3H). LCMS (Method 6): [M+H]$^+$ m/z 528, RT 1.94 minutes.

Example 78

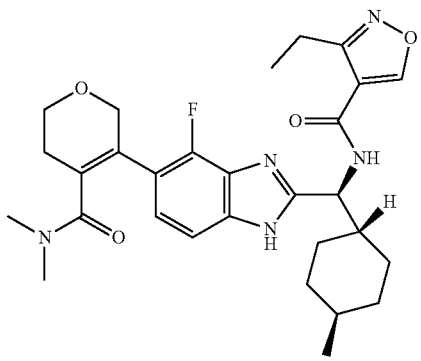 [SMILES: CCc1nocc1C(=O)N[C@H](c1nc2c(F)c(C3=C(C(=O)N(C)C)CCOC3)ccc2[nH]1)[C@H]1CC[C@H](C)CC1]

N-[(S)-{5-[4-(Dimethylcarbamoyl)-3,6-dihydro-2H-pyran-5-yl]-4-fluoro-1H-benzimidazol-2-yl}(4-methylcyclohexyl)methyl]-3-ethylisoxazole-4-carboxamide (Trans Isomer)

The title compound (17 mg, 24%), a white solid, was prepared from Intermediate 145 (58.35 mg, 0.13 mmol) and 3-ethylisoxazole-4-carboxylic acid (21.7 mg, 0.15 mmol) in accordance with Procedure A, using DCM (5 mL) as solvent. $\delta_H$ (400 MHz, DMSO-d6) 12.74 (s, 1H), 9.42 (s, 1H), 8.92-8.66 (m, 1H), 7.23 (d, J 8.3 Hz, 1H), 6.97-6.79 (m, 1H), 5.03 (t, J 8.3 Hz, 1H), 4.24 (s, 2H), 3.86 (t, J 5.5 Hz, 2H), 2.83 (qd, J 7.5, 2.6 Hz, 2H), 2.74 (s, 3H), 2.57 (s, 3H), 2.39-2.28 (m, 2H), 2.06-1.93 (m, 1H), 1.88 (d, J 12.9 Hz, 1H), 1.71 (d, J 12.8 Hz, 1H), 1.63 (d, J 12.6 Hz, 1H), 1.42-1.23 (m, 2H), 1.18-1.00 (m, 5H), 0.94-0.81 (m, 5H). LCMS (Method 6): [M+H]$^+$ m/z 538, RT 2.06 minutes.

Example 79

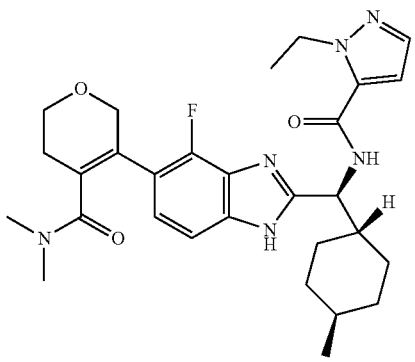 [SMILES: CCn1nccc1C(=O)N[C@H](c1nc2c(F)c(C3=C(C(=O)N(C)C)CCOC3)ccc2[nH]1)[C@H]1CC[C@H](C)CC1]

N-[(S)-{5-[4-(Dimethylcarbamoyl)-3,6-dihydro-2H-pyran-5-yl]-4-fluoro-1H-benzimidazol-2-yl}(4-methylcyclohexyl)methyl]-2-ethylpyrazole-3-carboxamide (Trans Isomer)

The title compound (14 mg, 20%), a white solid, was prepared from Intermediate 145 (58.35 mg, 0.13 mmol) and 2-ethylpyrazole-3-carboxylic acid (25 mg, 0.18 mmol) in accordance with Procedure A, using DCM (5 mL) as the solvent. $\delta_H$ (400 MHz, DMSO-d6) 12.75 (s, 1H), 8.82 (s, 1H), 7.48 (d, J 2.0 Hz, 1H), 7.31-7.12 (m, 1H), 7.04 (d, J 2.1 Hz, 1H), 6.92 (s, 1H), 5.02 (t, J 8.5 Hz, 1H), 4.51-4.39 (m, 2H), 4.24 (s, 2H), 3.86 (t, J 5.5 Hz, 2H), 2.73 (s, 3H), 2.57 (s, 3H), 2.37-2.31 (m, 2H), 2.12-1.97 (m, 1H), 1.89 (d, J 12.3 Hz, 1H), 1.71 (d, J 12.9 Hz, 1H), 1.62 (d, J 12.8 Hz, 1H), 1.39 (d, J 8.5 Hz, 1H), 1.32-1.22 (m, 4H), 1.16-0.98 (m, 2H), 0.96-0.80 (m, 5H). LCMS (Method 6): [M+H]$^+$ m/z 537, RT 1.99 minutes.

Example 80

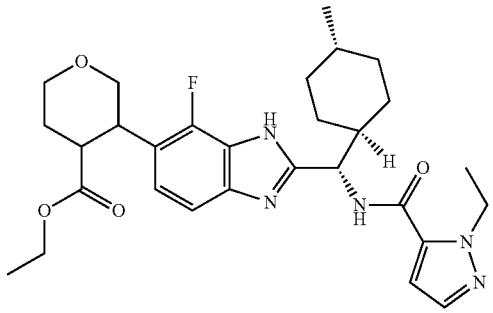 [SMILES: CCOC(=O)C1CCOCC1c1ccc2nc([C@@H](NC(=O)c3ccnn3CC)[C@H]3CC[C@H](C)CC3)[nH]c2c1F]

Ethyl 3-(2-{(S)-[(2-ethylpyrazole-3-carbonyl)amino](4-methylcyclohexyl)methyl}-4-fluoro-3H-benzimidazol-5-yl)tetrahydroyran-4-carboxylate (Trans Isomer)

The title compound (3 mg, 5%), a white solid, was prepared from Intermediate 146 (54 mg, 0.12 mmol) and 2-ethylpyrazole-3-carboxylic acid (25.2 mg, 0.18 mmol) in accordance with Procedure A, using DCM (5 mL) as the solvent. $\delta_H$ (400 MHz, DMSO-d6) 12.64 (s, 1H), 8.78 (s, 1H), 7.47 (t, J 1.7 Hz, 1H), 7.43-7.07 (m, 2H), 7.02 (s, 1H), 4.99 (s, 1H), 4.45 (q, J 7.2 Hz, 2H), 4.14-3.97 (m, 2H), 3.93-3.72 (m, 3H), 3.66-3.53 (m, 2H), 3.09 (s, 1H), 2.08-1.81 (m, 3H), 1.80-1.66 (m, 2H), 1.61 (d, J 13.3 Hz, 1H), 1.47-1.18 (m, 6H), 1.18-0.98 (m, 2H), 0.96-0.80 (m, 7H). LCMS (Method 6): [M+H]$^+$ m/z 540, RT 2.39 minutes.

Example 81

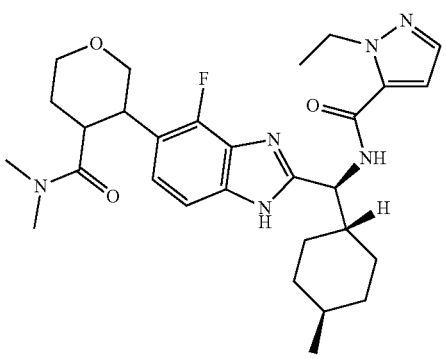 [SMILES: CCn1nccc1C(=O)N[C@H](c1nc2c(F)c(C3COCCC3C(=O)N(C)C)ccc2[nH]1)[C@H]1CC[C@H](C)CC1]

N-[(S)-{5-[4-(Dimethylcarbamoyl)tetrahydropyran-3-yl]-4-fluoro-1H-benzimidazol-2-yl}(4-methylcyclohexyl)methyl]-2-ethylpyrazole-3-carboxamide (Trans Isomer)

To a solution of Example 80 (17 mg, 0.03 mmol) in THF (2.5 mL) and water (2.5 mL) was added LiOH.H$_2$O (10 mg, 0.13 mmol). The reaction mixture was heated at 70° C. for 4h, then another aliquot of LiOH.H$_2$O (9 mg) was added. The mixture was heated overnight, then cooled, diluted with EtOAc, and neutralized with 2M aqueous HCl solution. The material was concentrated in vacuo. The yellow gum was taken up in DCM (2.5 mL) and treated with a 2M solution of dimethylamine in THF (60 μL, 0.12 mmol), in accordance with Procedure A, to yield the title compound (2 mg, 100%) as a white solid. $\delta_H$ (400 MHz, CD$_3$OD) 7.78-7.61 (m, 1H), 7.51 (dd J 2.1, 0.8 Hz, 1H), 7.29 (d, J 8.5 Hz, 1H), 6.94 (t, J 2.0 Hz, 1H), 5.09 (dd, J 8.6, 1.7 Hz, 1H), 4.59-4.47 (m, 2H), 4.34-4.19 (m, 2H), 3.95 (dd, J 11.5, 3.6 Hz, 1H), 3.80-3.63 (m, 2H), 3.57-3.47 (m, 1H), 3.07 (d, J 7.6 Hz, 3H), 2.79 (d, J 9.7 Hz, 3H), 2.18-1.95 (m, 3H), 1.87-1.76 (m, 1H), 1.71 (d, J 13.1 Hz, 1H), 1.66-1.57 (m, 1H), 1.48-1.26 (m, 6H), 1.26-1.07 (m, 2H), 1.07-0.86 (m, 4H). LCMS (Method 6): [M+H]$^+$ m/z 539, RT 2.02 minutes and 2.05 minutes (apparent separation of tetrahydropyran cis isomers).

Example 82

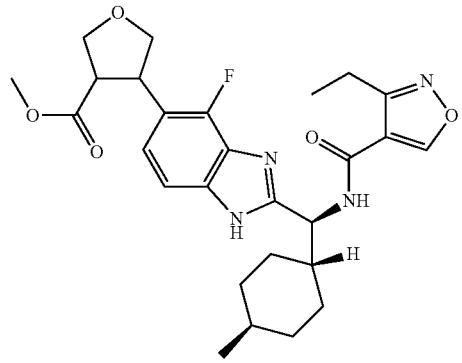 [SMILES: CCc1nocc1C(=O)N[C@H](c1nc2c(F)c(C3COCC3C(=O)OC)ccc2[nH]1)[C@H]1CC[C@H](C)CC1]

Methyl 4-(2-{(S)-[(3-ethylisoxazole-4-carbonyl)amino](4-methylcyclohexyl)methyl}-4-fluoro-1H-benzimidazol-5-yl)tetrahydrofuran-3-carboxylate (Trans Isomer)

The title compound (237 mg, quantitative), a white solid, was prepared from Intermediate 147 (180 mg, 0.46 mmol) and 3-ethylisoxazole-4-carboxylic acid (85 mg, 0.57 mmol) in accordance with Procedure A. LCMS (Method 5): [M+H]$^+$ m/z 513, RT 1.28 minutes.

Example 83

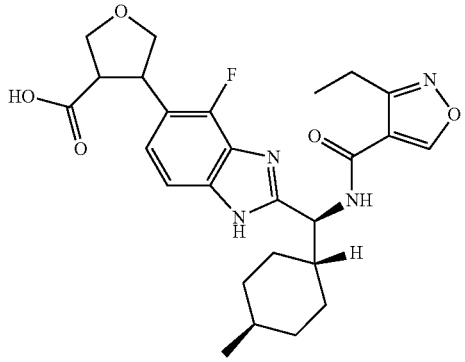 [SMILES: CCc1nocc1C(=O)N[C@H](c1nc2c(F)c(C3COCC3C(=O)O)ccc2[nH]1)[C@H]1CC[C@H](C)CC1]

4-(2-{(S')-[(3-Ethylisoxazole-4-carbonyl)amino](4-methylcyclohexyl)methyl}-4-fluoro-1H-benzimidazol-5-yl)tetrahydrofuran-3-carboxylic Acid (Trans Isomer)

To a solution of LiOH.H$_2$O (11 mg, 0.46 mmol) in water (0.5 mL) was added Example 82 (237 mg, 0.46 mmol) in EtOH (2 mL). The reaction mixture was stirred at r.t. overnight, then concentrated in vacuo. The crude material was purified by reverse-phase HPLC to yield the title compound (54 mg, 23%) as a white solid. $\delta_H$ (400 MHz, DMSO-d$_6$) 12.87 (s, 1H), 9.44 (s, 1H), 9.04 (s, 1H), 7.29-7.18 (m, 1H), 7.15 (t, J 7.4 Hz, 1H), 5.01 (t, J 8.6 Hz, 1H), 4.15 (dt, J 16.1, 8.2 Hz, 2H), 3.99-3.88 (m, 2H), 3.65 (t, J 8.1 Hz, 1H), 3.19 (q, J 7.8 Hz, 1H), 2.81 (qd, J 7.5, 2.2 Hz, 2H), 1.95 (d, J 10.3 Hz, 1H), 1.91-1.83 (m, 1H), 1.68 (d, J 12.4

Hz, 1H), 1.60 (d, J 12.7 Hz, 1H), 1.36-1.22 (m, 2H), 1.14 (t, J 7.5 Hz, 3H), 1.09-0.96 (m, 2H), 0.93-0.72 (m, 5H). LCMS (Method 6): [M+H]+ m/z 499, RT 2.08 minutes.

Example 84

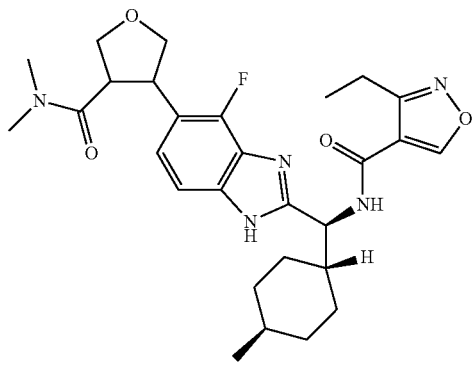 [SMILES: CCc1nocc1C(=O)N[C@H](c1nc2c(F)c(C3COCC3C(=O)N(C)C)ccc2[nH]1)[C@H]1CC[C@H](C)CC1]

N-[(S)-{5-[4-(Dimethylcarbamoyl)tetrahydrofuran-3-yl]-4-fluoro-1H-benzimidazol-2-yl}-(4-methylcyclohexyl)methyl]-3-ethylisoxazole-4-carboxamide (Trans Isomer)

The title compound (5 mg, 6%), a white solid, was prepared from Example 83 (85 mg, 0.17 mmol) and a 2M solution of dimethylamine in THF (170 µL, 0.34 mmol) in accordance with Procedure A. $\delta_H$ (400 MHz, DMSO-$d_6$) 12.74 (s, 1H), 9.43 (s, 1H), 8.75 (s, 1H), 7.24-7.18 (m, 1H), 7.11-7.04 (m, 1H), 4.99 (t, J 8.1 Hz, 1H), 4.22 (t, J 8.2 Hz, 1H), 4.10 (t, J 7.8 Hz, 1H), 4.01 (d, J 7.8 Hz, 1H), 3.81-3.76 (m, 1H), 3.74-3.58 (m, 3H), 2.86-2.72 (m, 6H), 1.94 (d, J 10.5 Hz, 1H), 1.85 (d, J 13.0 Hz, 1H), 1.69 (d, J 12.7 Hz, 1H), 1.60 (d, J 12.9 Hz, 1H), 1.39-1.33 (m, 1H), 1.30-1.24 (m, 1H), 1.15 (t, J 7.5 Hz, 3H), 1.11-0.95 (m, 3H), 0.93-0.75 (m, 5H). LCMS (Method 6): [M+H]+ m/z 526, RT 2.02 minutes.

Example 85

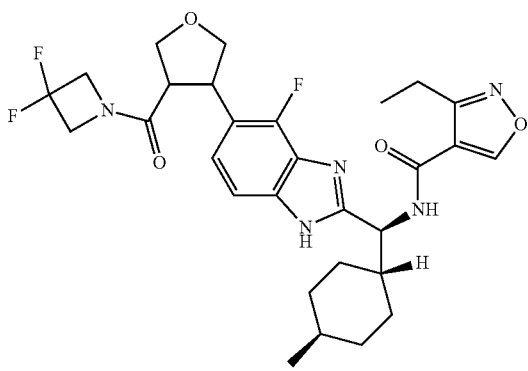 [SMILES: CCc1nocc1C(=O)N[C@H](c1nc2c(F)c(C3COCC3C(=O)N3CC(F)(F)C3)ccc2[nH]1)[C@H]1CC[C@H](C)CC1]

N-[(S)-{5-[4-(3,3-Difluoroazetidine-1-carbonyl)tetrahydrofuran-3-yl]-4-fluoro-1H-benzimidazol-2-yl}(4-methylcyclohexyl)methyl]-3-ethylisoxazole-4-carboxamide (trans isomer)

The title compound (9 mg, 9%), a white solid, was prepared from Example 83 (85 mg, 0.17 mmol) and 3,3-difluoroazetidine hydrochloride (35 mg, 0.34 mmol) in accordance with Procedure A. $\delta_H$ (400 MHz, DMSO-$d_6$) 12.89 (s, 1H), 9.45 (s, 1H), 8.74 (s, 1H), 7.19-7.14 (m, 1H), 7.05-6.97 (m, 1H), 5.00 (t, J 7.8 Hz, 1H), 4.55 (q, J 12.3 Hz, 2H), 4.27-4.14 (m, 3H), 4.10 (t, J 8.0 Hz, 1H), 4.02-3.96 (m, 1H), 3.87 (t, J 7.7 Hz, 1H), 3.70 (t, J 8.2 Hz, 1H), 2.83 (td, J 8.5, 6.6 Hz, 2H), 1.96-1.90 (m, 1H), 1.84-1.77 (m, 1H), 1.67 (d, J 13.4 Hz, 1H), 1.59 (d, J 11.2 Hz, 1H), 1.42-1.36 (m, 1H), 1.29-1.24 (m, 1H), 1.15 (t, J 7.5 Hz, 3H), 1.12-0.96 (m, 3H), 0.91-0.73 (m, 5H). LCMS (Method 6): [M+H]+ m/z 574, RT 2.17 minutes.

Example 86

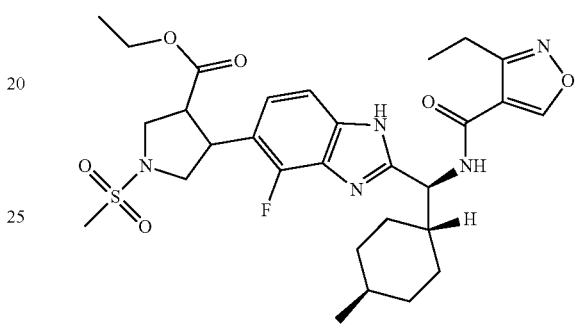

Ethyl 4-(2-{(S)-[(3-ethylisoxazole-4-carbonyl)amino](4-methylcyclohexyl)methyl}-4-fluoro-1H-benzimidazol-5-yl]-1-(methylsulfonyl)pyrrolidine-3-carboxylate (Trans Isomer)

The title compound (1 mg, 1%), a white solid, was prepared from Intermediate 159 (327 mg, 0.31 mmol) and 3-ethylisoxazole-4-carboxylic acid (55 mg, 0.31 mmol) in accordance with Procedure A. $\delta_H$ (400 MHz, CD$_3$OD) 9.18 (s, 1H), 7.29 (d, J 8.5 Hz, 1H), 7.13 (dd, J 8.5, 6.4 Hz, 1H), 5.05 (d, J 8.3 Hz, 1H), 4.54-4.49 (m, 1H), 4.29 (q, J 7.9 Hz, 1H), 3.84-3.61 (m, 6H), 3.03 (s, 3H), 2.88 (qd, J 7.5, 1.3 Hz, 2H), 2.06-1.93 (m, 2H), 1.82-1.74 (m, 1H), 1.69 (d, J 13.2 Hz, 1H), 1.43-1.31 (m, 2H), 1.22 (t, J 7.5 Hz, 3H), 1.19-0.91 (m, 4H), 0.89 (d, J 6.5 Hz, 3H), 0.67 (td, J 7.1, 0.8 Hz, 3H). LCMS (Method 6): [M+H]+ m/z 604, RT 2.27 minutes.

Example 87

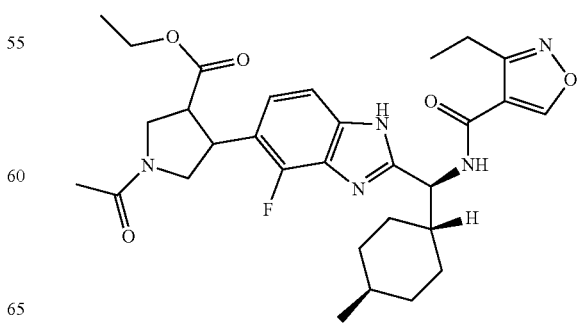

Ethyl 1-acetyl-4-(2-{(S)-[(3-ethylisoxazole-4-carbo-nyl)amino](4-methylcyclohexyl)-methyl}-4-fluoro-1H-benzimidazol-5-yl)pyrrolidine-3-carboxylate
(Trans Isomer)

The title compound (3 mg, 2%), a white solid, was prepared from Intermediate 160 (183 mg, 0.31 mmol) and 3-ethylisoxazole-4-carboxylic acid (55 mg, 0.37 mmol) in accordance with Procedure A. $\delta_H$ (400 MHz, CD$_3$OD) 9.18 (s, 1H), 7.29 (dd, J 8.5, 2.0 Hz, 1H), 7.05 (ddd, J 10.0, 8.5, 6.5 Hz, 1H), 5.05 (dd, J 8.3, 1.4 Hz, 1H), 4.27 (dq, J 24.9, 7.7 Hz, 1H), 4.04 (dd, J 8.0, 2.4 Hz, 1H), 4.01-3.56 (m, 6H), 2.88 (qd, J 7.5, 1.3 Hz, 2H), 2.16 (s, 3H), 2.06-1.92 (m, 2H), 1.78 (dt, J 13.1, 2.9 Hz, 1H), 1.69 (dt, J 12.8, 3.1 Hz, 1H), 1.44-1.29 (m, 2H), 1.22 (t, J 7.5 Hz, 3H), 1.19-0.91 (m, 4H), 0.89 (d, J 6.5 Hz, 3H), 0.83-0.64 (m, 3H). LCMS (Method 6): [M+H]$^+$ m/z 568, RT 2.09 minutes.

Example 88

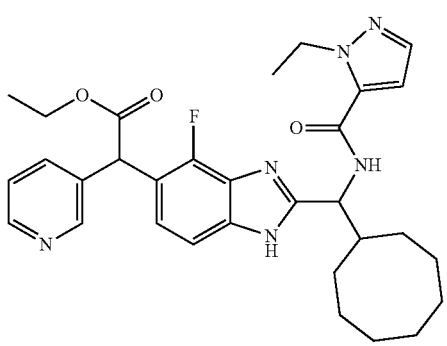 [SMILES: CCOC(=O)C(c1cccnc1)c1ccc2[nH]c(C(NC(=O)c3ccnn3CC)C3CCCCCCC3)nc2c1F]

Ethyl 2-(2-{cyclooctyl[(2-ethylpyrazole-3-carbonyl)amino]methyl}-4-fluoro-1H-benzimidazol-5-yl)-2-(pyridin-3-yl)acetate The title compound (24 mg, 25%), a white solid, was prepared from Intermediate 148 (80 mg, 0.17 mmol) and 2-ethylpyrazole-3-carboxylic acid (28 mg, 0.20 mmol) in accordance with Procedure A. $\delta_H$ (300 MHz, DMSO-d$_6$) 12.79 (s, 1H), 8.86 (br d, J 5.6 Hz, 1H), 8.55 (br s, J 2.1 Hz, 1H), 8.47 (dt, J 4.8, 1.3 Hz, 1H), 7.71 (dq, J 8.0, 2.0 Hz, 1H), 7.47 (t, J 1.8 Hz, 1H), 7.37 (dd, J 8.0, 4.8 Hz, 1H), 7.29 (d, J 8.4 Hz, 1H), 7.06-6.96 (m, 2H), 5.51 (s, 1H), 5.07 (t, J 8.9 Hz, 1H), 4.45 (q, J 7.2 Hz, 2H), 4.18 (q, J 7.1 Hz, 2H), 2.46-2.36 (m, 1H), 1.81-1.22 (m, 17H), 1.16 (t, J 7.2 Hz, 3H). LCMS (Method 6): [M+H]$^+$ m/z 561, RT 2.40 minutes.

Example 89 (Procedure CC)

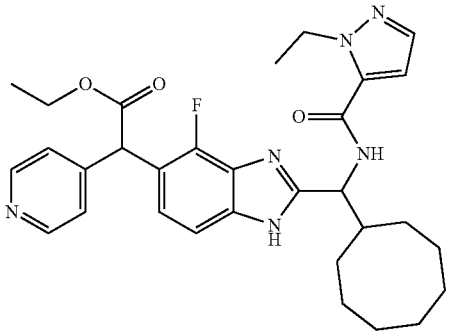 [SMILES: CCOC(=O)C(c1ccncc1)c1ccc2[nH]c(C(NC(=O)c3ccnn3CC)C3CCCCCCC3)nc2c1F]

Ethyl 2-(2-{cyclooctyl[(2-ethylpyrazole-3-carbonyl)amino]methyl}-4-fluoro-1H-benzimidazol-5-yl)-2-(pyridin-4-yl)acetate To a solution of Intermediate 150 (44.5 mg, 0.10 mmol) and 1-ethyl-H-pyrazole-5-carboxylic acid (17.0 mg, 0.12 mmol), dissolved in DMF (2 mL), were added T3P® (0.06 mL, 0.1 mmol) and DIPEA (0.03 mL, 0.2 mmol). The reaction mixture was placed in a sealed vial and heated at 70° C. overnight, then partitioned between EtOAc (10 mL) and water (10 mL). The aqueous layer was separated and re-extracted with EtOAc (10 mL). The organic layers were combined, and washed with water (10 mL) followed by 5% aqueous LiCl solution (10 mL), then dried over Na$_2$SO$_4$, and filtered under reduced pressure. The solvent was removed in vacuo. The isolated straw-coloured oil was purified by preparative HPLC to give, after freeze-drying, the title compound (mixture of diastereomers) (6 mg, 11%) as a white solid. $\delta_H$ (400 MHz, DMSO-d$_6$) 8.88 (s, 1H), 8.59-8.48 (m, 2H), 7.50-7.44 (m, 1H), 7.35-7.19 (m, 3H), 7.03-6.89 (m, 2H), 5.48 (s, 1H), 5.07 (t, J 8.8 Hz, 1H), 4.46 (q, J 7.1 Hz, 2H), 4.17 (q, J 7.1 Hz, 2H), 2.47-2.36 (m, 1H), 1.72-1.69 (m, 1H), 1.68-1.32 (m, 12H), 1.25-1.20 (m, 3H), 1.19-1.10 (m, 3H). LCMS (Method 6): [M+H]$^+$ m/z 561, RT 2.29 minutes.

Example 90

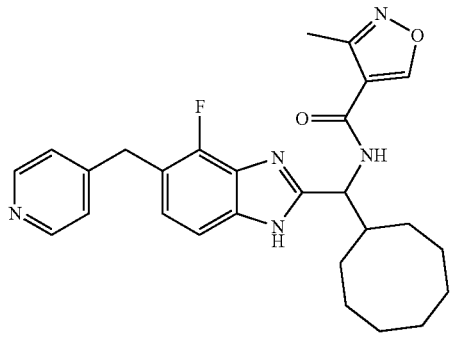 [SMILES: Cc1nocc1C(=O)NC(c1nc2c(F)c(Cc3ccncc3)ccc2[nH]1)C1CCCCCCC1]

N-{Cyclooctyl[4-fluoro-5-(pyridin-4-ylmethyl)-1H-benzimidazol-2-yl]methyl}-3-methyl-isoxazole-4-carboxamide The title compound (5 mg, 14%), a white solid, was prepared from Intermediate 151 (39 mg, 0.076 mmol) and 3-methylisoxazole-4-carboxylic acid (16.7 mg, 0.13 mmol) in accordance with Procedure CC. $\delta_H$ (400 MHz, DMSO-d$_6$) 12.80 (s, 1H), 9.43 (s, 1H), 8.95-8.78 (m, 1H), 8.52-8.28 (m, 2H), 7.30-7.17 (m, 3H), 7.11 (t, 1H), 5.08 (t, J 8.8 Hz, 1H), 4.08 (s, 2H), 2.44-2.34 (m, 4H), 1.79-1.19 (m, 14H). LCMS (Method 6): [M+H]$^+$ m/z 476, RT 2.36 minutes.

Example 91

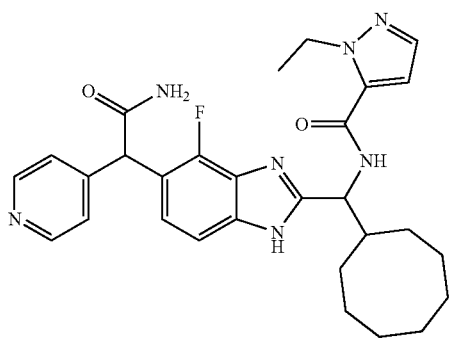 [SMILES: CCn1nccc1C(=O)NC(c1nc2c(F)c(C(C(N)=O)c3ccncc3)ccc2[nH]1)C1CCCCCCC1]

N-[{5-[2-Amino-2-oxo-1-(pyridin-4-yl)ethyl]-4-fluoro-1H-benzimidazol-2-yl}-(cyclooctyl)methyl]-2-ethylpyrazole-3-carboxamide The title compound (mixture of diastereomers) (4.0 mg, 16%), a white solid, was prepared from Intermediate 153 (19 mg, 0.046 mmol) and 2-ethylpyrazole-3-carboxylic acid (12 mg, 0.086 mmol) in accordance with Procedure A. $\delta_H$ (400 MHz, DMSO-d$_6$) 13.15-12.57 (m, 1H), 9.10-8.69 (m, 1H), 8.56-8.38 (m, 2H), 7.93-7.62 (m, 1H), 7.47 (t, J 1.9 Hz, 1H), 7.42-7.09 (m, 5H), 7.09-6.91 (m, 1H), 5.31 (s, 1H), 5.18-4.98 (m, 1H), 4.45 (q, J 7.1 Hz, 2H), 2.43 (s, 1H), 1.79-1.21 (m, 17H). LCMS (Method 6): [M+H]$^+$ m/z 532, RT 1.84 minutes.

Example 92

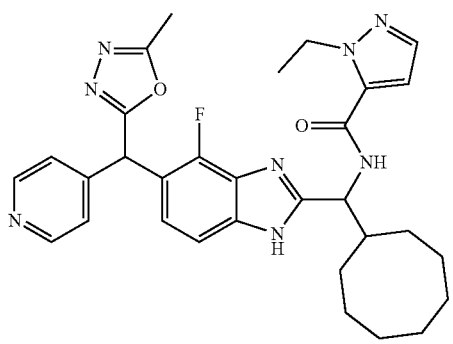 [SMILES: CCn1nccc1C(=O)NC(c1nc2c(F)c(C(c3ccncc3)c3nnc(C)o3)ccc2[nH]1)C1CCCCCCC1]

N-(Cyclooctyl{4-fluoro-5-[(5-methyl-1,3,4-oxadiazol-2-yl)(pyridin-4-yl)methyl]-1H-benzimidazol-2-yl}methyl)-2-ethylpyrazole-3-carboxamide The title compound (mixture of diastereomers) (2 mg, 2%), a white solid, was prepared from Intermediate 154 (80 mg, 0.16 mmol) and 2-ethylpyrazole-3-carboxylic acid (12 mg, 0.09 mmol) in accordance with Procedure A. LCMS (Method 6): [M+H]$^+$ m/z 571, RT 1.84 minutes. LCMS (Method 2): [M+H]$^+$ m/z 571, RT 2.08 minutes.

Example 93

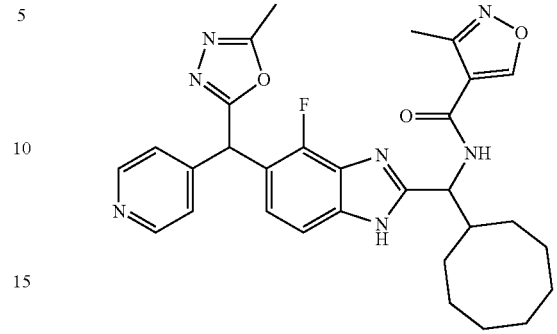

N-(Cyclooctyl{4-fluoro-5-[(5-methyl-1,3,4-oxadiazol-2-yl)(pyridin-4-yl)methyl]-1H-benzimidazol-2-yl}methyl)-3-methylisoxazole-4-carboxamide The title compound (mixture of diastereomers) (3 mg, 3%), a white solid, was prepared from Intermediate 154 (80 mg, 0.16 mmol) and 3-methylisoxazole-4-carboxylic acid (23 mg, 0.18 mmol) in accordance with Procedure A. LCMS (Method 6): [M+H]$^+$ m/z 558, RT 2.23 minutes. LCMS (Method 2): [M+H]$^+$ m/z 558, RT 2.02 minutes.

Example 94

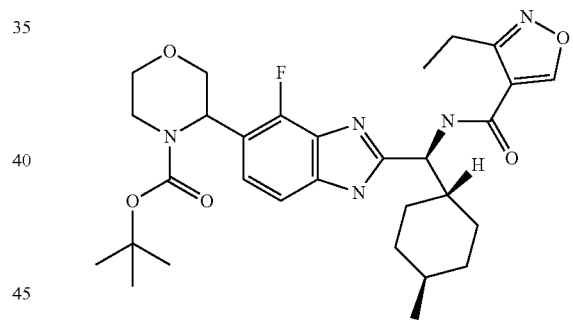

tert-Butyl 3-(2-{(S)-[(3-ethylisoxazole-4-carbonyl)amino](4-methylcyclohexyl)methyl}-4-fluoro-1H-benzimidazol-5-yl)morpholine-4-carboxylate (Trans Isomer)

To a solution of Intermediate 155 (48 mg, 0.07 mmol) in acetonitrile (1 mL) was added diethylamine (0.25 mL, 2.4 mmol). The mixture was stirred overnight, then concentrated in vacuo. The residue was filtered through an SCX column, washing with MeOH, then eluting with a 7N solution of NH$_3$ in MeOH. The semi-pure material was dissolved in DCM (2 mL), then 3-ethylisoxazole-4-carboxylic acid (10 mg, 0.07 mmol), DIPEA (25 µL, 0.14 mmol) and HATU (34 mg, 0.09 mmol) were added. The mixture was stirred for 3 h at r.t., then partitioned between DCM and water. The organic layers were separated and dried over MgSO$_4$, then concentrated in vacuo. The crude material was subject to preparative HPLC to yield the title compound (1:1 mixture of diastereomers) (12 mg, 29% overall). $\delta_H$ (400 MHz, DMSO-d$_6$) 12.94-12.69 (m, 1H), 9.43-9.42 (m, 1H), 8.86-8.78 (m, 1H), 7.33-7.16 (m, 2H), 5.30-5.26 (m, 1H), 5.02 (t, J 8.5 Hz, 1H), 4.08 (d, J 11.9 Hz, 1H), 3.95-3.88 (m, 1H), 3.83 (dd, J 11.9, 4.1 Hz, 1H), 3.78-3.70 (m, 1H), 3.53 (td, J 11.5, 3.3 Hz, 1H), 3.34-3.24 (m, 1H), 2.82 (q, J 7.6 Hz, 2H), 2.05-1.93 (m, 1H), 1.93-1.83 (m, 1H), 1.75-1.66 (m, 1H), 1.66-1.57 (m, 1H), 1.36-1.22 (m, 2H), 1.34-1.33 (m, 9H), 1.16-1.98 (m, 2H), 1.15 (td, J 7.5, 2.8 Hz, 3H), 0.96-0.77 (m, 2H), 0.85 (d, J 6.4 Hz, 3H). LCMS (Method 6): [M+H]$^+$ m/z 570, RT 2.66 minutes.

Examples 95 & 96

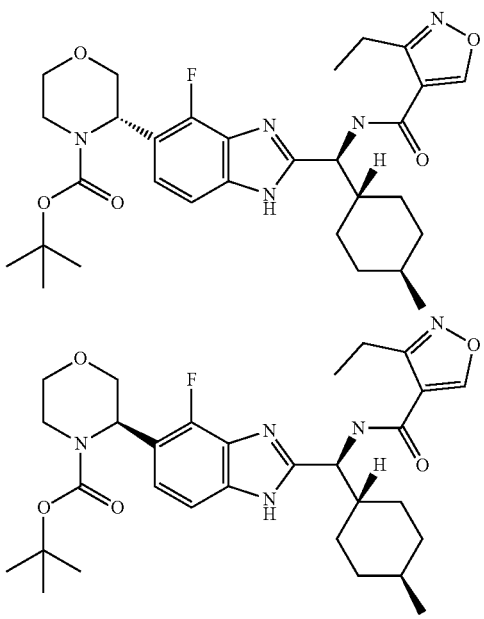

tert-Butyl (3S)-3-(2-{(S)-[(3-ethylisoxazole-4-carbonyl)amino](4-methylcyclohexyl)-methyl}-4-fluoro-1H-benzimidazol-5-yl)morpholine-4-carboxylate (Trans Isomer) (Example 95)

tert-Butyl (3R)-3-(2-{(S)-[(3-ethylisoxazole-4-carbonyl)amino](4-methylcyclohexyl)-methyl}-4-fluoro-1H-benzimidazol-5-yl)morpholine-4-carboxylate (Trans Isomer) (Example 96)

Example 94 was subject to chiral HPLC (Waters Prep 100-SQD2 equipped with a Lux Cellulose-1 250×21.2 mm, 5 μm column), flow rate 100 mL/min, column temperature 40° C., eluting with MeOH (+0.1% NH$_4$OH) and food fresh grade liquid C02 (gradient of 5-15%), to yield, after freeze drying, the title compounds (Peak 1, 2 mg; and Peak 2, 2 mg) as white solids.

Peak 1: δ$_H$ (400 MHz, DMSO-d$_6$) 12.94-12.69 (m, 1H), 9.42 (s, 1H), 8.86-8.78 (m, 1H), 7.33-7.16 (m, 2H), 5.30-5.26 (m, 1H), 5.02 (t, J 8.5 Hz, 1H), 4.08 (d, J 11.9 Hz, 1H), 3.95-3.88 (m, 1H), 3.83 (dd, J 11.9, 4.1 Hz, 1H), 3.78-3.70 (m, 1H), 3.53 (td, J 11.5, 3.3 Hz, 1H), 3.34-3.24 (m, 1H), 2.82 (q, J 7.6 Hz, 2H), 2.05-1.93 (m, 1H), 1.93-1.83 (m, 1H), 1.75-1.66 (m, 1H), 1.66-1.57 (m, 1H), 1.36-1.22 (m, 2H), 1.34 (s, 9H), 1.16-1.98 (m, 2H), 1.15 (td, J 7.5, 2.8 Hz, 3H), 0.96-0.77 (m, 2H), 0.85 (d, J 6.4 Hz, 3H). LCMS (Method 6): [M+H]$^+$ m/z 570, RT 2.66 minutes.

Peak 2: δ$_H$ (400 MHz, DMSO-d$_6$) 12.94-12.69 (m, 1H), 9.43 (s, 1H), 8.86-8.78 (m, 1H), 7.33-7.16 (m, 2H), 5.30-5.26 (m, 1H), 5.02 (t, J 8.5 Hz, 1H), 4.08 (d, J 11.9 Hz, 1H), 3.95-3.88 (m, 1H), 3.83 (dd, J 11.9, 4.1 Hz, 1H), 3.78-3.70 (m, 1H), 3.53 (td, J 11.5, 3.3 Hz, 1H), 3.34-3.24 (m, 1H), 2.82 (q, J 7.6 Hz, 2H), 2.05-1.93 (m, 1H), 1.93-1.83 (m, 1H), 1.75-1.66 (m, 1H), 1.66-1.57 (m, 1H), 1.36-1.22 (obscured m, 2H), 1.33 (s, 9H), 1.16-1.98 (m, 2H), 1.15 (td, J 7.5, 2.8 Hz, 3H), 0.96-0.77 (m, 2H), 0.85 (d, J 6.4 Hz, 3H). LCMS (Method 6): [M+H]$^+$ m/z 484, RT 2.65 minutes.

Example 97

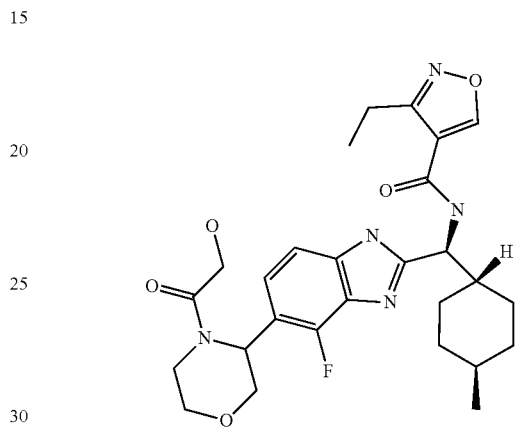

3-Ethyl-N-[(S)-{4-fluoro-5-[4-(2-hydroxyacetyl)morpholin-3-yl]-1H-benzimidazol-2-yl}-(4-methylcyclohexyl)methyl]isoxazole-4-carboxamide The title compound (mixture of diastereomers) (6 mg, 34%), a white solid, was prepared from Intermediate 156 (14 mg, 0.034 mmol) and 3-ethylisoxazole-4-carboxylic acid (12 mg, 0.084 mmol) in accordance with Procedure A, using DCM (3 mL) as solvent. δ$_H$ (400 MHz, CD$_3$OD) 9.25-9.13 (m, 1H), 7.57-7.50 (m, 1H), 7.36 (d, J 8.5 Hz, 1H), 5.07 (d, J 8.2 Hz, 1H), 4.47-4.24 (m, 3H), 4.06-3.93 (m, 2H), 3.68 (td, J 11.6, 3.2 Hz, 1H), 2.90 (qd, J 7.5, 1.5 Hz, 2H), 2.09-1.91 (m, 2H), 1.85-1.76 (m, 1H), 1.76-1.66 (m, 1H), 1.48-1.41 (m, 1H), 1.41-1.29 (m, 1H), 1.28-1.09 (m, 5H), 1.08-0.88 (m, 5H). LCMS (Method 6): [M+H]$^+$ m/z 528, RT 1.94 minutes.

Example 98

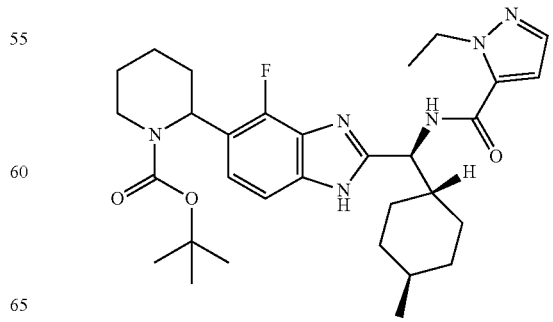

tert-Butyl 2-(2-{(S)-[(2-ethylpyrazole-3-carbonyl)amino](4-methylcyclohexyl)methyl}-4-fluoro-1H-benzimidazol-5-yl)piperidine-1-carboxylate (Trans Isomer)

The title compound (mixture of diastereomers) (72 mg, 13%), a white solid, was prepared from Intermediate 46 (130 mg, 0.44 mmol) and Intermediate 125 (140 mg, 0.45 mmol) in accordance with Procedure Y. $\delta_H$ (400 MHz, DMSO-$d_6$) 12.69 (s, 1H), 8.84 (s, 1H), 7.47 (dd, J 2.1, 1.1 Hz, 1H), 7.29-7.20 (m, 1H), 7.04 (t, J 2.7 Hz, 1H), 6.95 (t, J 7.7 Hz, 1H), 5.45 (t, J 4.9 Hz, 1H), 5.00 (t, J 8.3 Hz, 1H), 4.50-4.39 (m, 2H), 4.02-3.93 (m, 1H), 3.17-3.08 (m, 1H), 2.11-0.75 (m, 31H). LCMS (Method 6): [M+H]⁺ m/z 567, RT 2.84 minutes.

Example 99

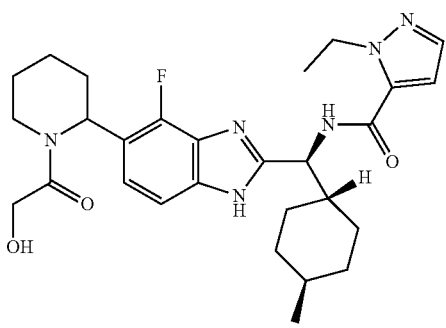 [SMILES: CCn1nccc1C(=O)N[C@H](c1nc2c(F)c(C3CCCCN3C(=O)CO)ccc2[nH]1)[C@H]1CC[C@H](C)CC1]

2-Ethyl-N-[{4-fluoro-5-[1-(2-hydroxyacetyl)piperidin-2-yl]-1H-benzimidazol-2-yl}(4-methylcyclohexyl)methyl]pyrazole-3-carboxamide (Trans Isomer)

Example 98 (36 mg, 0.06 mmol) in MeOH (2 mL) was treated with 4M HCl in 1,4-dioxane (0.3 mL). The reaction mixture was stirred at r.t. overnight, then concentrated in vacuo. The residue was dissolved in MeOH and run down an SCX column, eluting with a 7N solution of NH₃ in MeOH. The residue was taken up in DCM (1 mL) and triethylamine (9 μL, 0.06 mmol), and acetoxyacetyl chloride (7 μL, 0.06 mmol) was added. The reaction mixture was stirred overnight. Further aliquots of triethylamine (9 μL) and acetoxyacetyl chloride (7 μL) were added. The reaction mixture was left a further 24 h, then concentrated in vacuo. The residue was dissolved in MeOH, and NaOH (3 mg) in water (1 mL) was added. After 24 h, the reaction mixture was concentrated in vacuo, and partitioned between DCM and water. The organic layers were dried over Na₂SO₄ and concentrated in vacuo. The crude material was purified using preparative HPLC to yield the title compound (mixture of diastereomers) (7 mg, 21%) as a white solid. $\delta_H$ (400 MHz, DMSO-$d_6$) 12.97-12.59 (m, 1H), 8.90-8.70 (m, 1H), 7.47 (d, J 2.0 Hz, 1H), 7.24 (d, J 8.4 Hz, 1H), 7.03 (t, J 2.4 Hz, 1H), 6.98 (d, J 8.9 Hz, 1H), 5.65 (s, 1H), 4.98 (t, J 8.6 Hz, 1H), 4.58-4.34 (m, 4H), 4.23-4.19 (m, 1H), 3.20-3.10 (m, 1H), 2.18-1.83 (m, 6H), 1.74-1.38 (m, 7H), 1.25 (t, J 7.1 Hz, 3H), 1.06-1.02 (m, 3H), 0.95-0.80 (m, 4H). LCMS (Method 6): [M+H]⁺ m/z 525, RT 2.10 minutes.

Example 100

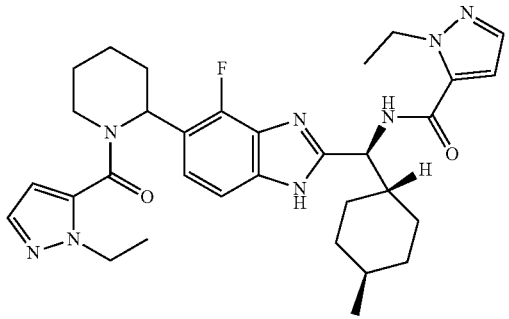 [SMILES: CCn1nccc1C(=O)N[C@H](c1nc2c(F)c(C3CCCCN3C(=O)c3ccnn3CC)ccc2[nH]1)[C@H]1CC[C@H](C)CC1]

2-Ethyl-N-[(S')-{5-[1-(2-ethylpyrazole-3-carbonyl)piperidin-2-yl]-4-fluoro-1H-benzimidazol-2-yl}(4-methylcyclohexyl)methyl]pyrazole-3-carboxamide (Trans Isomer)

Example 98 (36 mg, 0.06 mmol) in MeOH (2 mL) was treated with 4M HCl in 1,4-dioxane (0.3 mL). The reaction mixture was stirred at r.t. overnight, then concentrated in vacuo. The residue was dissolved in MeOH and eluted down an SCX column with a 7N solution of NH₃ in MeOH. After concentration in vacuo, the residue was taken up in DCM (2 mL) and combined with 2-ethylpyrazole-3-carboxylic acid (10 mg, 0.06 mmol), in accordance with Procedure A, to give the title compound (mixture of diastereomers) (20 mg, 57%) as a white solid. $\delta_H$ (400 MHz, DMSO-$d_6$) 12.65 (s, 1H), 9.03-8.59 (m, 2H), 7.55-7.21 (m, 3H), 7.13 (t, J 7.7 Hz, 1H), 7.06-7.00 (m, 1H), 6.42-6.22 (m, 1H), 5.86-5.68 (m, 1H), 4.99 (t, J 8.6 Hz, 1H), 4.44 (q, J 7.1 Hz, 2H), 4.23-3.89 (m, 3H), 3.28-3.16 (m, 1H), 2.23 (d, J 13.9 Hz, 1H), 2.12-1.85 (m, 3H), 1.82-1.42 (m, 6H), 1.40-1.17 (m, 7H), 1.17-0.73 (m, 7H). LCMS (Method 6): [M+H]⁺ m/z 589, RT 2.33

Example 101

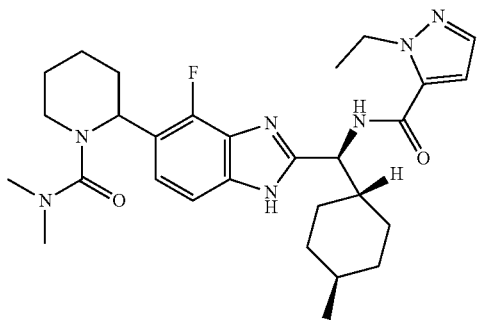 [SMILES: CCn1nccc1C(=O)N[C@H](c1nc2c(F)c(C3CCCCN3C(=O)N(C)C)ccc2[nH]1)[C@H]1CC[C@H](C)CC1]

2-(2-{(S')-[(2-Ethylpyrazole-3-carbonyl)amino](4-methylcyclohexyl)methyl}-4-fluoro-1H-benzimidazol-5-yl)-N,N-dimethylpiperidine-1-carboxamide (Trans Isomer)

A mixture of Example 98 (36 mg, 0.06 mmol) in MeOH (2 mL) and 4M HCl in 1,4-dioxane (0.3 mL) was stirred at r.t. overnight. The reaction mixture was concentrated in vacuo, then dissolved in MeOH and flashed down an SCX column, eluting with a 7N solution of NH₃ in MeOH. The residue was concentrated in vacuo, then taken up in DCM (1 mL). Triethylamine (9 µL, 0.06 mmol) and dimethylcarbamoyl chloride (6 µL, 0.06 mmol) were added. The reaction mixture was stirred for 1h at r.t., then further aliquots of triethylamine (3×9 µL) and dimethylcarbamoyl chloride (3×6 µL) were added over a 3 h period. The reaction mixture was left to stir overnight, then concentrated in vacuo.

The residue was purified by reverse-phase HPLC to yield the title compound (mixture of diastereomers) (5 mg, 15%) as a white solid. δ$_H$ (400 MHz, DMSO-d$_6$) 12.68-12.58 (s, 1H), 8.76-8.68 (s, 1H), 7.46 (d, J 2.0 Hz, 1H), 7.14-7.07 (m, 1H), 7.02-6.91 (m, 2H), 4.99-4.93 (m, 1H), 4.54-4.48 (m, 1H), 4.45 (q, J 7.0 Hz, 2H), 3.26-3.21 (m, 1H), 2.78 (d, J 1.5 Hz, 6H), 2.03-1.80 (m, 4H), 1.76-1.57 (m, 6H), 1.50-1.35 (m, 3H), 1.29-1.22 (m, 3H), 1.16-0.93 (m, 4H), 0.83 (d, J 6.5 Hz, 3H). LCMS (Method 6): [M+H]⁺ m/z 538, RT 2.44 minutes.

Example 102

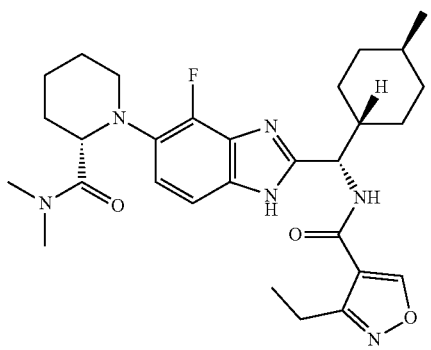

N-[(S)-{5-[(2S)-2-(Dimethylcarbamoyl)piperidin-1-yl]-4-fluoro-1H-benzimidazol-2-yl}-(4-methylcyclohexyl)methyl]-3-ethylisoxazole-4-carboxamide (Trans Isomer)

The title compound (30 mg, 13), a white solid, was prepared from Intermediate 157 (174 mg, 0.42 mmol) and 3-ethylisoxazole-4-carboxylic acid (75 mg, 0.51 mmol) in accordance with Procedure A. δ$_H$ (400 MHz, CD₃OD) 9.19 (s, 1H), 7.21 (d, J 8.7 Hz, 1H), 7.11 (dd, J 8.7, 7.3 Hz, 1H), 5.04 (d, J 8.3 Hz, 1H), 4.33 (dd, J 9.3, 3.3 Hz, 1H), 3.52-3.40 (m, 1H), 3.20 (s, 3H), 2.95-2.78 (m, 3H), 2.70 (s, 3H), 2.05-1.66 (m, 9H), 1.63-1.49 (m, 1H), 1.49-1.39 (m, 1H), 1.38-1.29 (m, 1H), 1.26-1.10 (m, 5H), 1.07-0.89 (m, 5H). LCMS (Method 6): [M+H]⁺ m/z 539, RT 2.30 minutes.

Example 103

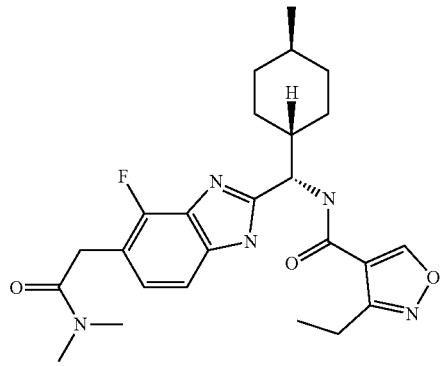

N-[(S)-{5-[2-(Dimethylamino)-2-oxoethyl]-4-fluoro-1H-benzimidazol-2-yl}(4-methyl-cyclohexyl)methyl]-3-ethylisoxazole-4-carboxamide (Trans Isomer)

The title compound (9 mg, 7%), a white solid, was prepared from Intermediate 158 (102 mg, 0.29 mmol) and 3-ethylisoxazole-4-carboxylic acid (55 mg, 0.37 mmol) in accordance with Procedure A. δ$_H$ (400 MHz, CD₃OD) 9.20 (s, 1H), 7.30 (d, J 8.3 Hz, 1H), 7.11 (dd, J 8.3, 6.6 Hz, 1H), 5.07 (d, J 8.3 Hz, 1H), 3.94-3.86 (m, 2H), 3.16 (s, 3H), 2.99 (s, 3H), 2.90 (qd, J 7.6, 1.5 Hz, 2H), 2.08-1.93 (m, 2H), 1.84-1.75 (m, 1H), 1.75-1.66 (m, 1H), 1.49-1.40 (m, 1H), 1.40-1.28 (m, 1H), 1.28-1.08 (m, 5H), 1.03-0.92 (m, 2H), 0.91 (d, J 6.5 Hz, 3H). LCMS (Method 6): [M+H]⁺ m/z 470, RT 2.05 minutes.

Example 104

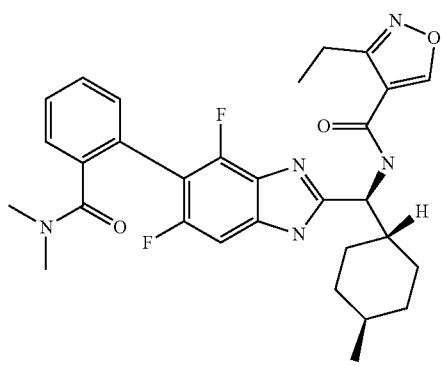 [SMILES: CCc1nocc1C(=O)N[C@H](c1nc2c(F)c(-c3ccccc3C(=O)N(C)C)c(F)cc2[nH]1)[C@H]1CC[C@H](C)CC1]

N-[(S)-{5-[2-(Dimethylcarbamoyl)phenyl]-4,6-difluoro-1H-benzimidazol-2-yl}(4-methylcyclohexyl)methyl]-3-ethylisoxazole-4-carboxamide (Trans Isomer)

The title compound (30 mg, 20%), a white solid, was prepared from Intermediate 161 (137 mg, 0.27 mmol) and 3-ethylisoxazole-4-carboxylic acid (39 mg, 0.28 mmol) in accordance with Procedure A, using DCM (5 mL) as solvent. δ$_H$ (373K, 400 MHz, DMSO-d$_6$) 12.51 (s, 1H), 9.34 (s, 1H), 8.35 (s, 1H), 7.56-7.44 (m, 2H), 7.44-7.34 (m, 2H), 7.13 (d, J 9.5 Hz, 1H), 5.11 (t, J 7.1 Hz, 1H), 2.91-2.82 (m, 2H), 2.78 (s, 6H), 2.02 (dtt, J 11.5, 7.2, 3.6 Hz, 1H), 1.93-1.81 (m, 1H), 1.77-1.63 (m, 2H), 1.61-1.51 (m, 1H), 1.39-1.26 (m, 1H), 1.24-1.06 (m, 5H), 0.98-0.85 (m, 5H). LCMS (Method 6): [M+H]⁺ m/z 550.0, RT 2.42 minutes.

Example 105

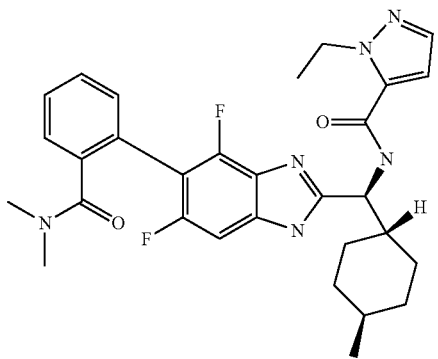 [SMILES: CCn1nccc1C(=O)N[C@H](c1nc2c(F)c(-c3ccccc3C(=O)N(C)C)c(F)cc2[nH]1)[C@H]1CC[C@H](C)CC1]

N-[(S)-{5-[2-(Dimethylcarbamoyl)phenyl]-4,6-difluoro-1H-benzimidazol-2-yl}(4-methylcyclohexyl)methyl]-2-ethylpyrazole-3-carboxamide (Trans Isomer)

The title compound (31 mg, 21%), a white solid, was prepared from Intermediate 161 (137 mg, 0.27 mmol) and 2-ethylpyrazole-3-carboxylic acid (44 mg, 0.31 mmol) in accordance with Procedure A, using DCM (5 mL) as the solvent. $\delta_H$ (400 MHz, DMSO-d6) 12.86 (s, 1H), 8.81 (s, 1H), 7.56-7.46 (m, 3H), 7.46-7.36 (m, 2H), 7.21 (s, 1H), 7.04 (d, J 2.0 Hz, 1H), 5.03 (t, J 8.6 Hz, 1H), 4.47 (qd, J 7.1, 1.4 Hz, 2H), 2.83-2.71 (m, 6H), 2.55 (s, 1H), 2.12-1.98 (m, 1H), 1.90 (d, J 12.8 Hz, 1H), 1.68 (dd, J 29.3, 12.7 Hz, 2H), 1.48-1.36 (m, 1H), 1.27 (td, J 7.1, 1.4 Hz, 4H), 1.20-0.98 (m, 2H), 0.98-0.77 (m, 5H). LCMS (Method 6): [M+H]⁺ m/z 549, RT 2.35 minutes.

Example 106

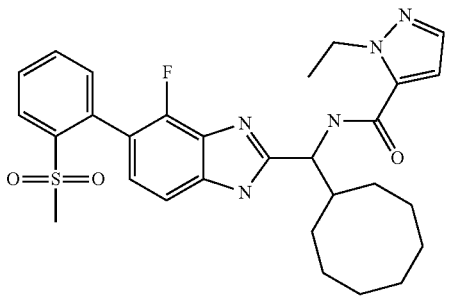 [SMILES: CCn1nccc1C(=O)NC(c1nc2c(F)c(-c3ccccc3S(C)(=O)=O)ccc2[nH]1)C1CCCCCCC1]

N-(Cyclooctyl{4-fluoro-5-[2-(methylsulfonyl)phenyl]-1H-benzimidazol-2-yl}methyl)-2-ethylpyrazole-3-carboxamide The title compound (2 mg, 6%), a white solid, was prepared from Intermediate 163 (31 mg, 0.064 mmol) and 4,4,5,5-tetramethyl-2-[2-(methylsulphonyl)phenyl]-1,3,2-dioxaborolane (23 mg, 0.08 mmol) in accordance with Procedure G. $\delta_H$ (400 MHz, DMSO-d6) 12.88 (s, 1H), 8.93 (s, 1H), 8.11 (d, J 7.9 Hz, 1H), 7.79-7.69 (m, 2H), 7.49-7.45 (m, 1H), 7.32 (s, 1H), 7.11 (s, 1H), 7.06-6.99 (m, 1H), 6.57-6.52 (m, 1H), 5.16-5.09 (m, 1H), 4.48 (q, J 7.5 Hz, 2H), 2.89 (s, 3H), 1.85-0.99 (m, 18H). LCMS (Method 6): [M+H]⁺ m/z 552, RT 2.35 minutes.

Example 107

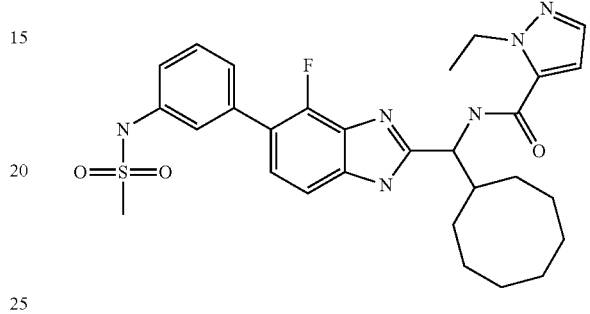

N-(Cyclooctyl{4-fluoro-5-[3-(methanesulfonamido)phenyl]-1H-benzimidazol-2-yl}-methyl)-2-ethylpyrazole-3-carboxamide The title compound (3 mg, 8%), a white solid, was prepared from Intermediate 163 (31 mg, 0.06 mmol) and 3-(methylsulfonylamino)phenylboronic acid (16 mg, 0.08 mmol) in accordance with Procedure G. $\delta_H$ (400 MHz, DMSO-d6) 12.79 (s, 1H), 9.84 (s, 1H), 8.93 (d, J 8.7 Hz, 1H), 7.48 (d, J 2.0 Hz, 1H), 7.44-7.18 (m, 5H), 7.03 (d, J 2.1 Hz, 1H), 5.11 (t, J 8.9 Hz, 1H), 4.46 (q, J 7.1 Hz, 2H), 3.01 (s, 3H), 1.84-1.18 (m, 18H). LCMS (Method 6): [M+H]⁺ m/z 567, RT 2.35 minutes.

Example 108

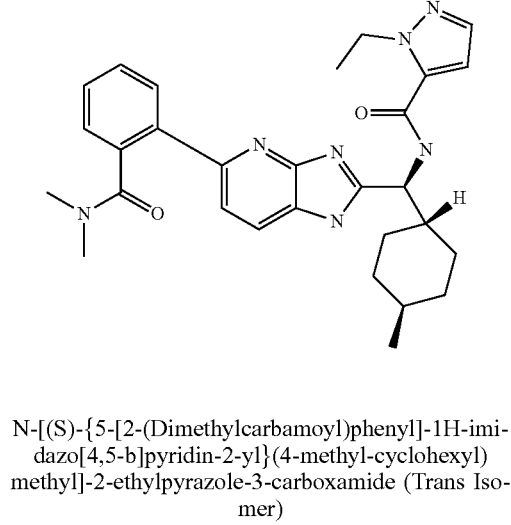

N-[(S)-{5-[2-(Dimethylcarbamoyl)phenyl]-1H-imidazo[4,5-b]pyridin-2-yl}(4-methyl-cyclohexyl)methyl]-2-ethylpyrazole-3-carboxamide (Trans Isomer)

The title compound (14 mg, 32%), a white solid, was prepared from Intermediate 166 (38 mg, 0.086 mmol) and N,N-dimethyl-2-(4,4,5,5-tetramethyl-1,3,2-dioxaborolan-2-yl)benzamide (30 mg, 0.1 mmol) in accordance with Procedure G. δ$_H$ (400 MHz, DMSO-d) 13.04-12.64 (m, 1H), 8.94-8.76 (m, 1H), 8.05-7.87 (m, 1H), 7.77 (dd, J 7.7, 1.4 Hz, 1H), 7.55-7.35 (m, 4H), 7.31 (dd, J 7.4, 1.5 Hz, 1H), 7.04 (d, J=2.1 Hz, 1H), 5.06 (t, J 8.5 Hz, 1H), 4.45 (qd, J 7.2, 1.4 Hz, 2H), 2.87 (s, 3H), 2.62 (s, 3H), 2.12-2.01 (m, 1H), 1.91 (d, J 12.7 Hz, 1H), 1.71 (d, J 12.9 Hz, 1H), 1.63 (d, J 12.9 Hz, 1H), 1.44-1.35 (m, 1H), 1.35-1.19 (m, 4H), 1.18-1.01 (m, 2H), 0.99-0.74 (m, 5H). LCMS (Method 6): [M+H]$^+$ m/z 514, RT 2.06 minutes.

Example 109

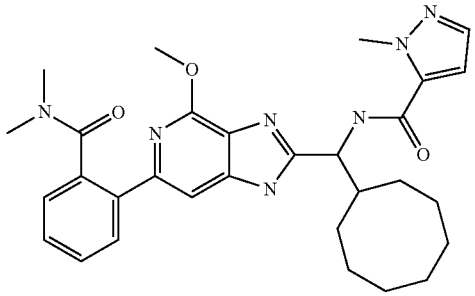 [SMILES: COc1nc(-c2ccccc2C(=O)N(C)C)cc2[nH]c(C(NC(=O)c3ccnn3C)C3CCCCCCC3)nc12]

N-(Cyclooctyl{6-[2-(dimethylcarbamoyl)phenyl]-4-methoxy-1H-imidazo[4,5-c]pyridin-2-yl}methyl)-2-methylpyrazole-3-carboxamide The title compound (18 mg, 12%), a white solid, was prepared from Intermediate 167 (130 mg, 0.27 mmol) and N,N-dimethyl-2-(4,4,5,5-tetramethyl-1,3,2-dioxaborolan-2-yl)benzamide (90 mg, 0.31 mmol) in accordance with Procedure G. δ$_H$ (400 MHz, DMSO-d$_6$) 8.94 (d, J 8.8 Hz, 1H), 8.84 (s, 1H), 7.76 (dd, J 7.7, 1.3 Hz, 1H), 7.51-7.34 (m, 3H), 7.29 (dd, J 7.5, 1.4 Hz, 1H), 7.07 (d, J 2.1 Hz, 1H), 5.10 (t, J 8.7 Hz, 1H), 4.07-3.90 (m, 6H), 2.89 (s, 3H), 2.66 (s, 3H), 2.46-2.39 (m, 1H), 1.78-1.25 (m, 14H). LCMS (Method 6): [M+H]$^+$ m/z 544, RT 2.25 minutes.

Example 110

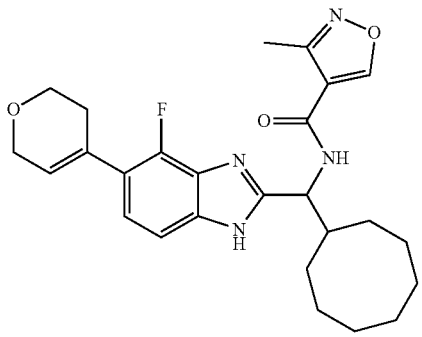 [SMILES: Cc1nocc1C(=O)NC(c1nc2c(F)c(C3=CCOCC3)ccc2[nH]1)C1CCCCCCC1]

N-{Cyclooctyl[6-(3,6-dihydro-2H-pyran-4-yl)-7-fluoro-3H-benzimidazol-2-yl]methyl}-3-methyl-isoxazole-4-carboxamide The title compound (5 mg, 17%), an off-white solid, was prepared from Intermediate 168 (60 mg, 0.06 mmol) and 2-(3,6-dihydro-2H-pyran-4-yl)-4,4,5,5-tetramethyl-1,3,2-dioxaborolane (15 mg, 0.06 mmol) in accordance with Procedure G. H (300 MHz, DMSO-d$_6$) 9.45 (s, 1H), 8.83 (s, 1H), 7.24 (d, J 8.3 Hz, 1H), 7.04 (t, J 7.6 Hz, 1H), 5.98 (s, 1H), 5.08 (t, J 8.5 Hz, 1H), 4.28-4.17 (m, 2H), 3.88-3.75 (m, 2H), 2.37 (s, 4H), 1.87-1.14 (m, 16H). LCMS (Method 6): [M+H]$^+$ m/z 467, RT 2.80 minutes.

Example 111

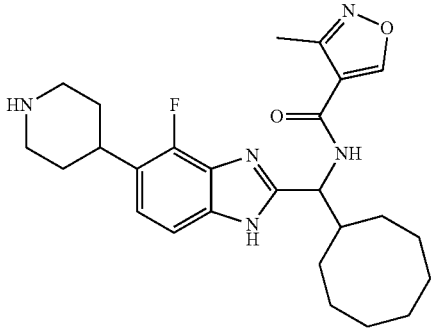 [SMILES: Cc1nocc1C(=O)NC(c1nc2c(F)c(C3CCNCC3)ccc2[nH]1)C1CCCCCCC1]

N-{Cyclooctyl[4-fluoro-5-(piperidin-4-yl)-1H-benzimidazol-2-yl]methyl}-3-methyl-isoxazole-4-carboxamide Intermediate 169 (463 mg, 0.59 mmol) was slurried in 4N HCl in 1,4-dioxane (5 mL, 20 mmol). The reaction mixture was stirred for 2 h, then concentrated in vacuo. The residue was dissolved in MeOH (2 mL) and eluted onto an Isolute SCX-2 cartridge (5 g), washing through with MeOH (20 mL). The material was released with a 4M solution of NH$_3$ in MeOH (20 mL) and concentrated in vacuo. A portion (95 mg) of the recovered crude material was purified by preparative HPLC, and lyophilised, to give the title compound (49 mg, 18%) as a white solid. δ$_H$ (300 MHz, DMSO-d$_6$) 9.45 (s, 1H), 8.95 (s, 1H), 7.39-7.16 (m, 1H), 7.14-6.97 (m, 1H), 5.08 (t, J 8.8 Hz, 1H), 3.19-2.87 (m, 4H), 2.72-2.54 (m, 2H), 2.45-2.29 (m, 4H), 1.88-1.14 (m, 18H). LCMS (Method 6): [M+H]$^+$ m/z 468, RT 1.79 minutes.

Example 112 (Method DD)

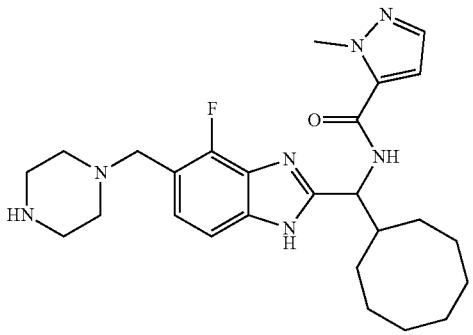 [SMILES: Cn1nccc1C(=O)NC(c1nc2c(F)c(CN3CCNCC3)ccc2[nH]1)C1CCCCCCC1]

N-{Cyclooctyl[4-fluoro-5-(piperazin-1-ylmethyl)-1H-benzimidazol-2-yl]methyl}-2-methylpyrazole-3-carboxamide To a solution of Example 33 (511 mg, 0.88 mmol) in DCM (5 mL) was added TFA (0.5 mL). The reaction mixture was stirred overnight, then concentrated in vacuo. The residue was loaded onto an SCX column in MeOH, eluting with a 7N solution of $NH_3$ in MeOH. The residue was concentrated in vacuo to afford crude material (430 mg, quantitative). Purification of a portion (15 mg) of this material was carried out by preparative HPLC to give, after freeze-drying, the title compound (6 mg, 1%) as a white solid. $\delta_H$ (400 MHz, $CD_3OD$) 7.50 (d, J 2.2 Hz, 1H), 7.33 (d, J 8.3 Hz, 1H), 7.26 (dd, J 8.3, 6.4 Hz, 1H), 6.94 (d, J 2.2 Hz, 1H), 5.18 (d, J 8.7 Hz, 1H), 4.09 (s, 3H), 3.74 (d, J 1.8 Hz, 2H), 2.85 (t, J 5.1 Hz, 4H), 2.58-2.39 (m, 5H), 1.85-1.43 (m, 14H). LCMS (Method 6): $[M+H]^+$ m/z 482, RT 1.70 minutes.

Example 113

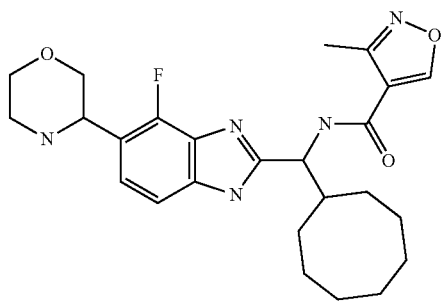 [SMILES: Cc1nocc1C(=O)NC(c1nc2c(F)c(C3COCCN3)ccc2[nH]1)C1CCCCCCC1]

N-{Cyclooctyl[4-fluoro-5-(morpholin-3-yl)-1H-benzimidazol-2-yl]methyl}-3-methyl-isoxazole-4-carboxamide The title compound (assumed 1:1 mixture of diastereomers) (4 mg, 17%), a white solid, was prepared from Example 43 (30 mg, 0.05 mmol) in accordance with Procedure DD. $\delta_H$ (300 MHz, DMSO-$d_6$) 12.79 (s, 1H), 9.44 (s, 1H), 8.86 (s, 1H), 7.57-6.85 (m, 2H), 5.08 (t, J 8.7 Hz, 1H), 4.18 (d, J 9.9 Hz, 1H), 3.76 (d, J 10.9 Hz, 1H), 3.72-3.61 (m, 1H), 3.48 (td, J 10.5, 3.8 Hz, 1H), 3.23 (t, J 10.4 Hz, 1H), 2.92 (d, J 10.4 Hz, 2H), 2.73 (s, 1H), 2.36 (m, 4H), 1.93-1.11 (m, 14H). LCMS (Method 6): $[M+H]^+$ m/z 470, RT 2.09 minutes.

Example 114

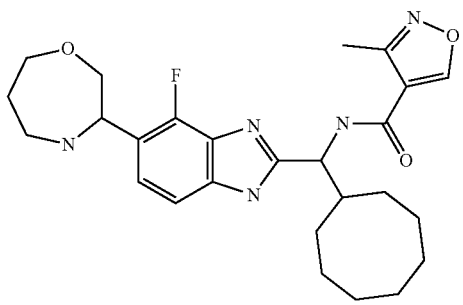 [SMILES: Cc1nocc1C(=O)NC(c1nc2c(F)c(C3COCCCN3)ccc2[nH]1)C1CCCCCCC1]

N-{Cyclooctyl[4-fluoro-5-(1,4-oxazepan-3-yl)-1H-benzimidazol-2-yl]methyl}-3-methyl-isoxazole-4-carboxamide The title compound (assumed 1:1 mixture of diastereomers) (2 mg, 23%), a white solid, was prepared from Example 44 (18 mg, 0.02 mmol) in accordance with Procedure DD. $\delta_H$ (300 MHz, DMSO-$d_6$) 12.92 (s, 1H), 9.46 (s, 1H), 8.94 (s, 1H), 7.30-7.12 (m, 2H), 5.07 (t, J 8.8 Hz, 1H), 4.28-4.13 (m, 1H), 3.98-3.62 (m, 3H), 3.40 (d, J 11.2 Hz, 1H), 3.18-2.98 (m, 1H), 2.84 (dt, J 13.7, 7.0 Hz, 1H), 2.36 (m, 4H), 1.87 (d, J 6.2 Hz, 2H), 1.79-1.17 (m, 14H). LCMS (Method 6): $[M+H]^+$ m/z 484, RT 2.15 minutes.

Example 115

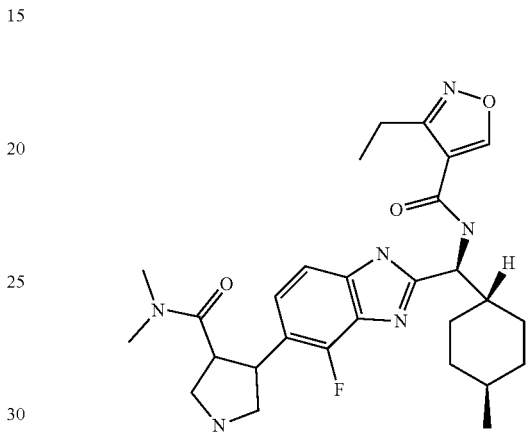

N-[(S)-{5-[4-(Dimethylcarbamoyl)pyrrolidin-3-yl]-4-fluoro-1H-benzimidazol-2-yl}(4-methylcyclohexyl)methyl]-3-ethylisoxazole-4-carboxamide (Trans Isomer)

The title compound (3 mg, 4%), a white solid, was prepared from Intermediate 172 (205 mg, 0.14 mmol) in accordance with Procedure DD, with purification by preparative HPLC. $\delta_H$ (400 MHz, DMSO-$d_6$) 12.47 (s, 1H), 9.38 (d, J 1.0 Hz, 1H), 8.60 (d, J 9.5 Hz, 1H), 7.25-6.95 (m, 2H), 6.24 (s, 1H), 5.06 (d, J 8.4 Hz, 1H), 4.02-3.68 (m, 2H), 3.58-3.12 (m, 4H), 3.06-2.60 (m, 9H), 2.47-2.38 (m, 1H), 2.05-1.93 (m, 1H), 1.87 (d, J 13.0 Hz, 1H), 1.76-1.58 (m, 2H), 1.45 (d, J 13.0 Hz, 1H), 1.35-1.24 (m, 1H), 1.24-0.98 (m, 4H), 0.98-0.79 (m, 4H). LCMS (Method 6): $[M+H]^+$ m/z 525, RT 1.81 minutes.

Example 116 (Procedure EE)

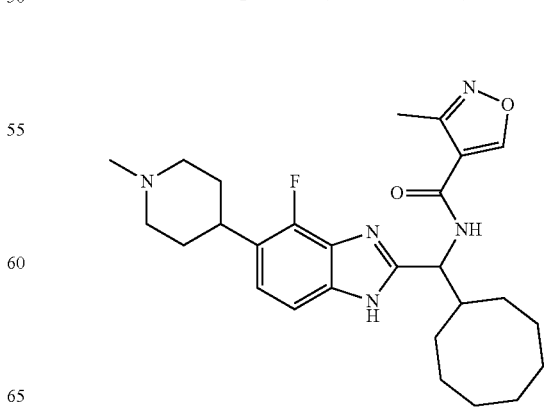

N-{Cyclooctyl[4-fluoro-5-(1-methylpiperidin-4-yl)-1H-benzimidazol-2-yl]methyl}-3-methylisoxazole-4-carboxamide To a suspension of Example 111 (95 mg, 0.15 mmol) in THF (5 mL) was added formaldehyde (0.06 mL, 0.8 mmol). The reaction mixture was stirred at r.t. for 5 minutes, then sodium triacetoxyborohydride (67 mg, 0.30 mmol) was added. The reaction mixture was stirred overnight, then additional formaldehyde (0.06 mL, 0.8 mmol) was added. The mixture was stirred for 10 minutes, then further sodium triacetoxyborohydride (67 mg, 0.30 mmol) was added. The reaction mixture was quenched with saturated aqueous NaHCO₃ solution (10 mL) and water (5 mL) and stirred for 5 minutes. The material was extracted with EtOAc (2×20 mL) and dried over Na₂SO₄, then filtered and concentrated in vacuo. Purification by preparative HPLC, followed by lyophilisation, gave the title compound (35 mg, 48%) as a white solid. $\delta_H$ (300 MHz, DMSO-d₆) 12.69 (s, 1H), 9.43 (s, 1H), 8.83 (d, J 8.7 Hz, 1H), 7.25 (d, J 8.3 Hz, 1H), 7.13-7.02 (m, 1H), 5.08 (t, J 8.5 Hz, 1H), 2.94-2.76 (m, 3H), 2.45-2.29 (m, 4H), 2.20 (s, 3H), 2.06-1.91 (m, 2H), 1.87-1.15 (m, 18H). LCMS (Method 6): [M+H]⁺ m/z 482, RT 2.07 minutes.

Example 117

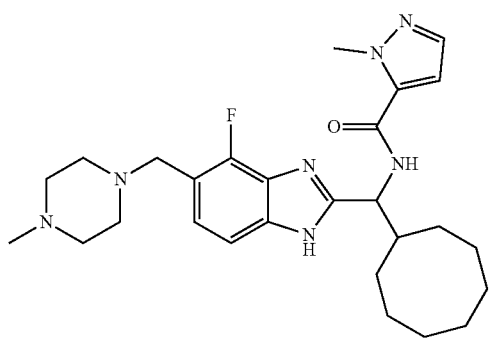 [SMILES: CN1CCN(Cc2ccc3[nH]c(C(NC(=O)c4ccnn4C)C4CCCCCCC4)nc3c2F)CC1]

N-(Cyclooctyl{4-fluoro-5-[(4-methylpiperazin-1-yl)methyl]-1H-benzimidazol-2-yl}-methyl)-2-methylpyrazole-3-carboxamide The title compound (19 mg, 18%), a white solid, was prepared from Example 112 (105 mg, 0.22 mmol) and formaldehyde in water (18.2 μL, 0.22 mmol, 36% by weight) in accordance with Procedure EE. $\delta_H$ (300 MHz, DMSO-d₆) 12.96-12.65 (m, 1H), 8.95-8.77 (m, 1H), 7.46 (d, J 2.1 Hz, 1H), 7.40-7.20 (m, 1H), 7.16-7.09 (m, 1H), 7.07 (d, J 2.0 Hz, 1H), 5.07 (t, J 9.1 Hz, 1H), 4.02 (s, 3H), 3.62-3.52 (m, 2H), 2.45-2.22 (m, 8H), 2.12 (s, 3H), 1.75-1.28 (m, 15H). LCMS (Method 6): [M+H]⁺ m/z 496, RT 1.73 minutes.

Example 118

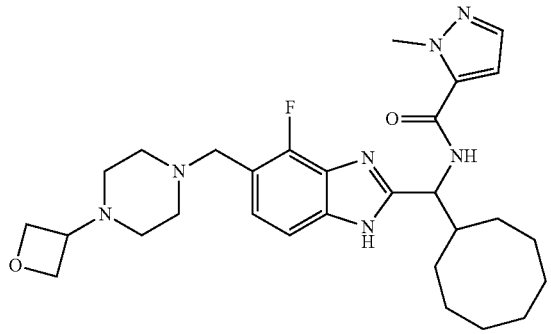 [SMILES: Cn1nccc1C(=O)NC(c1nc2c(F)c(CN3CCN(C4COC4)CC3)ccc2[nH]1)C1CCCCCCC1]

N-[Cyclooctyl(4-fluoro-5-{[4-(oxetan-3-yl)piperazin-1-yl]methyl}-1H-benzimidazol-2-yl)methyl]-2-methylpyrazole-3-carboxamide The title compound (2 mg, 2%), a white solid, was prepared from Example 112 (105 mg, 0.22 mmol) and 3-oxetanone (15 μL, 0.22 mmol) in accordance with Procedure EE. $\delta_H$ (400 MHz, DMSO-d₆) 13.49 (s, 1H), 9.31 (s, 1H), 7.44 (d, J 2.1 Hz, 1H), 7.23-7.19 (m, 1H), 7.14-7.05 (m, 2H), 5.08 (t, J 8.8 Hz, 1H), 4.50 (t, J 6.5 Hz, 2H), 4.39 (t, J 6.1 Hz, 2H), 4.02 (s, 3H), 3.60 (s, 2H), 3.36 (q, J 6.5 Hz, 1H), 2.46-2.37 (m, 4H), 2.31-2.14 (m, 4H), 1.78-1.71 (m, 1H), 1.63-1.22 (m, 14H). LCMS (Method 6): [M+H]⁺ m/z 538, RT 1.97 minutes.

Example 119 (Procedure FF)

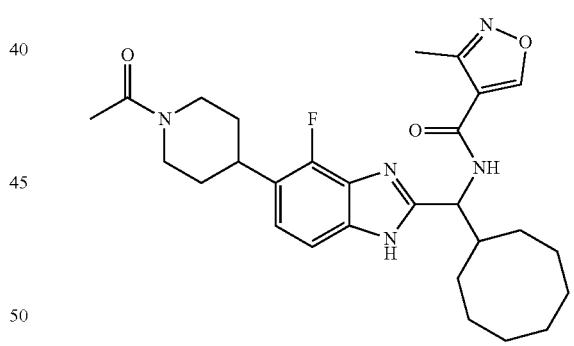

N-{[5-(1-Acetylpiperidin-4-yl)-4-fluoro-1H-benzimidazol-2-yl](cyclooctyl)methyl}-3-methylisoxazole-4-carboxamide To a solution of Example 111 (95 mg, 0.15 mmol) and DIPEA (0.029 mL, 0.17 mmol) in DCM (3 mL) and THF (3 mL) at 0° C. was added acetyl chloride (0.011 mL, 0.15 mmol) in one portion. The reaction mixture was allowed to warm to r.t. Additional acetyl chloride (0.011 mL, 0.15 mmol) was added. The reaction mixture was stirred for a further 2 h, then concentrated in vacuo. The residue was dissolved in DCM (20 mL) and washed with saturated aqueous NaHCO₃ solution (30 mL), then dried over Na₂SO₄, filtered and concentrated in vacuo. Purification by preparative HPLC gave the title compound (29 mg, 38%) as a white solid. $\delta_H$ (300 MHz, DMSO-d$_6$) 12.63 (s, 1H), 9.43 (s, 1H), 8.83 (d, J 8.7 Hz, 1H), 7.25 (d, J 8.3 Hz, 1H), 7.15-6.99 (m, 1H), 5.08 (t, J 8.7 Hz, 1H), 4.65-4.44 (m, 1H), 4.08-3.82 (m, 1H), 3.24-3.07 (m, 2H), 2.69-2.55 (m, 1H), 2.45-2.31 (m, 4H), 2.04 (s, 3H), 1.86-1.11 (m, 18H). LCMS (Method 6): [M+H]$^+$ m/z 510, RT 2.13 minutes.

Example 120

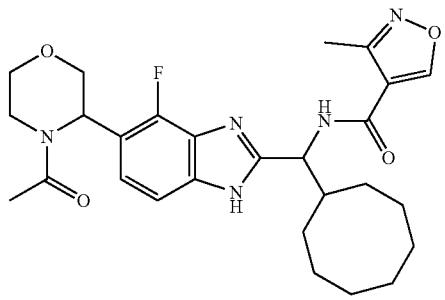 [SMILES: CC(=O)N1CCOCC1c1ccc2[nH]c(C(NC(=O)c3conc3C)C3CCCCCCC3)nc2c1F]

N-{[5-(4-Acetylmorpholin-3-yl)-4-fluoro-1H-benzimidazol-2-yl](cyclooctyl)methyl}-3-methylisoxazole-4-carboxamide The title compound (assumed 1:1 mixture of diastereomers) (6 mg, 820%), a white solid, was prepared from Example 113 (8 mg, 0.01 mmol) in accordance with Procedure FF. $\delta_H$ (373K, 400 MHz, DMSO-d$_6$) 12.36 (s, 1H), 9.34 (s, 1H), 8.34 (s, 1H), 7.32-7.23 (m, 2H), 5.50 (s, 1H), 5.16 (t, J 7.5 Hz, 1H), 4.19 (dt, J 11.9, 2.5 Hz, 1H), 4.02-3.91 (m, 2H), 3.87 (dd, J 11.9, 4.1 Hz, 1H), 3.57 (td, J 11.5, 3.4 Hz, 1H), 3.41-3.29 (m, 1H), 2.44-2.35 (m, 4H), 2.07-2.06 (m, 3H), 1.84-1.73 (m, 1H), 1.73-1.30 (m, 13H). LCMS (Method 6): [M+H]$^+$ m/z 512, RT 1.94 minutes.

Example 121 (Procedure GG)

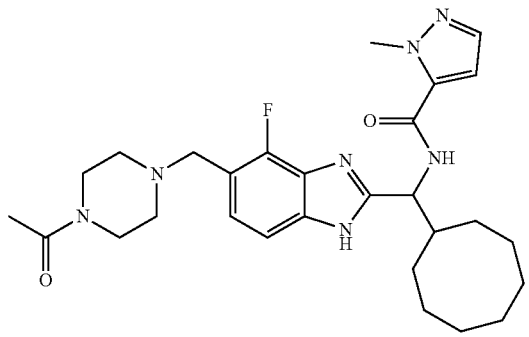 [SMILES: CC(=O)N1CCN(Cc2ccc3[nH]c(C(NC(=O)c4ccnn4C)C4CCCCCCC4)nc3c2F)CC1]

N-[{5-[(4-Acetylpiperazin-1-yl)methyl]-4-fluoro-1H-benzimidazol-2-yl}(cyclooctyl)-methyl]-2-methylpyrazole-3-carboxamide To a solution of Example 112 (105 mg, 0.22 mmol) in DCM (2 mL) were added triethylamine (30 µL, 0.22 mmol) and acetic anhydride (21 µL, 0.22 mmol). The reaction mixture was stirred at r.t. overnight, then concentrated in vacuo. The residue was purified by HPLC to yield the title compound (33 mg, 29%) as a white solid. $\delta_H$ (300 MHz, DMSO-d$_6$) 13.00-12.64 (m, 1H), 8.96-8.72 (m, 1H), 7.46 (d, J 2.0 Hz, 1H), 7.41-7.23 (m, 1H), 7.15 (t, J 7.3 Hz, 1H), 7.07 (d, J 2.0 Hz, 1H), 5.07 (t, J 8.8 Hz, 1H), 4.03 (s, 3H), 3.63 (s, 2H), 3.45-3.35 (m, 4H), 2.42-2.30 (m, 4H), 1.96 (s, 3H), 1.77-1.27 (m, 15H). LCMS (Method 6): [M+H]$^+$ m/z 524, RT 2.02 minutes.

Example 122

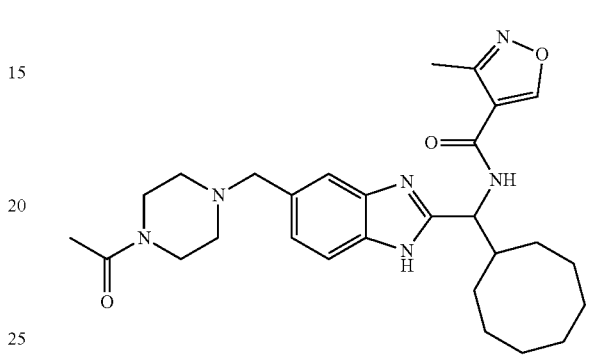

N-[{5-[(4-Acetylpiperazin-1-yl)methyl]-1H-benzimidazol-2-yl}(cyclooctyl)methyl]-3-methylisoxazole-4-carboxamide The title compound (4 mg, 9%), a white solid, was prepared from Intermediate 174 (40 mg, 0.09 mmol) in accordance with Procedure GG. $\delta_H$ (300 MHz, DMSO-d$_6$) 12.35 (d, J 8.6 Hz, 1H), 9.44 (d, J 0.6 Hz, 1H), 8.77 (d, J 6.6 Hz, 1H), 7.54-7.33 (m, 2H), 7.11 (t, J 9.0 Hz, 1H), 5.09 (t, J 8.6 Hz, 1H), 3.57 (s, 2H), 3.40 (s, 4H), 2.40-2.28 (m, 7H), 1.97 (s, 3H), 1.79-1.29 (m, 15H). LCMS (Method 6): [M+H]$^+$ m/z 507, RT 2.01 minutes.

Example 123

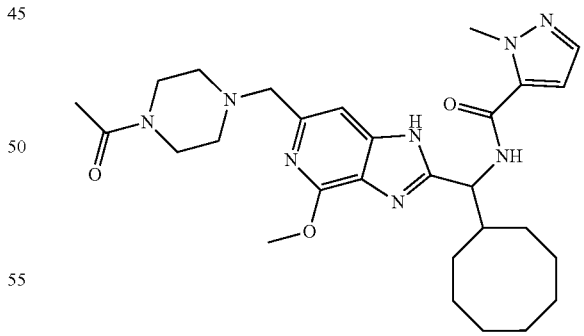

N-[{6-[(4-Acetylpiperazin-1-yl)methyl]-4-methoxy-1H-imidazo[4,5-c]pyridin-2-yl}-(cyclooctyl)methyl]-2-methylpyrazole-3-carboxamide The title compound (2 mg, 4%), a white solid, was prepared from Intermediate 176 (53 mg, 0.11 mmol) in accordance with Procedure GG. $\delta_H$ (400 MHz, DMSO-d$_6$) 12.94 (s, 1H), 8.61 (s, 1H), 7.45 (d, J 2.1 Hz, 1H), 7.02 (s, 1H), 6.73-6.60 (m, 1H), 5.03 (t, J 7.6 Hz, 1H), 4.03 (s, 3H), 3.91 (s, 3H), 3.55 (s, 2H), 3.49-3.36 (m, 4H), 2.48-2.39 (m, 4H), 2.39-2.35 (m, 1H), 1.97 (s, 3H), 1.77-1.26 (m, 14H). LCMS (Method 6): [M+H]$^+$ m/z 537, RT 2.01 minutes.

Example 124

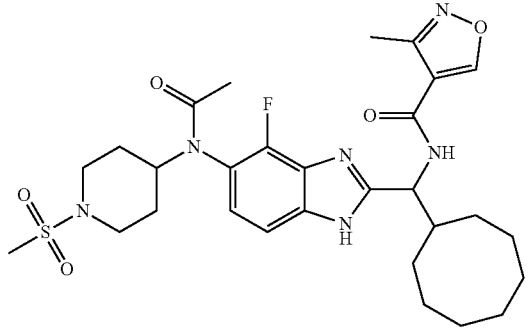 [SMILES: CC(=O)N(c1ccc2[nH]c(C(NC(=O)c3conc3C)C3CCCCCCC3)nc2c1F)C1CCN(S(C)(=O)=O)CC1]

N-[(5-{Acetyl[1-(methylsulfonyl)piperidin-4-yl]amino}-4-fluoro-1H-benzimidazol-2-yl)-(cyclooctyl)methyl]-3-methylisoxazole-4-carboxamide The title compound (25 mg, 25%), a white solid, was prepared from Example 32 (92 mg, 0.16 mmol) in accordance with Procedure GG. δ$_H$ (400 MHz, DMSO-d$_6$) 12.72 (s, 1H), 9.45-9.41 (m, 1H), 8.90-8.81 (m, 1H), 7.36 (d, J 8.4 Hz, 1H), 7.08 (t, J 7.7 Hz, 1H), 5.13 (td, J 8.7, 3.7 Hz, 1H), 4.58 (t, J 12.6 Hz, 1H), 3.55 (d, J 12.6 Hz, 2H), 2.89-2.75 (m, 5H), 2.46-2.34 (m, 4H), 2.00-1.24 (m, 21H). LCMS (Method 6): [M+H]$^+$ m/z 603, RT 2.21 minutes.

Example 125

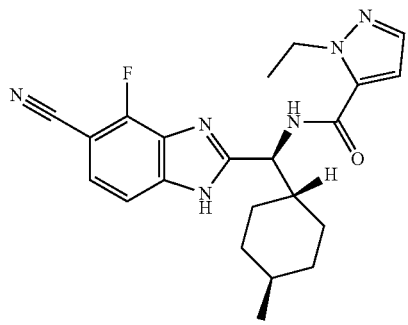 [SMILES: CCn1nccc1C(=O)N[C@H](c1nc2c(F)c(C#N)ccc2[nH]1)[C@H]1CC[C@H](C)CC1]

N-[(S)-(5-Cyano-4-fluoro-1H-benzimidazol-2-yl)(4-methylcyclohexyl)methyl]-2-ethyl-pyrazole-3-carboxamide (Trans Isomer)

The title compound (314 mg, 83%), a white solid, was prepared from Intermediate 177 (167 mg, 0.58 mmol) and 2-ethylpyrazole-3-carboxylic acid (105 mg, 0.71 mmol) in accordance with Procedure A. δ$_H$ (400 MHz, DMSO-d$_6$) 13.21 (s, 1H), 8.74 (s, 1H), 7.47 (d, J 2.0 Hz, 1H), 7.45-7.33 (m, 2H), 7.02 (d, J 2.1 Hz, 1H), 5.04 (t, J 8.4 Hz, 1H), 4.45 (q, J 7.1 Hz, 2H), 2.04 (d, J 11.1 Hz, 2H), 1.85 (d, J 12.6 Hz, 1H), 1.69-1.55 (m, 2H), 1.41 (d, J 12.8 Hz, 1H), 1.25 (t, J 7.1 Hz, 3H), 1.18-0.96 (m, 3H), 0.94-0.76 (m, 4H). LCMS (Method 6): [M+H]$^+$ m/z 409, RT 2.23 minutes.

Examples 126 & 127

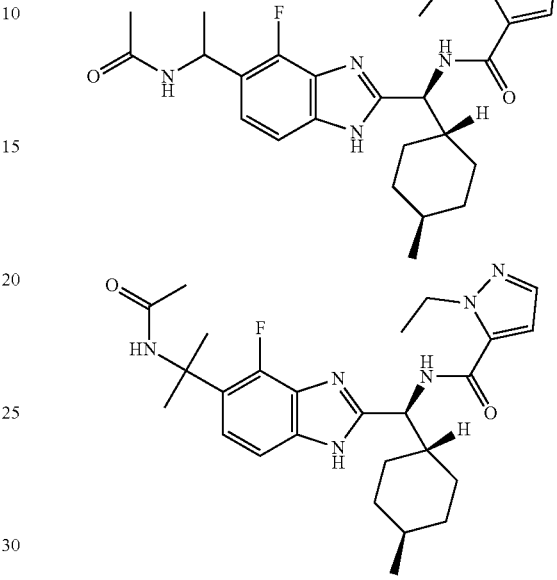

N-{(S)-[5-(1-Acetamidoethyl)-4-fluoro-1H-benzimidazol-2-yl](4-methylcyclohexyl)-methyl}-2-ethylpyrazole-3-carboxamide (Trans Isomer) (Example 126)

N-{(S)-[5-(1-Acetamido-1-methylethyl)-4-fluoro-1H-benzimidazol-2-yl](4-methyl-cyclohexyl)methyl}-2-ethylpyrazole-3-carboxamide (Trans Isomer) (Example 127)

To a solution of Example 125 (290 mg, 0.71 mmol) in anhydrous THF (5 mL) at −78° C. was added dropwise MeMgCl (3M in THF, 2.4 mL, 7.2 mmol). The reaction mixture was allowed to warm to r.t. over 1 h, then titanium (IV) isopropoxide (25.2 µL, 0.09 mmol) was added. The reaction mixture was stirred at r.t. overnight, then re-cooled to −78° C., and further MeMgCl (3M in THF, 2.4 mL, 7.2 mmol) was added. After further stirring at r.t. for 24 h, another aliquot of MeMgCl (3M in THF, 2.4 mL, 7.2 mmol) was added at −78° C. The reaction mixture was left another 24 h, then cooled to 0° C. MeOH (10 mL) was added dropwise, followed by the portionwise addition of NaBH$_4$ (55 mg, 1.45 mmol). The reaction mixture was warmed to r.t. and stirred overnight, then quenched with water and concentrated in vacuo. The residue was partitioned between DCM and water. The organic layers were separated and washed with saturated aqueous NaHCO$_3$ solution, then dried over Na$_2$SO$_4$ and concentrated in vacuo. The residue was flashed down an SCX column, eluting with a 7N solution of NH$_3$ in MeOH, then concentrated in vacuo. The crude recovered material was purified further by flash chromatography, eluting with EtOAc/hexanes (0-100% gradient). The recovered material was taken up in DCM (2 mL), with triethylamine (24 μL, 0.17 mmol) and acetic anhydride (16 μL, 0.17 mmol). The reaction mixture was stirred overnight, then concentrated in vacuo. The crude material was subject to purification using preparative HPLC, to yield the title compounds (Example 126, 16 mg, 20%; and Example 127, 2 mg, 2%) as white solids.

Example 126: $\delta_H$ (400 MHz, DMSO-d$_6$) 13.00-12.50 (m, 1H), 8.95-8.65 (m, 1H), 8.33 (d, J 8.0 Hz, 1H), 7.47 (dd, J 2.1, 0.8 Hz, 1H), 7.24 (d, J 8.3 Hz, 1H), 7.17-7.08 (m, 1H), 7.06-7.00 (m, 1H), 5.28-5.25 (m, 1H), 4.97 (t, J 8.8 Hz, 1H), 4.49-4.38 (m, 2H), 2.04 (d, J 11.5 Hz, 1H), 1.90 (d, J 12.4 Hz, 1H), 1.81 (s, 3H), 1.70 (d, J 12.7 Hz, 1H), 1.61 (d, J 12.8 Hz, 1H), 1.48-1.15 (m, 8H), 1.14-0.97 (m, 2H), 0.96-0.72 (m, 5H). LCMS (Method 6): [M+H]$^+$ m/z 469, RT 1.93 minutes.

Example 127: $\delta_H$ (400 MHz, CD$_3$OD) 8.55 (s, 1H), 7.49 (d, J 2.1 Hz, 1H), 7.28-7.18 (m, 2H), 6.92 (d, J 2.1 Hz, 1H), 5.06 (d, J 8.6 Hz, 1H), 4.50 (qd, J 7.2, 2.8 Hz, 2H), 2.04-1.95 (m, 2H), 1.92 (s, 3H), 1.84-1.64 (m, 8H), 1.44-1.31 (m, 5H), 1.21-1.09 (m, 2H), 1.05-0.93 (m, 2H), 0.89 (d, J 6.5 Hz, 3H). LCMS (Method 6): [M+H]$^+$ m/z 483, RT 2.02 minutes.

Example 128 (Procedure HH)

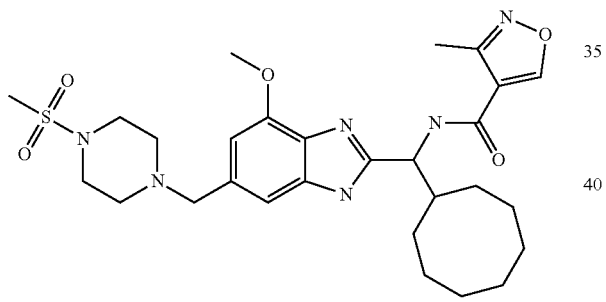

N-[Cyclooctyl(4-methoxy-6-{[4-(methylsulfonyl)piperazin-1-yl]methyl}-1H-benzimidazol-2-yl)methyl]-3-methylisoxazole-4-carboxamide To a solution of Intermediate 179 (25 mg, 0.05 mmol) in DCM (1 mL) were added triethylamine (7 μL, 0.05 mmol) and methanesulfonyl chloride (4 μL, 0.05 mmol). The reaction mixture was stirred at r.t. overnight, then concentrated in vacuo and subject to preparative HPLC purification, to give the title compound (7 mg, 24%) as a white solid. $\delta_H$ (300 MHz, DMSO-d$_6$) 12.66-12.24 (m, 1H), 9.44 (s, 1H), 8.91-8.57 (m, 1H), 7.16-6.88 (m, 1H), 6.76-6.55 (m, 1H), 5.16-4.94 (m, 1H), 3.90 (s, 3H), 3.57 (s, 2H), 3.23-3.00 (m, 4H), 2.87 (s, 3H), 2.50-2.44 (m, 4H), 2.40-2.24 (m, 4H), 1.81-1.26 (m, 14H). LCMS (Method 6): [M+H]$^+$ m/z 573, RT 2.25 minutes.

Example 129

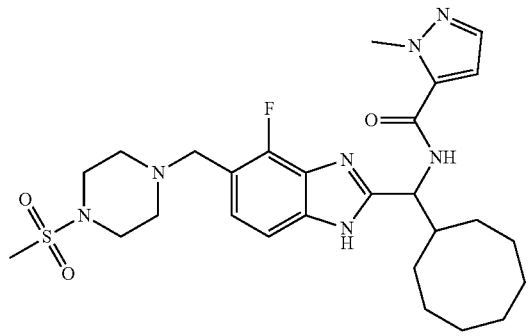 [SMILES: Cn1nccc1C(=O)NC(c1nc2c(F)c(CN3CCN(S(C)(=O)=O)CC3)ccc2[nH]1)C1CCCCCCC1]

N-[Cyclooctyl(4-fluoro-5-{[4-(methylsulfonyl)piperazin-1-yl]methyl}-1H-benzimidazol-2-yl)methyl]-2-methylpyrazole-3-carboxamide The title compound (39 mg, 32%), a white solid, was prepared from Example 112 (105 mg, 0.22 mmol) in accordance with Procedure HH. $\delta_H$ (300 MHz, DMSO-d$_6$) 12.99-12.65 (m, 1H), 8.96-8.72 (m, 1H), 7.46 (d, J 2.0 Hz, 1H), 7.41-7.23 (m, 1H), 7.19-7.11 (m, 1H), 7.07 (d, J 2.1 Hz, 1H), 5.07 (t, J 9.0 Hz, 1H), 4.03 (s, 3H), 3.65 (s, 2H), 3.08 (d, J 5.4 Hz, 4H), 2.85 (s, 3H), 2.49-2.42 (m, 4H), 1.80-1.26 (m, 15H). LCMS (Method 6): [M+H]$^+$ m/z 560, RT 2.21 minutes.

Example 130

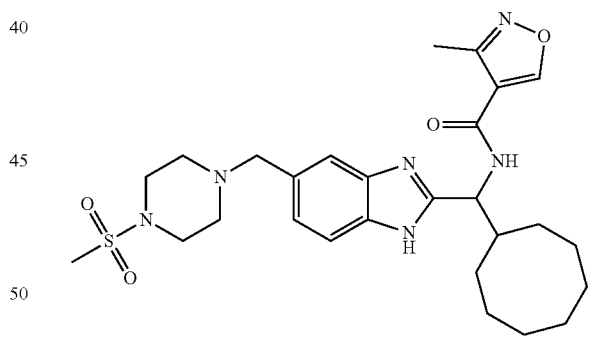

N-[Cyclooctyl(5-{[4-(methylsulfonyl)piperazin-1-yl]methyl}-1H-benzimidazol-2-yl)-methyl]-3-methyl-isoxazole-4-carboxamide The title compound (6 mg, 13%), a white solid, was prepared from Intermediate 174 (40 mg, 0.09 mmol) in accordance with Procedure HH. $\delta_H$ (300 MHz, DMSO-d$_6$) 12.40 (s, 1H), 9.44 (s, 1H), 8.80 (d, J 8.1 Hz, 1H), 7.58-7.28 (m, 2H), 7.11 (d, J 8.1 Hz, 1H), 5.09 (t, J 8.5 Hz, 1H), 3.59 (s, 2H), 3.09 (d, J 4.9 Hz, 4H), 2.86 (s, 3H), 2.46 (d, J 5.0 Hz, 4H), 2.37 (s, 3H), 1.83-1.19 (m, 15H). LCMS (Method 6): [M+H]$^+$ m/z 543, RT 2.20 minutes.

Example 131

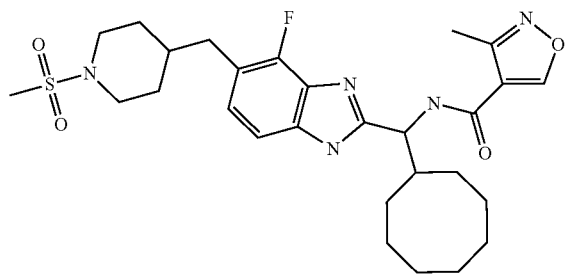 [SMILES: Cc1nocc1C(=O)NC(c1nc2c(F)c(CC3CCN(S(C)(=O)=O)CC3)ccc2[nH]1)C1CCCCCCC1]

N-[Cyclooctyl(4-fluoro-5-{[1-(methylsulfonyl)piperidin-4-yl]methyl}-1H-benzimidazol-2-yl)methyl]-3-methylisoxazole-4-carboxamide The title compound (3 mg, 27%), a white solid, was prepared from Intermediate 181 (19 mg, 0.02 mmol) in accordance with Procedure HH. $\delta_H$ (300 MHz, DMSO-d$_6$) 12.86-12.64 (m, 1H), 9.44 (s, 1H), 8.84-8.74 (m, 1H), 7.34-7.21 (m, 1H), 7.06-6.97 (m, 1H), 5.11-5.08 (m, 1H), 3.52 (d, J 11.7 Hz, 2H), 2.81 (s, 3H), 2.71-2.56 (m, 4H), 2.37-2.27 (m, 4H), 1.82-1.14 (m, 18H). LCMS (Method 6): [M+H]$^+$ m/z 560, RT 2.57 minutes.

Example 132

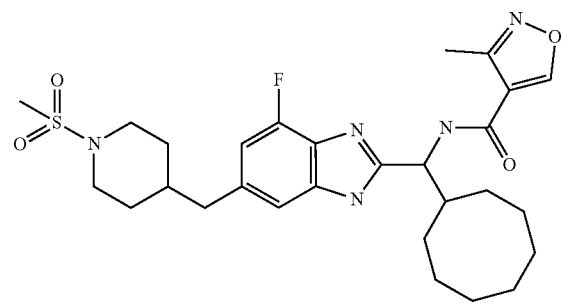 [SMILES: Cc1nocc1C(=O)NC(c1nc2c(F)cc(CC3CCN(S(C)(=O)=O)CC3)cc2[nH]1)C1CCCCCCC1]

N-[Cyclooctyl(4-fluoro-6-{[1-(methylsulfonyl)piperidin-4-yl]methyl}-1H-benzimidazol-2-yl)methyl]-3-methylisoxazole-4-carboxamide The title compound (12 mg, 10%), a white solid, was prepared from Intermediate 183 (100 mg, 0.21 mmol) in accordance with Procedure HH. $\delta_H$ (300 MHz, DMSO-d$_6$) 12.61 (s, 1H), 9.43 (s, 1H), 8.82 (d, J 8.6 Hz, 1H), 7.09 (s, 1H), 6.82 (d, J 11.9 Hz, 1H), 5.08 (t, J 8.7 Hz, 1H), 3.52 (d, J 11.7 Hz, 2H), 2.82 (s, 3H), 2.62 (m, 4H), 2.37 (m, 4H), 1.80-1.12 (m, 19H). LCMS (Method 6): [M+H]$^+$ m/z 560, RT 2.64 minutes.

Example 133

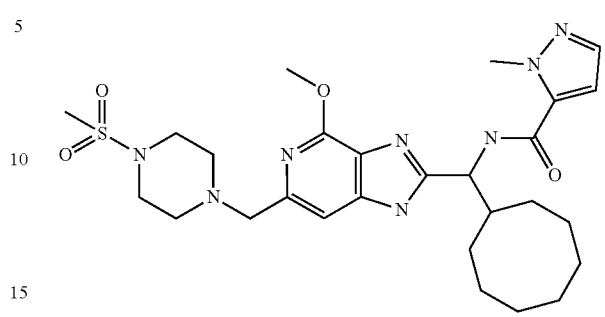

N-[Cyclooctyl(4-methoxy-6-{[4-(methylsulfonyl)piperazin-1-yl]methyl}-1H-imidazo-[4,5-c]pyridin-2-yl)methyl]-2-methylpyrazole-3-carboxamide The title compound (39 mg, 32%), a white solid, was prepared from Intermediate 176 (105 mg, 0.22 mmol) in accordance with Procedure HH. $\delta_H$ (400 MHz, DMSO-d$_6$) 12.82 (s, 1H), 8.85 (s, 1H), 7.46 (d, J 2.1 Hz, 1H), 7.10 (s, 1H), 7.06 (d, J 2.1 Hz, 1H), 5.07 (t, J 8.4 Hz, 1H), 4.02 (s, 3H), 3.95 (s, 3H), 3.62 (s, 2H), 3.13 (t, J 4.9 Hz, 4H), 2.88 (s, 3H), 2.62-2.53 (m, 4H), 2.43-2.39 (m, 1H), 1.72-1.29 (m, 14H). LCMS (Method 6): [M+H]$^+$ m/z 573, RT 2.19 minutes.

Example 134

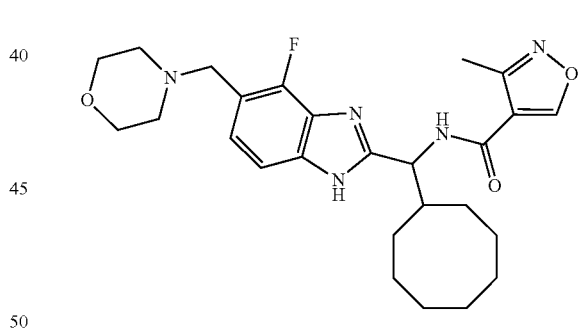

N-{Cyclooctyl[4-fluoro-5-(morpholin-4-ylmethyl)-1H-benzimidazol-2-yl]methyl}-3-methylisoxazole-4-carboxamide The title compound (6 mg, 7%), a white solid, was prepared from Intermediate 168 (88 mg, 0.19 mmol) and potassium [(morpholin-4-yl)methyl]trifluoroborane (60 mg, 0.29 mmol) in accordance with Procedure R. $\delta_H$ (300 MHz, DMSO-d$_6$) 9.47 (s, 1H), 9.30 (d, J 8.9 Hz, 1H), 8.37 (s, 1H), 7.24 (d, J 8.3 Hz, 1H), 7.12 (dd, J 8.2, 6.4 Hz, 1H), 5.08 (t, J 9.0 Hz, 1H), 3.58 (d, J 1.6 Hz, 2H), 3.54 (t, J 4.6 Hz, 4H), 2.42-2.30 (m, 8H), 1.63-1.39 (m, 10H), 1.29-1.22 (m, 4H). LCMS (Method 6): [M+H]$^+$ m/z 484, RT 2.07 minutes.

Example 135

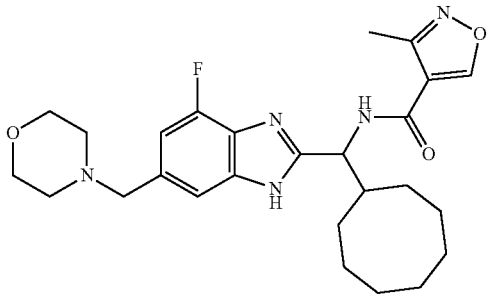 [SMILES: Cc1nocc1C(=O)NC(c1nc2c(F)cc(CN3CCOCC3)cc2[nH]1)C1CCCCCCC1]

N-{Cyclooctyl[4-fluoro-6-(morpholin-4-ylmethyl)-1H-benzimidazol-2-yl]methyl}-3-methylisoxazole-4-carboxamide The title compound (1 mg, 3%), a white solid, was prepared from Intermediate 184 (84 mg, 0.18 mmol) and potassium [(morpholin-4-yl)methyl]trifluoroborane (60 mg, 0.29 mmol) in accordance with Procedure MM. $\delta_H$ (300 MHz, CD$_3$OD) 9.18 (d, J 0.7 Hz, 1H), 7.32 (s, 1H), 7.02 (d, J 11.7 Hz, 1H), 5.14 (d, J 8.1 Hz, 1H), 3.69 (t, J 4.7 Hz, 4H), 3.61 (s, 2H), 2.51-2.44 (m, 4H), 2.42 (d, J 0.6 Hz, 3H), 2.10-2.02 (m, 1H), 1.76-1.43 (m, 14H). LCMS (Method 6): [M+H]$^+$ m/z 484, RT 2.13 minutes.

Example 136

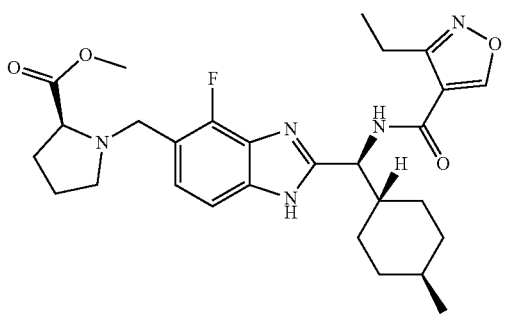 [SMILES: CCc1nocc1C(=O)N[C@H](c1nc2c(F)c(CN3CCC[C@H]3C(=O)OC)ccc2[nH]1)[C@H]1CC[C@H](C)CC1]

Methyl (2S)-1-[(2-{(S)-[(3-ethylisoxazole-4-carbonyl)amino](4-methylcyclohexyl)-methyl}-4-fluoro-1H-benzimidazol-5-yl)methyl]pyrrolidine-2-carboxylate (Trans Isomer)

The title compound (43 mg, 25%), a white solid, was prepared from Intermediate 185 (127 mg, 0.32 mmol) and 3-ethylisoxazole-4-carboxylic acid (58 mg, 0.41 mmol) in accordance with Procedure A, using DCM as solvent. $\delta_H$ (500 MHz, DMSO-d$_6$) 12.64 (br s, 1H), 9.41 (s, 1H), 8.82 (br s, 1H), 7.22 (br s, 1H), 7.15-7.07 (m, 1H), 5.02 (t, J 8.4 Hz, 1H), 3.90 (d, J 13.0 Hz, 1H), 3.76 (d, J 13.0 Hz, 1H), 3.57 (s, 3H), 3.24 (dd, J 8.9, 5.9 Hz, 1H), 2.91-2.77 (m, 3H), 2.39 (q, J 8.1 Hz, 1H), 2.07-1.92 (m, 2H), 1.88 (d, J 12.5 Hz, 1H), 1.84-1.74 (m, 1H), 1.74-1.65 (m, 3H), 1.65-1.58 (m, 1H), 1.40-1.22 (m, 2H), 1.15 (t, J 7.5 Hz, 3H), 1.12-1.00 (m, 2H), 0.95-0.78 (m, 5H). LCMS (Method 2): [M+H]$^+$ m/z 526, RT 2.11 minutes.

Example 137

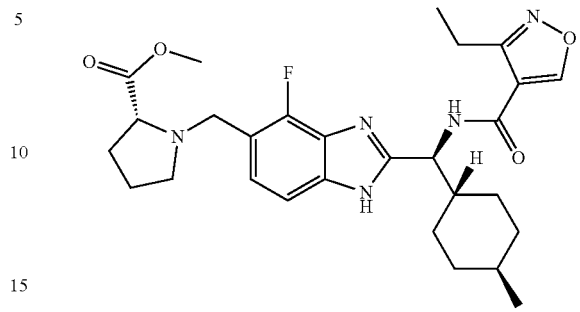

Methyl (2R)-1-[(2-{(S)-[(3-ethylisoxazole-4-carbonyl)amino](4-methylcyclohexyl)-methyl}-4-fluoro-1H-benzimidazol-5-yl)methyl]pyrrolidine-2-carboxylate (Trans Isomer)

The title compound (43 mg, 25%), a white solid, was prepared from Intermediate 186 (102 mg, 0.25 mmol) and 3-ethylisoxazole-4-carboxylic acid (47 mg, 0.33 mmol) in accordance with Procedure A, using DCM as solvent. $\delta_H$ (500 MHz, DMSO-d$_6$) 12.63 (br s, 1H), 9.41 (s, 1H), 8.81 (br s, 1H), 7.22 (br s, 1H), 7.15-7.07 (m, 1H), 5.02 (t, J 8.4 Hz, 1H), 3.90 (d, J 13.0 Hz, 1H), 3.76 (d, J 13.0 Hz, 1H), 3.57 (s, 3H), 3.25 (dd, J 8.9, 5.9 Hz, 1H), 2.90-2.75 (m, 3H), 2.39 (q, J 8.2 Hz, 1H), 2.10-1.93 (m, 2H), 1.92-1.84 (m, 1H), 1.84-1.58 (m, 5H), 1.41-1.22 (m, 2H), 1.15 (t, J 7.5 Hz, 3H), 1.12-0.99 (m, 2H), 0.95-0.78 (m, 5H). LCMS (Method 2): [M+H]$^+$ m/z 526, RT 2.11 minutes.

Example 138 (Procedure II)

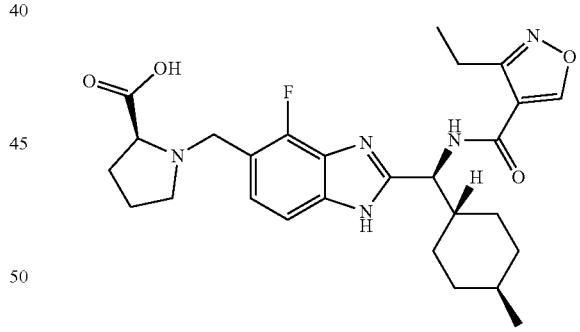

(2S)-1-[(2-{(S)-[(3-Ethylisoxazole-4-carbonyl)amino](4-methylcyclohexyl)methyl}-4-fluoro-1H-benzimidazol-5-yl)methyl]pyrrolidine-2-carboxylic Acid (Trans Isomer)

LiOH.H$_2$O (9.4 mg, 0.22 mmol) was added to a stirred solution of Example 136 (76 mg, 0.15 mmol) in 4:1 MeOH/water (3 mL). The mixture was stirred at 20° C. for 16 h. An additional portion of LiOH.H$_2$O (9.4 mg, 0.22 mmol) was added, and stirring was continued at 20° C. for 48 h. The volatiles were removed in vacuo. The residue was diluted with water (30 mL), and the pH was adjusted to pH 4 with 1M aqueous HCl. The material was extracted successively with EtOAc (3×30 mL), then 2-methyltetrahydro-furan/ EtOAc (1:1, 6×20 mL). The combined organic extracts were washed with brine (20 mL), dried over MgSO$_4$ and concentrated in vacuo. The resultant tan gum was purified by preparative HPLC to afford, after freeze-drying, the title compound (10.1 mg, 14%) as a white powder. $\delta_H$ (500 MHz, DMSO-d$_6$) 12.88 (br s, 1H), 9.43 (s, 1H), 8.94 (br s, 1H), 7.44-7.15 (m, 2H), 5.03 (t, J 8.5 Hz, 1H), 4.16 (d, J 13.0 Hz, 1H), 3.97 (d, J 13.2 Hz, 1H), 3.69-3.16 (obscured m, 1H), 3.12-3.04 (m, 1H), 2.88-2.76 (m, 2H), 2.66-2.58 (m, 1H), 2.15-2.04 (m, 1H), 1.99 (d, J 7.4 Hz, 1H), 1.93-1.82 (m, 2H), 1.81-1.56 (m, 4H), 1.41-1.21 (m, 2H), 1.15 (t, J 7.5 Hz, 3H), 1.11-0.99 (m, 2H), 0.95-0.75 (m, 5H). LCMS (Method 2): [M+H]$^+$ m/z 512, RT 2.32 minutes.

Example 139

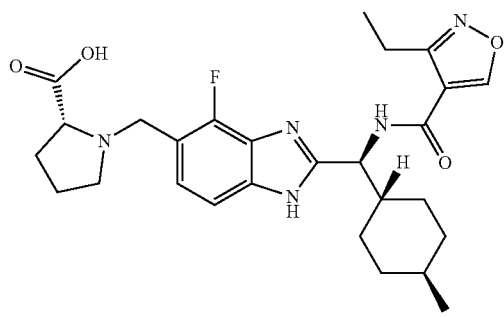 [SMILES: CCc1nocc1C(=O)N[C@H](c1nc2c(F)c(CN3CCC[C@@H]3C(=O)O)ccc2[nH]1)[C@H]1CC[C@H](C)CC1]

(2R)-1-[(2-{(S)-[(3-Ethylisoxazole-4-carbonyl) amino](4-methylcyclohexyl)methyl}-4-fluoro-1H-benzimidazol-5-yl)methyl]pyrrolidine-2-carboxylic Acid (Trans Isomer)

The title compound (10 mg, 13%) was prepared from Example 137 (82 mg, 0.16 mmol) in accordance with Procedure II. $\delta_H$ (500 MHz, DMSO-d$_6$) 12.88 (br s, 1H), 9.43 (s, 1H), 8.94 (br s, 1H), 7.48-7.15 (m, 2H), 5.03 (t, J 8.5 Hz, 1H), 4.16 (d, J 13.1 Hz, 1H), 3.97 (d, J 13.1 Hz, 1H), 3.78-3.16 (obscured m, 1H), 3.12-3.05 (m, 1H), 2.88-2.76 (m, 2H), 2.67-2.57 (m, 1H), 2.09 (dq, J 12.5, 8.5 Hz, 1H), 2.03-1.94 (m, 1H), 1.92-1.82 (m, 2H), 1.80-1.57 (m, 4H), 1.40-1.22 (m, 2H), 1.15 (t, J 7.5 Hz, 3H), 1.11-1.00 (m, 2H), 0.94-0.77 (m, 5H). LCMS (Method 2): [M+H]$^+$ m/z 512, RT 2.32 minutes.

Example 140

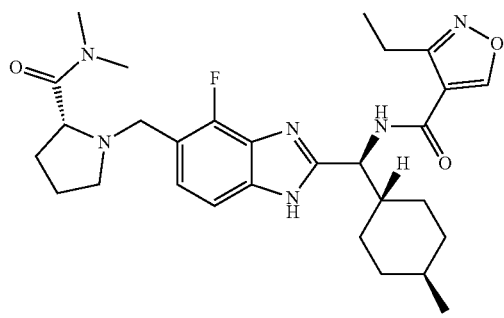 [SMILES: CCc1nocc1C(=O)N[C@H](c1nc2c(F)c(CN3CCC[C@@H]3C(=O)N(C)C)ccc2[nH]1)[C@H]1CC[C@H](C)CC1]

N-[(S)-(5-{[(2R)-2-(Dimethylcarbamoyl)pyrrolidin-1-yl]methyl}-4-fluoro-1H-benzimidazol-2-yl)(4-methylcyclohexyl)methyl]-3-ethylisoxazole-4-carboxamide (Trans Isomer)

The title compound (30 mg, 47%), a white solid, was prepared from Example 139 (60 mg, 0.12 mmol) and dimethylamine hydrochloride (48 mg, 0.59 mmol) in accordance with Procedure A. $\delta_H$ (500 MHz, DMSO-d$_6$) 12.69 (br s, 1H), 9.41 (s, 1H), 8.82 (br s, 1H), 7.23 (br s, 1H), 7.17-7.05 (m, 1H), 5.01 (t, J 8.4 Hz, 1H), 3.84 (d, J 13.1 Hz, 1H), 3.64 (d, J 12.8 Hz, 1H), 3.45 (dd, J 8.5, 6.3 Hz, 1H), 2.98 (s, 3H), 2.91-2.76 (m, 6H), 2.31 (q, J 7.9 Hz, 1H), 2.11-1.92 (m, 2H), 1.88 (d, J 12.8 Hz, 1H), 1.76-1.58 (m, 5H), 1.40-1.22 (m, 2H), 1.15 (t, J 7.5 Hz, 3H), 1.18-0.99 (m, 2H), 0.94-0.78 (m, 5H). LCMS (Method 2): [M+H]$^+$ m/z 539, RT 2.04 minutes.

Example 141

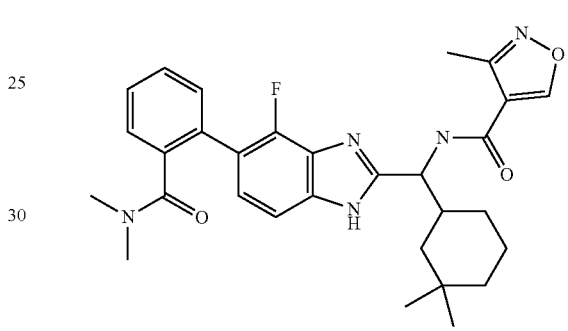

N-[{5-[2-(Dimethylcarbamoyl)phenyl]-4-fluoro-1H-benzimidazol-2-yl}(3,3-dimethyl-cyclohexyl) methyl]-3-methylisoxazole-4-carboxamide The title compound (1:1 mixture of diastereomers) (5.9 mg, 9%), a white solid, was prepared from Intermediate 117 (40 mg, 0.14 mmol) and Intermediate 34 (35 mg, 0.13 mmol) in accordance with Procedure Y. $\delta_H$ (373K, 400 MHz, DMSO-d$_6$) 12.42 (br s, 2H), 9.37 (s, 2H), 8.29 (s, 2H), 7.50-7.39 (m, 6H), 7.37-7.33 (m, 2H), 7.28-7.23 (m, 2H), 6.93 (t, J 6.8 Hz, 2H), 5.09 (t, J 7.2 Hz, 2H), 2.80-2.58 (br s, 12H), 2.41 (s, 6H), 2.33-2.22 (m, 2H), 1.89-0.92 (m, 16H), 0.93 (s, 6H), 0.89 (s, 3H), 0.88 (s, 3H). LCMS (Method 6): [M+H]$^+$ m/z 532, RT 2.25 minutes.

Example 142

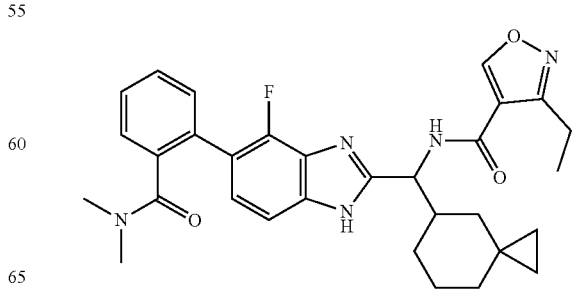

N-[{5-[2-(Dimethylcarbamoyl)phenyl]-4-fluoro-1H-benzimidazol-2-yl}(spiro[2.5]octan-7-yl)methyl]-3-ethylisoxazole-4-carboxamide The title compound (1:1 mixture of diastereomers) (3 mg, 4%), a white solid, was prepared from Intermediate 120 (41 mg, 0.14 mmol) and Intermediate 34 (35 mg, 0.13 mmol) in accordance with Procedure Y. $\delta_H$ (373K, 400 MHz, DMSO-$d_6$) 9.35 (s, 1H), 9.32 (s, 1H), 8.42-8.22 (s, 2H), 7.50-7.39 (m, 6H), 7.38-7.32 (m, 2H), 7.30-7.21 (m, 2H), 7.00-6.98 (m, 2H), 5.22-5.16 (m, 1H), 5.16-5.10 (m, 1H), 2.88 (ddd, J 7.8, 6.1, 2.0 Hz, 4H), 2.80-2.59 (v br s, 12H), 2.36-2.25 (m, 2H), 1.92-1.83 (m, 1H), 1.77-1.52 (m, 7H), 1.48-1.32 (m, 2H), 1.21 (td, J 7.5, 5.8 Hz, 6H), 1.14-1.04 (m, 2H), 0.91-0.79 (m, 4H), 0.31-0.16 (m, 7H), 0.16-0.10 (m, 1H). LCMS (Method 6): [M+H]$^+$ m/z 544, RT 2.34

Example 143

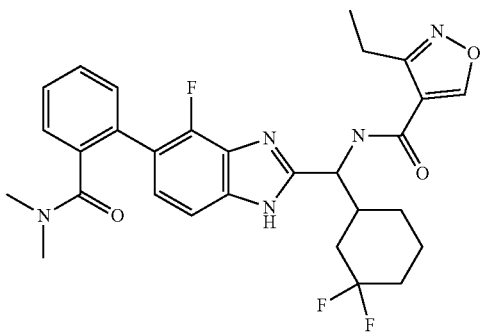 [SMILES: CCc1nocc1C(=O)NC(c1nc2c(F)c(-c3ccccc3C(=O)N(C)C)ccc2[nH]1)C1CCCC(F)(F)C1]

N-[(3,3-Difluorocyclohexyl){5-[2-(dimethylcarbamoyl)phenyl]-4-fluoro-1H-benzimidazol-2-yl]methyl}-3-ethylisoxazole-4-carboxamide The title compound (1:1 mixture of diastereomers) (3.0 mg, 4%), a white solid, was prepared from Intermediate 123 (43 mg, 0.14 mmol) and Intermediate 34 (35 mg, 0.13 mmol) in accordance with Procedure Y. $\delta_H$ (373K, 400 MHz, DMSO-$d_6$) 9.38 (s, 2H), 8.28 (s, 2H), 7.48-7.22 (m, 8H), 7.21-7.12 (m, 2H), 6.77 (s, 2H), 5.21 (t, J 4.6 Hz, 2H), 2.97-2.87 (m, 4H), 2.80-2.67 (v br s, 6H), 2.67-2.56 (v br s, 6H), 2.49-2.35 (m, 2H), 2.22-1.04 (m, 16H), 1.24 (t, J 7.5 Hz, 6H). LCMS (Method 6): [M+H]$^+$ m/z 554, RT 2.09 minutes.

Example 144

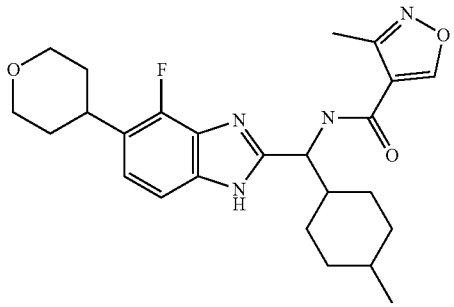 [SMILES: Cc1nocc1C(=O)NC(c1nc2c(F)c(C3CCOCC3)ccc2[nH]1)C1CCC(C)CC1]

N-{[4-Fluoro-5-(tetrahydropyran-4-yl)-1H-benzimidazol-2-yl](4-methylcyclohexyl)-methyl}-3-methylisoxazole-4-carboxamide The title compound (175 mg, quantitative), a white solid, was prepared from Intermediate 128 (137 mg, 0.39 mmol) and 3-methylisoxazole-4-carboxylic acid (51 mg, 0.4 mmol) in accordance with Procedure A. LCMS (Method 5): [M+H]$^+$ m/z 455, RT 1.38 minutes.

Examples 145 & 146

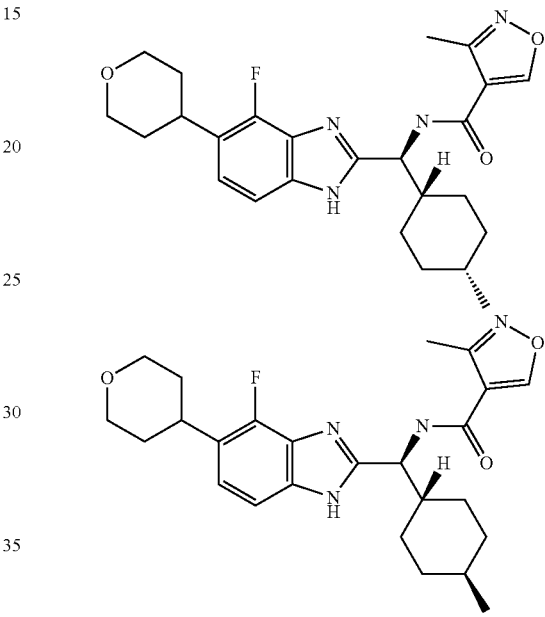

N-{(S)-[4-Fluoro-5-(tetrahydropyran-4-yl)-1H-benzimidazol-2-yl](4-methylcyclohexyl)-methyl}-3-methylisoxazole-4-carboxamide (Cis Isomer) (Example 145)

N-{(S)-[4-Fluoro-5-(tetrahydropyran-4-yl)-1H-benzimidazol-2-yl](4-methylcyclohexyl)-methyl}-3-methylisoxazole-4-carboxamide (Trans Isomer) (Example 146)

Example 144 was subject to preparative HPLC (Waters Prep 100-SQD2 equipped with a Lux Cellulose-4 250×21.2 mm, 5 μm column), flow rate 100 mL/min, column temperature 40° C., eluting with MeOH (+0.1% NH$_4$OH) and food fresh grade liquid C02 (gradient of 5-15%) over 16 minutes, to yield, after freeze-drying, the title compounds (Example 145, 1.6 mg; Example 146, 2.0 mg) as white solids.

Example 145: $\delta_H$ (400 MHz, DMSO-$d_6$) 13.00 (s, 1H), 9.45 (s, 1H), 8.87 (s, 1H), 7.27-7.13 (m, 1H), 7.07-6.91 (m, 1H), 5.28 (t, J 9.4 Hz, 1H), 3.96 (dd, J 11.3, 4.0 Hz, 2H), 3.53-3.43 (m, 2H), 3.20-3.10 (m, 1H), 2.36 (s, 3H), 2.27-2.17 (m, 1H), 1.86-1.72 (m, 2H), 1.69-1.06 (m, 11H), 0.91 (d, J 6.6 Hz, 3H). LCMS (Method 6): [M+H]$^+$ m/z 455, RT 2.23 minutes.

Example 146: $\delta_H$ (400 MHz, DMSO-$d_6$) 12.81 (s, 1H), 9.46 (s, 1H), 8.86 (s, 1H), 7.24 (d, J 8.2 Hz, 1H), 7.05 (s, 1H), 5.01 (t, J 8.4 Hz, 1H), 3.96 (dd, J 11.3, 4.1 Hz, 2H), 3.53-3.43 (m, 2H), 3.24-3.08 (m, 1H), 2.36 (s, 3H), 2.03-1.92 (m, 1H), 1.92-1.57 (m, 7H), 1.40-1.17 (m, 2H), 1.16-0.97 (m, 2H), 0.96-0.77 (m, 2H), 0.85 (d, J 6.5 Hz, 3H). LCMS (Method 6): [M+H]$^+$ m/z 455, =2.24 minutes.

Example 147 (Procedure JJ)

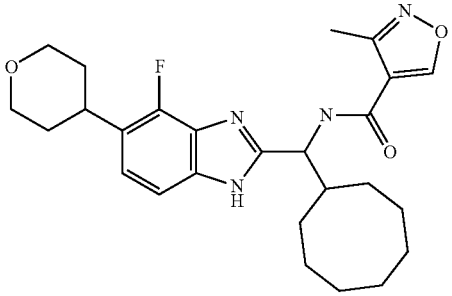 [SMILES: Cc1nocc1C(=O)NC(c1nc2c(F)c(C3CCOCC3)ccc2[nH]1)C1CCCCCCC1]

N-{Cycloheptyl[4-fluoro-5-(tetrahydropyran-4-yl)-1H-benzimidazol-2-yl]methyl}-3-methylisoxazole-4-carboxamide To a solution of Intermediate 195 (103 mg, 0.29 mmol) in THF (2.5 mL) at –40° C. was added n-butyllithium (1.2M, 1.05 equiv.) dropwise over 5 minutes. The resulting dark yellow solution was stirred for 20 minutes at –40° C., then Intermediate 187 (134 mg, 0.58 mmol) in THF (2.5 mL) was added dropwise over 10 minutes. The reaction mixture was stirred at –40° C. for 2 h, then warmed to r.t. and stirred for 1 h. Water (3 mL) was added, and the mixture was extracted with EtOAc (3×20 mL), then dried (MgSO$_4$) and concentrated in vacuo. The crude residue was dissolved in MeOH (5 mL) at r.t., and 4N HCl in 1,4-dioxane (30.0 equiv.) was added. The mixture was stirred for 16 h, then concentrated in vacuo. The residue was purified by flash column chromatography, eluting with EtOAc/hexanes (50-100% gradient), then 10% MeOH in DCM. The resulting material was taken up in DMF (1 mL), and 3-methyl-4-isoxazolecarboxylic acid (1.05 equiv.), DIPEA (3.0 equiv.) and HATU (1.2 equiv.) were sequentially added at r.t. The reaction mixture was stirred for 16 h, then H$_2$O (5 mL) and EtOAc (15 mL) were added. The layers were separated. The aqueous layer was extracted with EtOAc (2×20 mL). The combined organic layers were washed with brine (2×30 mL), then dried (MgSO$_4$) and concentrated in vacuo. Purification by flash column chromatography, eluting with EtOAc/hexanes (30-100% gradient), followed by preparative HPLC, gave the title compound (9 mg, 31% overall) as a white solid. δ$_H$ (300 MHz, DMSO-d$_6$) 12.95-12.72 (m, 1H), 9.45 (s, 1H), 8.90-8.78 (m, 1H), 7.36-7.24 (m, 1H), 7.16-7.02 (m, 1H), 5.11 (t, J 8.5 Hz, 1H), 3.96 (dd, J 11.2, 3.7 Hz, 2H), 3.48 (td, J 11.6, 2.1 Hz, 2H), 3.24-2.94 (tt, J 11.8, 3.1 Hz, 1H), 2.36 (s, 3H), 2.34-2.23 (m, 1H), 1.91-1.15 (m, 16H). LCMS (Method 6): [M+H]$^+$ m/z 455, RT 2.20 minutes.

Example 148

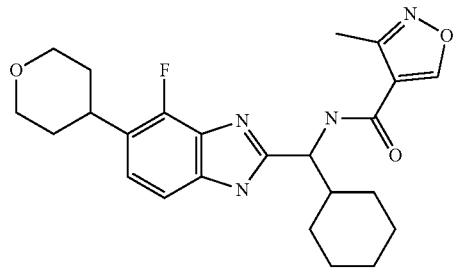 [SMILES: Cc1nocc1C(=O)NC(c1nc2c(F)c(C3CCOCC3)ccc2[nH]1)C1CCCCC1]

N-{Cyclohexyl[4-fluoro-5-(tetrahydropyran-4-yl)-1H-benzimidazol-2-yl]methyl}-3-methylisoxazole-4-carboxamide The title compound (2 mg, 3%), a white solid, was prepared from Intermediate 195 (120 mg, 0.34 mmol), Intermediate 188 (148 mg, 0.68 mmol) and 3-methylisoxazole-4-carboxylic acid (25 mg, 0.19 mmol) in accordance with Procedure JJ. δ$_H$ (300 MHz, DMSO-d$_6$) 12.64 (s, 1H), 9.45 (s, 1H), 8.80 (s, 1H), 7.32-7.19 (m, 1H), 7.17-6.99 (m, 1H), 5.03 (t, J 8.5 Hz, 1H), 3.96 (dd, J 11.2, 4.0 Hz, 2H), 3.54-3.42 (m, 2H), 3.17 (tt, J 11.7, 3.5 Hz, 1H), 2.36 (s, 3H), 2.13-2.96 (m, 1H), 1.92-1.53 (m, 8H), 1.43-1.30 (m, 1H), 1.30-0.92 (m, 5H). LCMS (Method 6): [M+H]$^+$ m/z 441, RT 2.20 minutes.

Example 149

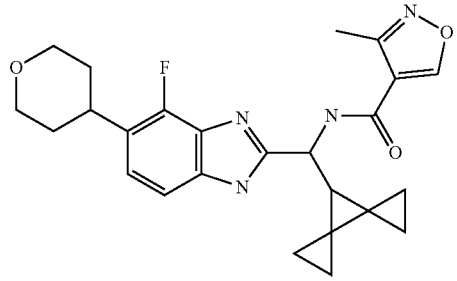 [SMILES: Cc1nocc1C(=O)NC(c1nc2c(F)c(C3CCOCC3)ccc2[nH]1)C1C2(CC2)C12CC2]

N-{Dispiro[2.0.24.13]heptan-7-yl[4-fluoro-5-(tetrahydropyran-4-yl)-1H-benzimidazol-2-yl]methyl}-3-methylisoxazole-4-carboxamide The title compound (assumed mixture of diastereomers) (41 mg, 27%), a white solid, was prepared from Intermediate 195 (148 mg, 0.42 mmol), Intermediate 189 (189 mg, 0.84 mmol) and 3-methylisoxazole-4-carboxylic acid (25 mg, 0.19 mmol) in accordance with Procedure JJ. δ$_H$ (400 MHz, DMSO-d$_6$) 12.49 (s, 1H), 9.32 (s, 1H), 9.01 (s, 1H), 7.23 (s, 1H), 7.09 (t, J 7.7 Hz, 1H), 4.92 (t, J 8.5 Hz, 1H), 4.20-3.77 (m, 2H), 3.48 (t, J 11.8 Hz, 2H), 3.17 (t, J 12.2 Hz, 1H), 2.37 (s, 3H), 2.17 (d, J 9.9 Hz, 1H), 1.87-1.73 (m, 2H), 1.70-1.60 (m, 2H), 0.99-0.55 (m, 8H). LCMS (Method 6): [M+H]$^+$ m/z 451, RT 2.21 minutes.

Example 150

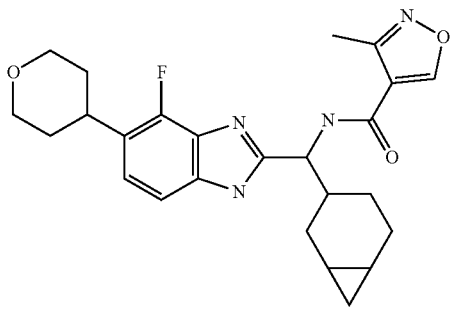 [SMILES: Cc1nocc1C(=O)NC(c1nc2c(F)c(C3CCOCC3)ccc2[nH]1)C1CCC2CC2C1]

N-{[4-Fluoro-5-(tetrahydropyran-4-yl)-1H-benzimidazol-2-yl](norcaran-3-yl)methyl}-3-methylisoxazole-4-carboxamide The title compound (assumed mixture of diastereomers) (30 mg, 40%), a white solid, was prepared from Intermediate 195 (294 mg, 0.84 mmol), Intermediate 190 (382 mg, 1.68 mmol) and 3-methylisoxazole-4-carboxylic acid (22 mg, 0.17 mmol) in accordance with Procedure JJ. $\delta_H$ (400 MHz, DMSO-$d_6$) 12.82-12.56 (m, 1H), 9.44 (s, 1H), 8.80-8.69 (m, 1H), 7.36-7.23 (m, 1H), 7.14-7.07 (m, 1H), 4.95-4.92 (m, 1H), 4.00-3.92 (m, 2H), 3.54-3.43 (m, 2H), 3.23-3.12 (m, 1H), 2.36 (s, 3H), 2.29-2.15 (m, 1H), 2.03-1.87 (m, 1H), 1.87-1.74 (m, 3H), 1.73-1.60 (m, 3H), 1.31-1.07 (m, 2H), 0.94-0.73 (m, 3H), 0.53 (td, J 8.8, 4.2 Hz, 1H), 0.05-0.03 (m, 1H). LCMS (Method 5): [M+H]$^+$ m/z 453, RT 1.09 minutes.

Example 151

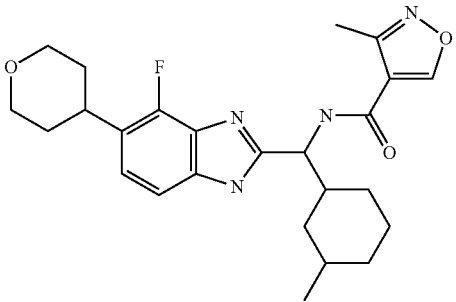 [SMILES: Cc1nocc1C(=O)NC(c1nc2c(F)c(C3CCOCC3)ccc2[nH]1)C1CCCC(C)C1]

N-{[4-Fluoro-5-(tetrahydropyran-4-yl)-1H-benzimidazol-2-yl](3-methylcyclohexyl)-methyl}-3-methylisoxazole-4-carboxamide The title compound (assumed mixture of diastereomers) (100 mg, 69%), a white solid, was prepared from Intermediate 195 (202 mg, 0.58 mmol), Intermediate 191 (264 mg, 1.15 mmol) and 3-methylisoxazole-4-carboxylic acid (43 mg, 0.33 mmol) in accordance with Procedure JJ. $\delta_H$ (600 MHz, DMSO-$d_6$) 12.92-12.69 (m, 1H), 9.43 (s, 1H), 8.87-8.74 (m, 1H), 7.37-7.25 (m, 1H), 7.14-7.07 (m, 1H), 5.24 (t, J 9.4 Hz, 1H), 3.96 (dd, J 11.7, 3.9 Hz, 2H), 3.48 (td, J 11.8, 2.1 Hz, 2H), 3.17 (tt, J 11.8, 3.7 Hz, 1H), 2.45-2.38 (m, 1H), 2.35 (s, 3H), 1.90-1.74 (m, 3H), 1.71-1.41 (m, 7H), 1.18-1.03 (m, 3H), 0.80 (d, J 6.8 Hz, 3H). LCMS (Method 5): [M+H]$^+$ m/z 455, RT 1.31 minutes.

Example 152

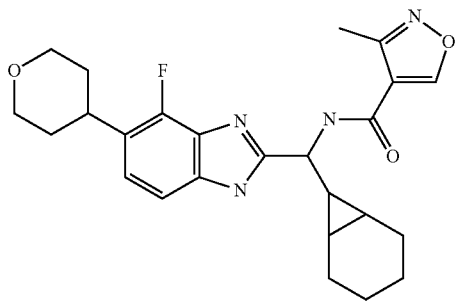 [SMILES: Cc1nocc1C(=O)NC(c1nc2c(F)c(C3CCOCC3)ccc2[nH]1)C1C2CCCCC21]

N-{[4-Fluoro-5-(tetrahydropyran-4-yl)-1H-benzimidazol-2-yl](norcaran-7-yl)methyl}-3-methylisoxazole-4-carboxamide The title compound (assumed mixture of diastereomers) (24 mg, 28%), a white solid, was prepared from Intermediate 195 (148 mg, 0.42 mmol), Intermediate 192 (192 mg, 0.84 mmol) and 3-methylisoxazole-4-carboxylic acid (26 mg, 0.20 mmol) in accordance with Procedure JJ. $\delta_H$ (300 MHz, DMSO-$d_6$) 12.59 (s, 1H), 9.43-9.40 (m, 1H), 9.14-9.02 (m, 1H), 7.26 (d, J 8.3 Hz, 1H), 7.09 (t, J 7.5 Hz, 1H), 5.10-4.63 (m, 1H), 3.96 (dd, J 11.3, 3.9 Hz, 2H), 3.49 (td, J 11.7, 2.1 Hz, 2H), 3.24-3.10 (m, 1H), 2.37-2.36 (m, 3H), 1.92-0.89 (m, 15H). LCMS (Method 6): [M+H]$^+$ m/z 453, RT 2.17 and 2.26 minutes (observable diastereomers).

Example 153

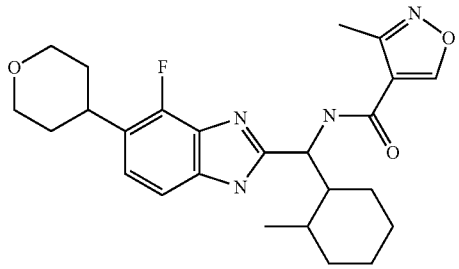 [SMILES: Cc1nocc1C(=O)NC(c1nc2c(F)c(C3CCOCC3)ccc2[nH]1)C1CCCCC1C]

N-{[4-Fluoro-5-(tetrahydropyran-4-yl)-1H-benzimidazol-2-yl](2-methylcyclohexyl)-methyl}-3-methylisoxazole-4-carboxamide The title compound (assumed mixture of diastereomers) (2 mg, 1%), a white solid, was prepared from Intermediate 195 (202 mg, 0.57 mmol), Intermediate 193 (264 mg, 1.15 mmol) and 3-methylisoxazole-4-carboxylic acid (12 mg, 0.09 mmol) in accordance with Procedure JJ. LCMS (Method 6): [M+H]$^+$ m/z 455, RT 2.18 minutes.

Example 154

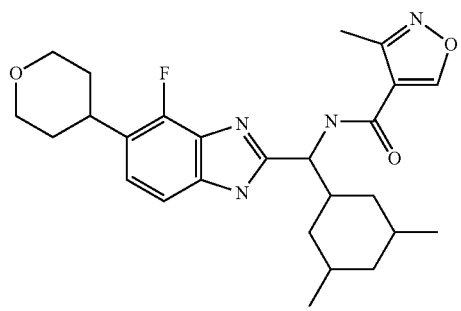 [SMILES: Cc1nocc1C(=O)NC(c1nc2c(F)c(C3CCOCC3)ccc2[nH]1)C1CC(C)CC(C)C1]

N-{(3,5-Dimethylcyclohexyl)[4-fluoro-5-(tetrahydropyran-4-yl)-1H-benzimidazol-2-yl]-methyl}-3-methylisoxazole-4-carboxamide The title compound (assumed mixture of diastereomers) (31 mg, 11%), a white solid, was prepared from Intermediate 195 (202 mg, 0.58 mmol), Intermediate 194 (281 mg, 1.15 mmol) and 3-methylisoxazole-4-carboxylic acid (47 mg, 0.37 mmol) in accordance with Procedure JJ. LCMS (Method 6): [M+H]$^+$ m/z 469.0, RT 2.55 minutes.

Example 155

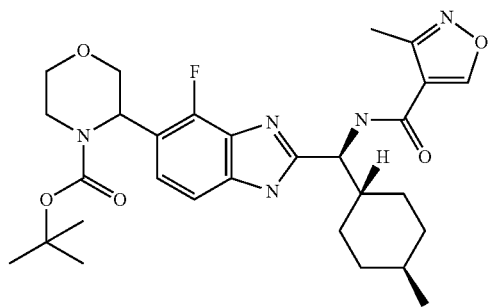 [SMILES: Cc1nocc1C(=O)N[C@H](c1nc2c(F)c(C3COCCN3C(=O)OC(C)(C)C)ccc2[nH]1)[C@H]1CC[C@H](C)CC1]

tert-Butyl 3-(4-fluoro-2-{(S)-(4-methylcyclohexyl)[(3-methylisoxazole-4-carbonyl)-amino]methyl}-1H-benzimidazol-5-yl)morpholine-4-carboxylate (Trans Isomer)

The title compound (assumed mixture of diastereomers) (213 mg, 22%) was prepared from Intermediate 216 (300 mg, 0.67 mmol) and 3-methylisoxazole-4-carboxylic acid (81 mg, 0.67 mmol) in accordance with Procedure A, in DCM (12 mL) as solvent. δ$_H$ (400 MHz, DMSO-d$_6$) 12.74 (s, 1H), 9.46 (s, 1H), 8.82 (s, 1H), 7.25 (br s, 2H), 5.28 (d, J 2.8 Hz, 1H), 5.02 (t, J 8.4 Hz, 1H), 4.08 (d, J 11.8 Hz, 1H), 3.91 (dd, J 11.4, 3.7 Hz, 1H), 3.83 (dd, J 11.9, 4.1 Hz, 1H), 3.74 (app. d, J 11.9 Hz, 1H), 3.52 (td, J 11.5, 3.3 Hz, 1H), 3.32-3.32 (m, 1H), 2.36 (s, 3H), 2.04-1.94 (m, 1H), 1.94-1.85 (m, 1H), 1.75-1.66 (m, 1H), 1.66-1.57 (m, 1H), 1.41-1.22 (m, 2H), 1.34 (s, 9H), 1.14-0.98 (m, 2H), 0.96-0.78 (m, 2H), 0.85 (d, J 6.4 Hz, 3H). LCMS (Method 5): [M+H]$^+$ m/z 556, RT 1.39 minutes.

Example 156 (Procedure KK)

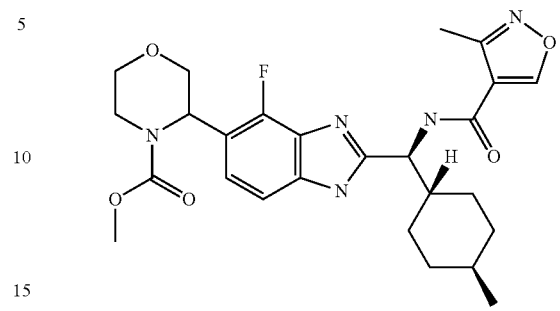

Methyl 3-(4-fluoro-2-{(S)-(4-methylcyclohexyl)[(3-methylisoxazole-4-carbonyl)amino]-methyl}-1H-benzimidazol-5-yl)morpholine-4-carboxylate (Trans Isomer)

To a solution of Example 155 (0.16 mmol) in DCM (2 mL) was added TFA (0.9 mL). The reaction mixture was stirred overnight, then concentrated in vacuo. The residue was passed through an SCX column, eluting initially with MeOH, then with a 7N solution of NH$_3$ in MeOH. The washings were concentrated in vacuo, and taken up in DCM (2 mL). Triethylamine (22 μL, 0.16 mmol), followed by methyl chloroformate (10 μL, 0.2 mmol), were added at r.t. The mixture was stirred overnight, then concentrated in vacuo. The residue was purified by flash chromatography, eluting with EtOAc/hexanes (0-100% gradient), to give the title compound (assumed mixture of diastereomers) (50 mg, 60.8% overall). δ$_H$ (400 MHz, DMSO-d$_6$) 12.73 (s, 1H), 9.45 (s, 1H), 8.79 (s, 1H), 7.25 (br s, 2H), 5.32 (d, J 3.4 Hz, 1H), 5.00 (t, J 8.4 Hz, 1H), 4.10 (d, J 11.9 Hz, 1H), 3.92 (dd, J 11.4, 3.4 Hz, 1H), 3.86 (dd, J 11.9, 4.1 Hz, 1H), 3.83-3.77 (m, 1H), 3.60 (s, 3H), 3.58-3.50 (m, 1H), 3.42-3.35 (m, 1H), 2.36 (s, 3H), 2.04-1.92 (m, 1H), 1.92-1.85 (m, 1H), 1.76-1.66 (m, 1H), 1.66-1.57 (m, 1H), 1.41-1.21 (m, 2H), 1.17-0.98 (m, 2H), 0.95-0.78 (m, 2H), 0.85 (d, J 6.4 Hz, 3H). LCMS (Method 6): [M+H]$^+$ m/z 514, RT 2.07 minutes.

Example 157

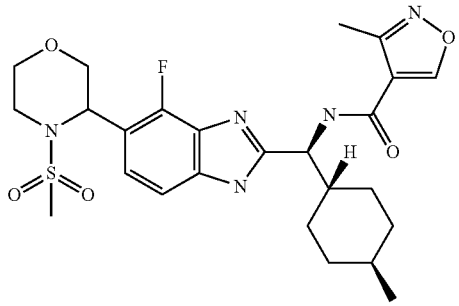 [SMILES: Cc1nocc1C(=O)N[C@H](c1nc2c(F)c(C3COCCN3S(C)(=O)=O)ccc2[nH]1)[C@H]1CC[C@H](C)CC1]

N-[(S)-{4-Fluoro-5-[4-(methylsulfonyl)morpholin-3-yl]-1H-benzimidazol-2-yl}(4-methylcyclohexyl)methyl]-3-methylisoxazole-4-carboxamide (Trans Isomer)

The title compound (assumed mixture of diastereomers) (22 mg, 52%), a white solid, was prepared from Example 155 (0.08 mmol) and methanesulfonyl chloride (10 µL, 0.1 mmol) in accordance with Procedure KK. $\delta_H$ (400 MHz, DMSO-$d_6$) 12.73 (s, 1H), 9.45 (s, 1H), 8.79 (s, 1H), 7.55-7.42 (m, 1H), 7.38-7.20 (m, 1H), 5.06-4.98 (m, 2H), 4.02-3.86 (m, 3H), 3.72 (td, J 11.6, 10.5, 3.7 Hz, 1H), 3.54-3.39 (m, 2H), 2.74 (s, 3H), 2.36 (s, 3H), 2.05-1.93 (m, 1H), 1.93-1.84 (m, 1H), 1.75-1.66 (m, 1H), 1.66-1.57 (m, 1H), 1.42-1.19 (m, 3H), 1.17-0.98 (m, 2H), 0.96-0.78 (m, 1H), 0.85 (d, J 6.4 Hz, 3H). LCMS (Method 6): [M+H]$^+$ m/z 534, RT 1.97 minutes.

Example 158

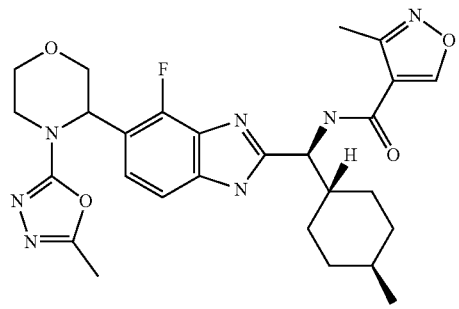 [SMILES: Cc1nnc(N2CCOCC2c2ccc3[nH]c([C@@H](NC(=O)c4conc4C)[C@H]4CC[C@H](C)CC4)nc3c2F)o1]

N-[(S)-{4-Fluoro-5-[4-(5-methyl-1,3,4-oxadiazol-2-yl)morpholin-3-yl]-1H-benzimidazol-2-yl}(4-methylcyclohexyl)methyl]-3-methylisoxazole-4-carboxamide (Trans Isomer)

To a solution of Example 155 (0.10 mmol) in DCM (2 mL) was added TFA (0.9 mL). The reaction mixture was stirred overnight, then concentrated in vacuo. The residue was passed through an SCX column, eluting initially with MeOH, then with a 7N solution of NH$_3$ in MeOH. The washings were concentrated in vacuo, and taken up in EtOH (2 mL). Triethylamine (60 µL, 0.40 mmol) and 2-bromo-5-methyl-1,3,4-oxadiazole (35 mg, 0.21 mmol) were added. The reaction mixture was heated in a sealed tube at 130° C. overnight. A further aliquot of triethylamine (60 µL, 0.40 mmol) was added, and the reaction mixture was heated a further 60 h. After cooling, the reaction mixture was concentrated in vacuo. The residue was re-dissolved in DCM (10 mL) and water (10 mL). The aqueous layer was further extracted with DCM (3×10 mL). The organic layers were combined, dried over Na$_2$SO$_4$ and concentrated in vacuo. Purification by flash chromatography, eluting with EtOAc/hexanes (0-100% gradient), then MeOH/DCM (0-10% gradient), followed by reverse-phase HPLC, gave the title compound (assumed mixture of diastereomers) (18 mg, 34%) as a white solid. $\delta_H$ (400 MHz, DMSO-$d_6$) 12.74 (s, 1H), 9.45 (s, 1H), 8.74 (s, 1H), 7.40-7.11 (m, 2H), 5.09 (t, J 3.8 Hz, 1H), 5.00 (t, J 8.4 Hz, 1H), 4.02-3.93 (m, 3H), 3.77 (unresolved t, J 10.3 Hz, 1H), 3.68-3.58 (m, 1H), 3.57-3.50 (m, 1H), 2.36 (s, 3H), 2.28 (s, 3H), 2.03-1.91 (m, 1H), 1.91-1.81 (m, 1H), 1.74-1.65 (m, 1H), 1.65-1.57 (m, 1H), 1.43-1.20 (m, 3H), 1.17-0.96 (m, 2H), 0.95-0.77 (m, 1H), 0.85 (d, J 6.4 Hz, 3H). LCMS (Method 6): [M+H]$^+$ m/z 538, RT 1.92 minutes.

Example 159

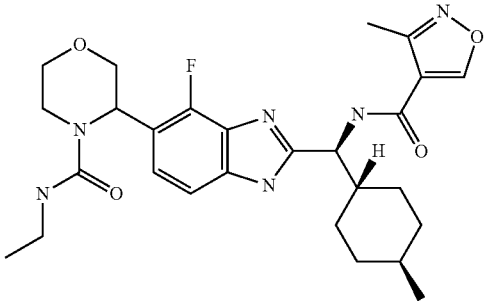 [SMILES: CCNC(=O)N1CCOCC1c1ccc2[nH]c([C@@H](NC(=O)c3conc3C)[C@H]3CC[C@H](C)CC3)nc2c1F]

N-Ethyl-3-(4-fluoro-2-{(S)-(4-methylcyclohexyl) [(3-methylisoxazole-4-carbonyl)amino]-methyl}-1H-benzimidazol-5-yl)morpholine-4-carboxamide (Trans Isomer)

The title compound (assumed mixture of diastereomers) (25 mg, 34%), a white solid, was prepared from Example 155 (0.14 mmol) and ethyl isocyanate (33 µL, 0.41 mmol) in accordance with Procedure KK. $\delta_H$ (400 MHz, DMSO-$d_6$) 12.72 (s, 1H), 9.46 (s, 1H), 8.81 (s, 1H), 7.30-7.16 (m, 1H), 7.10-6.99 (m, 1H), 6.51 (s, 1H), 5.31 (s, 1H), 5.00 (t, J 8.4 Hz, 1H), 4.11 (d, J 11.6 Hz, 1H), 3.87 (dd, J 10.5, 2.2 Hz, 1H), 3.80 (dd, J 11.7, 3.9 Hz, 1H), 3.72 (d, J 12.7 Hz, 1H), 3.49 (td, J 11.3, 3.2 Hz, 1H), 3.36-3.25 (m, 1H), 3.06-2.98 (m, 2H), 2.36 (s, 3H), 2.03-1.92 (m, 1H), 1.92-1.83 (m, 1H), 1.75-1.66 (m, 1H), 1.65-1.57 (m, 1H), 1.40-1.16 (m, 2H), 1.16-1.00 (m, 2H), 0.96 (t, J 7.1 Hz, 3H), 0.92-0.77 (m, 2H), 0.85 (d, J 6.4 Hz, 3H). LCMS (Method 6): [M+H]$^+$ m/z 527, RT 1.65 minutes.

Example 160

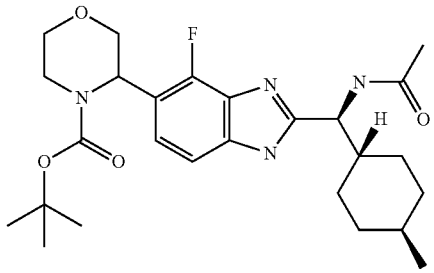 [SMILES: CC(=O)N[C@H](c1nc2c(F)c(C3COCCN3C(=O)OC(C)(C)C)ccc2[nH]1)[C@H]1CC[C@H](C)CC1]

tert-Butyl 3-{2-[(S)-acetamido(4-methylcyclohexyl) methyl]-4-fluoro-1H-benzimidazol-5-yl}morpholine-4-carboxylate To a solution of Intermediate 216 (50 mg, 0.11 mmol) in THF (0.5 mL) at 0° C. was added DIPEA (21 µL, 0.12 mmol), followed by acetyl chloride (10 µL, 0.1 mmol). The reaction mixture was stirred, and allowed to warm to r.t. A 7N solution of NH$_3$ in MeOH (0.5 mL) was added, and the reaction mixture was concentrated in vacuo. Purification by flash chromatography, eluting with EtOAc/hexanes (0-100% gradient), then MeOH/DCM (0-10% gradient), followed by reverse-phase HPLC, gave the title compound (assumed mixture of diastereomers) (3 mg, 6%) as a white solid. δ$_H$ (400 MHz, DMSO-d$_6$) 12.82-12.55 (m, 1H), 8.40-8.30 (m, 1H), 7.37-7.17 (m, 2H), 5.28 (d, J 3.7 Hz, 1H), 4.87 (t, J 8.3 Hz, 1H), 4.13-4.04 (m, 1H), 3.95-3.88 (m, 1H), 3.83 (dd, J 11.9, 4.1 Hz, 1H), 3.74 (d, J 13.3 Hz, 1H), 3.53 (td, J 11.5, 3.2 Hz, 1H), 3.36-3.24 (m, 1H), 1.89 (s, 3H), 1.89-1.73 (m, 2H), 1.72-1.56 (m, 2H), 1.39-1.13 (m, 2H), 1.34 (s, 9H), 1.11-0.95 (m, 1H), 0.93-0.76 (m, 2H), 0.84 (d, J 6.6 Hz, 3H). LCMS (Method 6): [M+H]$^+$ m/z 489, RT 1.93 minutes.

Example 161

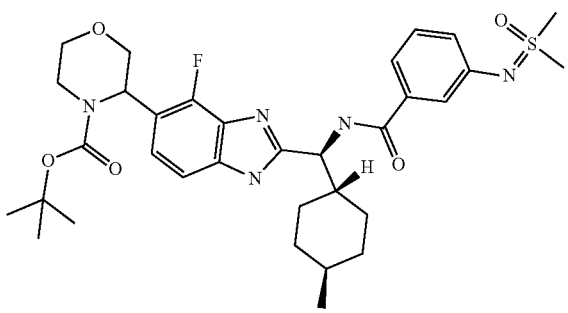 [SMILES: CC(C)(C)OC(=O)N1CCOCC1c1ccc2[nH]c([C@@H](NC(=O)c3cccc(N=S(C)(C)=O)c3)[C@H]3CC[C@H](C)CC3)nc2c1F]

tert-Butyl 3-(2-{(S)-[(3-{[dimethyl(oxo)-λ$^6$-sulfanylidene]amino}benzoyl)amino](4-methylcyclohexyl)methyl}-4-fluoro-1H-benzimidazol-5-yl)morpholine-4-carboxylate (Trans Isomer)

The title compound (assumed mixture of diastereomers) (10 mg, 14%) was prepared from Intermediate 216 (50 mg, 0.11 mmol) and 3-{[dimethyl(oxo)-)$^6$-sulfanylidene]amino}benzoic acid (24 mg, 0.11 mmol) in accordance with Procedure A, in DCM (2 mL) as solvent. δ$_H$ (400 MHz, DMSO-d$_6$) 12.70 (s, 1H), 8.56 (s, 1H), 7.44-7.37 (m, 2H), 7.27 (t, J 8.0 Hz, 1H), 7.26-7.12 (v br m, 2H), 7.12-7.06 (m, 1H), 5.27 (d, J 2.6 Hz, 1H), 5.01 (t, J 8.1 Hz, 1H), 4.09 (d, J 11.8 Hz, 1H), 3.91 (d, J 10.9, 3.2 Hz, 1H), 3.82 (dd, J 11.9, 4.0 Hz, 1H), 3.74 (d, J 12.9 Hz, 1H), 3.51 (dt, J 11.5, 3.1 Hz, 1H), 3.41-3.26 (m, 1H), 3.23 (2×s, 6H), 2.10-1.93 (m, 1H), 1.93-1.77 (m, 1H), 1.74-1.53 (m, 2H), 1.48-0.75 (m, 6H), 1.34 (s, 9H), 0.84 (d, J 6.4 Hz, 3H). LCMS (Method 5): [M+H]$^+$ m/z 642, RT 1.33 minutes.

Example 162

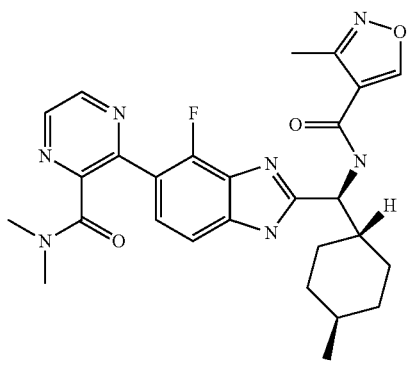 [SMILES: Cc1nocc1C(=O)N[C@H](c1nc2c(F)c(-c3nccnc3C(=O)N(C)C)ccc2[nH]1)[C@H]1CC[C@H](C)CC1]

N-[(S)-{5-[3-(Dimethylcarbamoyl)pyrazin-2-yl]-4-fluoro-1H-benzimidazol-2-yl}(4-methylcyclohexyl)methyl]-3-methylisoxazole-4-carboxamide (Trans Isomer)

The title compound (32 mg, 67%), a white solid, was prepared from Intermediate 199 (41.1 mg, 0.09 mmol) and 3-methylisoxazole-4-carboxylic acid (24 mg, 0.19 mmol) in accordance with Procedure A, using DCM (3 mL) as solvent. δ$_H$ (400 MHz, DMSO-d6) 12.89 (s, 1H), 9.46 (s, 1H), 8.93-8.74 (m, 2H), 8.69 (d, J 2.5 Hz, 1H), 7.58-7.35 (m, 1H), 7.29 (t, J 7.4 Hz, 1H), 5.06 (t, J 8.5 Hz, 1H), 2.93 (s, 3H), 2.89 (s, 3H), 2.37 (s, 3H), 2.11-1.97 (m, 1H), 1.92 (d, J 12.9 Hz, 1H), 1.72 (d, J 12.6 Hz, 1H), 1.64 (d, J 12.7 Hz, 1H), 1.42 (d, J 12.6 Hz, 1H), 1.37-1.23 (m, 1H), 1.20-1.02 (m, 2H), 0.97-0.79 (m, 5H). LCMS (Method 6): [M+H]$^+$ m/z 520, RT 1.77 minutes.

Example 163

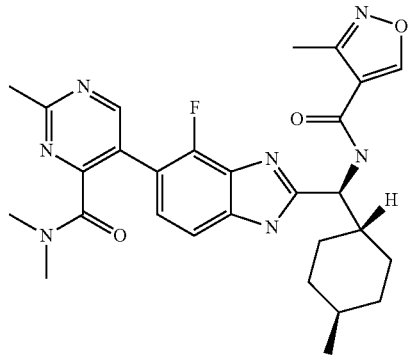 [SMILES: Cc1ncc(-c2ccc3[nH]c([C@@H](NC(=O)c4conc4C)[C@H]4CC[C@H](C)CC4)nc3c2F)c(C(=O)N(C)C)n1]

N-[(S)-{5-[4-(Dimethylcarbamoyl)-2-methylpyrimidin-5-yl]-4-fluoro-1H-benzimidazol-2-yl}(4-methylcyclohexyl)methyl]-3-methylisoxazole-4-carboxamide (Trans Isomer)

The title compound (3 mg, 46%), a white solid, was prepared from Intermediate 202 (5.6 mg, 0.01 mmol) and 3-methylisoxazole-4-carboxylic acid (5.3 mg, 0.04 mmol) in accordance with Procedure A, using DCM (3 mL) as solvent. δ$_H$ (400 MHz, CD$_3$OD) 9.22 (s, 1H), 8.88 (d, J 1.2 Hz, 1H), 7.45 (d, J 8.4 Hz, 1H), 7.22 (dd, J 8.4, 6.6 Hz, 1H), 5.09 (d, J 8.3 Hz, 1H), 2.95 (s, 3H), 2.89 (s, 3H), 2.80 (s, 3H), 2.43 (s, 3H), 2.12-1.97 (m, 2H), 1.88-1.78 (m, 1H), 1.78-1.69 (m, 1H), 1.52-1.44 (m, 1H), 1.44-1.31 (m, 1H), 1.27-1.12 (m, 2H), 1.10-0.95 (m, 2H), 0.92 (d, J 6.5 Hz, 3H). LCMS (Method 6): [M+H]$^+$ m/z 534, RT 1.82 minutes.

Example 164

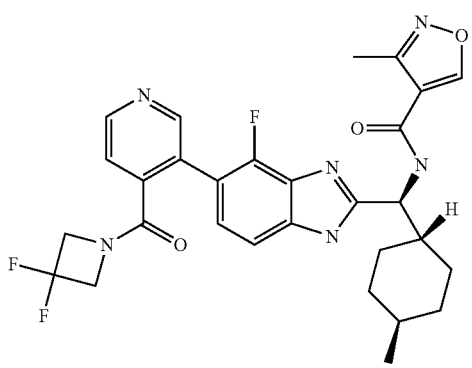

N-[(S)-{5-[4-(3,3-Difluoroazetidine-1-carbonyl)
pyridin-3-yl]-4-fluoro-1H-benzimidazol-2-yl}(4-
methylcyclohexyl)methyl]-3-methylisoxazole-4-
carboxamide (Trans Isomer)

The title compound (16 mg, 57%), a white solid, was prepared from Intermediate 204 (24.4 mg, 0.049 mmol) and 3-methylisoxazole-4-carboxylic acid (21.3 mg, 0.17 mmol) in accordance with Procedure A, using DCM (3 mL) as solvent. $\delta_H$ (400 MHz, DMSO-$d_6$) 13.24-12.60 (m, 1H), 9.47 (s, 1H), 9.03-8.77 (m, 1H), 8.71 (d, J 4.8 Hz, 2H), 7.63 (d, J 5.0 Hz, 1H), 7.59-7.37 (m, 1H), 7.18 (dd, J 8.2, 6.7 Hz, 1H), 5.06 (t, J 8.5 Hz, 1H), 4.38 (dt, J 24.0, 12.5 Hz, 4H), 2.37 (s, 3H), 2.09-1.96 (m, 1H), 1.92 (d, J 12.7 Hz, 1H), 1.72 (d, J 12.7 Hz, 1H), 1.64 (d, J 12.6 Hz, 1H), 1.38 (d, J 12.8 Hz, 1H), 1.35-1.23 (m, 1H), 1.18-1.01 (m, 2H), 0.97-0.80 (m, 5H). LCMS (Method 6): [M+H]$^+$ m/z 567, RT 2.00 minutes.

Example 165

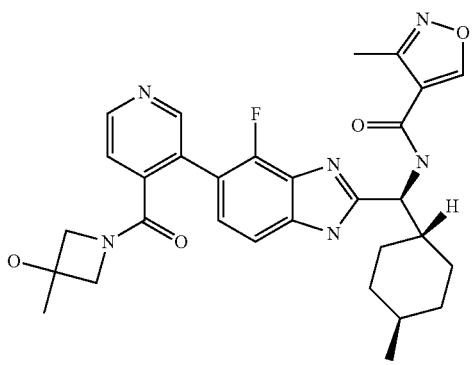 [SMILES: Cc1nocc1C(=O)N[C@H](c1nc2c(F)c(-c3cnccc3C(=O)N3CC(F)(F)C3)ccc2[nH]1)[C@H]1CC[C@H](C)CC1]

N-[(S)-{4-Fluoro-5-[4-(3-hydroxy-3-methylazeti-
dine-1-carbonyl)pyridin-3-yl]-1H-benzimidazol-2-
yl}(4-methylcyclohexyl)methyl]-3-methylisoxazole-
4-carboxamide (Trans Isomer)

The title compound (9 mg, 19%), a white solid, was prepared from Intermediate 206 (41.8 mg, 0.086 mmol) and 3-methylisoxazole-4-carboxylic acid (25.5 mg, 0.20 mmol) in accordance with Procedure A, using DCM (3 mL) as solvent. $\delta_H$ (400 MHz, DMSO-$d_6$) 12.87 (s, 1H), 9.46 (s, 1H), 8.98-8.74 (m, 1H), 8.74-8.62 (m, 2H), 7.50 (d, J 5.0 Hz, 1H), 7.39 (d, J 8.3 Hz, 1H), 7.12 (t, J 7.0 Hz, 1H), 5.62 (d, J 1.9 Hz, 1H), 5.05 (t, J 8.4 Hz, 1H), 3.71-3.60 (m, 3H), 3.51 (t, J 7.5 Hz, 1H), 2.37 (d, J 1.2 Hz, 3H), 2.08-1.96 (m, 1H), 1.91 (d, J 12.9 Hz, 1H), 1.72 (d, J 12.6 Hz, 1H), 1.63 (d, J 12.7 Hz, 1H), 1.45-1.21 (m, 3H), 1.17-1.00 (m, 4H), 0.97-0.80 (m, 5H). LCMS (Method 6): [M+H]$^+$ m/z 561, RT 1.69 minutes.

Examples 166 & 167

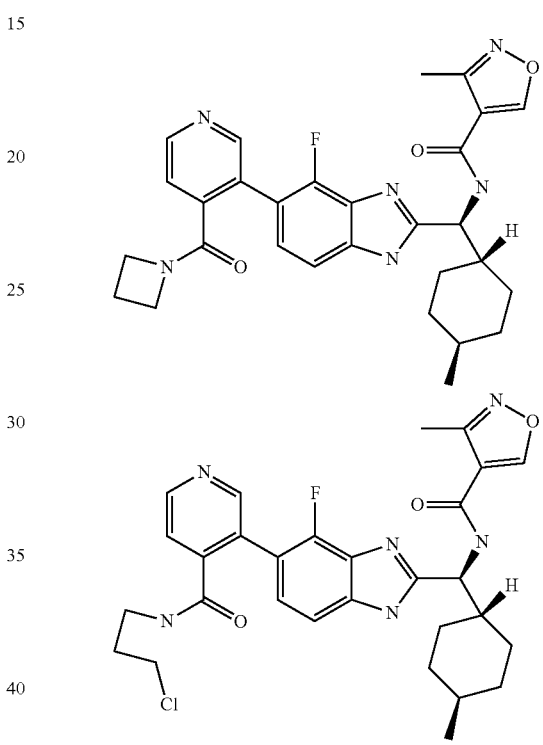

N-[(S)-{5-[4-(Azetidine-1-carbonyl)pyridin-3-yl]-4-
fluoro-1H-benzimidazol-2-yl}(4-methylcyclohexyl)
methyl]-3-methylisoxazole-4-carboxamide (Trans
Isomer) (Example 16)

N-[(S)-{5-[4-(3-Chloropropylcarbamoyl)pyridin-3-
yl]-4-fluoro-1H-benzimidazol-2-yl}(4-methylcyclo-
hexyl)methyl]-3-methylisoxazole-4-carboxamide
(Trans Isomer) (Example 16)

To the inseparable mixture of Intermediates 208 and 209 (90 mg, 0.20 mmol) in DCM (3 mL) were added HATU (90 mg, 0.23 mmol), 3-methylisoxazole-4-carboxylic acid (50 mg, 0.39 mmol) and DIPEA (0.10 mL, 0.58 mmol). The reaction mixture was stirred at r.t. for 3 h, then partitioned between DCM (10 mL) and water (10 mL). The organic layers were separated and concentrated in vacuo. The resulting brown oil was purified by preparative HPLC to yield the title compounds (Example 166, 15 mg, 15%; Example 167, 10 mg, 9%) as white solids.

Example 166: $\delta_H$ (400 MHz, DMSO-$d_6$) 12.85 (d, J 2.2 Hz, 1H), 9.46 (s, 1H), 8.88 (d, J 8.5 Hz, 1H), 8.72-8.64 (m, 2H), 7.54-7.46 (m, 1H), 7.39 (d, J 8.3 Hz, 1H), 7.20-7.11 (m, 1H), 5.12-5.01 (m, 1H), 3.87 (t, J 7.9 Hz, 4H), 2.37 (s, 3H), 2.21-2.09 (m, 2H), 2.09-1.97 (m, 1H), 1.93 (d, J 9.7 Hz, 1H), 1.73 (d, J 12.8 Hz, 1H), 1.65 (d, J 12.9 Hz, 1H), 1.42 (d, J 12.5 Hz, 1H), 1.31 (br s, 1H), 1.19-1.03 (m, 2H), 0.97-0.83 (m, 5H). LCMS (Method 6): [M+H]$^+$ m/z 531, RT 1.83 minutes.

Example 167: $\delta_H$ (400 MHz, DMSO-d$_6$) 12.86 (s, 1H), 9.46 (s, 1H), 8.98-8.73 (m, 1H), 8.72-8.60 (m, 2H), 8.42 (s, 1H), 7.49 (d, J 5.0 Hz, 1H), 7.33 (d, J 8.1 Hz, 1H), 7.10 (s, 1H), 5.03 (t, J 8.5 Hz, 1H), 3.16 (q, J 6.3 Hz, 2H), 2.36 (s, 3H), 1.96-1.78 (m, 2H), 1.76-1.60 (m, 4H), 1.40 (d, J 12.6 Hz, 1H), 1.36-1.22 (m, 2H), 1.18-1.02 (m, 2H), 0.96-0.81 (m, 6H). LCMS (Method 6): [M+H]$^+$ m/z 567, RT 1.95 minutes.

Example 168

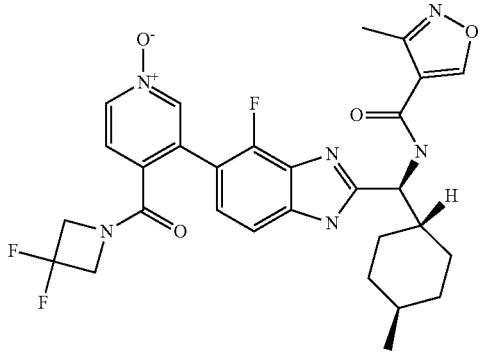 [SMILES: Cc1nocc1C(=O)N[C@H](c1nc2c(F)c(-c3c[n+]([O-])ccc3C(=O)N3CC(F)(F)C3)ccc2[nH]1)[C@H]1CC[C@H](C)CC1]

N-[(S)-{5-[4-(3,3-Difluoroazetidine-1-carbonyl)-1-oxidopyridin-1-ium-3-yl]-4-fluoro-1H-benzimidazol-2-yl}(4-methylcyclohexyl)methyl]-3-methyl-isoxazole-4-carboxamide (Trans Isomer)

To Example 164 (11 mg, 0.02 mmol) in DCM (1 mL) was added MCPBA (7.4 mg, 0.033 mmol). The reaction mixture was stirred at r.t. for 2 h, then further MCPBA (3.2 mg) was added. The reaction mixture was stirred at r.t. for 1 h. Saturated aqueous NaHCO$_3$ solution (2 mL), water (1 mL) and DCM (2 mL) were added. The organic layer was further diluted with DCM (5 mL), then filtered through a phase separation frit, washing with water and DCM. The organic phase was concentrated in vacuo. The resulting yellow oil was purified by preparative HPLC to give the title compound (4 mg, 36%) as a colourless film. $\delta_H$ (400 MHz, DMSO-d$_6$) 12.85 (s, 1H), 9.46 (s, 1H), 8.87 (d, J 8.4 Hz, 1H), 8.30 (d, J 6.2 Hz, 2H), 7.65 (d, J 6.7 Hz, 1H), 7.37 (d, J 8.3 Hz, 1H), 7.13 (t, J 7.5 Hz, 1H), 5.04 (t, J 8.4 Hz, 1H), 4.48-4.22 (m, 4H), 2.36 (s, 3H), 1.99 (dtt, J 11.7, 7.2, 3.4 Hz, 1H), 1.89 (dt, J 12.7, 3.1 Hz, 1H), 1.70 (dd, J 12.6, 3.2 Hz, 1H), 1.66-1.57 (m, 1H), 1.41-1.34 (m, 1H), 1.28 (dq, J 8.3, 4.2, 3.8 Hz, 1H), 1.08 (dqd, J 20.6, 12.7, 3.3 Hz, 2H), 0.95-0.77 (m, 5H). LCMS (Method 6): [M+H]$^+$ m/z 583, RT 1.56 minutes.

Example 169

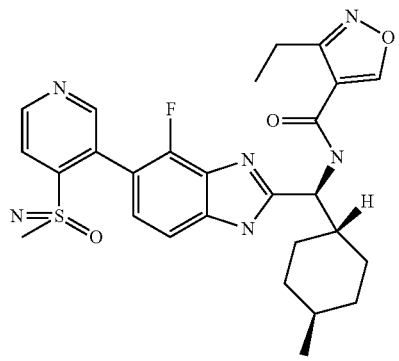 [SMILES: CCc1nocc1C(=O)N[C@H](c1nc2c(F)c(-c3cnccc3S(C)(=N)=O)ccc2[nH]1)[C@H]1CC[C@H](C)CC1]

3-Ethyl-N-[(S)-{4-fluoro-5-[4-(methylsulfonimidoyl)pyridin-3-yl]-1H-benzimidazol-2-yl}(4-methyl-cyclohexyl)methyl]isoxazole-4-carboxamide (Trans Isomer)

Intermediate 211 (109 mg, 0.22 mmol), (diacetoxyiodo)benzene (175 mg, 0.54 mmol) and ammonium carbamate (35 mg, 0.45 mmol) were placed in a flask containing a stirrer bar, then MeOH (1 mL) was added. The reaction mixture was stirred at r.t. for 4 h, then concentrated in vacuo. The residue was purified by flash column chromatography, eluting with MeOH/EtOAc (0-20% gradient), then further purified using preparative HPLC, to give the title compound (19 mg, 16%). $\delta_H$ (400 MHz, DMSO-d$_6$) 12.88 (s, 1H), 9.43 (s, 1H), 8.91 (d, J 5.2 Hz, 1H), 8.85 (s, 1H), 8.65-8.59 (m, 1H), 8.06 (d, J 5.2 Hz, 1H), 7.37-7.31 (m, 1H), 7.21-7.13 (m, 1H), 5.07 (t, J 8.5 Hz, 1H), 4.50 (s, 1H), 2.92-2.74 (m, 5H), 2.02 (d, J 11.2 Hz, 1H), 1.93-1.87 (m, 1H), 1.71 (d, J 13.0 Hz, 1H), 1.64 (d, J 12.8 Hz, 1H), 1.47-1.38 (m, 1H), 1.34-1.25 (m, 1H), 1.19-1.01 (m, 5H), 0.97-0.79 (m, 5H). LCMS (Method 6): [M+H]$^+$ m/z 539, RT 1.86 minutes.

Example 170

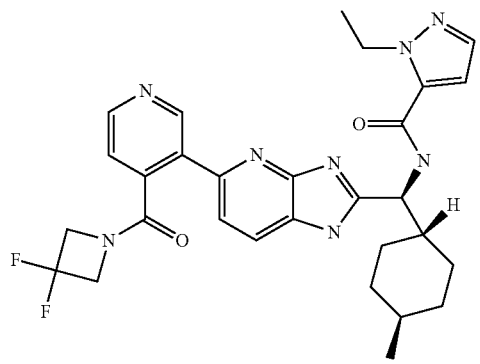 [SMILES: CCn1nccc1C(=O)N[C@H](c1nc2nc(-c3cnccc3C(=O)N3CC(F)(F)C3)ccc2[nH]1)[C@H]1CC[C@H](C)CC1]

N-[(S)-{5-[4-(3,3-Difluoroazetidine-1-carbonyl)pyridin-3-yl]-1H-imidazo[4,5-b]pyridin-2-yl}(4-methylcyclohexyl)methyl]-2-ethylpyrazole-3-carboxamide (Trans Isomer)

The title compound (5 mg, 12%), a white solid, was prepared from Intermediate 212 (36 mg, 0.07 mmol) and 3,3-difluoroazetidine hydrochloride (16 mg, 0.16 mmol) in accordance with Procedure A. $\delta_H$ (400 MHz, DMSO-$d_6$) 12.88 (s, 1H), 9.11 (s, 1H), 8.81-8.61 (m, 2H), 7.98-7.84 (m, 1H), 7.68-7.56 (m, 1H), 7.48 (d, J 2.0 Hz, 1H), 7.45-7.38 (m, 1H), 7.04-6.95 (m, 1H), 5.05 (t, J 8.0 Hz, 1H), 4.65-4.37 (m, 4H), 4.15-3.99 (m, 2H), 2.08-1.98 (m, 1H), 1.90-1.78 (m, 1H), 1.69 (d, J 13.2 Hz, 1H), 1.61 (d, J 12.7 Hz, 1H), 1.56-1.34 (m, 2H), 1.30-1.03 (m, 5H), 1.02-0.74 (m, 5H). LCMS (Method 6): [M+H]$^+$ m/z 563, RT 1.73 minutes.

Examples 171 & 172

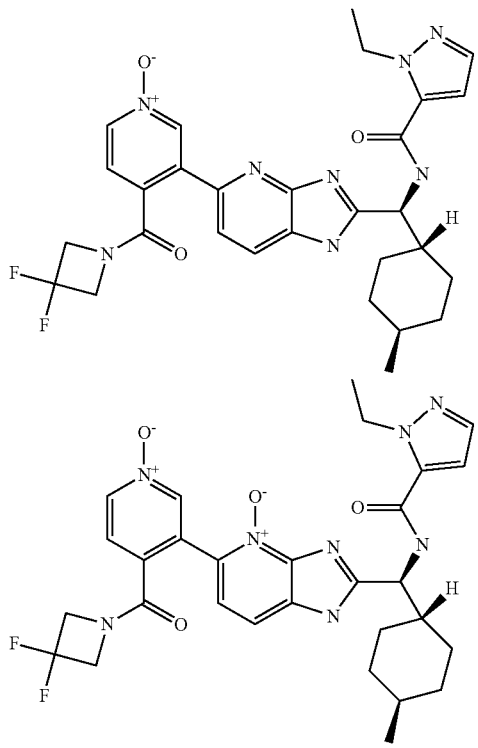

N-[(S)-{5-[4-(3,3-Difluoroazetidine-1-carbonyl)-1-oxidopyridin-3-yl]-1H-imidazo[4,5-b]-pyridin-2-yl}(4-methylcyclohexyl)methyl]-2-ethylpyrazole-3-carboxamide (Trans Isomer) (Example 171)

N-[(S)-{5-[4-(3,3-Difluoroazetidine-1-carbonyl)-1-oxidopyridin-3-yl]-4-hydroxy-1H-imidazo[4,5-b]pyridin-2-yl}(4-methylcyclohexyl)methyl]-2-ethylpyrazole-3-carboxamide (Trans Isomer) (Example 172)

To a solution of Example 170 (43 mg, 0.08 mmol) in DCM (2 mL) was added MCPBA (13 mg, 0.08 mmol). The reaction mixture was stirred at r.t. overnight. Further MCPBA (13 mg, 0.08 mmol) was added. The reaction mixture was stirred for a further 24 h, then partitioned between DCM and saturated aqueous Na$_2$CO$_3$ solution. The organic layers were separated, dried over Na$_2$SO$_4$ and concentrated in vacuo. The residue was purified by preparative HPLC to give the title compounds (Example 171, 1 mg, 2%; and Example 172, 2 mg, 4%) as white solids.

Example 171: $\delta_H$ (400 MHz, CD$_3$OD) 8.80 (d, J 1.7 Hz, 1H), 8.41 (dd, J 6.6, 1.8 Hz, 1H), 8.10 (d, J 8.3 Hz, 1H), 7.68 (dd, J 18.2, 7.4 Hz, 2H), 7.50 (d, J 2.1 Hz, 1H), 6.94 (d, J 2.2 Hz, 1H), 5.14 (d, J 8.6 Hz, 1H), 4.55-4.42 (m, 4H), 4.14 (t, J 11.9 Hz, 2H), 2.16-2.07 (m, 1H), 2.02 (dq, J 12.7, 3.6, 3.0 Hz, 1H), 1.80 (dt, J 13.0, 3.0 Hz, 1H), 1.70 (dt, J 13.2, 3.1 Hz, 1H), 1.46 (dt, J 12.7, 3.1 Hz, 1H), 1.33 (t, J 7.2 Hz, 3H), 1.25-1.12 (m, 2H), 1.10-0.80 (m, 6H). LCMS (Method 6): [M+H]$^+$ m/z 579, RT 1.54 minutes.

Example 172: $\delta_H$ (400 MHz, CD$_3$OD) 8.53 (d, J 1.8 Hz, 1H), 8.40 (dd, J 6.6, 1.8 Hz, 1H), 7.78-7.65 (m, 2H), 7.50 (d, J 2.2 Hz, 1H), 7.26 (d, J 8.1 Hz, 1H), 6.94 (d, J 2.1 Hz, 1H), 5.23 (d, J 8.1 Hz, 1H), 4.69-4.63 (m, 2H), 4.54 (q, J 7.2 Hz, 2H), 4.49-4.39 (m, 2H), 1.99-1.88 (m, 2H), 1.75 (d, J 13.0 Hz, 1H), 1.66 (d, J 13.1 Hz, 1H), 1.48 (d, J 13.1 Hz, 1H), 1.36 (t, J 7.2 Hz, 3H), 1.27-1.11 (m, 3H), 1.00-0.83 (m, 5H). LCMS (Method 6): [M+H]$^+$ m/z 595, RT 1.25 minutes.

Example 173

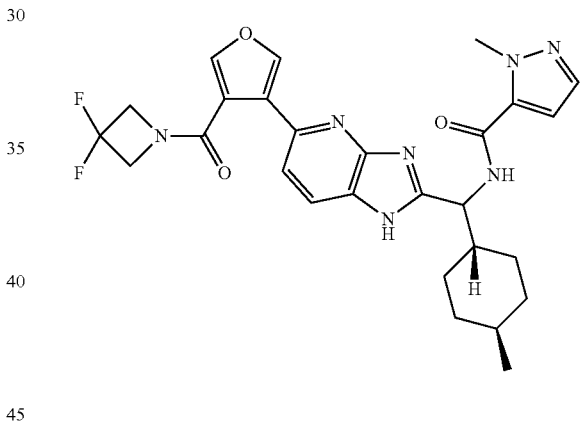

N-[(S)-{5-[4-(3,3-Difluoroazetidine-1-carbonyl)furan-3-yl]-1H-imidazo[4,5-b]pyridin-2-yl}(4-methylcyclohexyl)methyl]-2-methylpyrazole-3-carboxamide (Trans Isomer)

The title compound (139 mg, quantitative), a white solid, was prepared from Intermediate 215 (120 mg, 0.26 mmol) and 3,3-difluoroazetidine hydrochloride (55 mg, 0.53 mmol) in accordance with Procedure A. $\delta_H$ (400 MHz, DMSO-$d_6$) 13.10 (s, 1H), 8.81 (s, 1H), 8.34 (d, J 1.0 Hz, 1H), 8.04-7.95 (m, 1H), 7.67 (d, J 8.3 Hz, 1H), 7.47 (d, J 2.1 Hz, 1H), 7.23 (d, J 0.9 Hz, 1H), 7.08 (d, J 2.1 Hz, 1H), 5.04 (t, J 8.4 Hz, 1H), 4.99-4.77 (m, 2H), 4.57-4.35 (m, 2H), 4.02 (d, J 7.9 Hz, 3H), 2.11-2.00 (m, 1H), 1.90 (d, J 12.8 Hz, 1H), 1.71 (d, J 12.8 Hz, 1H), 1.63 (d, J 12.9 Hz, 1H), 1.42 (d, J 12.7 Hz, 1H), 1.34-1.23 (m, 1H), 1.20-1.02 (m, 2H), 1.00-0.67 (m, 5H). LCMS (Method 6): [M+H]$^+$ m/z 538, RT 1.77 minutes.

Example 174

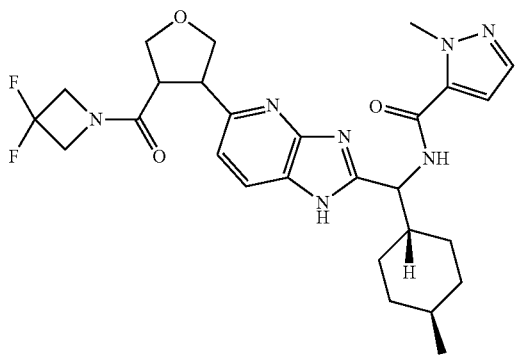

N-[(S)-{5-[4-(3,3-Difluoroazetidine-1-carbonyl) tetrahydrofuran-3-yl]-1H-imidazo[4,5-b]-pyridin-2-yl}(4-methylcyclohexyl)methyl]-2-methylpyrazole-3-carboxamide (Trans Isomer To a solution of Example 173 (104 mg, 0.19 mmol) in MeOH (5 mL) was added 10% Pd/C (10 mg). The reaction mixture was stirred under an atmosphere of hydrogen for 4 days, then filtered through Celite®, and concentrated in vacuo. The residue was dissolved in MeOH (10 mL) and charged again with 10% Pd/C (10 mg), then stirred under an atmosphere of hydrogen for 7 days. The reaction mixture was filtered through Celite®, and concentrated in vacuo. The residue was purified by preparative HPLC to give the title compound (1 mg, 1%) as a white solid. $\delta_H$ (400 MHz, DMSO-d$_6$) 7.94 (d, J 8.3 Hz, 1H), 7.57-7.40 (m, 2H), 6.94 (d, J 2.2 Hz, 1H), 5.14-5.02 (m, 2H), 4.67 (t, J 12.0 Hz, 2H), 4.31 (t, J 12.0 Hz, 2H), 4.22 (dd, J 8.5, 6.9 Hz, 1H), 4.15 (t, J 8.3 Hz, 1H), 4.06 (s, 3H), 3.43-3.35 (m, 1H), 2.71 (dddd, J 12.3, 8.2, 6.2, 1.8 Hz, 1H), 2.18 (dt, J 12.4, 9.4 Hz, 1H), 2.12-1.96 (m, 2H), 1.79 (dt, J 12.9, 3.0 Hz, 1H), 1.70 (dt, J 13.0, 3.0 Hz, 1H), 1.44 (d, J 13.0 Hz, 1H), 1.39-1.30 (m, 1H), 1.25-1.10 (m, 2H), 1.06-0.86 (m, 5H). LCMS (Method 6): [M+H]$^+$ m/z 542, RT 1.59 minutes.

Example 175

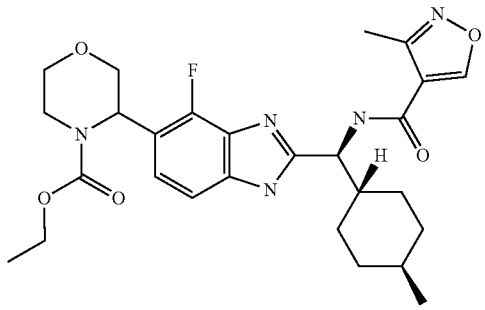 [SMILES: CCOC(=O)N1CCOCC1c1ccc2[nH]c([C@@H](NC(=O)c3conc3C)[C@H]3CC[C@H](C)CC3)nc2c1F]

Ethyl 3-(4-fluoro-2-{(S)-(4-methylcyclohexyl)[(3-methylisoxazole-4-carbonyl)amino]-methyl}-1H-benzimidazol-5-yl)morpholine-4-carboxylate (Trans Isomer)

The title compound (18 mg, 40%), a white solid, was prepared from Example 155 (40 mg, 0.08 mmol) and ethyl chloroformate (16 μL, 0.16 mmol) in accordance with Procedure KK. $\delta_H$ (400 MHz, DMSO-d$_6$) 12.93 (v br s, 1H), 9.48 (s, 1H), 9.10 (br s, 1H), 7.34-7.21 (m, 2H), 5.34 (d, J 3.7 Hz, 1H), 5.01 (t, J 8.6 Hz, 1H), 4.12 (d, J 11.9 Hz, 1H), 4.04 (q, J 7.1 Hz, 2H), 3.93 (dd, J 11.5, 3.7 Hz, 1H), 3.86 (dd, J 12.0, 4.1 Hz, 1H), 3.79 (d, J 13.4, 2.1 Hz, 1H), 3.54 (td, J 11.6, 3.2 Hz, 1H), 3.37-3.27 (m, 1H), 2.35 (s, 3H), 2.04-1.94 (m, 1H), 1.92-1.84 (m, 1H), 1.75-1.66 (m, 1H), 1.66-1.57 (m, 1H), 1.37-1.21 (m, 2H), 1.14 (t, J 7.1 Hz, 3H), 1.16-0.96 (m, 2H), 0.96-0.75 (m, 2H), 0.85 (d, J 6.5 Hz, 3H). LCMS (Method 5): [M+H]$^+$ m/z 528, RT 1.29 minutes.

Example 176

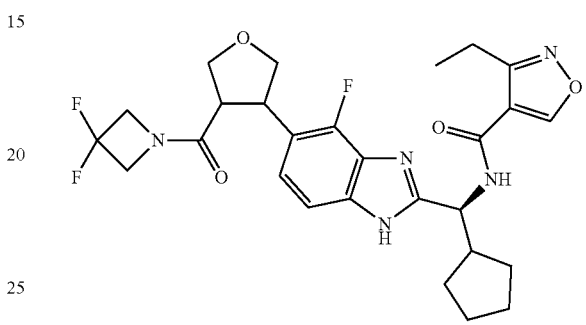

N-[(S)-Cyclopentyl{5-[4-(3,3-difluoroazetidine-1-carbonyl)tetrahydrofuran-3-yl]-4-fluoro-1H-benzimidazol-2-yl}methyl]-3-ethylisoxazole-4-carboxamide The title compound (11 mg, 17%), a white solid, was prepared from Intermediate 221 (56 mg, 0.12 mmol) and 3,3-difluoroazetidine hydrochloride (25 mg, 0.0.24 mmol) in accordance with Procedure A. $\delta_H$ (400 MHz, DMSO-d$_6$) 12.78 (s, 1H), 9.40 (s, 1H), 8.85 (s, 1H), 7.26-7.19 (m, 1H), 7.11-7.02 (m, 1H), 5.05 (t, J 8.8 Hz, 1H), 4.56 (q, J 12.1 Hz, 2H), 4.31-4.15 (m, 3H), 4.11 (t, J 7.9 Hz, 1H), 4.06-3.99 (m, 1H), 3.88 (dt, J 15.4, 7.8 Hz, 2H), 3.70 (t, J 8.1 Hz, 1H), 2.83 (qd, J 7.5, 2.7 Hz, 2H), 2.63-2.56 (m, 1H), 1.81-1.73 (m, 1H), 1.69-1.35 (m, 6H), 1.28-1.22 (m, 1H), 1.15 (t, J 7.5 Hz, 3H). LCMS (Method 6): [M+H]$^+$ m/z 546, RT 1.61 minutes.

Example 177

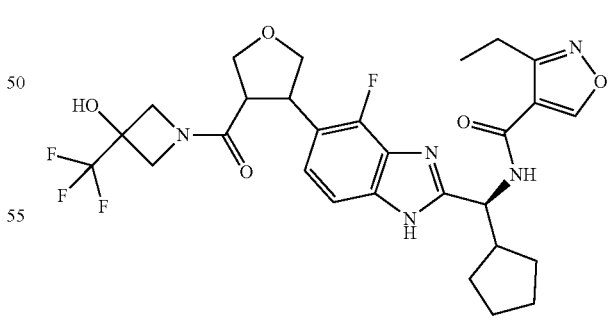

N-[(S)-Cyclopentyl(4-fluoro-5-{4-[3-hydroxy-3-(trifluoromethyl)azetidine-1-carbonyl]-tetrahydrofuran-3-yl}-1H-benzimidazol-2-yl)methyl]-3-ethylisoxazole-4-carboxamide The title compound (11 mg, 16%), a white solid, was prepared from crude Intermediate 221 (56 mg, 0.12 mmol)

and 3-(trifluoromethyl)azetidin-3-ol (35 mg, 0.24 mmol) in accordance with Procedure A. $\delta_H$ (400 MHz, DMSO-d$_6$) 12.68 (s, 1H), 9.38 (d, J 2.2 Hz, 1H), 8.96 (s, 1H), 7.42-7.24 (m, 2H), 7.21-7.12 (m, 1H), 5.08-4.99 (m, 1H), 4.40-3.63 (m, 10H), 3.30-3.27 (m, 1H), 2.83 (tt, J 9.1, 7.5, 5.5 Hz, 2H), 2.60 (m, 1H), 1.88-1.78 (m, 1H), 1.64-1.37 (m, 5H), 1.28-1.20 (m, 1H), 1.15 (td, J 7.5, 4.6 Hz, 3H). LCMS (Method 6): [M+H]$^+$ m/z 594, RT 1.55 minutes.

Example 178

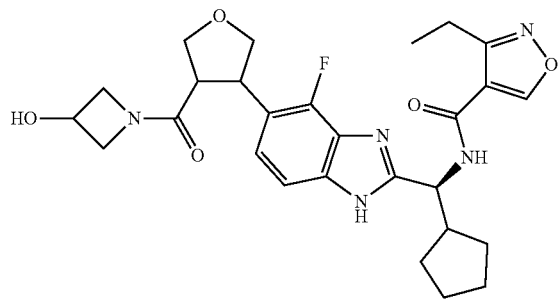 [SMILES: CCc1nocc1C(=O)N[C@H](c1nc2c(F)c(C3COCC3C(=O)N3CC(O)C3)ccc2[nH]1)C1CCCC1]

N-[(S)-Cyclopentyl{4-fluoro-5-[4-(3-hydroxyazetidine-1-carbonyl)tetrahydrofuran-3-yl]-1H-benzimidazol-2-yl}methyl]-3-ethylisoxazole-4-carboxamide The title compound (6 mg, 10%), a white solid, was prepared from crude Intermediate 221 (56 mg, 0.12 mmol) and azetidin-3-ol (20 mg, 0.26 mmol) in accordance with Procedure A. $\delta_H$ (400 MHz, DMSO-d$_6$) 12.72 (s, 1H), 9.39 (s, 1H), 8.93 (s, 1H), 7.31-7.21 (m, 1H), 7.18-7.09 (m, 1H), 5.67-5.54 (m, 1H), 5.09-5.01 (m, 1H), 4.41-4.06 (m, 4H), 4.01-3.85 (m, 2H), 3.77 (q, J 7.0, 6.1 Hz, 1H), 3.67 (q, J 7.8 Hz, 1H), 3.49 (ddd, J 24.7, 9.6, 4.5 Hz, 2H), 3.28-3.21 (m, 1H), 2.83 (qd, J 7.5, 3.0 Hz, 2H), 2.65-2.56 (m, 1H), 1.86-1.76 (m, 1H), 1.68-1.33 (m, 5H), 1.29-1.22 (m, 1H), 1.15 (t, J 7.5 Hz, 3H). LCMS (Method 6): [M+H]$^+$ m/z 526, RT 1.31 minutes.

Example 179

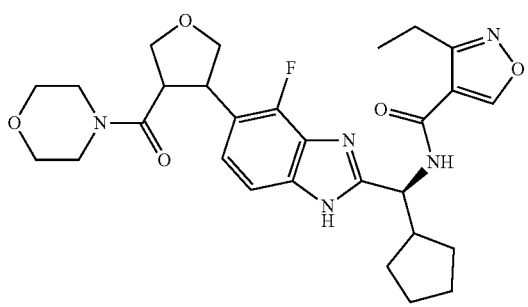 [SMILES: CCc1nocc1C(=O)N[C@H](c1nc2c(F)c(C3COCC3C(=O)N3CCOCC3)ccc2[nH]1)C1CCCC1]

N-[(S)-Cyclopentyl{4-fluoro-5-[4-(morpholine-4-carbonyl)tetrahydrofuran-3-yl]-1H-benzimidazol-2-yl}methyl]-3-ethylisoxazole-4-carboxamide The title compound (6 mg, 9%), a white solid, was prepared from crude Intermediate 221 (56 mg, 0.12 mmol) and morpholine (20 μL, 0.20 mmol) in accordance with Procedure A. $\delta_H$ (400 MHz, DMSO-d$_6$) 12.69 (s, 1H), 9.39 (s, 1H), 8.97 (s, 1H), 7.25 (d, J 8.3 Hz, 1H), 7.18 (t, J 7.4 Hz, 1H), 5.03 (t, J 9.0 Hz, 1H), 4.21 (t, J 8.2 Hz, 1H), 4.15-4.01 (m, 2H), 3.84 (dd, J 8.3, 6.6 Hz, 1H), 3.70 (t, J 7.3 Hz, 1H), 3.63 (d, J 7.4 Hz, 1H), 3.57-3.13 (m, 9H), 2.82 (qd, J 7.4, 2.7 Hz, 2H), 2.65-2.57 (m, 1H), 1.86-1.78 (m, 1H), 1.65-1.35 (m, 5H), 1.27-1.21 (m, 1H), 1.15 (t, J 7.5 Hz, 3H). LCMS (Method 6): [M+H]$^+$ m/z 540, RT 1.46 minutes.

Example 180

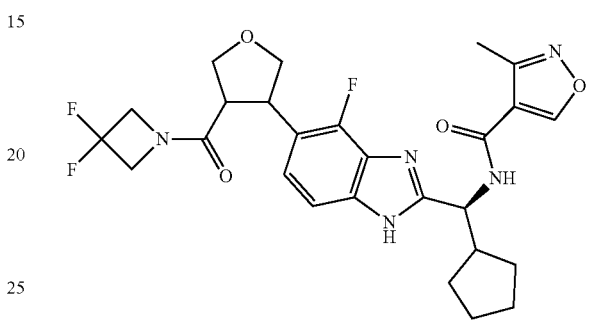

N-[(S)-Cyclopentyl{5-[4-(3,3-difluoroazetidine-1-carbonyl)tetrahydrofuran-3-yl]-4-fluoro-1H-benzimidazol-2-yl}methyl]-3-methylisoxazole-4-carboxamide The title compound (14 mg, 19% yield), a white solid, was prepared from crude Intermediate 222 (58 mg, 0.14 mmol) and 3-methylisoxazole-4-carboxylic acid (22 mg, 0.16 mmol) in accordance with Procedure A, in DCM (2 mL) as solvent. $\delta_H$ (400 MHz, DMSO-d$_6$) 12.71 (s, 1H), 9.41 (s, 1H), 8.94 (s, 1H), 7.27 (d, J 8.3 Hz, 1H), 7.17 (t, J 7.4 Hz, 1H), 5.03 (t, J 8.9 Hz, 1H), 4.57 (q, J 12.0 Hz, 2H), 4.30-4.16 (m, 3H), 4.14-4.04 (m, 2H), 3.94 (q, J 7.8 Hz, 1H), 3.85 (dd, J 8.5, 6.9 Hz, 1H), 3.71 (t, J 8.0 Hz, 1H), 2.65-2.56 (m, 1H), 2.35 (s, 3H), 1.87-1.78 (m, 1H), 1.63-1.37 (m, 6H), 1.27-1.19 (m, 1H). LCMS (Method 6): [M+H]$^+$ m/z 532, RT 1.48 minutes.

Example 181

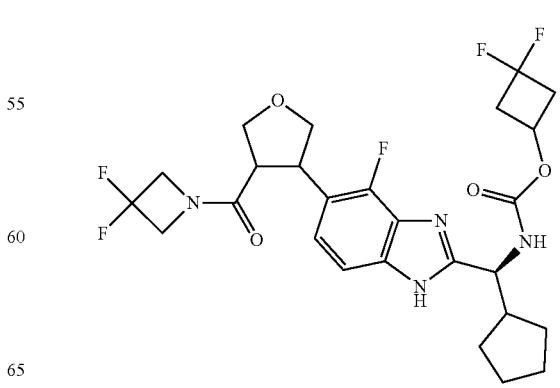

3,3-Difluorocyclobutyl N-[(S)-cyclopentyl{5-[4-(3,3-difluoroazetidine-1-carbonyl)-tetrahydrofuran-3-yl]-4-fluoro-1H-benzimidazol-2-yl}methyl]carbamate To a solution of 3,3-difluorocyclobutanol (20 mg, 0.18 mmol) in DCM (1 mL) were added triethylamine (40 μL, 0.3 mmol) and N,N'-disuccinimidyl carbonate (75 mg, 0.29 mmol). The reaction mixture was stirred at r.t. for 30 minutes, then a solution of Intermediate 222 (60 mg, 0.14 mmol) in DCM (1 mL) was added dropwise. After stirring for 80 minutes, the reaction mixture was partitioned between DCM and water. The organic layers were separated, dried over Na$_2$SO$_4$, and concentrated in vacuo. The residue was purified by preparative HPLC to give the title compound (12 mg, 15%) as a white solid. δ$_H$ (400 MHz, DMSO-d$_6$) 7.35 (d, J 8.4 Hz, 1H), 7.26 (dd, J 8.4, 6.4 Hz, 1H), 4.64 (d, J 9.4 Hz, 1H), 4.48 (q, J 11.7 Hz, 2H), 4.32-4.20 (m, 3H), 4.04 (dt, J 11.7, 7.6 Hz, 2H), 3.94 (t, J 8.0 Hz, 1H), 3.86 (t, J 10.9 Hz, 1H), 3.38-3.33 (m, 1H), 2.95 (dtd, J 17.9, 13.3, 12.6, 6.6 Hz, 2H), 2.73-2.45 (m, 3H), 1.91 (dd, J 12.7, 5.8 Hz, 1H), 1.74-1.40 (m, 6H), 1.27 (d, J 11.9 Hz, 1H). LCMS (Method 6): [M+H]$^+$ m/z 557, RT 1.66 minutes.

Example 182

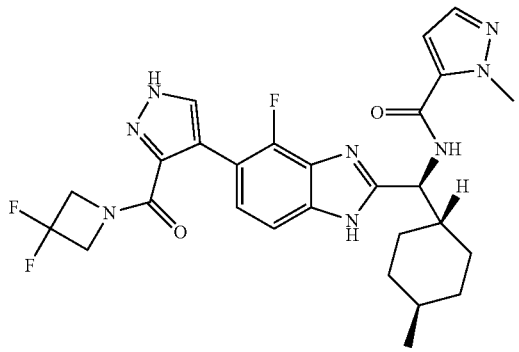 [SMILES: Cn1nccc1C(=O)N[C@H](c1nc2c(F)c(-c3c[nH]nc3C(=O)N3CC(F)(F)C3)ccc2[nH]1)[C@H]1CC[C@H](C)CC1]

N-[(S)-{5-[3-(3,3-Difluoroazetidine-1-carbonyl)-1H-pyrazol-4-yl]-4-fluoro-1H-benzimidazol-2-yl}(4-methylcyclohexyl)methyl]-2-methylpyrazole-3-carboxamide (Trans Isomer The title compound (3 mg, 5%) was prepared from Intermediate 225 (50 mg, 0.10 mmol) and Intermediate 226 (35 mg, 0.13 mmol) in accordance with Procedure G. δ$_H$ (400 MHz, DMSO-d$_6$) 13.15 (s, 1H), 8.78 (s, 1H), 7.93 (s, 1H), 7.45 (d, J 2.1 Hz, 1H), 7.27-7.19 (m, 1H), 7.13-7.02 (m, 2H), 5.01 (t, J 8.4 Hz, 1H), 4.79-4.65 (m, 2H), 4.39 (t, J 12.6 Hz, 2H), 4.02 (s, 3H), 2.07-2.00 (m, 1H), 1.88 (d, J 12.7 Hz, 1H), 1.70 (d, J 12.7 Hz, 1H), 1.62 (d, J 12.8 Hz, 1H), 1.40 (d, J 12.5 Hz, 1H), 1.32-1.25 (m, 1H), 1.15-1.01 (m, 2H), 0.95-0.78 (m, 5H). LCMS (Method 6): [M+H]$^+$ m/z 555, RT 1.68 minutes.

Example 183

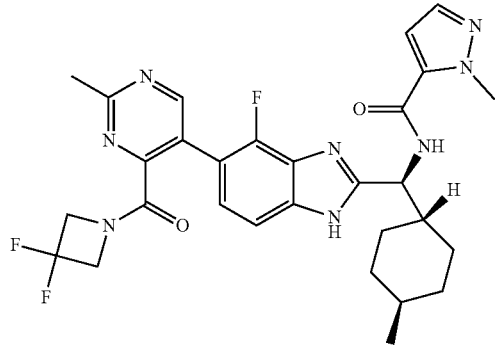 [SMILES: Cc1ncc(-c2ccc3[nH]c([C@@H](NC(=O)c4ccnn4C)[C@H]4CC[C@H](C)CC4)nc3c2F)c(C(=O)N2CC(F)(F)C2)n1]

N-[(S)-{5-[4-(3,3-Difluoroazetidine-1-carbonyl)-2-methylpyrimidin-5-yl]-4-fluoro-1H-benzimidazol-2-yl}(4-methylcyclohexyl)methyl]-2-methylpyrazole-3-carboxamide (Trans Isomer The title compound (6 mg, 10%) was prepared from Intermediate 225 (50 mg, 0.10 mmol) and Intermediate 227 (35 mg, 0.12 mmol) in accordance with Procedure G. δ$_H$ (400 MHz, DMSO-d$_6$) 12.86 (s, 1H), 8.91-8.78 (m, 2H), 7.46 (d, J 2.1 Hz, 1H), 7.38 (d, J 8.2 Hz, 1H), 7.22-7.16 (m, 1H), 7.08 (d, J 2.1 Hz, 1H), 5.02 (t, J 8.6 Hz, 1H), 4.70 (t, J 12.3 Hz, 2H), 4.46 (t, J 12.4 Hz, 2H), 4.02 (s, 3H), 2.73 (s, 3H), 2.11-2.02 (m, 1H), 1.92 (d, J 12.8 Hz, 1H), 1.71 (d, J 12.7 Hz, 1H), 1.63 (d, J 12.8 Hz, 1H), 1.38 (d, J 12.7 Hz, 1H), 1.33-1.25 (m, 1H), 1.15-1.01 (m, 2H), 0.98-0.71 (m, 5H). LCMS (Method 6): [M+H]$^+$ m/z 581, RT 1.85 minutes.

Example 184

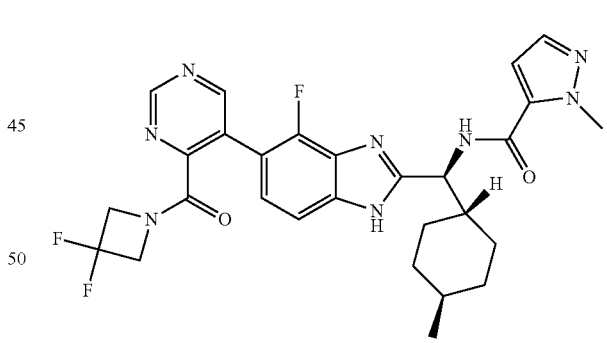

N-[(S)-{5-[4-(3,3-Difluoroazetidine-1-carbonyl)pyrimidin-5-yl]-4-fluoro-1H-benzimidazol-2-yl}(4-methylcyclohexyl)methyl]-2-methylpyrazole-3-carboxamide (Trans Isomer The title compound (11 mg, 19%) was prepared from Intermediate 225 (50 mg, 0.10 mmol) and Intermediate 228 (35 mg, 0.13 mmol) in accordance with Procedure G. δ$_H$ (400 MHz, DMSO-d$_6$) 12.90 (s, 1H), 9.27 (s, 1H), 9.03 (s, 1H), 8.83 (s, 1H), 7.46 (d, J 2.1 Hz, 1H), 7.42-7.36 (m, 1H), 7.22-7.14 (m, 1H), 7.07 (d, J 2.1 Hz, 1H), 5.03 (t, J 8.5 Hz, 1H), 4.70 (t, J 12.2 Hz, 2H), 4.47 (t, J 12.4 Hz, 2H), 4.02 (s, 3H), 2.09-2.01 (m, 1H), 1.91 (d, J 12.6 Hz, 1H), 1.71 (d, J 12.8 Hz, 1H), 1.63 (d, J 12.9 Hz, 1H), 1.40 (d, J 12.6 Hz, 1H), 1.33-1.25 (m, 1H), 1.16-1.02 (m, 2H), 1.02-0.75 (m, 5H). LCMS (Method 6): [M+H]+ m/z 567, RT 1.78 minutes.

Example 185

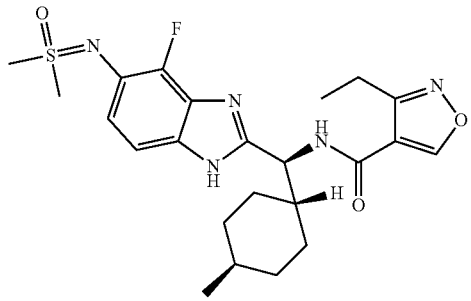 [SMILES: CCc1nocc1C(=O)N[C@H](c1nc2c(F)c(N=S(C)(C)=O)ccc2[nH]1)[C@H]1CC[C@H](C)CC1]

N-[(S)-(5-{[Dimethyl(oxo)-λ⁶-sulfanylidene]amino}-4-fluoro-1H-benzimidazol-2-yl)(4-methylcyclohexyl)methyl]-3-ethylisoxazole-4-carboxamide (Trans Isomer)

TFA (0.75 mL, 10.1 mmol) was added to a solution of Intermediate 232 (90 mg, 0.16 mmol) in DCM (0.75 mL). The reaction mixture was stirred at 20° C. under air for 2 days, then partitioned between DCM (10 mL) and saturated aqueous Na₂CO₃ solution (10 mL). The phases were separated using a hydrophobic frit, and the aqueous phase was extracted with DCM (2×10 mL). The organic filtrate was concentrated in vacuo. The residue was dissolved in acetonitrile (1.5 mL). Aqueous NH₃ (35%, 0.5 mL) was added, and the mixture was stirred at 20° C. under air for 30 minutes. The volatiles were removed in vacuo. The resultant tan powder was dissolved in DCM (2 mL) and adsorbed onto an SCX-2 column (2 g), which was eluted sequentially with DCM, MeOH and a 1M solution of ammonia in MeOH. The ammonia-MeOH fractions were combined and concentrated in vacuo. The resultant tan powder was dissolved in DCM (1 mL). A solution of 3-ethyl-isoxazole-4-carboxylic acid (41 mg, 0.29 mmol), HATU (116 mg, 0.31 mmol) and DIPEA (0.08 mL, 0.46 mmol) in DCM (1.0 mL), pre-mixed at 20° C. under N₂ for 30 minutes, was added. The reaction mixture was stirred at 20° C. under nitrogen for 16 h, then diluted with DCM (10 mL), and quenched with saturated aqueous Na₂CO₃ solution (5 mL) and water (5 mL). The biphasic mixture was stirred at 20° C. for 30 minutes, then the organic phase was separated using a hydrophobic frit. The aqueous layer was extracted with DCM (2×10 mL), and the organic filtrate was concentrated in vacuo. The resultant orange viscous oil was separated by preparative HPLC to afford, after freeze-drying, the title compound (14.9 mg, 19%) as a white powder. δ_H (353K, 250 MHz, DMSO-d₆) 12.16 (br s, 1H), 9.33 (s, 1H), 8.38 (br s, 1H), 7.20-7.04 (m, 1H), 6.94 (dd, J 8.3, 7.7 Hz, 1H), 5.07 (t, J 7.5 Hz, 1H), 3.16 (s, 6H), 2.85 (q, J 7.5 Hz, 2H), 2.11-1.81 (m, 2H), 1.80-1.59 (m, 2H), 1.56-1.42 (m, 1H), 1.40-0.77 (m, 11H). uPLCMS (Method 9): [M+H]+ m/z 476, RT 2.55 minutes.

Example 186

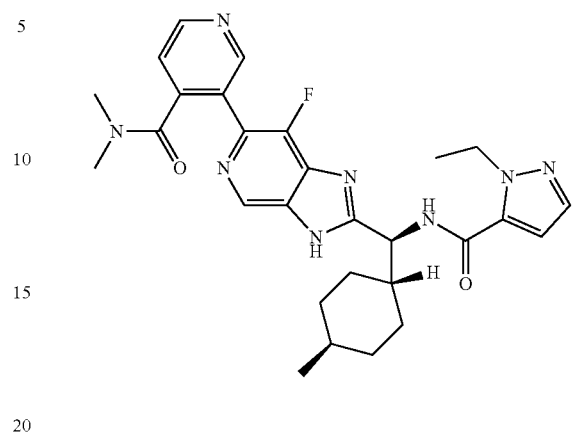

3-(2-{(S')-[(2-Ethylpyrazole-3-carbonyl)amino](4-methylcyclohexyl)methyl}-7-fluoro-3H-imidazo[4,5-c]pyridin-6-yl)-N,N-dimethylpyridine-4-carboxamide (Trans Isomer)

DIPEA (58 μL, 0.33 mmol) was added to a stirred suspension of Intermediate 237 (53 mg, 0.13 mmol), 1-ethyl-1H-pyrazole-5-carboxylic acid (28 mg, 0.20 mmol) and HATU (82 mg, 0.22 mmol) in anhydrous DCM (1.8 mL). The mixture was stirred at 20° C. under N₂ for 16 h, then diluted with DCM (10 mL) and quenched with saturated aqueous Na₂CO₃ solution (10 mL). The organic phase was separated using a hydrophobic frit, and the aqueous layer was extracted with DCM (2×10 mL). The organic filtrate was concentrated in vacuo. The resultant tan gum was separated by flash column chromatography, eluting with EtOAc/heptane (0-100% gradient). The resultant tan powder was combined with Intermediate 229 (45 mg, 0.23 mmol). The reagents were suspended in a mixture of 1,4-dioxane (0.6 mL) and a 2M aqueous Na₂CO₃ solution (0.2 mL, 0.40 mmol), and the suspension was sparged with N₂ whilst sonicating for 5 minutes. Pd₂(dba)₃ (2.6 mg, 2.84 μmol) and XPhos (2.7 mg, 5.66 μmol) were added, and the suspension was sparged with nitrogen whilst sonicating for 5 minutes. The reaction mixture was sealed under N₂ and heated at 100° C. for 16 h. The mixture was re-treated four times with Intermediate 229 (45 mg, 0.23 mmol), twice with 2M aqueous sodium carbonate solution (0.2 mL, 0.40 mmol), and three times with Pd₂(dba)₃ (2.6 mg, 2.84 μmol) and XPhos (2.7 mg, 5.66 μmol), whilst heating at 110° C. for 54 h. After cooling to r.t., the mixture was diluted with water (20 mL) and extracted with EtOAc (3×30 mL). The combined organic extracts were washed with brine (20 mL), dried over MgSO₄ and concentrated in vacuo. The resultant brown viscous oil was purified by preparative HPLC to afford, after freeze-drying, the title compound (1.1 mg, 2%) as an off-white powder. δ_H (500 MHz, CDCl₃) 11.71 (br s, 1H), 9.11-8.88 (m, 1H), 8.73 (d, J 5.0 Hz, 1H), 8.62 (s, 0.5H), 8.05 (s, 0.5H), 7.55-7.08 (m, 3H), 6.75 (s, 0.5H), 6.58 (s, 0.5H), 5.32-4.89 (m, 1H), 4.76-4.44 (m, 2H), 3.39-2.81 (m, 6H), 1.97-1.85 (m, 1H), 1.82-1.14 (obs. m, 10H), 1.12-0.95 (m, 2H), 0.94-0.67 (m, 5H). uPLCMS (Method 9): [M+H]+ m/z 533, RT 2.66 minutes.

Example 187

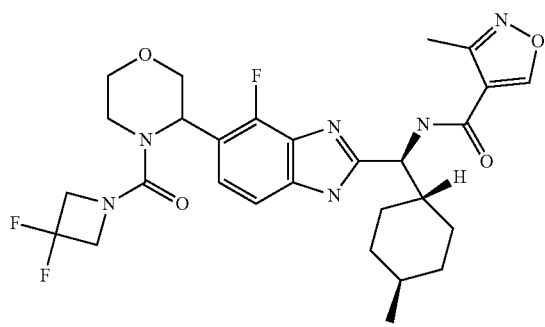

N-[(S)-{5-[4-(3,3-Difluoroazetidine-1-carbonyl)morpholin-3-yl]-4-fluoro-1H-benzimidazol-2-yl}(4-methylcyclohexyl)methyl]-3-methylisoxazole-4-carboxamide (Trans Isomer)

To a solution of Example 155 (0.17 mmol) in DCM (2 mL) was added TFA (0.9 mL). The reaction mixture was stirred overnight, then concentrated in vacuo. The residue was passed through an SCX column, eluting initially with MeOH, then with a 7N solution of NH$_3$ in MeOH. The washings were concentrated in vacuo, then taken up in DCM (3 mL) and stirred with triethylamine (0.05 mL, 0.40 mmol) and Intermediate 230 (70.0 mg, 0.35 mmol). The reaction mixture was stirred at r.t. for 6 h, then additional triethylamine (0.05 mL, 0.40 mmol) and Intermediate 230 (70.0 mg, 0.35 mmol) were added. The reaction mixture was re-treated with triethylamine (0.05 mL, 0.40 mmol) and Intermediate 230 (70.0 mg, 0.35 mmol) on two further occasions at 17 h intervals. A 7N solution of NH$_3$ in MeOH (1.5 mL) was added, and the mixture was stirred vigorously for 16 h, then concentrated in vacuo. The residue was subject to purification by flash column chromatography, eluting with EtOAc/hexanes (0-100% gradient) then MeOH/DCM (0-10% gradient), to furnish the title compound (mixture of diastereomers) (48 mg, 48%). $\delta_H$ (400 MHz, DMSO-d$_6$) 12.79 (s, 1H), 9.46 (s, 1H), 8.97 (s, 1H), 7.37-7.30 (m, 1H), 7.29-7.22 (m, 1H), 5.26 (s, 1H), 5.00 (t, J 8.7 Hz, 1H), 4.39 (q, J 12.5 Hz, 2H), 4.22 (q, J 12.2 Hz, 2H), 4.12 (unresolved dd, J 12.0, 1.2 Hz, 1H), 3.89-3.81 (m, 2H), 3.61-3.46 (m, 2H), 3.38-3.26 (m, 1H), 2.35 (s, 3H), 2.04-1.84 (m, 2H), 1.75-1.67 (m, 1H), 1.66-1.57 (m, 1H), 1.39-1.21 (m, 2H), 1.16-0.98 (m, 2H), 0.96-0.77 (m, 2H), 0.85 (d, J 6.4 Hz, 3H). LCMS (Method 6): [M+H]$^+$ m/z 575, RT 1.85 minutes.

Example 188

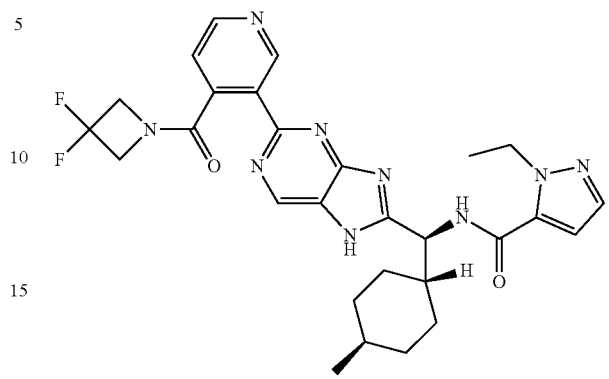

N-[(S)-{2-[4-(3,3-difluoroazetidine-1-carbonyl)pyridin-3-yl]-7H-purin-8-yl}(4-methyl-cyclohexyl)methyl]-2-ethylpyrazole-3-carboxamide (Trans Isomer)

A sealed tube was charged with Intermediate 240 (52 mg, 0.09 mmol) and 3-boronopyridine-4-carboxylic acid (37 mg, 0.22 mmol) in 1,4-dioxane (0.6 mL) and 2M aqueous Na$_2$CO$_3$ solution (0.16 mL, 0.33 mmol). The suspension was sparged with N$_2$ whilst sonicating for 5 minutes. Pd$_2$(dba)$_3$ (2.6 mg, 0.003 mmol) and XPhos (2.2 mg, 0.004 mmol) were added, and the suspension was further sparged with N$_2$ whilst sonicating for 5 minutes. The reaction mixture was sealed and heated at 100° C. for 18 h. The reaction mixture was re-treated four times with 3-boronopyridine-4-carboxylic acid (37 mg, 0.22 mmol), twice with 2M aqueous Na$_2$CO$_3$ solution (0.16 mL, 0.33 mol) and four times with Pd$_2$(dba)$_3$ (2.6 mg, 0.003 mmol) and XPhos (2.2 mg, 0.004 mmol), whilst heating at 110° C. for 60 h. After cooling, the mixture was further diluted with 2M aqueous Na$_2$CO$_3$ solution (2 mL) and extracted with EtOAc (3×5 mL). The pH of the aqueous layer was adjusted to pH 4 using 6M aqueous HCl. The aqueous layer was extracted with 1:1 2-methyltetrahydrofuran/EtOAc (3×5 mL). The combined organic layers were dried over Na$_2$SO$_4$, and the solvent was concentrated in vacuo. The resulting pink solid was purified by flash column chromatography (SNAP Ultra C18 12 g), eluting with water (+0.1% formic acid)/acetonitrile (10-100% gradient). The resulting off-white solid (5.7 mg) was suspended in DMF (1 mL). HATU (7.1 mg, 0.02 mmol) and DIPEA (10 μL, 0.06 mmol) were added, and the reaction mixture was stirred at 20° C. for 10 minutes. 3,3-Difluoroazetidine hydrochloride (1:1) (2.3 mg, 0.017 mmol) was added, and the reaction mixture was stirred for 18 h at 20° C. The reaction mixture was re-treated twice with HATU (10 mg, 0.026 mmol), DIPEA (10 μL, 0.06 mmol) and 3,3-difluoro-azetidine hydrochloride (1:1) (5 mg, 0.038 mmol), whilst stirring at 20° C. for 24 h. The reaction mixture was concentrated in vacuo. The residue was purified by preparative HPLC to afford, after freeze-drying, the title compound (1.0 mg, 1%) as a white solid. $\delta_H$ (500 MHz, CDCl$_3$) 13.41 (br s, 1H), 10.17 (s, 1H), 9.08 (s, 1H), 8.88 (d, J 4.9 Hz, 1H), 7.49 (d, J 2.0 Hz, 1H), 7.43 (d, J 4.9 Hz, 1H), 6.97 (d, J 8.5 Hz, 1H), 6.65 (d, J 2.0 Hz, 1H), 5.33-5.22 (m, 1H), 4.68-4.62 (m, 2H), 4.59 (q, J 7.2 Hz, 2H), 4.36-4.29 (m, 2H), 2.24-2.18 (m, 1H), 1.98-1.89 (m, 1H), 1.82-1.75 (m, 1H), 1.75-1.69

(m, 2H), 1.43 (t, J 7.2 Hz, 3H), 1.34-1.30 (m, 1H), 1.24-1.14 (m, 2H), 1.02-0.93 (m, 2H), 0.88 (d, J 6.5 Hz, 3H). uPLCMS (Method 9): [M+H]+ m/z 564, RT 2.97 minutes.

Example 189

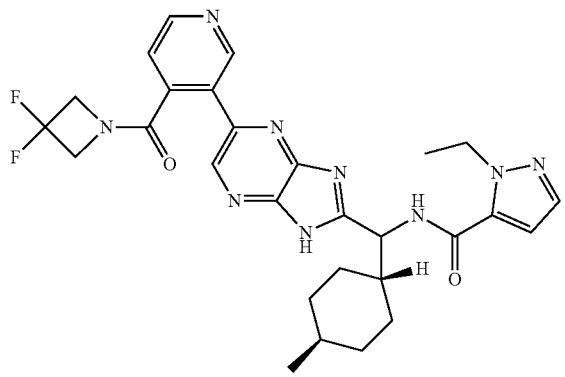 [SMILES: CCn1nccc1C(=O)NC(c1nc2nc(-c3cnccc3C(=O)N3CC(F)(F)C3)cnc2[nH]1)[C@H]1CC[C@H](C)CC1]

N-[(S)-{5-[4-(3,3-Difluoroazetidine-1-carbonyl)pyridin-3-yl]-1H-imidazo[4,5-b]pyrazin-2-yl}(4-methylcyclohexyl)methyl]-2-ethylpyrazole-3-carboxamide (Trans Isomer)

A sealed tube was charged with Intermediate 241 (96 mg, 0.21 mmol), and 3-boronopyridine-4-carboxylic acid (93 mg, 0.5 mmol) in 1,4-dioxane (1 mL) and 2M aqueous sodium carbonate solution (0.37 mL, 0.73 mmol). The suspension was sparged with $N_2$ whilst sonicating for 5 minutes. $Pd_2(dba)_3$ (5.7 mg, 0.06 mmol) and XPhos (5.0 mg, 0.01 mmol) were added, and the suspension was sparged with $N_2$ whilst sonicating for 5 minutes. The reaction mixture was sealed and heated at 100° C. for 18 h. The reaction mixture was re-treated four times with 3-boronopyridine-4-carboxylic acid (93 mg, 0.5 mmol), twice with 2M aqueous sodium carbonate solution (0.37 mL, 0.73 mmol), and four times with $Pd_2(dba)_3$ (5.7 mg, 0.006 mmol) and XPhos (5.0 mg, 0.01 mmol), whilst heating at 110° C. for 60 h. After cooling, the mixture was diluted with 2M aqueous sodium carbonate solution (2 mL) and extracted with EtOAc (3×5 mL). The pH of the aqueous layer was adjusted to pH 4 using 6M HCl. The aqueous layer was extracted with 1:1 2-methyltetrahydrofuran/EtOAc (3×5 mL). The combined organic layers were dried over $Na_2SO_4$, and the solvent was concentrated in vacuo. The resulting off-white solid was separated by flash column chromatography (SNAP Ultra C18 12 g), eluting with water (+0.1% formic acid)/acetonitrile (10-100% gradient). The resulting yellow solid (13 mg) was suspended in DMF (1 mL). HATU (16 mg, 0.042 mmol) and DIPEA (23 μL, 0.13 mmol) were added, and the reaction mixture was stirred at 20° C. for 10 minutes. 3,3-Difluoroazetidine hydrochloride (1:1) (5.1 mg, 0.039 mmol) was added, and the reaction mixture was stirred for 18 h at 20° C. The reaction mixture was re-treated twice with HATU (20 mg, 0.05 mmol), DIPEA (25 μL, 0.143 mmol) and 3,3-difluoroazetidine hydrochloride (1:1) (10 mg, 0.077 mmol), whilst stirring at 20° C. for 24 h. The reaction mixture was concentrated in vacuo. The residue was purified by preparative HPLC to afford, after freeze-drying, the title compound (1.9 mg, 2%) as a cream solid. $\delta_H$ (500 MHz, $CD_3OD$) 9.25 (s, 1H), 8.90 (s, 1H), 8.84 (d, J 5.3 Hz, 1H), 7.80 (d, J 5.2 Hz, 1H), 7.51 (d, J 2.1 Hz, 1H), 6.95 (d, J 2.1 Hz, 1H), 5.15 (d, J 8.6 Hz, 1H), 4.60-4.54 (m, 2H), 4.52-4.46 (m, 2H), 4.39-4.29 (m, 2H), 2.19-2.10 (m, 1H), 2.08-2.01 (m, 1H), 1.85-1.78 (m, 1H), 1.75-1.69 (m, 1H), 1.54-1.45 (m, 1H), 1.40-1.35 (m, 1H), 1.32 (d, J 7.2 Hz, 3H), 1.27-1.19 (m, 2H), 1.09-0.94 (m, 2H), 0.90 (d, J 6.5 Hz, 3H). uPLCMS (Method 9): [M+H]+ m/z 564, RT 2.91 minutes.

Example 190

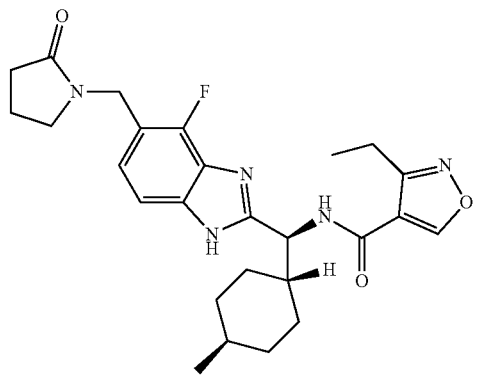 [SMILES: CCc1nocc1C(=O)N[C@H](c1nc2c(F)c(CN3CCCC3=O)ccc2[nH]1)[C@H]1CC[C@H](C)CC1]

3-Ethyl-N-[(S)-{4-fluoro-5-[(2-oxopyrrolidin-1-yl)methyl]-1H-benzimidazol-2-yl}(4-methylcyclohexyl)methyl]isoxazole-4-carboxamide (Trans Isomer)

The title compound (25 mg, 47%), a white solid, was prepared from Intermediate 246 (40 mg, 0.11 mmol) and 3-ethylisoxazole-4-carboxylic acid (19 mg, 0.14 mmol) in accordance with Procedure A, in DCM (2 mL) as solvent. $\delta_H$ (500 MHz, DMSO-$d_6$) 12.70 (br s, 1H), 9.41 (s, 1H), 8.82 (d, J 6.9 Hz, 1H), 7.27 (br s, 1H), 7.04 (dd, J 8.0, 6.8 Hz, 1H), 5.01 (t, J 8.5 Hz, 1H), 4.49 (s, 2H), 3.21 (t, J 7.0 Hz, 2H), 2.81 (qd, J 7.5, 3.6 Hz, 2H), 2.25 (t, J 8.1 Hz, 2H), 2.04-1.93 (m, 1H), 1.93-1.84 (m, 3H), 1.70 (d, J 12.4 Hz, 1H), 1.62 (d, J 12.8 Hz, 1H), 1.41-1.22 (m, 2H), 1.14 (t, J 7.5 Hz, 3H), 1.12-0.99 (m, 2H), 0.95-0.78 (m, 5H). uPLCMS (Method 9): [M+H]+ m/z 482, RT 3.03 minutes.

Examples 191 & 192

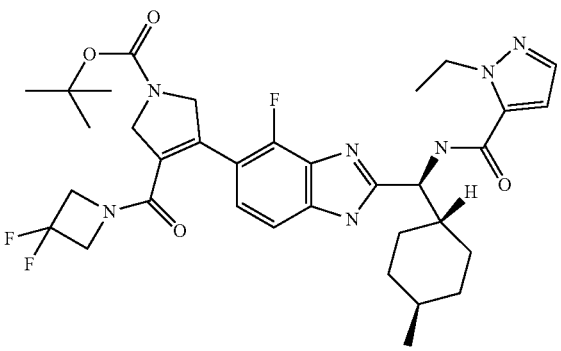

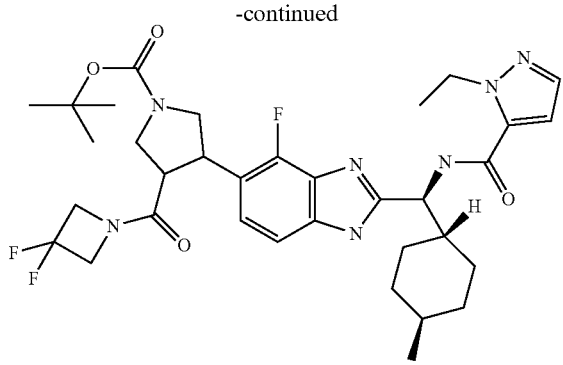

tert-Butyl 3-(3,3-difluoroazetidine-1-carbonyl)-4-(2-{(S)-[(2-ethylpyrazole-3-carbonyl-amino](4-methyl-cyclohexyl)methyl}-4-fluoro-1H-benzimidazol-5-yl)-2,5-dihydro-pyrrole-1-carboxylate (Trans Isomer) (Example 191)

tert-Butyl 3-(3,3-difluoroazetidine-1-carbonyl)-4-(2-{(S)-[(2-ethylpyrazole-3-carbonyl)-amino](4-methylcyclohexyl)methyl}-4-fluoro-1H-benzimidazol-5-yl)pyrrolidine-1-carboxylate (Trans Isomer) (Example 192)

To a solution of Intermediate 249 (553 mg, 0.9 mmol) in EtOH (20 mL) was added 10% Pd/C (20 mg). The reaction mixture was stirred under an atmosphere of hydrogen for 1 week, then filtered through Celite®, washing with EtOAc. The filtrate was concentrated in vacuo. The material was redissolved in EtOH (20 mL), and 10% Pd/C (20 mg) was added. The reaction mixture was again stirred under an atmosphere of hydrogen for a further 2 days, then filtered through Celite®, washing with EtOAc. The filtrate was concentrated in vacuo. The crude material was purified by flash column chromatography, eluting with EtOAc/hexanes (0-100% gradient). The resulting white solid—30% O¹-tert-butyl O³-ethyl 4-(2-{(S)-[(2-ethylpyrazole-3-carbonyl)amino](4-methylcyclohexyl)methyl}-4-fluoro-1H-benzimidazol-5-yl)pyrrolidine-1,3-dicarboxylate (assumed 1:1 mixture of cis isomers of reduced pyrrolidine moiety) and 70% unreduced inseparable Intermediate 249—was taken up in EtOH (4 mL) and treated with LiOH.H₂O (10 mg, 0.40 mmol) in water (1 mL). The reaction mixture was stirred for 2 days, then concentrated in vacuo. The 70:30 mixture respectively of unreduced and reduced carboxylic acids was taken up in DMF (4 mL) and treated with DIPEA (0.36 mL, 2.10 mmol), followed by HATU (195 mg, 0.50 mmol). The reaction mixture was stirred at r.t. for 10 minutes, then 3,3-difluoroazetidine hydrochloride (85.0 mg, 0.80 mmol) was added. The reaction mixture was stirred at r.t. for 6 h, then partitioned between DCM and water. The organic layers were separated, dried over Na₂SO₄ and concentrated in vacuo. The residue was purified by reverse-phase HPLC to yield Example 192 (48 mg, 8% overall) and Example 193 (assumed 1:1 mixture of cis isomers of reduced pyrrolidine moiety) (57 mg, 9% overall) as white solids.

Example 191: $\delta_H$ (400 MHz, DMSO-d$_6$) 12.77 (s, 1H), 8.87 (s, 1H), 7.48 (d, J 2.0 Hz, 1H), 7.39-7.29 (m, 1H), 7.13 (t, J 7.4 Hz, 1H), 7.04 (d, J 2.1 Hz, 1H), 5.02 (t, J 8.6 Hz, 1H), 4.53 (t, J 4.3 Hz, 2H), 4.48-4.35 (m, 4H), 4.31-4.15 (m, 2H), 4.07-3.88 (m, 2H), 2.06 (d, J 12.1 Hz, 1H), 1.90 (d, J 12.7 Hz, 1H), 1.70 (d, J 12.7 Hz, 1H), 1.61 (d, J 13.1 Hz, 1H), 1.44 (d, J 3.3 Hz, 9H), 1.37-1.22 (m, 5H), 1.05 (dtd, J 24.5, 12.2, 3.3 Hz, 2H), 0.95-0.78 (m, 5H). LCMS (Method 6): [M+H]⁺ m/z 670, RT 2.22 minutes.

Example 192: $\delta_H$ (400 MHz, DMSO-d$_6$) 12.74 (s, 1H), 8.83 (s, 1H), 7.47 (d, J 2.0 Hz, 1H), 7.32-7.24 (m, 1H), 7.17 (t, J 7.4 Hz, 1H), 7.03 (t, J 1.8 Hz, 1H), 4.99 (t, J 8.5 Hz, 1H), 4.63 (q, J 12.2 Hz, 1H), 4.44 (q, J 7.1 Hz, 2H), 4.30-4.03 (m, 3H), 3.93-3.80 (m, 2H), 3.75 (t, J 8.9 Hz, 2H), 3.38 (d, J 8.7 Hz, 2H), 2.07-1.98 (m, 1H), 1.89 (d, J 12.6 Hz, 1H), 1.70 (d, J 12.7 Hz, 1H), 1.60 (d, J 12.6 Hz, 1H), 1.41 (d, J 11.2 Hz, 9H), 1.35-1.20 (m, 5H), 1.13-0.97 (m, 2H), 0.94-0.76 (m, 5H). LCMS (Method 6): [M+H]⁺ m/z 672, RT 2.18 minutes.

Example 193

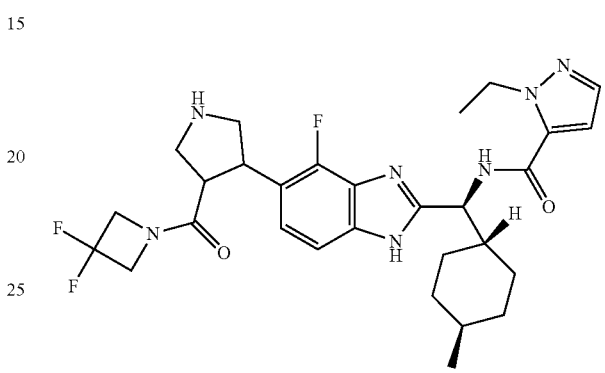

N-[(S)-{5-[4-(3,3-Difluoroazetidine-1-carbonyl)pyrrolidin-3-yl]-4-fluoro-1H-benzimidazol-2-yl}(4-methylcyclohexyl)methyl]-2-ethylpyrazole-3-carboxamide (Trans Isomer)

Example 192 (53 mg, 0.10 mmol) was dissolved in DCM (1 mL, 15.6 mmol), and 4M HCl in 1,4-dioxane (0.1 mL, 0.40 mmol) was added. The reaction mixture was stirred at r.t. for 16 h, then flashed down an SCX column, eluting with a 7N solution of NH₃ in MeOH, to give the title compound (1:1 mixture of cis isomers of pyrrolidine moiety) (45 mg, quantitative) as an off-white solid. $\delta_H$ (400 MHz, CD₃OD) 7.50 (d, J 2.1 Hz, 1H), 7.37 (d, J 8.4 Hz, 1H), 7.26 (dd, J 8.4, 6.4 Hz, 1H), 6.92 (q, J 2.0, 1.5 Hz, 1H), 5.07 (dd, J 8.7, 2.6 Hz, 1H), 4.55-4.38 (m, 3H), 4.32-4.12 (m, 2H), 3.84 (q, J 8.8 Hz, 1H), 3.70-3.58 (m, 1H), 3.49-3.42 (m, 1H), 3.39-3.23 (m, 2H), 3.19 (dd, J 8.6, 6.6 Hz, 1H), 3.08 (t, J 10.5 Hz, 1H), 2.08-1.96 (m, 2H), 1.82-1.75 (m, 1H), 1.69 (d, J 13.0 Hz, 1H), 1.44-1.30 (m, 5H), 1.26-1.13 (m, 2H), 1.06-0.86 (m, 5H). LCMS (Method 5): [M+H]⁺ m/z 572, RT 1.14 minutes.

Examples 194 & 195

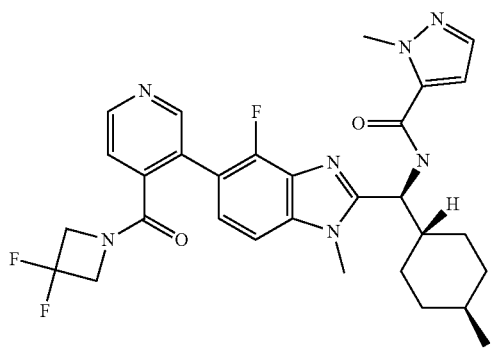

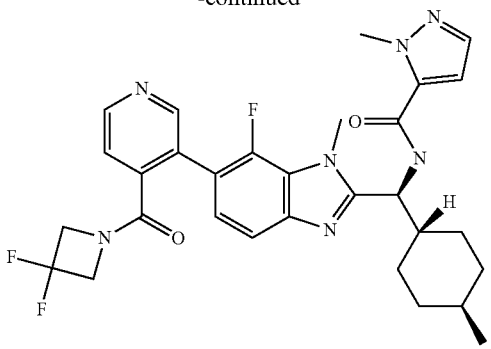

N-[(S)-{5-[4-(3,3-Difluoroazetidine-1-carbonyl)
pyridin-3-yl]-4-fluoro-1-methyl-benzimidazol-2-yl}
(4-methylcyclohexyl)methyl]-2-methylpyrazole-3-
carboxamide (Trans Isomer) (Example 194)

N-[(S)-{6-[4-(3,3-Difluoroazetidine-1-carbonyl)
pyridin-3-yl]-7-fluoro-1-methyl-benzimidazol-2-yl}
(4-methylcyclohexyl)methyl]-2-methylpyrazole-3-
carboxamide (Trans Isomer) (Example 195)

To Intermediate 250 (mixture of isomers, 140 mg, 0.30 mmol), under nitrogen, were added bis(pinacolato)diboron (92 mg, 0.36 mmol), Pd(dppf)Cl$_2$.DCM (13 mg, 0.016 mmol), potassium acetate (90 mg, 0.92 mmol) and 1,4-dioxane (3 mL). The mixture was degassed and placed under nitrogen, then heated at 100° C. with stirring for 18 h. (3-Bromopyridin-4-yl)(3,3-difluoroazetidin-1-yl)methanone (75% purity, 132 mg, 0.35 mmol) and saturated aqueous sodium carbonate solution (1 mL) were added. The mixture was heated at 100° C. overnight, then partitioned between EtOAc and brine, dried (sodium sulfate) and concentrated in vacuo. The residue was purified by chromatography (silica, 0-100% EtOAc in isohexane) to give the title compounds (1:1 mixture) (5.0 mg, 5.7%) as a white solid. $\delta_H$ (300 MHz, DMSO-d$_6$) 9.06 (dd, J 24.9, 8.2 Hz, 1H), 8.78-8.65 (m, 2H), 7.64 (d, J 4.9 Hz, 1H), 7.53 (dd, J 8.4, 4.0 Hz, 1H), 7.45 (dd, J 2.2, 1.1 Hz, 1H), 7.24 (ddd, J 18.7, 8.2, 6.9 Hz, 1H), 7.08 (t, J 2.2 Hz, 1H), 5.11 (t, J 9.1 Hz, 1H), 4.41 (dq, J 25.0, 12.7, 12.1 Hz, 4H), 4.03 (3 s, 4.5H, 3-NMe), 3.96 (s, 1.5H, 1-NMe), 2.33-2.14 (m, 1H), 2.04 (m, 1H), 1.75 (m, 1H), 1.62 (m, 1H), 1.47-0.69 (m, 9H). LCMS (pH 10): [M+H]$^+$ 580.4, RT 1.90 and 1.93 minutes (97% purity, ~1:1).

The invention claimed is:

1. A compound of formula (I) or an N-oxide thereof, or a pharmaceutically acceptable salt thereof:

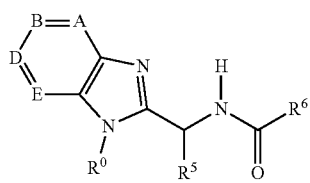

(I)

wherein

A represents C—R$^1$ or N;

B represents C—R$^2$ or N;

D represents C—R$^3$ or N;

E represents C—R$^4$ or N;

R$^0$ represents hydrogen or C$_{1-6}$ alkyl;

R$^1$, R$^2$, R$^3$ and R$^4$ independently represent hydrogen, halogen, cyano, nitro, hydroxy, trifluoromethyl, trifluoromethoxy, —OR$^a$, —SR$^a$, —SOR$^a$, —SO$_2$R$^a$, —NR$^b$R$^c$, —NR$^c$COR$^d$, —NR$^c$CO$_2$R$^d$, —NHCONR$^b$R$^c$, —NR$^c$SO$_2$R$^e$, —NHSO$_2$NR$^b$R$^c$, —N=S(O)R$^b$R$^c$, —COR$^d$, —CO$_2$R$^d$, —CONR$^b$R$^c$, —CON(OR$^a$)R$^b$, —SO$_2$NR$^b$R$^c$ or —S(O)(NR$^c$)R$^a$; or C$_{1-6}$ alkyl, C$_{2-6}$ alkenyl, C$_{2-6}$ alkynyl, C$_{3-9}$ cycloalkyl, C$_{3-9}$ cycloalkyl(C$_{1-6}$)alkyl, C$_{4-9}$ cycloalkenyl, aryl, aryl(C$_{1-6}$)alkyl, C$_{3-7}$ heterocycloalkyl, C$_{3-7}$ heterocycloalkyl(C$_{1-6}$)alkyl, C$_{3-7}$ hetero-cycloalkenyl, C$_{4-9}$ heterobicycloalkyl, heteroaryl or heteroaryl (C$_{1-6}$)alkyl, any of which groups may be optionally substituted by one or more substituents;

R$^5$ represents C$_{3-9}$ cycloalkyl, C$_{4-12}$ bicycloalkyl, C$_{5-9}$ spirocycloalkyl(C$_{1-6}$)alkyl, or C$_{7-13}$ dispirocycloalkyl, any of which groups is optionally substituted by one or more substituents;

R$^6$ represents —OR$^{6a}$; or R$^6$ represents C$_{1-6}$ alkyl, aryl or heteroaryl, any of which groups may be optionally substituted by one, two or three substituents independently selected from C$_{1-6}$ alkyl, tetrahydropyranyl and di(C$_{1-6}$)alkylsulfoximinyl;

R$^{6a}$ represents C$_{3-9}$ cycloalkyl, which group may be optionally substituted by one or more substituents;

R$^a$ represents trifluoromethyl; or R$^a$ represents C$_{1-6}$ alkyl, C$_{3-9}$ cycloalkyl, C$_{3-9}$ cycloalkyl(C$_{1-6}$)alkyl, aryl, aryl(C$_{1-6}$)alkyl, C$_{3-7}$ heterocycloalkyl, C$_{3-7}$ heterocycloalkyl-(C$_{1-6}$)alkyl, heteroaryl or heteroaryl (C$_{1-6}$)alkyl, any of which groups may be optionally substituted by one or more substituents;

R$^b$ and R$^c$ independently represent hydrogen or trifluoromethyl; or C$_{1-6}$ alkyl, C$_{3-9}$ cycloalkyl, C$_{3-9}$ cycloalkyl(C$_{1-6}$)alkyl, aryl, aryl(C$_{1-6}$)alkyl, C$_{3-7}$ heterocycloalkyl, C$_{3-7}$ heterocycloalkyl(C$_{1-6}$)alkyl, heteroaryl or heteroaryl(C$_{1-6}$)alkyl, any of which groups may be optionally substituted by one or more substituents; or R$^b$ and R$^c$, when taken together with the nitrogen atom to which they are both attached, represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents;

R$^d$ represents hydrogen; or R$^d$ represents C$_{1-6}$ alkyl, C$_{3-9}$ cycloalkyl, aryl, C$_{3-7}$ heterocycloalkyl or heteroaryl, any of which groups may be optionally substituted by one or more substituents; and R$^e$ represents C$_{1-6}$ alkyl, aryl or heteroaryl, any of which groups may be optionally substituted by one or more substituents.

2. A compound as claimed in claim 1 represented by formula (I-1), (I-2), (I-3), (I-4), (I-5) or (I-6) or an N-oxide thereof, or a pharmaceutically acceptable salt thereof:

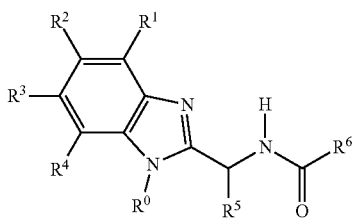

(I-1)

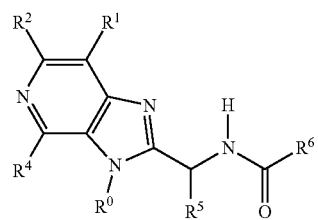

(I-2)

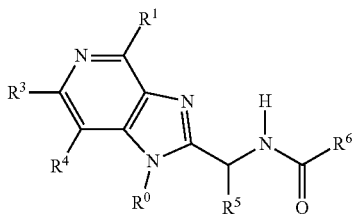

(I-3)

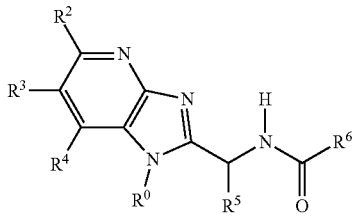

(I-4)

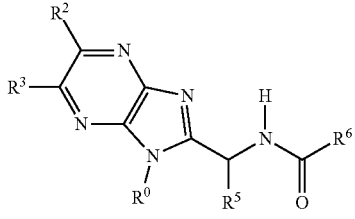

(I-5)

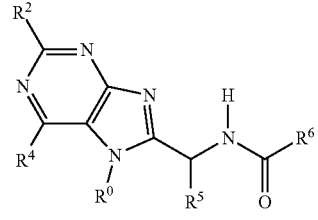

(I-6)

wherein $R^0$, $R^1$, $R^2$, $R^3$, $R^4$, $R^5$ and $R^6$ are as defined in claim 1.

3. A compound as claimed in claim 1 wherein $R^1$ represents hydrogen, halogen, cyano or —$OR^a$, in which $R^a$ is as defined in claim 1.

4. A compound as claimed in claim 1 wherein $R^3$ represents hydrogen, halogen or —$NR^bR^c$, in which $R^b$ and $R^c$ are as defined in claim 1; or $R^3$ represents $C_{1-6}$ alkyl, aryl, $C_{3-7}$ heterocycloalkyl, $C_{3-7}$ heterocycloalkyl($C_{1-6}$)alkyl or heteroaryl, any of which groups may be optionally substituted by one, two or three substituents independently selected from $C_{1-6}$ alkylsulfonyl, $C_{2-6}$ alkylcarbonyl, $C_{2-6}$ alkoxycarbonyl, di($C_{1-6}$)alkylaminocarbonyl and difluoroazetidinylcarbonyl.

5. A compound as claimed in claim 1 wherein $R^4$ represents hydrogen, halogen or —$OR^a$, in which $R^a$ is as defined in claim 1.

6. A compound as claimed in claim 1 represented by formula (IIA) or an N-oxide thereof, or a pharmaceutically acceptable salt thereof:

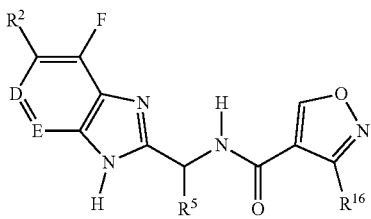

(IIA)

wherein $R^{16}$ represents methyl or ethyl; and

D, E, $R^2$ and $R^5$ are as defined in claim 1.

7. A compound as claimed in claim 1 represented by formula (IIB) or an N-oxide thereof, or a pharmaceutically acceptable salt thereof:

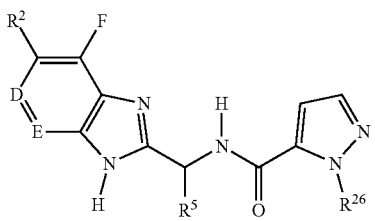

(IIB)

wherein $R^{26}$ represents methyl or ethyl; and

D, E, $R^2$ and $R^5$ are as defined in claim 1.

8. A compound as claimed in claim 1 wherein $R^2$ represents hydrogen, cyano, —$OR^a$, —$SOR^a$, —$NR^bR^c$, —$NR^c$-$COR^d$ or —$N=S(O)R^bR^c$, in which $R^a$, $R^b$, $R^c$ and $R^d$ are as defined in claim 1; or $R^2$ represents $C_{1-6}$ alkyl, aryl, aryl($C_{1-6}$)-alkyl, $C_{3-7}$ heterocycloalkyl, $C_{3-7}$ heterocycloalkyl($C_{1-6}$)alkyl, $C_{3-7}$ heterocycloalkenyl, heteroaryl or heteroaryl($C_{1-6}$)alkyl, any of which groups may be optionally substituted by one, two or three substituents independently selected from halogen, cyano, $C_{1-6}$ alkyl, oxetanyl, oxadiazolyl, ($C_{1-6}$)alkyloxadiazolyl, hydroxy, oxo, ($C_{1-6}$)alkyl (imino)sulfinyl, $C_{1-6}$ alkylsulfonyl, $C_{2-6}$ alkylcarbonylamino, $C_{1-6}$ alkylsulfonylamino, $C_{2-6}$ alkylcarbonyl, hydroxy($C_{1-6}$)alkylcarbonyl, carboxy, $C_{2-6}$ alkoxycarbonyl, aminocarbonyl, $C_{1-6}$ alkyl-aminocarbonyl, chloro($C_{1-6}$)alkylaminocarbonyl, di($C_{1-6}$)alkylaminocarbonyl, azetidinylcarbonyl, hydroxyazetidinylcarbonyl, difluoroazetidinylcarbonyl, (hydroxy)(trifluoro-methyl)azetidinylcarbonyl, (hydroxy)(methyl)azetidinylcarbonyl, morpholinylcarbonyl and ($C_{1-6}$)alkylpyrazolylcarbonyl.

9. A compound as claimed in claim 1 wherein the optional substituents on $R^5$ are one, two or three substituents independently selected from halogen, cyano, $C_{1-6}$ alkyl, trifluoromethyl, phenyl, hydroxy, $C_{1-6}$ alkoxy and aminocarbonyl.

10. A compound as claimed in claim 1 which is
N-[Cyclooctyl(4-methoxy-1H-benzimidazol-2-yl)
methyl]-3-methylisoxazole-4-carboxamide;
N-[Cyclooctyl(4-fluoro-1H-benzimidazol-2-yl)methyl]-
3-methylisoxazole-4-carboxamide;
N-{Cyclooctyl[4-fluoro-5-(tetrahydropyran-4-yl)-1H-
benzimidazol-2-yl]methyl}-3-methylisoxazole-4-carboxamide;
N-{Cyclooctyl[4-fluoro-5-(4-methylpiperazin-1-yl)-1H-
benzimidazol-2-yl]methyl}-3-methylisoxazole-4-carboxamide;
N-[Cyclooctyl(4,7-difluoro-1H-benzimidazol-2-yl)
methyl]-3-methylisoxazole-4-carboxamide;
N-[Cyclooctyl(4-fluoro-1H-benzimidazol-2-yl)methyl]-
5-methyl-1-(tetrahydropyran-4-yl)pyrazole-4-carboxamide;
N-[(4-Fluoro-1H-benzimidazol-2-yl)(trans-4-methylcyclohexyl)methyl]-3-methyl-isoxazole-4-carboxamide;
N-[(4-Chloro-1H-benzimidazol-2-yl)(cyclooctyl)
methyl]-3-methylisoxazole-4-carboxamide;
N-[Cyclooctyl(4-fluoro-1H-benzimidazol-2-yl)methyl]-
2-methylpyrazole-3-carboxamide;
N-[Cyclooctyl(4-methoxy-1H-imidazolo[4,5-c]pyridin-
2-yl)methyl]-3-methylisoxazole-4-carboxamide;
N-[Cyclooctyl(4-fluoro-5-methoxy-1H-benzimidazol-2-
yl)methyl]-3-methylisoxazole-4-carboxamide;
N-[(4-Cyano-1H-benzimidazol-2-yl)(cyclooctyl)methyl]-
3-methylisoxazole-4-carboxamide;
N-{Cyclooctyl[5-(tetrahydropyran-4-yl)-1H-benzimidazol-2-yl]methyl}-3-methyl-isoxazole-4-carboxamide;
N-{Cyclooctyl[4-fluoro-5-(1H-pyrazol-5-yl)-1H-benzimidazol-2-yl]methyl}-3-methyl-isoxazole-4-carboxamide;
N-{[5-(Benzenesulfinyl)-4-fluoro-1H-benzimidazol-2-
yl](cyclooctyl)methyl}-3-methyl-isoxazole-4-carboxamide;
tert-Butyl 2-(2-{cyclooctyl[(3-methylisoxazole-4-carbonyl)amino]methyl}-4-fluoro-1H-benzimidazol-5-yl)
acetate;
tert-Butyl rel-(2S)-2-(4-acetylpiperazin-1-yl)-2-(4-fluoro-2-{rel-(S)-cyclooctyl[(3-methyl-isoxazole-4-carbonyl)amino]methyl}-1H-benzimidazol-5-yl)acetate;
tert-Butyl rel-(2R)-2-(4-acetylpiperazin-1-yl)-2-(4-fluoro-2-{rel-(R)-cyclooctyl[(3-methylisoxazole-4-carbonyl)amino]methyl}-1H-benzimidazol-5-yl)acetate;
tert-Butyl 3-(2-{cyclooctyl[(3-methylisoxazole-4-carbonyl)amino]methyl}-4-fluoro-1H-benzimidazol-5-yl)
propanoate;
tert-Butyl 2-(2-{cyclooctyl[(3-methylisoxazole-4-carbonyl)amino]methyl}-4-fluoro-1H-benzimidazol-5-yl)
benzoate;
N-{Cyclooctyl[4-(cyclopentoxy)-1H-benzimidazol-2-yl]
methyl}-3-methylisoxazole-4-carboxamide;
N-{Cyclooctyl[7-methoxy-6-(tetrahydropyran-4-yl)-1H-
benzimidazol-2-yl]methyl}-3-methylisoxazole-4-carboxamide;
N-{Cyclooctyl[4-fluoro-7-methoxy-5-(tetrahydropyran-
4-yl)-1H-benzimidazol-2-yl]-methyl}-3-methylisoxazole-4-carboxamide;
N-{Cyclooctyl[4-fluoro-6-(morpholin-4-yl)-1H-benzimidazol-2-yl]methyl}-3-methyl-isoxazole-4-carboxamide;
N-[{5-[Cyano(pyridin-3-yl)methyl]-4-fluoro-1H-benzimidazol-2-yl}(cyclooctyl)methyl]-3-methylisoxazole-4-carboxamide;
N-(Cyclooctyl{4-fluoro-5-[1-(pyridin-4-yl)ethyl]-1H-
benzimidazol-2-yl}methyl)-2-methylpyrazole-3-carboxamide;
N-[Cyclooctyl(4-fluoro-5-{[1-(methylsulfonyl)piperidin-
4-yl]oxy}-1H-benzimidazol-2-yl)methyl]-3-methyl-isoxazole-4-carboxamide;
N-{Cyclooctyl[4-fluoro-5-(morpholin-4-yl)-1H-benzimidazol-2-yl]methyl}-3-methyl-isoxazole-4-carboxamide;
tert-Butyl 6-(2-{cyclooctyl[(3-methylisoxazole-4-carbonyl)amino]methyl}-4-fluoro-1H-benzimidazol-5-yl)-3,4-dihydro-2H-pyridine-1-carboxylate;
tert-Butyl 2-(2-{cyclooctyl[(3-methylisoxazole-4-carbonyl)amino]methyl}-4-fluoro-1H-benzimidazol-5-yl)piperidine-1-carboxylate;
N-[Cyclooctyl(4-fluoro-5-{[1-(methylsulfonyl)piperidin-
4-yl]amino}-1H-benzimidazol-2-yl)methyl]-3-methyl-isoxazole-4-carboxamide;
tert-Butyl 4-[(2-{cyclooctyl[(2-methylpyrazole-3-carbonyl)amino]methyl}-4-fluoro-1H-benzimidazol-5-yl)
methyl]piperazine-1-carboxylate;
N-[Cyclooctyl(4,7-difluoro-6-{[4-(methylsulfonyl)piperazin-1-yl]methyl}-1H-benzimidazol-2-yl)methyl]-3-methylisoxazole-4-carboxamide;
N-[Cyclooctyl(4,7-difluoro-6-{[4-(methylsulfonyl)piperazin-1-yl]methyl}-1H-benzimidazol-2-yl)methyl]-2-ethylpyrazole-3-carboxamide;
N-[(S)-Cyclooctyl(4,7-difluoro-6-{[4-(methylsulfonyl)
piperazin-1-yl]methyl}-1H-benzimidazol-2-yl)
methyl]-2-ethylpyrazole-3-carboxamide;
N-[(R)-Cyclooctyl(4,7-difluoro-6-{[4-(methylsulfonyl)
piperazin-1-yl]methyl}-1H-benzimidazol-2-yl)
methyl]-2-ethylpyrazole-3-carboxamide;
N-[Cyclooctyl(4-fluoro-6-{[4-(methylsulfonyl)piperazin-
1-yl]methyl}-1H-benzimidazol-2-yl)methyl]-3-methylisoxazole-4-carboxamide;
N-[{6-[(4-Acetylpiperazin-1-yl)methyl]-4-fluoro-1H-
benzimidazol-2-yl}(cyclooctyl)-methyl]-3-methyl-isoxazole-4-carboxamide;
tert-Butyl 2-(2-{cyclooctyl[(3-methylisoxazole-4-carbonyl)amino]methyl}-4-fluoro-1H-benzimidazol-5-yl)
pyrrolidine-1-carboxylate;
tert-Butyl 5-(2-{cyclooctyl[(3-methylisoxazole-4-carbonyl)amino]methyl}-4-fluoro-1H-benzimidazol-5-yl)-2,3-dihydro-1,4-oxazine-4-carboxylate;
tert-Butyl 3-(2-{cyclooctyl[(3-methylisoxazole-4-carbonyl)amino]methyl}-4-fluoro-1H-benzimidazol-5-yl)-6,7-dihydro-5H-1,4-oxazepine-4-carboxylate;
tert-Butyl 3-(2-{cyclooctyl[(3-methylisoxazole-4-carbonyl)amino]methyl}-4-fluoro-1H-benzimidazol-5-yl)
morpholine-4-carboxylate;
tert-Butyl 3-(2-{cyclooctyl[(3-methylisoxazole-4-carbonyl)amino]methyl}-4-fluoro-1H-benzimidazol-5-yl)-1,4-oxazepane-4-carboxylate;
Ethyl 2-(2-{cyclooctyl[(3-methylisoxazole-4-carbonyl)
amino]methyl}-4-fluoro-1H-benzimidazol-5-yl)-2-phenylacetate;
tert-Butyl 3-(2-{cyclooctyl[(3-methylisoxazole-4-carbonyl)amino]methyl}-7-fluoro-3H-benzimidazol-5-yl)
propanoate;
3-(2-{Cyclooctyl[(3-methylisoxazole-4-carbonyl)amino]
methyl}-4-fluoro-1H-benzimidazol-5-yl)propanoic
acid;
N-(Cyclooctyl{5-[3-(dimethylamino)-3-oxopropyl]-4-fluoro-1H-benzimidazol-2-yl}-methyl)-3-methylisoxazole-4-carboxamide;

- N-(Cyclooctyl{4-fluoro-5-[3-(methylamino)-3-oxopropyl]-1H-benzimidazol-2-yl}-methyl)-3-methylisoxazole-4-carboxamide;
- N-{Cyclooctyl[4,6-difluoro-5-(tetrahydropyran-4-yl)-1H-benzimidazol-2-yl]methyl}-3-methylisoxazole-4-carboxamide;
- N-{Cyclooctyl[4,7-difluoro-5-(tetrahydropyran-4-yl)-1H-benzimidazol-2-yl]methyl}-3-methylisoxazole-4-carboxamide;
- Ethyl 2-(2-{cyclooctyl[(3-methylisoxazole-4-carbonyl)amino]methyl}-4-fluoro-1H-benzimidazol-5-yl)-2-(pyridin-4-yl)acetate;
- N-(Cyclooctyl{4-fluoro-5-[2-hydroxy-1-(pyridin-4-yl)ethyl]-1H-benzimidazol-2-yl}-methyl)-3-methylisoxazole-4-carboxamide;
- N-[{5-[Cyano(pyridin-4-yl)methyl]-4-fluoro-1H-benzimidazol-2-yl}(cyclooctyl)methyl]-3-methylisoxazole-4-carboxamide;
- N-[Cyclooctyl(7-fluoro-4-methoxy-1H-benzimidazol-2-yl)methyl]-3-methylisoxazole-4-carboxamide;
- N-{Cyclooctyl[4-fluoro-5-(pyridin-4-yloxy)-1H-benzimidazol-2-yl]methyl}-3-methyl-isoxazole-4-carboxamide;
- N-{Cyclooctyl[4-fluoro-5-(tetrahydropyran-4-yloxy)-1H-benzimidazol-2-yl]methyl}-3-methylisoxazole-4-carboxamide;
- N-{Cyclooctyl[4-fluoro-5-(oxetan-3-yloxy)-1H-benzimidazol-2-yl]methyl}-3-methyl-isoxazole-4-carboxamide;
- N-{Cyclooctyl[6-fluoro-4-(tetrahydropyran-4-yloxy)-1H-benzimidazol-2-yl]methyl}-3-methylisoxazole-4-carboxamide;
- N-{Cyclooctyl[4-fluoro-5-(pyridazin-4-yloxy)-1H-benzimidazol-2-yl]methyl}-3-methyl-isoxazole-4-carboxamide;
- N-{Cyclooctyl[4-fluoro-5-(tetrahydropyran-4-ylamino)-1H-benzimidazol-2-yl]methyl}-3-methylisoxazole-4-carboxamide;
- Methyl (2S)-1-(2-{cyclooctyl[(3-methylisoxazole-4-carbonyl)amino]methyl}-4-fluoro-1H-benzimidazol-5-yl)pyrrolidine-2-carboxylate;
- Methyl (2R)-1-(2-{cyclooctyl[(3-methylisoxazole-4-carbonyl)amino]methyl}-4-fluoro-1H-benzimidazol-5-yl)pyrrolidine-2-carboxylate;
- Methyl 1-(2-{cyclooctyl[(3-methylisoxazole-4-carbonyl)amino]methyl}-4-fluoro-1H-benzimidazol-5-yl)piperidine-3-carboxylate;
- Methyl 1-(2-{cyclooctyl[(3-methylisoxazole-4-carbonyl)amino]methyl}-4-fluoro-1H-benzimidazol-5-yl)piperidine-2-carboxylate;
- N-{Cyclooctyl[4-fluoro-6-(tetrahydropyran-4-ylamino)-1H-benzimidazol-2-yl]methyl}-3-methylisoxazole-4-carboxamide;
- N-[(S)-{5-[(4-Acetylpiperazin-1-yl)methyl]-4-fluoro-1H-benzimidazol-2-yl}(4-methyl-cyclohexyl)methyl]-2-ethylpyrazole-3-carboxamide;
- N-[(S)-{5-[2-(Dimethylcarbamoyl)phenyl]-4-fluoro-1H-benzimidazol-2-yl}(4-methyl-cyclohexyl)methyl]-2-ethylpyrazole-3-carboxamide;
- N-(Cyclooctyl{5-[2-(dimethylcarbamoyl)phenyl]-4-fluoro-1H-benzimidazol-2-yl}-methyl)-2-ethylpyrazole-3-carboxamide;
- Ethyl 3-(2-{cyclooctyl[(2-ethylpyrazole-3-carbonyl)amino]methyl}-4-fluoro-1H-benzimidazol-5-yl)pyridine-4-carboxylate;
- N-{[5-(7-Acetyl-6,8-dihydro-5H-[1,2,4]triazolo[4,3-a]pyrazin-3-yl)-4-fluoro-1H-benzimidazol-2-yl](cyclooctyl)methyl]-2-ethylpyrazole-3-carboxamide;
- 2-Ethyl-N-{(S)-[4-fluoro-5-(tetrahydropyran-3-yl)-1H-benzimidazol-2-yl](4-methyl-cyclohexyl)methyl}pyrazole-3-carboxamide;
- N-[(S)-{5-[4-(Dimethylcarbamoyl)-5-fluoropyridin-3-yl]-4-fluoro-1H-benzimidazol-2-yl}(4-methylcyclohexyl)methyl]-3-ethylisoxazole-4-carboxamide;
- N-[(S)-{5-[4-(Dimethylcarbamoyl)pyridin-3-yl]-4-fluoro-1H-benzimidazol-2-yl}(4-methylcyclohexyl)methyl]-3-ethylisoxazole-4-carboxamide;
- N-[(S)-{5-[4-(Dimethylcarbamoyl)-1-oxopyridin-3-yl]-4-fluoro-1H-benzimidazol-2-yl}-(4-methylcyclohexyl)methyl]-3-ethylisoxazole-4-carboxamide;
- N-[(S)-{5-[3-(Dimethylcarbamoyl)pyridin-2-yl]-4-fluoro-1H-benzimidazol-2-yl}(4-methylcyclohexyl)methyl]-3-ethylisoxazole-4-carboxamide;
- Ethyl 5-(2-{(S)-[(2-ethylpyrazole-3-carbonyl)amino](4-methylcyclohexyl)methyl}-4-fluoro-1H-benzimidazol-5-yl)-3,6-dihydro-2H-pyran-4-carboxylate;
- N-[(S)-{5-[4-(Dimethylcarbamoyl)-3,6-dihydro-2H-pyran-5-yl]-4-fluoro-1H-benzimidazol-2-yl}(4-methylcyclohexyl)methyl]-3-ethylisoxazole-4-carboxamide;
- N-[(S)-{5-[4-(Dimethylcarbamoyl)-3,6-dihydro-2H-pyran-5-yl]-4-fluoro-1H-benzimidazol-2-yl}(4-methylcyclohexyl)methyl]-2-ethylpyrazole-3-carboxamide;
- Ethyl 3-(2-{(S)-[(2-ethylpyrazole-3-carbonyl)amino](4-methylcyclohexyl)methyl}-4-fluoro-3H-benzimidazol-5-yl)tetrahydropyran-4-carboxylate;
- N-[(S)-{5-[4-(Dimethylcarbamoyl)tetrahydropyran-3-yl]-4-fluoro-1H-benzimidazol-2-yl}(4-methylcyclohexyl)methyl]-2-ethylpyrazole-3-carboxamide;
- Methyl 4-(2-{(S)-[(3-ethylisoxazole-4-carbonyl)amino](4-methylcyclohexyl)methyl}-4-fluoro-1H-benzimidazol-5-yl)tetrahydrofuran-3-carboxylate;
- 4-(2-{(S)-[(3-Ethylisoxazole-4-carbonyl)amino](4-methylcyclohexyl)methyl}-4-fluoro-1H-benzimidazol-5-yl)tetrahydrofuran-3-carboxylic acid;
- N-[(S)-{5-[4-(Dimethylcarbamoyl)tetrahydrofuran-3-yl]-4-fluoro-1H-benzimidazol-2-yl}-(4-methylcyclohexyl)methyl]-3-ethylisoxazole-4-carboxamide;
- N-[(S)-{5-[4-(3,3-Difluoroazetidine-1-carbonyl)tetrahydrofuran-3-yl]-4-fluoro-1H-benzimidazol-2-yl}(4-methylcyclohexyl)methyl]-3-ethylisoxazole-4-carboxamide;
- Ethyl 4-(2-{(S)-[(3-ethylisoxazole-4-carbonyl)amino](4-methylcyclohexyl)methyl}-4-fluoro-1H-benzimidazol-5-yl)-1-(methylsulfonyl)pyrrolidine-3-carboxylate;
- Ethyl 1-acetyl-4-(2-{(S)-[(3-ethylisoxazole-4-carbonyl)amino](4-methylcyclohexyl)-methyl}-4-fluoro-1H-benzimidazol-5-yl)pyrrolidine-3-carboxylate;
- Ethyl 2-(2-{cyclooctyl[(2-ethylpyrazole-3-carbonyl)amino]methyl}-4-fluoro-1H-benzimidazol-5-yl)-2-(pyridin-3-yl)acetate;
- Ethyl 2-(2-{cyclooctyl[(2-ethylpyrazole-3-carbonyl)amino]methyl}-4-fluoro-1H-benzimidazol-5-yl)-2-(pyridin-4-yl)acetate;
- N-{Cyclooctyl[4-fluoro-5-(pyridin-4-ylmethyl)-1H-benzimidazol-2-yl]methyl}-3-methyl-isoxazole-4-carboxamide;
- N-[{5-[2-Amino-2-oxo-1-(pyridin-4-yl)ethyl]-4-fluoro-1H-benzimidazol-2-yl}-(cyclooctyl)methyl]-2-ethylpyrazole-3-carboxamide;

N-(Cyclooctyl{4-fluoro-5-[(5-methyl-1,3,4-oxadiazol-2-yl)(pyridin-4-yl)methyl]-1H-benzimidazol-2-yl}methyl)-2-ethylpyrazole-3-carboxamide;

N-(Cyclooctyl{4-fluoro-5-[(5-methyl-1,3,4-oxadiazol-2-yl)(pyridin-4-yl)methyl]-1H-benzimidazol-2-yl}methyl)-3-methylisoxazole-4-carboxamide;

tert-Butyl 3-(2-{(S)-[(3-ethylisoxazole-4-carbonyl)amino](4-methylcyclohexyl)methyl}-4-fluoro-1H-benzimidazol-5-yl)morpholine-4-carboxylate;

tert-Butyl (3S)-3-(2-{(S)-[(3-ethylisoxazole-4-carbonyl)amino](4-methylcyclohexyl)-methyl}-4-fluoro-1H-benzimidazol-5-yl)morpholine-4-carboxylate;

tert-Butyl (3R)-3-(2-{(S)-[(3-ethylisoxazole-4-carbonyl)amino](4-methylcyclohexyl)-methyl}-4-fluoro-1H-benzimidazol-5-yl)morpholine-4-carboxylate;

3-Ethyl-N-[(S)-{4-fluoro-5-[4-(2-hydroxyacetyl)morpholin-3-yl]-1H-benzimidazol-2-yl}-(4-methylcyclohexyl)methyl]isoxazole-4-carboxamide;

tert-Butyl 2-(2-{(S)-[(2-ethylpyrazole-3-carbonyl)amino](4-methylcyclohexyl)methyl}-4-fluoro-1H-benzimidazol-5-yl)piperidine-1-carboxylate;

2-Ethyl-N-[{4-fluoro-5-[1-(2-hydroxyacetyl)piperidin-2-yl]-1H-benzimidazol-2-yl}(4-methylcyclohexyl)methyl]pyrazole-3-carboxamide;

2-Ethyl-N-[(S)-{5-[1-(2-ethylpyrazole-3-carbonyl)piperidin-2-yl]-4-fluoro-1H-benzimidazol-2-yl}(4-methylcyclohexyl)methyl]pyrazole-3-carboxamide;

2-(2-{(S)-[(2-Ethylpyrazole-3-carbonyl)amino](4-methylcyclohexyl)methyl}-4-fluoro-1H-benzimidazol-5-yl)-N,N-dimethylpiperidine-1-carboxamide;

N-[(S)-{5-[(2S)-2-(Dimethylcarbamoyl)piperidin-1-yl]-4-fluoro-1H-benzimidazol-2-yl}-(4-methylcyclohexyl)methyl]-3-ethylisoxazole-4-carboxamide;

N-[(S)-{5-[2-(Dimethylamino)-2-oxoethyl]-4-fluoro-1H-benzimidazol-2-yl}(4-methyl-cyclohexyl)methyl]-3-ethylisoxazole-4-carboxamide;

N-[(S)-{5-[2-(Dimethylcarbamoyl)phenyl]-4,6-difluoro-1H-benzimidazol-2-yl}(4-methylcyclohexyl)methyl]-3-ethylisoxazole-4-carboxamide;

N-[(S)-{5-[2-(Dimethylcarbamoyl)phenyl]-4,6-difluoro-1H-benzimidazol-2-yl}(4-methylcyclohexyl)methyl]-2-ethylpyrazole-3-carboxamide;

N-(Cyclooctyl{4-fluoro-5-[2-(methylsulfonyl)phenyl]-1H-benzimidazol-2-yl}methyl)-2-ethylpyrazole-3-carboxamide;

N-(Cyclooctyl{4-fluoro-5-[3-(methanesulfonamido)phenyl]-1H-benzimidazol-2-yl}-methyl)-2-ethylpyrazole-3-carboxamide;

N-[(S)-{5-[2-(Dimethylcarbamoyl)phenyl]-1H-imidazo[4,5-b]pyridin-2-yl}(4-methyl-cyclohexyl)methyl]-2-ethylpyrazole-3-carboxamide;

N-(Cyclooctyl{6-[2-(dimethylcarbamoyl)phenyl]-4-methoxy-1H-imidazo[4,5-c]pyridin-2-yl}methyl)-2-methylpyrazole-3-carboxamide;

N-{Cyclooctyl[6-(3,6-dihydro-2H-pyran-4-yl)-7-fluoro-3H-benzimidazol-2-yl]methyl}-3-methylisoxazole-4-carboxamide;

N-{Cyclooctyl[4-fluoro-5-(piperidin-4-yl)-1H-benzimidazol-2-yl]methyl}-3-methyl-isoxazole-4-carboxamide;

N-{Cyclooctyl[4-fluoro-5-(piperazin-1-ylmethyl)-1H-benzimidazol-2-yl]methyl}-2-methylpyrazole-3-carboxamide;

N-{Cyclooctyl[4-fluoro-5-(morpholin-3-yl)-1H-benzimidazol-2-yl]methyl}-3-methyl-isoxazole-4-carboxamide;

N-{Cyclooctyl[4-fluoro-5-(1,4-oxazepan-3-yl)-1H-benzimidazol-2-yl]methyl}-3-methyl-isoxazole-4-carboxamide;

N-[(S)-{5-[4-(Dimethylcarbamoyl)pyrrolidin-3-yl]-4-fluoro-1H-benzimidazol-2-yl}(4-methylcyclohexyl)methyl]-3-ethylisoxazole-4-carboxamide;

N-{Cyclooctyl[4-fluoro-5-(1-methylpiperidin-4-yl)-1H-benzimidazol-2-yl]methyl}-3-methylisoxazole-4-carboxamide;

N-(Cyclooctyl{4-fluoro-5-[(4-methylpiperazin-1-yl)methyl]-1H-benzimidazol-2-yl}-methyl)-2-methylpyrazole-3-carboxamide;

N-[Cyclooctyl(4-fluoro-5-{[4-(oxetan-3-yl)piperazin-1-yl]methyl}-1H-benzimidazol-2-yl)methyl]-2-methylpyrazole-3-carboxamide;

N-{[5-(1-Acetylpiperidin-4-yl)-4-fluoro-1H-benzimidazol-2-yl](cyclooctyl)methyl}-3-methylisoxazole-4-carboxamide;

N-{[5-(4-Acetylmorpholin-3-yl)-4-fluoro-1H-benzimidazol-2-yl](cyclooctyl)methyl}-3-methylisoxazole-4-carboxamide;

N-[{5-[(4-Acetylpiperazin-1-yl)methyl]-4-fluoro-1H-benzimidazol-2-yl}(cyclooctyl)-methyl]-2-methylpyrazole-3-carboxamide;

N-[{5-[(4-Acetylpiperazin-1-yl)methyl]-1H-benzimidazol-2-yl}(cyclooctyl)methyl]-3-methylisoxazole-4-carboxamide;

N-[{6-[(4-Acetylpiperazin-1-yl)methyl]-4-methoxy-1H-imidazo[4,5-c]pyridin-2-yl}-(cyclooctyl)methyl]-2-methylpyrazole-3-carboxamide;

N-[(5-{Acetyl[1-(methylsulfonyl)piperidin-4-yl]amino}-4-fluoro-1H-benzimidazol-2-yl)-(cyclooctyl)methyl]-3-methylisoxazole-4-carboxamide;

N-[(S)-(5-Cyano-4-fluoro-1H-benzimidazol-2-yl)(4-methylcyclohexyl)methyl]-2-ethyl-pyrazole-3-carboxamide;

N-{(S)-[5-(1-Acetamidoethyl)-4-fluoro-1H-benzimidazol-2-yl](4-methylcyclohexyl)-methyl}-2-ethylpyrazole-3-carboxamide;

N-{(S)-[5-(1-Acetamido-1-methylethyl)-4-fluoro-1H-benzimidazol-2-yl](4-methyl-cyclohexyl)methyl}-2-ethylpyrazole-3-carboxamide;

N-[Cyclooctyl(4-methoxy-6-{[4-(methylsulfonyl)piperazin-1-yl]methyl}-1H-benzimidazol-2-yl)methyl]-3-methylisoxazole-4-carboxamide;

N-[Cyclooctyl(4-fluoro-5-{[4-(methylsulfonyl)piperazin-1-yl]methyl}-1H-benzimidazol-2-yl)methyl]-2-methylpyrazole-3-carboxamide;

N-[Cyclooctyl(5-{[4-(methylsulfonyl)piperazin-1-yl]methyl}-1H-benzimidazol-2-yl)-methyl]-3-methyl-isoxazole-4-carboxamide;

N-[Cyclooctyl(4-fluoro-5-{[1-(methylsulfonyl)piperidin-4-yl]methyl}-1H-benzimidazol-2-yl)methyl]-3-methylisoxazole-4-carboxamide;

N-[Cyclooctyl(4-fluoro-6-{[1-(methylsulfonyl)piperidin-4-yl]methyl}-1H-benzimidazol-2-yl)methyl]-3-methylisoxazole-4-carboxamide;

N-[Cyclooctyl(4-methoxy-6-{[4-(methylsulfonyl)piperazin-1-yl]methyl}-1H-imidazo-[4,5-c]pyridin-2-yl)methyl]-2-methylpyrazole-3-carboxamide;

N-{Cyclooctyl[4-fluoro-5-(morpholin-4-ylmethyl)-1H-benzimidazol-2-yl]methyl}-3-methylisoxazole-4-carboxamide;

N-{Cyclooctyl[4-fluoro-6-(morpholin-4-ylmethyl)-1H-benzimidazol-2-yl]methyl}-3-methylisoxazole-4-carboxamide;

Methyl (2S)-1-[(2-{(S)-[(3-ethylisoxazole-4-carbonyl)amino](4-methylcyclohexyl)-methyl}-4-fluoro-1H-benzimidazol-5-yl)methyl]pyrrolidine-2-carboxylate;

Methyl (2R)-1-[(2-{(S)-[(3-ethylisoxazole-4-carbonyl)amino](4-methylcyclohexyl)-methyl}-4-fluoro-1H-benzimidazol-5-yl)methyl]pyrrolidine-2-carboxylate;

(2S)-1-[(2-{(S)-[(3-Ethylisoxazole-4-carbonyl)amino](4-methylcyclohexyl)methyl}-4-fluoro-1H-benzimidazol-5-yl)methyl]pyrrolidine-2-carboxylic acid;

(2R)-1-[(2-{(S)-[(3-Ethylisoxazole-4-carbonyl)amino](4-methylcyclohexyl)methyl}-4-fluoro-1H-benzimidazol-5-yl)methyl]pyrrolidine-2-carboxylic acid;

N-[(S)-(5-{[(2R)-2-(Dimethylcarbamoyl)pyrrolidin-1-yl]methyl}-4-fluoro-1H-benzimidazol-2-yl)(4-methylcyclohexyl)methyl]-3-ethylisoxazole-4-carboxamide;

N-[{5-[2-(Dimethylcarbamoyl)phenyl]-4-fluoro-1H-benzimidazol-2-yl}(3,3-dimethyl-cyclohexyl)methyl]-3-methylisoxazole-4-carboxamide;

N-[{5-[2-(Dimethylcarbamoyl)phenyl]-4-fluoro-1H-benzimidazol-2-yl}(spiro[2.5]octan-7-yl)methyl]-3-ethyl-isoxazole-4-carboxamide;

N-[(3,3-Difluorocyclohexyl){5-[2-(dimethylcarbamoyl)phenyl]-4-fluoro-1H-benzimidazol-2-yl}methyl]-3-ethylisoxazole-4-carboxamide;

N-{[4-Fluoro-5-(tetrahydropyran-4-yl)-1H-benzimidazol-2-yl](4-methylcyclohexyl)-methyl}-3-methyl-isoxazole-4-carboxamide;

N-{(S)-[4-Fluoro-5-(tetrahydropyran-4-yl)-1H-benzimidazol-2-yl](4-methylcyclohexyl)-methyl}-3-methyl-isoxazole-4-carboxamide;

N-{(S)-[4-Fluoro-5-(tetrahydropyran-4-yl)-1H-benzimidazol-2-yl](4-methylcyclohexyl)-methyl}-3-methyl-isoxazole-4-carboxamide;

N-{Cycloheptyl[4-fluoro-5-(tetrahydropyran-4-yl)-1H-benzimidazol-2-yl]methyl}-3-methylisoxazole-4-carboxamide;

N-{Cyclohexyl[4-fluoro-5-(tetrahydropyran-4-yl)-1H-benzimidazol-2-yl]methyl}-3-methylisoxazole-4-carboxamide;

N-{Dispiro[2.0.24.13]heptan-7-yl[4-fluoro-5-(tetrahydropyran-4-yl)-1H-benzimidazol-2-yl]methyl}-3-methylisoxazole-4-carboxamide;

N-{[4-Fluoro-5-(tetrahydropyran-4-yl)-1H-benzimidazol-2-yl](norcaran-3-yl)methyl}-3-methylisoxazole-4-carboxamide;

N-{[4-Fluoro-5-(tetrahydropyran-4-yl)-1H-benzimidazol-2-yl](3-methylcyclohexyl)-methyl}-3-methylisoxazole-4-carboxamide;

N-{[4-Fluoro-5-(tetrahydropyran-4-yl)-1H-benzimidazol-2-yl](norcaran-7-yl)methyl}-3-methylisoxazole-4-carboxamide;

N-{[4-Fluoro-5-(tetrahydropyran-4-yl)-1H-benzimidazol-2-yl](2-methylcyclohexyl)-methyl}-3-methylisoxazole-4-carboxamide;

N-{(3,5-Dimethylcyclohexyl)[4-fluoro-5-(tetrahydropyran-4-yl)-1H-benzimidazol-2-yl]-methyl}-3-methylisoxazole-4-carboxamide;

tert-Butyl 3-(4-fluoro-2-{(S)-(4-methylcyclohexyl)[(3-methylisoxazole-4-carbonyl)-amino]methyl}-1H-benzimidazol-5-yl)morpholine-4-carboxylate;

Methyl 3-(4-fluoro-2-{(S)-(4-methylcyclohexyl)[(3-methylisoxazole-4-carbonyl)amino]-methyl}-1H-benzimidazol-5-yl)morpholine-4-carboxylate;

N-[(S)-{4-Fluoro-5-[4-(methylsulfonyl)morpholin-3-yl]-1H-benzimidazol-2-yl}(4-methylcyclohexyl)methyl]-3-methylisoxazole-4-carboxamide;

N-[(S)-{4-Fluoro-5-[4-(5-methyl-1,3,4-oxadiazol-2-yl)morpholin-3-yl]-1H-benzimidazol-2-yl}(4-methylcyclohexyl)methyl]-3-methylisoxazole-4-carboxamide;

N-Ethyl-3-(4-fluoro-2-{(S)-(4-methylcyclohexyl)[(3-methylisoxazole-4-carbonyl)amino]-methyl}-1H-benzimidazol-5-yl)morpholine-4-carboxamide;

tert-Butyl 3-{2-[(S)-acetamido(4-methylcyclohexyl)methyl]-4-fluoro-1H-benzimidazol-5-yl}morpholine-4-carboxylate;

tert-Butyl 3-(2-{(S)-[(3-{[dimethyl(oxo)-λ⁶-sulfanylidene]amino}benzoyl)amino](4-methylcyclohexyl)methyl}-4-fluoro-1H-benzimidazol-5-yl)morpholine-4-carboxylate;

N-[(S)-{5-[3-(Dimethylcarbamoyl)pyrazin-2-yl]-4-fluoro-1H-benzimidazol-2-yl}(4-methylcyclohexyl)methyl]-3-methylisoxazole-4-carboxamide;

N-[(S)-{5-[4-(Dimethylcarbamoyl)-2-methylpyrimidin-5-yl]-4-fluoro-1H-benzimidazol-2-yl}(4-methylcyclohexyl)methyl]-3-methylisoxazole-4-carboxamide;

N-[(S)-{5-[4-(3,3-Difluoroazetidine-1-carbonyl)pyridin-3-yl]-4-fluoro-1H-benzimidazol-2-yl}(4-methylcyclohexyl)methyl]-3-methylisoxazole-4-carboxamide;

N-[(S)-{4-Fluoro-5-[4-(3-hydroxy-3-methylazetidine-1-carbonyl)pyridin-3-yl]-1H-benzimidazol-2-yl}(4-methylcyclohexyl)methyl]-3-methylisoxazole-4-carboxamide;

N-[(S)-{5-[4-(Azetidine-1-carbonyl)pyridin-3-yl]-4-fluoro-1H-benzimidazol-2-yl}(4-methylcyclohexyl)methyl]-3-methylisoxazole-4-carboxamide;

N-[(S)-{5-[4-(3-Chloropropylcarbamoyl)pyridin-3-yl]-4-fluoro-1H-benzimidazol-2-yl}(4-methylcyclohexyl)methyl]-3-methylisoxazole-4-carboxamide;

N-[(S)-{5-[4-(3,3-Difluoroazetidine-1-carbonyl)-1-oxidopyridin-1-ium-3-yl]-4-fluoro-1H-benzimidazol-2-yl}(4-methylcyclohexyl)methyl]-3-methylisoxazole-4-carboxamide;

3-Ethyl-N-[(S)-{4-fluoro-5-[4-(methylsulfonimidoyl)pyridin-3-yl]-1H-benzimidazol-2-yl}(4-methylcyclohexyl)methyl]isoxazole-4-carboxamide;

N-[(S)-{5-[4-(3,3-Difluoroazetidine-1-carbonyl)pyridin-3-yl]-1H-imidazo[4,5-b]pyridin-2-yl}(4-methylcyclohexyl)methyl]-2-ethylpyrazole-3-carboxamide;

N-[(S)-{5-[4-(3,3-Difluoroazetidine-1-carbonyl)-1-oxidopyridin-3-yl]-1H-imidazo[4,5-b]-pyridin-2-yl}(4-methylcyclohexyl)methyl]-2-ethylpyrazole-3-carboxamide;

N-[(S)-{5-[4-(3,3-Difluoroazetidine-1-carbonyl)-1-oxidopyridin-3-yl]-4-hydroxy-1H-imidazo[4,5-b]pyridin-2-yl}(4-methylcyclohexyl)methyl]-2-ethylpyrazole-3-carboxamide;

N-[(S)-{5-[4-(3,3-Difluoroazetidine-1-carbonyl)furan-3-yl]-1H-imidazo[4,5-b]pyridin-2-yl}(4-methylcyclohexyl)methyl]-2-methylpyrazole-3-carboxamide;

N-[(S)-{5-[4-(3,3-Difluoroazetidine-1-carbonyl)tetrahydrofuran-3-yl]-1H-imidazo[4,5-b]-pyridin-2-yl}(4-methylcyclohexyl)methyl]-2-methylpyrazole-3-carboxamide;

Ethyl 3-(4-fluoro-2-{(S)-(4-methylcyclohexyl)[(3-methylisoxazole-4-carbonyl)amino]-methyl}-1H-benzimidazol-5-yl)morpholine-4-carboxylate;

N-[(S)-Cyclopentyl{5-[4-(3,3-difluoroazetidine-1-carbonyl)tetrahydrofuran-3-yl]-4-fluoro-1H-benzimidazol-2-yl}methyl]-3-ethylisoxazole-4-carboxamide;

N-[(S)-Cyclopentyl(4-fluoro-5-{4-[3-hydroxy-3-(trifluoromethyl)azetidine-1-carbonyl]-tetrahydrofuran-3-yl}-1H-benzimidazol-2-yl)methyl]-3-ethylisoxazole-4-carboxamide;

N-[(S)-Cyclopentyl{4-fluoro-5-[4-(3-hydroxyazetidine-1-carbonyl)tetrahydrofuran-3-yl]-1H-benzimidazol-2-yl}methyl]-3-ethylisoxazole-4-carboxamide;

N-[(S)-Cyclopentyl{4-fluoro-5-[4-(morpholine-4-carbonyl)tetrahydrofuran-3-yl]-1H-benzimidazol-2-yl}methyl]-3-ethylisoxazole-4-carboxamide;

N-[(S)-Cyclopentyl{5-[4-(3,3-difluoroazetidine-1-carbonyl)tetrahydrofuran-3-yl]-4-fluoro-1H-benzimidazol-2-yl}methyl]-3-methylisoxazole-4-carboxamide;

3,3-Difluorocyclobutyl N-[(S)-cyclopentyl{5-[4-(3,3-difluoroazetidine-1-carbonyl)-tetrahydrofuran-3-yl]-4-fluoro-1H-benzimidazol-2-yl}methyl]carbamate;

N-[(S)-{5-[3-(3,3-Difluoroazetidine-1-carbonyl)-1H-pyrazol-4-yl]-4-fluoro-1H-benzimidazol-2-yl}(4-methylcyclohexyl)methyl]-2-methylpyrazole-3-carboxamide;

N-[(S)-{5-[4-(3,3-Difluoroazetidine-1-carbonyl)-2-methylpyrimidin-5-yl]-4-fluoro-1H-benzimidazol-2-yl}(4-methylcyclohexyl)methyl]-2-methylpyrazole-3-carboxamide;

N-[(S)-{5-[4-(3,3-Difluoroazetidine-1-carbonyl)pyrimidin-5-yl]-4-fluoro-1H-benzimidazol-2-yl}(4-methylcyclohexyl)methyl]-2-methylpyrazole-3-carboxamide;

N-[(S)-(5-{[Dimethyl(oxo)-$\lambda^6$-sulfanylidene]amino}-4-fluoro-1H-benzimidazol-2-yl)(4-methylcyclohexyl)methyl]-3-ethylisoxazole-4-carboxamide;

3-(2-{(S)-[(2-Ethylpyrazole-3-carbonyl)amino](4-methylcyclohexyl)methyl}-7-fluoro-3H-imidazo[4,5-c]pyridin-6-yl)-N,N-dimethylpyridine-4-carboxamide;

N-[(S)-{5-[4-(3,3-Difluoroazetidine-1-carbonyl)morpholin-3-yl]-4-fluoro-1H-benzimidazol-2-yl}(4-methylcyclohexyl)methyl]-3-methylisoxazole-4-carboxamide;

N-[(S)-{2-[4-(3,3-difluoroazetidine-1-carbonyl)pyridin-3-yl]-7H-purin-8-yl}(4-methyl-cyclohexyl)methyl]-2-ethylpyrazole-3-carboxamide;

N-[(S)-{5-[4-(3,3-Difluoroazetidine-1-carbonyl)pyridin-3-yl]-1H-imidazo[4,5-b]pyrazin-2-yl}(4-methylcyclohexyl)methyl]-2-ethylpyrazole-3-carboxamide;

3-Ethyl-N-[(S)-{4-fluoro-5-[(2-oxopyrrolidin-1-yl)methyl]-1H-benzimidazol-2-yl}(4-methylcyclohexyl)methyl]isoxazole-4-carboxamide;

tert-Butyl 3-(3,3-difluoroazetidine-1-carbonyl)-4-(2-{(S)-[(2-ethylpyrazole-3-carbonyl)-amino](4-methylcyclohexyl)methyl}-4-fluoro-1H-benzimidazol-5-yl)-2,5-dihydro-pyrrole-1-carboxylate;

tert-Butyl 3-(3,3-difluoroazetidine-1-carbonyl)-4-(2-{(S)-[(2-ethylpyrazole-3-carbonyl)-amino](4-methylcyclohexyl)methyl}-4-fluoro-1H-benzimidazol-5-yl)pyrrolidine-1-carboxylate;

N-[(S)-{5-[4-(3,3-Difluoroazetidine-1-carbonyl)pyrrolidin-3-yl]-4-fluoro-1H-benzimidazol-2-yl}(4-methylcyclohexyl)methyl]-2-ethylpyrazole-3-carboxamide;

N-[(S)-{5-[4-(3,3-Difluoroazetidine-1-carbonyl)pyridin-3-yl]-4-fluoro-1-methyl-benzimidazol-2-yl}(4-methylcyclohexyl)methyl]-2-methylpyrazole-3-carboxamide; or N-[(S)-{6-[4-(3,3-Difluoroazetidine-1-carbonyl)pyridin-3-yl]-7-fluoro-1-methyl-benzimidazol-2-yl}(4-methylcyclohexyl)methyl]-2-methylpyrazole-3-carboxamide.

11. A pharmaceutical composition comprising a compound of formula (I) as defined in claim 1 or an N-oxide thereof, or a pharmaceutically acceptable salt thereof, in association with a pharmaceutically acceptable carrier.

12. A pharmaceutical composition comprising a first pharmaceutically active ingredient which is a compound of formula (I) as defined in claim 1 or an N-oxide thereof, or a pharmaceutically acceptable salt thereof, in association with a pharmaceutically acceptable carrier, and further comprising an additional pharmaceutically active ingredient.

* * * * *